(12) United States Patent
Schenkel et al.

(10) Patent No.: US 10,562,891 B2
(45) Date of Patent: Feb. 18, 2020

(54) QUINAZOLINONES AS PARP14 INHIBITORS

(71) Applicant: Ribon Therapeutics Inc., Lexington, MA (US)

(72) Inventors: Laurie B. Schenkel, Somerville, MA (US); Melissa Marie Vasbinder, Newton, MA (US); Kevin Wayne Kuntz, Woburn, MA (US); Kerren Kalai Swinger, Lexington, MA (US)

(73) Assignee: Ribon Therapeutics Inc., Cambridge, MA (US)

( * ) Notice: Subject to any disclaimer, the term of this patent is extended or adjusted under 35 U.S.C. 154(b) by 0 days.

(21) Appl. No.: 16/227,132

(22) Filed: Dec. 20, 2018

(65) Prior Publication Data

US 2019/0194174 A1 Jun. 27, 2019

Related U.S. Application Data

(60) Provisional application No. 62/691,025, filed on Jun. 28, 2018, provisional application No. 62/608,747, filed on Dec. 21, 2017.

(51) Int. Cl.
| | | |
|---|---|---|
| *C07D 405/12* | (2006.01) | |
| *C07D 401/12* | (2006.01) | |
| *C07D 403/12* | (2006.01) | |
| *C07D 401/14* | (2006.01) | |
| *C07D 239/88* | (2006.01) | |
| *A61P 35/00* | (2006.01) | |
| *C07D 405/14* | (2006.01) | |
| *C07D 417/14* | (2006.01) | |
| *C07D 471/04* | (2006.01) | |
| *C07D 409/12* | (2006.01) | |
| *C07D 413/14* | (2006.01) | |

(52) U.S. Cl.
CPC ............ *C07D 405/12* (2013.01); *A61P 35/00* (2018.01); *C07D 239/88* (2013.01); *C07D 401/12* (2013.01); *C07D 401/14* (2013.01); *C07D 403/12* (2013.01); *C07D 405/14* (2013.01); *C07D 409/12* (2013.01); *C07D 413/14* (2013.01); *C07D 417/14* (2013.01); *C07D 471/04* (2013.01)

(58) Field of Classification Search
CPC .. C07D 405/12; C07D 239/88; C07D 401/12; C07D 401/14; C07D 403/12; C07D 405/14; C07D 409/12; C07D 413/14; C07D 417/14; C07D 471/04; A61P 35/00
USPC ........................................................ 544/283
See application file for complete search history.

(56) References Cited

U.S. PATENT DOCUMENTS

| 9,359,367 | B2 * | 6/2016 | Jana ...................... C07D 239/88 |
| 2004/0077667 | A1 * | 4/2004 | Matsuoka ............ C07D 239/88 |
| | | | 514/266.2 |
| 2005/0043333 | A1 * | 2/2005 | Ishida .................. C07D 239/88 |
| | | | 514/266.2 |
| 2005/0054658 | A1 | 3/2005 | Thompson et al. |
| 2015/0225396 | A1 * | 8/2015 | Bregman ............. C07D 403/12 |
| | | | 514/252.17 |
| 2016/0184310 | A1 * | 6/2016 | Dorsch ................ C07D 401/14 |
| | | | 514/252.02 |
| 2016/0289685 | A1 | 10/2016 | Iwata et al. |

FOREIGN PATENT DOCUMENTS

| WO | WO2002/048177 | 6/2002 |
| WO | WO2011/036576 | 3/2011 |
| WO | WO2013/091773 | 6/2013 |
| WO | WO2014/036022 | 3/2014 |
| WO | WO2018/046933 | 3/2018 |

OTHER PUBLICATIONS

National Center for Biotechnology Information. PubChem Database. CID9289985, SID=53380422, https://pubchem.ncbi.nlm.nih.gov/substance/53380422 (accessed on May 10, 2019). Available on Sep. 12, 2008 (Year: 2008).*
National Center for Biotechnology Information. PubChem Database. SID 43973648, SID=43973648, https://pubchem.ncbi.nlm.nih.gov/substance/43973648 (accessed on May 9, 2019). Available on Dec. 5, 2007 (Year: 2007).*
Wahlberg; Nature Biotechnology vol. 30, pp. 283-288 (2012). (Year: 2012).*
Anderson et al, "Discovery of Ligands for ADP-Ribosyltransferases via Docking-Based Virtual Screening," Journal of Medicinal Chemistry, Aug. 2012, 55:17:7706-7718.
PCT International Search Report and Written Opinion in International Appln. No. PCT/US2018/066700, dated Apr. 20, 2019, 13 pages.
Aguiar et al, "B-aggressive Lymphoma Family Proteins Have Unique Domains That Modulate Transcription and Exhibit Poly(ADP-ribose) Polymerase Activity," J Biol Chem., Oct. 7, 2005;280(40):33756-33765.
Aguiar et al, "BAL is a novel risk-related gene in diffuse large B-cell lymphomas that enhances cellular migration," Blood, Dec. 15, 2000, 96(13):4328-4334.
Bachmann et al, "DTX3L and ARTD9 inhibit IRF1 expression and mediate in cooperation with ARTD8 survival and proliferation of metastatic prostate cancer cells," Mol Cancer., May 27, 2014, 13:125.
Barbarulo et al, "Poly(ADP-ribose) polymerase family member 14 (PARP14) is a novel effector of the JNK2-dependent pro-survival signal in multiple myeloma," Oncogene, Oct. 8, 2012, 32(36):4231-4242.
Camicia et al, "Novel drug targets for personalized precision medicine in relapsed/refractory diffuse large B-cell lymphoma: a comprehensive review," Molecular Cancer, 2015, 14:207:62 pages.

(Continued)

*Primary Examiner* — Daniel R Carcanague
(74) *Attorney, Agent, or Firm* — Fish & Richardson P.C.

(57) ABSTRACT

The present invention relates to quinazolinones and related compounds which are inhibitors of PARP14 and are useful, for example, in the treatment of cancer and inflammatory diseases.

4 Claims, 4 Drawing Sheets

(56) References Cited

OTHER PUBLICATIONS

Chang et al, "POSTER: NAD+ Metabolism and Signaling," Presented at the Federation of American Societies for Experimental Biology, Jul. 9-14, 2017, New Orleans, Louisiana, 1 page.
Cho et al, "B Cell-Intrinsic and -Extrinsic Regulation of Antibody Responses by PARP14, an Intracellular (ADP-Ribosyl)Transferase," J. Immunol., Aug., 2013, 191:3169-3178.
Cho et al, "Glycolytic rate and lymphomagenesis depend on PARP14, an ADP ribosyltransferase of the B aggressive lymphoma (BAL) family," Proc Natl Acad Sci USA, Sep. 20, 2011, 108(38): 15972-15977.
Cho et al, "PARP-14, a member of the B aggressive lymphoma family, transduces survival signals in primary B cells," Blood, Jan. 2009, 113(11):2416-2425.
Ekblad et al, "Towards small molecule inhibitors of mono-ADP-ribosyltransferases," European Journal of Medicine, 2015, 95:546-551.
GenBank Accession No. NM_017554, "Homo sapiens poly(ADP-ribose) polymerase family member 14 (PARP14), mRNA," Apr. 1, 2018, 8 pages.
Goenka et al, "Collaborator of Stat6 (CoaSt6)-associated Poly(ADP-ribose) Polymerase Activity Modulates Stat6-dependent Gene Transcription," J Biol Chem, May 10, 2007, 282(26):18732-18739.
Goenka et al, "Selective potentiation of Stat-dependent gene expression by collaborator of Stat6 (CoaSt6), a transcriptional cofactor," Proc Natl Acad Sci USA, Mar. 6, 2006, 103(11):4210-4215.
Iansante et al, "PARP14 promotes the Warburg effect in hepatocellular carcinoma by inhibiting JNK1-dependent PKM2 phosphorylation and activation," Nat Commun. Aug. 10, 2015, 6:7882.
Iqbal et al, "PARP-14 combines with tristeraprolin in the selective posttranscriptional control of macrophage tissue factor expression," Blood, Dec., 2014, 124:24:3646-3655.
Iwata et al, "PARP9 and PARP14 cross-regulate macrophage activation via STAT1 ADP-ribosylation," Nat Commun. Oct. 31, 2016, 7:12849.
Juszczynski et al, "BAL1 and BBAP Are Regulated by a Gamma Interferon-Responsive Bidirectional Promoter and Are Overexpressed in Diffuse Large B-Cell Lymphomas with a Prominent Inflammatory Infiltrate," Mol Cell Biol. Jul., 2006, 26(14):5348-5359.
Kirby et al, "A Potent and Selective PARP11 Inhibitor Suggests Coupling between Cellular Localization and Catalytic Activity," Cell Chemical Biology, Dec. 20, 2018, 25:1-7.
Kirby et al, "Abstract: Structure-guided Design of H-Y-F Triad Motif-containing PARP Inhibitors," Presented at Proceedings of NAD+ Metabolism and Signaling: Federation of American Societies for Experimental Biology, New Orleans, Jul. 9-14, 2017, 1 page.
Kirby et al, Abstract: Structure-guided Design of H-Y-F Triad Motif-containing PARP Inhibitors, Presented at the Federation of American Societies for Experimental Biology, Jul. 9-14, 2017, New Orleans, Louisiana, 1 page.
Krishnamurthy et al, "Poly-ADP ribose polymerase-14 limits severity of allergic skin disease," Immunology, Jul. 27, 2017, 152(3):451-461.
Liu et al, "New Methylene Homologation Method for Cyclic Ketones," Chem. Eur. J., 2012, 18(38):11889-11893.
Mehrotra et al, "Poly (ADP-ribose) polymerase 14 and its enzyme activity regulates T(H)2 differentiation and allergic airway disease," J Allergy Clin Immunol, Jul. 25, 2012, 131(2):521-531.
Mehrotra et al "PARP-14 functions as a transcriptional switch for Stat6-dependent gene activation," J Biol Chem, Nov. 16, 2010, 286(3):1767-1776.
Monti et al, "Molecular profiling of diffuse large B-cell lymphoma identifies robust subtypes including one characterized by host inflammatory response," Blood, Mar., 2005, 105(5):1851.
Moustakim et al, "Discovery of a novel allosteric inhibitor scaffold for polyadenosine-diphosphate-ribose polymerase 14 (PARP14) macrodomain 2," Bioorganic & Medicinal Chemistry, 2018, 26:2965-2972.
Ohmoto et al, "Current status of poly(ADP-ribose) polymerase inhibitors and future directions," Onco Targets and Therapy. 2017, 10:5195-5208.
Peng et al, "Small Molecule Microarray Based Discovery of PARP14 Inhibitors," Angew. Chem., 2017, 129:254-259.
Schweiker et al, "Structure, Function and Inhibition of Poly(ADP-ribose)polymerase, Member 14 (PARP14)," Medicinal Chemistry, 2018, 12:1659-1669.
STN Search, conducted Oct. 3, 2017, 42 pages.
STN Search, conducted Sep. 29, 2017, 21 pages.
Upton et al, "Design and synthesis of potent inhibitors of the mono(ADP-ribosyl)transferase, PARP14," Bioorganic & Medicinal Chemistry Letters, 2017, 27:2907-2911.
Vyas et al, "A systematic analysis of the PARP protein family identifies new functions critical for cell physiology," Nat Commun., Aug. 7, 2013, 4:2240, 27 pages.
Vyas et al, "New PARP targets for cancer therapy Nat Rev Cancer," Jun. 5, 2014, 14:502-509.
Yanagawa et al, "Regulation of Phosphoglucose Isomerase/Autocrine Motility Factor Activities by the Poly(ADP-Ribose) Polymerase Family-14," Cancer Res., 2007, 67:18:8682-8689.
Yoneyama-Hirozane et al, "Identification of PARP14 inhibitors using novel methods for detecting auto-ribosylation," 2017, 486:626-631.
Zhang et al, "Design, synthesis, and preliminary SAR study of 3- and 6-side-chain-extended tetrahydro-pyran analogues of cis- and trans-(6-benzhydryl-tetrahydropyran-3-yl)-benzylamine," Bioorg. Med. Chem. 2006, 14:3953-3966.
Camicia et al, "BAL1/ARTD9 represses the anti-proliferative and pro-apoptotic IFNc-STAT1-IRF1-p53 axis in diffuse large B-cell lymphoma,"Journal of Cell Science, 2013, 126: 1969-1980.
Caprara et al, "PARP14 Controls the Nuclear Accumulation of a Subset of Type I IFN—Inducible Proteins," The Journal of Immunology, Mar. 2018, 16 pages.
Ekblad et al, "Identification of Poly(ADP-Ribose) Polymerase Macrodomain Inhibitors Using an AlphaScreen Protocol," SLAS Discovery, 2017, 10 pages.
Holechek et al, "Design, synthesis and evaluation of potent and selective inhibitors of mono-(ADP-ribosyl)transferases PARP10 and PARP14," Bioorg. Med. Chem. Lett., 2018, 5 pages.
Passerini et al, "PARP14 Is a Novel Therapeutic Target in STAT6 mutant Follicular Lymphoma," Blood, Nov. 29, 2018, 5 pages.
Riley et al, "PARP-14 Binds Specific DNA Sequences to Promote Th2 Cell Gene Expression," PLOS One, Dec. 2013, 8(12):e83127, 11 pages.
Schuller et al, "Human Poly (ADP-ribose) Polymerase Family Member 14 (PARP14) a Target Enabling Packaged (TEP)," Zenodo, 2018, 17 pages.

\* cited by examiner

QUINAZOLINONES AS PARP14 INHIBITORS

FIELD OF THE INVENTION

The present invention relates to quinazolinones and related compounds which are inhibitors of PARP14 and are useful in the treatment of cancer.

BACKGROUND OF THE INVENTION

Poly(ADP-ribose) polymerases (PARPs) are members of a family of seventeen enzymes that regulate fundamental cellular processes including gene expression, protein degradation, and multiple cellular stress responses (Vyas S, et al. Nat Rev Cancer. 2014 Jun. 5; 14(7):502-509). The ability of cancer cells to survive under stress is a fundamental cancer mechanism and an emerging approach for novel therapeutics. One member of the PARP family, PARP1, has already been shown to be an effective cancer target in connection to cellular stress induced by DNA damage, either induced by genetic mutation or with cytotoxic chemotherapy, with three approved drugs in the clinic and several others in late stage development (Ohmoto A, et al. OncoTargets and Therapy. 2017; Volume 10:5195).

The seventeen members of the PARP family were identified in the human genome based on the homology within their catalytic domains (Vyas S, et al. Nat Commun. 2013 Aug. 7; 4:2240). However, their catalytic activities fall into 3 different categories. The majority of PARP family members catalyze the transfer of mono-ADP-ribose units onto their substrates (monoPARPs), while others (PARP1, PARP2, TNKS, TNKS2) catalyze the transfer of poly-ADP-ribose units onto substrates (polyPARPs). Finally, PARP13 is thus far the only PARP for which catalytic activity could not be demonstrated either in vitro or in vivo. PARP14 is a cytosolic as well as nuclear monoPARP. It was originally identified as BAL2 (B Aggressive Lymphoma 2), a gene associated with inferior outcome of diffuse large B cell lymphoma (DLBCL), together with two other monoPARPs (PARP9 or BAL1 and PARP15 or BAL3) (Aguiar R C, et al. Blood. 2000 Dec. 9; 96(13):4328-4334 and Juszczynski P, et al. Mol Cell Biol. 2006 Jul. 1; 26(14):5348-5359). PARP14, PARP9 and PARP15 are also referred to as macro-PARPs due to the presence of macro-domains in their N-terminus. The genes for the three macroPARPs are located in the same genomic locus suggesting co-regulation. Indeed, the gene expression of PARP14 and PARP9 is highly correlated across normal tissues and cancer types. PARP14 is overexpressed in tumors compared to normal tissues, including established cancer cell lines in comparison to their normal counterparts. Literature examples of cancers with high PARP14 expression are DLBCL (Aguiar R C T, et al. J Biol Chem. 2005 Aug. 1; 280(40):33756-33765), multiple myeloma (MM) (Barbarulo A, et al. Oncogene. 2012 Oct. 8; 32(36):4231-4242) and hepatocellular carcinoma (HCC) (Iansante V, et al. Nat Commun. 2015 Aug. 10; 6:7882). In MM and HCC cell lines RNA interference (RNAi) mediated PARP14 knockdown inhibits cell proliferation and survival. Other studies show that the enzymatic activity of PARP14 is required for survival of prostate cancer cell lines in vitro (Bachmann S B, et al. Mol Cancer. 2014 May 27; 13:125).

PARP14 has been identified as a downstream regulator of IFN-γ and IL-4 signaling, influencing transcription downstream of STAT1 (in the case of IFN-γ) (Iwata H, et al. Nat Commun. 2016 Oct. 31; 7:12849) or STAT6 (in the case of IL-4) (Goenka S, et al. Proc Natl Acad Sci USA. 2006 Mar. 6; 103(11):4210-4215; Goenka S, et al. J Biol Chem. 2007 May 3; 282(26):18732-18739; and Mehrotra P, et al. J Biol Chem. 2010 Nov. 16; 286(3):1767-1776). Parp14−/− knockout (KO) mice have reduced marginal zone B cells, and the ability of IL-4 to confer B cell survival in vitro was reduced as well in the Parp14 KO setting (Cho S H, et al. Blood. 2009 Jan. 15; 113(11):2416-2425). This decreased survival signaling was linked mechanistically to decreased abilities of Parp14 KO B cells to sustain metabolic fitness and to increased Mcl-1 expression. Parp14 KO can extend survival in the Eμ-Myc lymphoma model, suggesting a role of PARP14 in Myc-driven lymphomagenesis (Cho S H, et al. Proc Natl Acad Sci USA. 2011 Sep. 12; 108(38):15972-15977). Gene expression data point towards roles of PARP14 in human B cell lymphoma as well. The BAL proteins, including PARP14, are highly expressed in host response (HR) DLBCLs, a genomically defined B cell lymphoma subtype characterized with a brisk inflammatory infiltrate of T and dendritic cells and presence of an IFN-γ gene signature (Molecular profiling of diffuse large B-cell lymphoma identifies robust subtypes including one characterized by host inflammatory response. Monti S, et al. Blood. 2005; 105(5):1851). Indeed, PARP14 is believed to be an interferon stimulated gene with its mRNA increased by stimulation of various cell systems with all types of interferon (I, II and III; www.interferome.org).

Due to its role downstream of IL-4 and IFN-γ signaling pathways PARP14 has been implicated in T helper cell and macrophage differentiation. Genetic PARP14 inactivation in macrophages skews to a pro-inflammatory M1 phenotype associated with antitumor immunity while reducing a pro-tumor M2 phenotype. M1 gene expression, downstream of IFN-γ, was found to be increased while M2 gene expression, downstream of IL-4, was decreased with PARP14 knockout or knockdown in human and mouse macrophage models. Similarly, genetic PARP14 knockout has been shown to reduce a Th2 T helper cell phenotype in the setting of skin and airway inflammation, again pertaining to the regulatory role of PARP14 in IL-4 signal transduction (Mehrotra P, et al. J Allergy Clin Immunol. 2012 Jul. 25; 131(2):521 and Krishnamurthy P, et al. Immunology. 2017 Jul. 27; 152(3): 451-461).

PARP14 was shown to regulate the transcription of STAT6 (activator of transcription 6) and promotes $T_H2$ responses in T cells and B cells, which are known to promote allergic airway disease (asthmatic condition). Genetic depletion of PARP14 and its enzymatic activity in a model of allergic airway disease led to reduced lung inflammation and IgE levels, which are key readouts of the asthmatic process in this model. In addition, the enzymatic activity of PARP14 promoted a $T_H2$ phenotype differentiation in a STAT6 dependent manner. (Mehrotra P, et al. J Allergy Clin Immunol. 2012 Jul. 25; 131(2):521) Therefore, inhibition of the PARP14 catalytic activity may be a potential novel therapy for allergic airway disease.

There is an ongoing need for new medications that can treat diseases such as certain cancers and inflammatory conditions characterized by abnormal expression or activity of PARP14. The compounds, compositions, and methods described herein help meet these and other needs.

SUMMARY OF THE INVENTION

The present invention is directed to a compound of Formula I:

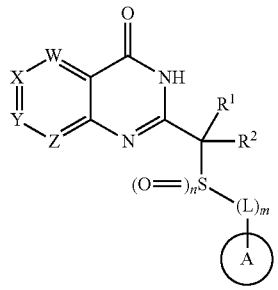

or a pharmaceutically acceptable salt thereof, wherein constituent members are defined below.

The present invention is further directed to a pharmaceutical composition comprising a compound of Formula I, or a pharmaceutically acceptable salt thereof, and at least one pharmaceutically acceptable carrier.

The present invention is further directed to a method of inhibiting the activity of PARP14 comprising contacting a compound of Formula I, or a pharmaceutically acceptable salt thereof, with PARP14.

The present invention is further directed to a method of decreasing IL-10 in a cell comprising contacting a compound of Formula I, or a pharmaceutically acceptable salt thereof, with the cell.

The present invention is further directed to a method of treating a disease or disorder in a patient in need of treatment, where the disease or disorder is characterized by overexpression or increased activity of PARP14, comprising administering to the patient a therapeutically effective amount of a compound Formula I, or a pharmaceutically acceptable salt thereof.

The present invention is further directed to a method of treating cancer in a patient in need of treatment comprising administering to the patient a therapeutically effective amount of a compound of Formula I, or a pharmaceutically acceptable salt thereof.

The present invention is further directed to a method of treating an inflammatory disease in a patient in need of treatment comprising administering to the patient a therapeutically effective amount of a compound of Formula I, or a pharmaceutically acceptable salt thereof.

DETAILED DESCRIPTION

Figure 1:
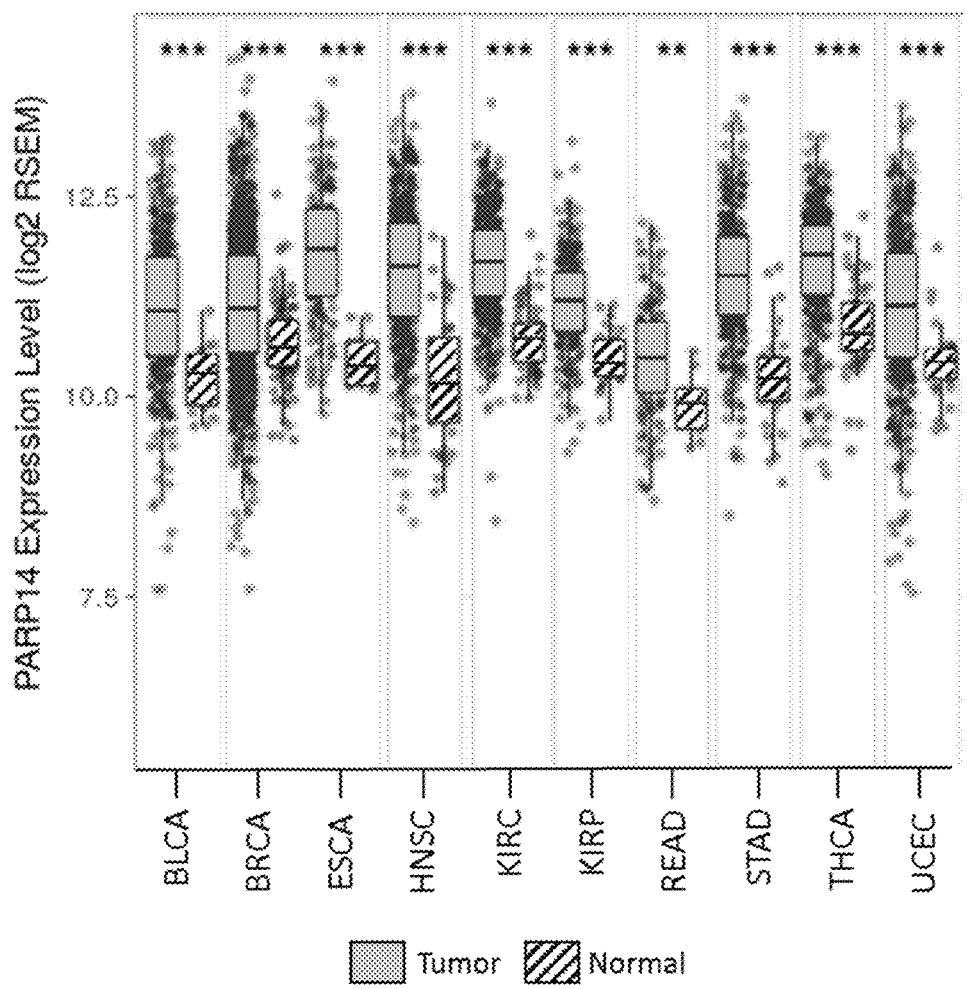
FIG. 1 illustrates the mRNA expression levels of PARP14 in various cancer types, compared to their matched normal tissue.

The present invention is directed to a compound of Formula I:

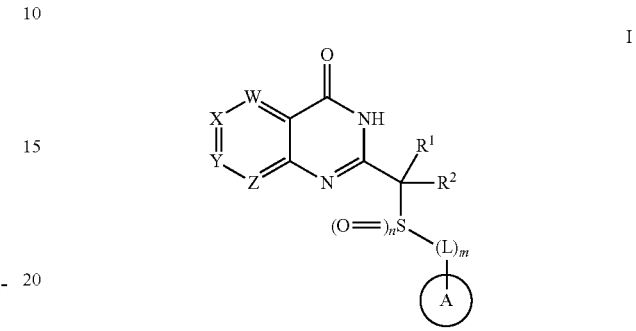

or a pharmaceutically acceptable salt thereof, wherein:
W is $CR^W$ or N;
X is $CR^X$ or N;
Y is $CR^Y$ or N;
Z is $CR^Z$ or N;
wherein no more than two of W, X, Y, and Z are simultaneously N;
Ring A is monocyclic or polycyclic $C_{3-14}$ cycloalkyl or Ring A is monocyclic or polycyclic 4-18 membered heterocycloalkyl, wherein Ring A is optionally substituted by 1, 2, 3, or 4 $R^4$, and Ring A is attached to the $-(L)_m$-moiety of Formula I through a non-aromatic ring when Ring A is polycyclic;
L is $(CR^5R^6)_t$—, —$(CR^5R^6)_p$—O—$(CR^5R^6)_q$—, —$(CR^5R^6)_p$—S—$(CR^5$—O—$(CR^5R^6)_q$, —$(CR^5R^6)_p$—$NR^3$—$(CR^5R^6)_q$—, —$(CR^5R^6)_p$—CO—$(CR^5R^6)_q$—, —$(CR^5R^6)_r$—C(O)O—$(CR^5R^6)_s$—, —$(CR^5R^6)_r$—$CONR^3$—$(CR^5R^6)_s$—, —$(CR^5R^6)_p$—SO—$(CR^5R^6)_q$—, —$(CR^5R^6)_p$—$SO_2$—$(CR^5R^6)_q$—, —$(CR^5R^6)_r$—$SONR^3$—$(CR^5R^6)_s$—, or —$NR^3CONR^4$—;
$R^1$ and $R^2$ are each, independently, selected from H and methyl;
$R^3$ and $R^4$ are each, independently, selected from H and $C_{1-4}$ alkyl;
$R^5$ and $R^6$ are each, independently, selected from H, halo, $C_{1-4}$ alkyl, $C_{1-4}$ alkoxy, $C_{1-4}$ haloalkyl, amino, $C_{1-4}$ alkylamino, and $C_{2-8}$ dialkylamino;
each $R^4$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^A$ are each optionally substituted with 1, 2, 3, 4, or 5 substituents independently selected from $Cy^1$, $Cy^1$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})$ $NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^W$, $R^X$, $R^Y$, and $R^Z$ are each, independently, selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$; wherein said $C_{1-6}$ alkyl, $C_{2-6}$ alkenyl, $C_{2-6}$ alkynyl, $C_{1-6}$ haloalkyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^W$, $R^X$, $R^Y$, or $R^Z$ are each optionally substituted with 1, 2, 3, 4, or 5 substituents independently selected from $Cy^2$, $Cy^2$-$C_{1-4}$ alkyl, halo, $C_{1-6}$ alkyl, $C_{2-6}$ alkenyl, $C_{2-6}$ alkynyl, $C_{1-6}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

wherein when W is $CR^W$, X is $CR^X$, Y is $CR^Y$, and Z is $CR^Z$, then at least one of $R^W$, $R^X$, $R^Y$, and $R^Z$ is other than H;

each $Cy^1$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

each $Cy^2$ is independently selected from $C_{6-10}$ aryl, $C_{3-7}$ cycloalkyl, 5-10 membered heteroaryl, and 4-10 membered heterocycloalkyl, each optionally substituted by 1, 2, 3, or 4 substituents independently selected from halo, $C_{1-6}$ alkyl, $C_{2-6}$ alkenyl, $C_{2-6}$ alkynyl, $C_{1-6}$ haloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, 4-10 membered heterocycloalkyl-$C_{1-4}$ alkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^{a1}$, $R^{b1}$, $R^{c1}$, $R^{d1}$, $R^{a2}$, $R^{b2}$, $R^{c2}$, and $R^{d2}$ is independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl of $R^{a1}$, $R^{b1}$, $R^{c1}$, $R^{d1}$, $R^{a2}$, $R^{b2}$, $R^{c2}$, or $R^{d2}$ is optionally substituted with 1, 2, 3, 4, or 5 substituents independently selected from $Cy^3$, $Cy^3$-$C_{1-4}$ alkyl, halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$, $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $Cy^3$ is $C_{6-10}$ aryl, $C_{3-7}$ cycloalkyl, 5-10 membered heteroaryl, or 4-10 membered heterocycloalkyl, each optionally substituted by 1, 2, 3, or 4 substituents independently selected from halo, $C_{1-4}$ alkyl, $C_{1-4}$ haloalkyl, $C_{1-6}$ haloalkyl, $C_{2-6}$ alkenyl, $C_{2-6}$ alkynyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$ $NR^{c3}C(O)OR^{a3}$, $C(=NR^{e3})NR^{c3}R^{d3}$, $NR^{c3}C(=NR^{e3})$ $NR^{c3}R^{d3}$ $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

$R^{a3}$, $R^{b3}$, $R^{c3}$, and $R^{d3}$ are independently selected from H, $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl, wherein said $C_{1-6}$ alkyl, $C_{1-6}$ haloalkyl, $C_{2-6}$ alkenyl, $C_{2-6}$ alkynyl, $C_{6-10}$ aryl, $C_{3-7}$ cycloalkyl, 5-10 membered heteroaryl, 4-10 membered heterocycloalkyl, $C_{6-10}$ aryl-$C_{1-4}$ alkyl, $C_{3-7}$ cycloalkyl-$C_{1-4}$ alkyl, 5-10 membered heteroaryl-$C_{1-4}$ alkyl, and 4-10 membered heterocycloalkyl-$C_{1-4}$ alkyl are each optionally substituted with 1, 2, or 3 substituents independently selected from OH, CN, amino, halo, $C_{1-6}$ alkyl, $C_{1-6}$ alkoxy, $C_{1-6}$ haloalkyl, and $C_{1-6}$ haloalkoxy;

or $R^{c1}$ and $R^{d1}$, together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$ $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$ and $S(O)_2NR^{c3}R^{d3}$;

or $R^{c2}$ and $R^{d2}$, together with the N atom to which they are attached form a 4-7 membered heterocycloalkyl group optionally substituted with 1, 2, or 3 substituents independently selected from halo, $C_{1-4}$ alkyl, $C_{1-4}$ haloalkyl, CN, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)NR^{c3}R^{d3}$ $NR^{c3}C(O)OR^{a3}$, $C(=NR^{e3})NR^{c3}R^{d3}$, $NR^{c3}C(=NR^{e3})NR^{c3}R^{d3}$, $S(O)R^{b3}$, $S(O)NR^{c3}R^{d3}$, $S(O)_2R^{b3}$, $NR^{c3}S(O)_2R^{b3}$, $NR^{c3}S(O)_2NR^{c3}R^{d3}$, and $S(O)_2NR^{c3}R^{d3}$;

each $R^{e1}$, $R^{e2}$, and $R^{e3}$ is independently selected from H, $C_{1-4}$ alkyl, and CN;

m is 0 or 1, n is 0, 1, or 2;

p is 0, 1, or 2;

q is 0, 1, or 2, wherein p+q is 0, 1, or 2;

r is 0 or 1;

s is 0 or 1, where r+s is 0 or 1; and t is 1, 2, or 3;

wherein any aforementioned heteroaryl or heterocycloalkyl group comprises 1, 2, 3, or 4 ring-forming heteroatoms independently selected from O, N, and S;

wherein one or more ring-forming C or N atoms of any aforementioned heterocycloalkyl group is optionally substituted by an oxo (=O) group;

wherein one or more ring-forming S atoms of any aforementioned heterocycloalkyl group is optionally substituted by one or two oxo (=O) groups;

wherein when W is $CR^W$, X is $CR^X$, Y is $CR^Y$, and Z is $CR^Z$ and when m is 1 or 2, then $R^X$ and $R^Y$ are not both methoxy;

wherein the compound is other than:

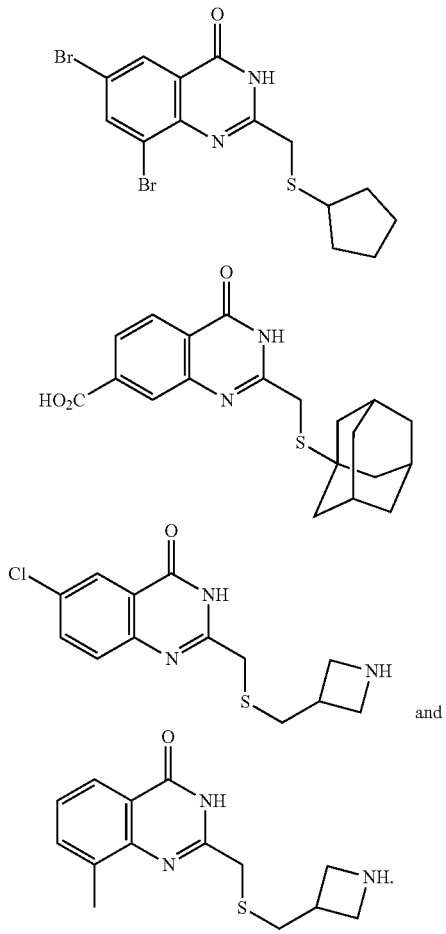

In some embodiments, W is $CR^W$; X is $CR^X$; Y is $CR^Y$; and Z is $CR^Z$.

In some embodiments, W is N; X is $CR^X$; Y is $CR^Y$; and Z is $CR^Z$.

In some embodiments, W is $CR^W$; X is N; Y is $CR^Y$; and Z is $CR^Z$.

In some embodiments, W is $CR^W$; X is $CR^X$; Y is N; and Z is $CR^Z$.

In some embodiments, W is $CR^W$; X is $CR^X$; Y is $CR^Y$; and Z is N.

In some embodiments, Ring A is monocyclic or polycyclic $C_{3-14}$ cycloalkyl optionally substituted by 1, 2, 3, or 4 $R^A$, wherein Ring A is attached to the -(L)$_m$-moiety of Formula I through a non-aromatic ring when Ring A is polycyclic.

In some embodiments, Ring A is monocyclic $C_{3-7}$ cycloalkyl optionally substituted by 1, 2, 3, or 4 $R^A$.

In some embodiments, Ring A is cyclobutyl, cyclopentyl, cyclohexyl, or cycloheptyl optionally substituted by 1, 2, 3, or 4 $R^A$.

In some embodiments, Ring A is cyclobutyl, cyclopentyl, cyclohexyl, or cycloheptyl.

In some embodiments, Ring A is cyclohexyl or cycloheptyl optionally substituted by 1, 2, 3, or 4 $R^A$.

In some embodiments, Ring A is cyclohexyl or cycloheptyl.

In some embodiments, Ring A is cyclohexyl optionally substituted by 1, 2, 3, or 4 $R^A$.

In some embodiments, Ring A is cyclohexyl.

In some embodiments, Ring A is monocyclic or polycyclic 4-18 membered heterocycloalkyl optionally substituted by 1, 2, 3, or 4 $R^A$, and wherein Ring A is attached to the -(L)$_m$-moiety of Formula I through a non-aromatic ring when Ring A is polycyclic.

In some embodiments, Ring A is monocyclic 4-7 membered heterocycloalkyl optionally substituted by 1, 2, 3, or 4 $R^A$.

In some embodiments, Ring A is monocyclic 4-7 membered heterocycloalkyl.

In some embodiments, Ring A is oxetanyl, tetrahydropyranyl, oxepanyl, azetidinyl, pyrrolidinyl, piperidinyl, or azepanyl, optionally substituted by 1, 2, 3, or 4 $R^A$.

In some embodiments, Ring A is oxetanyl, tetrahydropyranyl, oxepanyl, azetidinyl, pyrrolidinyl, piperidinyl, or azepanyl.

In some embodiments, Ring A is oxetanyl, tetrahydropyranyl, oxepanyl, azetidinyl, pyrrolidinyl, piperidinyl, azepanyl, or tetrahydrothiopyranyl optionally substituted by 1, 2, 3, or 4 $R^A$.

In some embodiments, Ring A is oxetanyl, tetrahydropyranyl, oxepanyl, azetidinyl, pyrrolidinyl, piperidinyl, azepanyl, or tetrahydrothiopyranyl.

In some embodiments, Ring A is piperidinyl optionally substituted by 1, 2, 3, or 4 $R^A$.

In some embodiments, Ring A is piperidinyl.

In some embodiments, Ring A is piperidin-4-yl optionally substituted by 1, 2, 3, or 4 $R^A$.

In some embodiments, Ring A is piperidin-4-yl.

In some embodiments, Ring A is tetrahydropyranyl optionally substituted by 1, 2, 3, or 4 $R^A$.

In some embodiments, Ring A is tetrahydropyranyl.

In some embodiments, Ring A is tetrahydropyran-4-yl optionally substituted by 1, 2, 3, or 4 $R^A$.

In some embodiments, Ring A is tetrahydropyran-4-yl.

In some embodiments, L is —(CR$^5$R$^6$)$_t$—.

In some embodiments, L is —(CR$^5$R$^6$)$_t$— and t is 1.

In some embodiments, L is —(CR$^5$R$^6$)$_t$— and t is 2.

In some embodiments, L is —(CR$^5$R$^6$)$_t$— and t is 3.

In some embodiments, L is —CH$_2$—.

In some embodiments, m is 0.

In some embodiments, m is 1.

In some embodiments, n is 0.

In some embodiments, n is 1.

In some embodiments, n is 2.

In some embodiments, $R^1$ and $R^2$ are both H.

In some embodiments, one of $R^1$ and $R^2$ is H and the other is methyl.

In some embodiments, each $R^A$ is independently selected from $C_{1-6}$ alkyl, OR$^{a1}$, C(O)R$^{b1}$, NR$^{c1}$R$^{d1}$, and S(O)$_2$R$^{b1}$; wherein said $C_{1-6}$ alkyl is optionally substituted with 1, 2, 3, 4, or 5 substituents independently selected from Cy$^1$, Cy$^1$-$C_{1-4}$ alkyl, halo, $C_{1-6}$ alkyl, $C_{2-6}$ alkenyl, $C_{2-6}$ alkynyl, $C_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments, each R$^A$ is independently selected from C$_{1-6}$ alkyl, halo, C$_{1-6}$ haloalkyl, OR$^{a1}$, C(O)R$^{b1}$, C(O)NR$^{c1}$R$^{d1}$, C(O)OR$^{a1}$, NR$^{c1}$R$^{d1}$, S(O)$_2$R$^{b1}$, 4-10 membered heterocycloalkyl, 5-10 membered heteroaryl, 4-10 membered heterocycloalkyl-C$_{1-4}$ alkyl and 5-10 membered heteroaryl-C$_{1-4}$ alkyl; wherein said C$_{1-6}$ alkyl, C$_{1-6}$ haloalkyl, 4-10 membered heterocycloalkyl, 5-10 membered heteroaryl, 4-10 membered heterocycloalkyl-C$_{1-4}$ alkyl and 5-10 membered heteroaryl-C$_{1-4}$ alkyl are each optionally substituted with 1, 2, 3, 4, or 5 substituents independently selected from Cy$^1$, Cy$^1$-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, C(=NR$^{e1}$)NR$^{c1}$R$^{d1}$, NR$^{c1}$C(=NR$^{e1}$)NR$^{c1}$R$^{d1}$, NR$^{c1}$R$^{d1}$, NR$^{c1}$C(O)R$^{b1}$, NR$^{c1}$C(O)OR$^{a1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, and S(O)$_2$NR$^{c1}$R$^{d1}$.

In some embodiments, each R$^A$ is independently selected from halo, C$_{1-6}$ haloalkyl, OR$^{a1}$, C(O)NR$^{c1}$R$^{d1}$, and C(O)OR$^{a1}$.

In some embodiments, R$^A$ is OR$^{a1}$.

In some embodiments, each R$^A$ is independently selected from halo, C$_{1-6}$ alkyl, C$_{1-6}$ haloalkyl, C$_{6-10}$ aryl-C$_{1-4}$ alkyl, 5-10 membered heteroaryl-C$_{1-4}$ alkyl, 4-10 membered heterocycloalkyl-C$_{1-4}$ alkyl, CN, OR$^{a1}$, NR$^{c1}$R$^{d1}$, C(O)NR$^{c1}$R$^{d1}$, NR$^{c1}$C(O)R$^{b1}$, C(O)R$^{b1}$, C(O)OR$^{a1}$, and S(O)$_2$R$^{b1}$, wherein said C$_{1-6}$ alkyl, C$_{1-6}$ haloalkyl, C$_{6-10}$ aryl-C$_{1-4}$ alkyl, 5-10 membered heteroaryl-C$_{1-4}$ alkyl, and 4-10 membered heterocycloalkyl-C$_{1-4}$ alkyl are each optionally substituted with 1, 2, 3, 4, or 5 substituents independently selected from halo, CN, OR$^{a1}$, NR$^{c1}$R$^{d1}$, C(O)R$^{b1}$, and NR$^{c1}$C(O)R$^{b1}$.

In some embodiments, each R$^W$, R$^X$, R$^Y$, and R$^Z$ is independently selected from H, halo, C$_{1-6}$ alkyl, C$_{1-6}$ haloalkyl, 5-10 membered heteroaryl, 4-10 membered heterocycloalkyl, C$_{6-10}$ aryl-C$_{1-4}$ alkyl, CN, OR$^{a2}$, C(O)NR$^{c2}$R$^{d2}$, NR$^{c2}$R$^{d2}$, NR$^{c2}$C(O)R$^{b2}$, NR$^{c2}$C(O)OR$^{a2}$ NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, and NR$^{c2}$S(O)$_2$NR$^{c2}$R$^{d2}$; wherein said C$_{1-6}$ alkyl, C$_{1-6}$ haloalkyl, 5-10 membered heteroaryl, 4-10 membered heterocycloalkyl, and C$_{6-10}$ aryl-C$_{1-4}$ alkyl of R$^W$, R$^X$, R$^Y$, and R$^Z$ are each optionally substituted with 1, 2, 3, 4, or 5 substituents independently selected from Cy$^2$, Cy$^2$-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, each R$^W$, R$^X$, R$^Y$, and R$^Z$ is independently selected from H, halo, C$_{1-6}$ alkyl, C$_{1-6}$ haloalkyl, 5-10 membered heteroaryl, 4-10 membered heterocycloalkyl, C$_{6-10}$ aryl-C$_{1-4}$ alkyl, CN, OR$^{a2}$, C(O)NR$^{c2}$R$^{d2}$, NR$^{c2}$R$^{d2}$, and NR$^{c2}$C(O)R$^{b2}$; wherein said C$_{1-6}$ alkyl, C$_{1-6}$ haloalkyl, 5-10 membered heteroaryl, 4-10 membered heterocycloalkyl, and C$_{6-10}$ aryl-C$_{1-4}$ alkyl of R$^W$, R$^X$, R$^Y$, and R$^Z$ are each optionally substituted with 1, 2, 3, 4, or 5 substituents independently selected from Cy$^2$, Cy$^2$-C$_{1-4}$ alkyl, halo, C$_{1-6}$ alkyl, C$_{2-6}$ alkenyl, C$_{2-6}$ alkynyl, C$_{1-6}$ haloalkyl, CN, NO$_2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, C(=NR$^{e2}$) NR$^{c2}$R$^{d2}$, NR$^{c2}$C(=NR$^{e2}$)NR$^{c2}$R$^{d2}$, NR$^{c2}$R$^{d2}$, NR$^{c2}$C(O) R$^{b2}$, NR$^{c2}$C(O)OR$^{a2}$, NR$^{c2}$C(O)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$.

In some embodiments, W is CR$^W$ and R$^W$ is other than H.

In some embodiments, W is CR$^W$ and R$^W$ is H.

In some embodiments, R$^W$ is halo.

In some embodiments, R$^W$ is F.

In some embodiments, R$^W$ is selected from C$_{1-6}$ alkyl, C$_{1-6}$ haloalkyl, halo, and OR$^{a2}$, wherein said C$_{1-6}$ alkyl and C$_{1-6}$ haloalkyl are each optionally substituted with OR$^{a2}$.

In some embodiments, R$^W$ is selected from C$_{1-6}$ alkyl, C$_{1-6}$ haloalkyl, CN, halo, and OR$^{a2}$, wherein said C$_{1-6}$ alkyl and C$_{1-6}$ haloalkyl are each optionally substituted with OR$^Z$.

In some embodiments, R$^X$ and R$^Z$ are not both halogen.

In some embodiments, R$^Z$ is H.

In some embodiments, when W is CR$^W$, X is CR$^X$, Y is CR$^Y$, and Z is CR$^Z$ and when m is 1 or 2, then R$^X$ and R$^Y$ are not both C$_{1-6}$ alkoxy.

In some embodiments, when W is CR$^W$, X is CR$^X$, Y is CR$^Y$, and Z is CR$^Z$ and when m is 1 or 2, then R$^X$ and R$^Y$ are not the same.

In some embodiments, X is CR$^X$ and R$^X$ is other than H.

In some embodiments, X is CR$^X$ and R$^X$ is H.

In some embodiments, R$^X$ is selected from C$_{1-6}$ alkyl, halo, and OR$^{a2}$.

In some embodiments, Y is CR$^Y$ and R$^Y$ is other than H.

In some embodiments, Y is CR$^Y$ and R$^Y$ is H.

In some embodiments, Y is CR$^Y$ and R$^Y$ is independently selected from NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, and NR$^{c2}$S(O)$_2$NR$^{c2}$R$^{d2}$.

In some embodiments, Y is CR$^Y$ and R$^Y$ is independently selected from C$_{1-6}$ alkyl, OR$^{a2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, and NR$^{c2}$S(O)$_2$NR$^{c2}$R$^{d2}$.

In some embodiments, Y is CR$^Y$ and R$^Y$ is independently selected from NR$^{c2}$R$^{d2}$ and NR$^{c2}$C(O)R$^{b2}$.

In some embodiments, R$^Y$ is independently selected from C$_{1-6}$ alkyl, C$_{3-7}$ cycloalkyl-C$_{1-4}$ alkyl, 5-10 membered heteroaryl, 4-10 membered heterocycloalkyl, halo, CN, OR$^{a2}$, SR$^{a2}$, C(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$ S(O)R$^{b2}$, NR$^{c2}$S(O)$_2$R$^{b2}$, and NR$^{c2}$S(O)$_2$NR$^{c2}$R$^{d2}$, wherein said C$_{1-6}$ alkyl, C$_{3-7}$ cycloalkyl-C$_{1-4}$ alkyl, 5-10 membered heteroaryl, and 4-10 membered heterocycloalkyl of R$^Y$ are each optionally substituted with 1, 2, 3, 4, or 5 substituents independently selected from halo, C$_{1-6}$ alkyl, C$_{1-6}$ haloalkyl, CN, NO$_2$, OR$^{a2}$, NR$^{c2}$R$^{d2}$, and S(O)$_2$R$^{b2}$.

In some embodiments, Y is CR$^Y$ and R$^Y$ is independently selected from C$_{1-6}$ alkyl and OR$^{a2}$.

In some embodiments, Y is CR$^Y$ and R$^Y$ is OR$^{a2}$.

In some embodiments, Z is CR$^Z$ and R$^Z$ is other than H.

In some embodiments, Z is CR$^Z$ and R$^Z$ is H.

In some embodiments, Z is CR$^Z$ and R$^Z$ is C$_{1-6}$ alkyl.

In some embodiments, Z is CR$^Z$ and R$^Z$ is C$_{1-6}$ alkyl, halo, or CN.

In some embodiments, each R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, and C$_{1-6}$ haloalkyl, wherein the C$_{1-6}$ alkyl is optionally substituted with 1, 2, 3, 4, or 5 substituents independently selected from Cy$^3$, Cy$^3$-C$_{1-4}$ alkyl, halo, C$_{1-4}$ alkyl, C$_{1-4}$ haloalkyl, C$_{1-6}$ haloalkyl, C$_{2-6}$ alkenyl, C$_{2-6}$ alkynyl, CN, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$ NR$^{c3}$C(O)R$^{b3}$, NR$^{c3}$C(O)NR$^{c3}$R$^{d3}$ NR$^{c3}$C(O)OR$^{a3}$, C(=NR$^{e3}$)NR$^{c3}$R$^{d3}$, NR$^{c3}$C(=NR$^{e3}$)NR$^{c3}$R$^{d3}$, S(O)R$^{b3}$, S(O)NR$^{c3}$R$^{d3}$, S(O)$_2$R$^{b3}$, NR$^{c3}$S(O)$_2$R$^{b3}$, NR$^{c3}$S(O)$_2$NR$^{c3}$R$^{d3}$, and S(O)$_2$NR$^{c3}$R$^{d3}$.

In some embodiments, each R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, and C$_{1-6}$ haloalkyl.

In some embodiments, each R$^{a1}$, R$^{b1}$, R$^{c1}$, R$^{d1}$, R$^{a2}$, R$^{b2}$, R$^{c2}$, and R$^{d2}$ is independently selected from H, C$_{1-6}$ alkyl, C$_{1-6}$ haloalkyl, C$_{6-10}$ aryl, C$_{3-7}$ cycloalkyl, 4-10 membered heterocycloalkyl, C$_{6-10}$ aryl-C$_{1-4}$ alkyl, C$_{3-7}$ cycloalkyl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{6-10}$ aryl, C$_{3-7}$ cycloalkyl, 4-10 membered heterocycloalkyl, C$_{6-10}$ aryl-C$_{1-4}$ alkyl, C$_{3-7}$ cycloalkyl-C$_{1-4}$ alkyl, and 4-10 membered heterocycloalkyl-C$_{1-4}$ alkyl are each optionally substituted with 1, 2, 3, 4, or 5 substituents independently selected from C$_{1-4}$ alkyl, C$_{1-4}$ haloalkyl, halo, CN, OR$^{a3}$, C(O)R$^{b3}$, C(O)OR$^{a3}$ and S(O)$_2$R$^{b3}$.

In some embodiments, R$^{a2}$ is selected from H, C$_{1-6}$ alkyl, C$_{1-6}$ haloalkyl, C$_{6-10}$ aryl, C$_{3-7}$ cycloalkyl, 4-10 membered heterocycloalkyl, C$_{6-10}$ aryl-C$_{1-4}$ alkyl, C$_{3-7}$ cycloalkyl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{6-10}$ aryl, C$_{3-7}$ cycloalkyl, 4-10 membered heterocycloalkyl, C$_{6-10}$ aryl-C$_{1-4}$ alkyl, C$_{3-7}$ cycloalkyl-C$_{1-4}$ alkyl, and 4-10 membered heterocycloalkyl-C$_{1-4}$ alkyl are each optionally substituted with 1, 2, 3, 4, or 5 substituents independently selected from C$_{1-4}$ alkyl, C$_{1-4}$ haloalkyl, halo, CN, OR$^{a3}$, C(O)R$^{b3}$, C(O)OR$^{a3}$ and S(O)$_2$R$^{b3}$.

In some embodiments, R$^{c2}$ and R$^{d2}$, are each independently selected from H, C$_{1-6}$ alkyl, C$_{1-6}$ haloalkyl, C$_{6-10}$ aryl, C$_{3-7}$ cycloalkyl, 4-10 membered heterocycloalkyl, C$_{6-10}$ aryl-C$_{1-4}$ alkyl, C$_{3-7}$ cycloalkyl-C$_{1-4}$ alkyl, and 4-10 membered heterocycloalkyl-C$_{1-4}$ alkyl, wherein said C$_{1-6}$ alkyl, C$_{1-6}$ haloalkyl, C$_{6-10}$ aryl, C$_{3-7}$ cycloalkyl, 4-10 membered heterocycloalkyl, C$_{6-10}$ aryl-C$_{1-4}$ alkyl, C$_{3-7}$ cycloalkyl-C$_{1-4}$ alkyl, and 4-10 membered heterocycloalkyl-C$_{1-4}$ alkyl are each optionally substituted with 1, 2, 3, 4, or 5 substituents independently selected from C$_{1-4}$ alkyl, C$_{1-4}$ haloalkyl, halo, CN, OR$^{a3}$, C(O)R$^{b3}$, C(O)OR$^{a3}$ and S(O)$_2$R$^{b3}$.

In some embodiments, Cy$^3$ is 4-10 membered heterocycloalkyl optionally substituted with 1, 2, 3, 4, or 5 substituents independently selected from C$_{1-4}$ alkyl, C$_{1-4}$ haloalkyl, halo, CN, OR$^{a3}$, C(O)R$^{b3}$, C(O)OR$^{a3}$ and S(O)$_2$R$^{b3}$.

In some embodiments, Cy$^3$ is 4-10 membered heterocycloalkyl optionally substituted with 1, 2, 3, 4, or 5 substituents independently selected from C(O)R$^{b3}$.

In some embodiments, Cy$^3$ is piperidinyl optionally substituted with 1, 2, 3, 4, or 5 substituents independently selected from halo and C(O)CH$_3$.

In some embodiments, the compounds of the invention have Formula II:

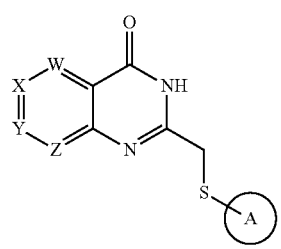

II

In some embodiments, the compounds of the invention have Formula IIIA, IIIB, IIIC, IIID, or IIIE:

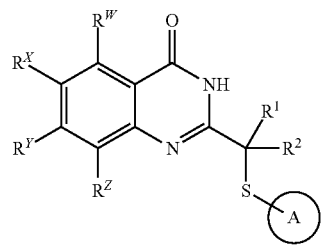

IIIA

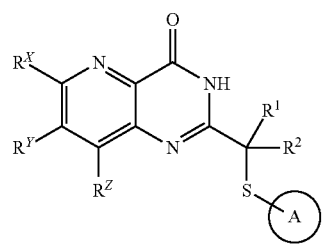

IIIB

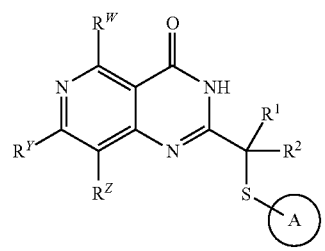

IIIC

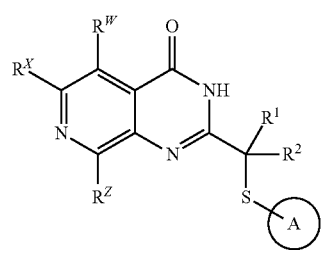

IIID

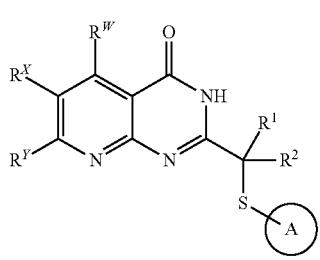

IIIE

In some embodiments, the compounds of the invention have Formula IVA or IVB:

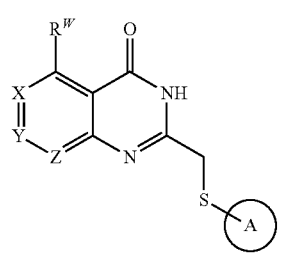

IVA

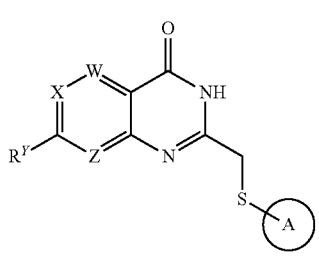

IVB

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "pyridinyl," "pyridyl," or "a pyridine ring" may refer to a pyridin-2-yl, pyridin-3-yl, or pyridin-4-yl ring.

The term "n-membered," where "n" is an integer, typically describes the number of ring-forming atoms in a moiety where the number of ring-forming atoms is "n". For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the phrase "optionally substituted" means unsubstituted or substituted.

As used herein, the term "substituted" means that a hydrogen atom is replaced by a non-hydrogen group. It is to be understood that substitution at a given atom is limited by valency.

As used herein, the term "$C_{i-j}$," where i and j are integers, employed in combination with a chemical group, designates a range of the number of carbon atoms in the chemical group with i-j defining the range. For example, $C_{1-6}$ alkyl refers to an alkyl group having 1, 2, 3, 4, 5, or 6 carbon atoms.

As used herein, the term "alkyl," employed alone or in combination with other terms, refers to a saturated hydrocarbon group that may be straight-chain or branched. In some embodiments, the alkyl group contains 1 to 7, 1 to 6, 1 to 4, or 1 to 3 carbon atoms. Examples of alkyl moieties include, but are not limited to, chemical groups such as methyl, ethyl, n-propyl, isopropyl, n-butyl, isobutyl, sec-butyl, tert-butyl, n-pentyl, 2-methyl-1-butyl, 3-pentyl, n-hexyl, 1,2,2-trimethylpropyl, n-heptyl, and the like. In some embodiments, the alkyl group is methyl, ethyl, or propyl.

As used herein, "alkenyl," employed alone or in combination with other terms, refers to an alkyl group having one or more carbon-carbon double bonds. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "alkynyl," employed alone or in combination with other terms, refers to an alkyl group having one or more carbon-carbon triple bonds. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, "halo" or "halogen", employed alone or in combination with other terms, includes fluoro, chloro, bromo, and iodo. In some embodiments, halo is F or $C_1$.

As used herein, the term "haloalkyl," employed alone or in combination with other terms, refers to an alkyl group having up to the full valency of halogen atom substituents, which may either be the same or different. In some embodiments, the halogen atoms are fluoro atoms. In some embodiments, the alkyl group has 1 to 6 or 1 to 4 carbon atoms. Example haloalkyl groups include $CF_3$, $C_2F_5$, $CHF_2$, $CCl_3$, $CHCl_2$, $C_2Cl_5$, and the like.

As used herein, the term "alkoxy," employed alone or in combination with other terms, refers to a group of formula —O-alkyl. Example alkoxy groups include methoxy, ethoxy, propoxy (e.g., n-propoxy and isopropoxy), t-butoxy, and the like. In some embodiments, the alkyl group has 1 to 6 or 1 to 4 carbon atoms.

As used herein, "haloalkoxy," employed alone or in combination with other terms, refers to a group of formula —O-(haloalkyl). In some embodiments, the alkyl group has 1 to 6 or 1 to 4 carbon atoms. An example haloalkoxy group is —$OCF_3$.

As used herein, "amino," employed alone or in combination with other terms, refers to $NH_2$.

As used herein, the term "alkylamino," employed alone or in combination with other terms, refers to a group of formula —NH(alkyl). In some embodiments, the alkylamino group has 1 to 6 or 1 to 4 carbon atoms. Example alkylamino groups include methylamino, ethylamino, propylamino (e.g., n-propylamino and isopropylamino), and the like.

As used herein, the term "dialkylamino," employed alone or in combination with other terms, refers to a group of formula —$N(alkyl)_2$. Example dialkylamino groups include dimethylamino, diethylamino, dipropylamino (e.g., di(n-propyl)amino and di(isopropyl)amino), and the like. In some embodiments, each alkyl group independently has 1 to 6 or 1 to 4 carbon atoms.

As used herein, the term "cycloalkyl," employed alone or in combination with other terms, refers to a non-aromatic cyclic hydrocarbon including cyclized alkyl and alkenyl groups. Cycloalkyl groups can include mono- or polycyclic (e.g., having 2, 3, or 4 fused, bridged, or spiro rings) ring systems. Also included in the definition of cycloalkyl are moieties that have one or more aromatic rings (e.g., aryl or heteroaryl rings) fused (i.e., having a bond in common with) to the cycloalkyl ring, for example, benzo derivatives of cyclopentane, cyclohexene, cyclohexane, and the like, or pyrido derivatives of cyclopentane or cyclohexane. Ring-forming carbon atoms of a cycloalkyl group can be optionally substituted by oxo. Cycloalkyl groups also include cycloalkylidenes. The term "cycloalkyl" also includes bridgehead cycloalkyl groups (e.g., non-aromatic cyclic hydrocarbon moieties containing at least one bridgehead carbon, such as admantan-1-yl) and spirocycloalkyl groups (e.g., non-aromatic hydrocarbon moieties containing at least two rings fused at a single carbon atom, such as spiro[2.5] octane and the like). In some embodiments, the cycloalkyl group has 3 to 10 ring members, or 3 to 7 ring members. In some embodiments, the cycloalkyl group is monocyclic or bicyclic. In some embodiments, the cycloalkyl group is monocyclic. In some embodiments, the cycloalkyl group is a $C_{3-7}$ monocyclic cycloalkyl group. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, tetrahydronaphthalenyl, octahydronaphthalenyl, indanyl, and the like. In some embodiments, the cycloalkyl group is cyclopropyl, cyclobutyl, cyclopentyl, or cyclohexyl.

As used herein, the term "cycloalkylalkyl," employed alone or in combination with other terms, refers to a group of formula cycloalkyl-alkyl-. In some embodiments, the alkyl portion has 1 to 4, 1 to 3, 1 to 2, or 1 carbon atom(s). In some embodiments, the alkyl portion is methylene. In some embodiments, the cycloalkyl portion has 3 to 10 ring members or 3 to 7 ring members. In some embodiments, the cycloalkyl group is monocyclic or bicyclic. In some embodiments, the cycloalkyl portion is monocyclic. In some embodiments, the cycloalkyl portion is a $C_{3-7}$ monocyclic cycloalkyl group.

As used herein, the term "heterocycloalkyl," employed alone or in combination with other terms, refers to a non-aromatic ring or ring system, which may optionally contain one or more alkenylene or alkynylene groups as part of the ring structure, which has at least one heteroatom ring member independently selected from nitrogen, sulfur, oxygen, and phosphorus. Heterocycloalkyl groups can include mono- or polycyclic (e.g., having 2, 3 or 4 fused, bridged, or spiro rings) ring systems. In some embodiments, the heterocycloalkyl group is a monocyclic or bicyclic group having 1, 2, 3, or 4 heteroatoms independently selected from nitrogen, sulfur and oxygen. Also included in the definition of heterocycloalkyl are moieties that have one or more aromatic rings (e.g., aryl or heteroaryl rings) fused (i.e., having a bond in common with) to the non-aromatic heterocycloalkyl ring, for example, 1,2,3,4-tetrahydro-quinoline and the like. Heterocycloalkyl groups can also include bridgehead heterocycloalkyl groups (e.g., a heterocycloalkyl moiety containing at least one bridgehead atom, such as azaadmantan-1-yl and the like) and spiroheterocycloalkyl groups (e.g., a heterocycloalkyl moiety containing at least two rings fused at a single atom, such as [1,4-dioxa-8-aza-spiro[4.5]decan-N-yl] and the like). In some embodiments, the heterocycloalkyl group has 3 to 10 ring-forming atoms, 4 to 10 ring-forming atoms, or about 3 to 8 ring forming atoms. In some embodiments, the heterocycloalkyl group has 2 to 20 carbon atoms, 2 to 15 carbon atoms, 2 to 10 carbon atoms, or about 2 to 8 carbon atoms. In some embodiments, the heterocycloalkyl group has 1 to 5 heteroatoms, 1 to 4 heteroatoms, 1 to 3 heteroatoms, or 1 to 2 heteroatoms. The carbon atoms or heteroatoms in the ring(s) of the heterocycloalkyl group can be oxidized to form a carbonyl, an N-oxide, or a sulfonyl group (or other oxidized linkage) or a nitrogen atom can be quaternized. In some embodiments, the heterocycloalkyl portion is a $C_{2-7}$ monocyclic heterocycloalkyl group. In some embodiments, the heterocycloalkyl group is a morpholine ring, pyrrolidine ring, piperazine ring, piperidine ring, tetrahydropyran ring, tetrahyropyridine, azetidine ring, or tetrahydrofuran ring.

As used herein, the term "heterocycloalkylalkyl," employed alone or in combination with other terms, refers to a group of formula heterocycloalkyl-alkyl-. In some embodiments, the alkyl portion has 1 to 4, 1 to 3, 1 to 2, or 1 carbon atom(s). In some embodiments, the alkyl portion is methylene. In some embodiments, the heterocycloalkyl portion has 3 to 10 ring members, 4 to 10 ring members, or 3 to 7 ring members. In some embodiments, the heterocycloalkyl group is monocyclic or bicyclic. In some embodiments, the heterocycloalkyl portion is monocyclic. In some embodiments, the heterocycloalkyl portion is a $C_{2-7}$ monocyclic heterocycloalkyl group.

As used herein, the term "aryl," employed alone or in combination with other terms, refers to a monocyclic or polycyclic (e.g., a fused ring system) aromatic hydrocarbon moiety, such as, but not limited to, phenyl, 1-naphthyl, 2-naphthyl, and the like. In some embodiments, aryl groups have from 6 to 10 carbon atoms or 6 carbon atoms. In some embodiments, the aryl group is a monocyclic or bicyclic group. In some embodiments, the aryl group is phenyl or naphthyl.

As used herein, the term "arylalkyl," employed alone or in combination with other terms, refers to a group of formula aryl-alkyl-. In some embodiments, the alkyl portion has 1 to 4, 1 to 3, 1 to 2, or 1 carbon atom(s). In some embodiments, the alkyl portion is methylene. In some embodiments, the aryl portion is phenyl. In some embodiments, the aryl group is a monocyclic or bicyclic group. In some embodiments, the arylalkyl group is benzyl.

As used herein, the term "heteroaryl," employed alone or in combination with other terms, refers to a monocyclic or polycyclic (e.g., a fused ring system) aromatic hydrocarbon moiety, having one or more heteroatom ring members independently selected from nitrogen, sulfur and oxygen. In some embodiments, the heteroaryl group is a monocyclic or a bicyclic group having 1, 2, 3, or 4 heteroatoms independently selected from nitrogen, sulfur and oxygen. Example heteroaryl groups include, but are not limited to, pyridyl, pyrimidinyl, pyrazinyl, pyridazinyl, triazinyl, furyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, pyrrolyl, azolyl, quinolinyl, isoquinolinyl, benzisoxazolyl, imidazo[1,2-b] thiazolyl or the like. The carbon atoms or heteroatoms in the ring(s) of the heteroaryl group can be oxidized to form a carbonyl, an N-oxide, or a sulfonyl group (or other oxidized linkage) or a nitrogen atom can be quaternized, provided the aromatic nature of the ring is preserved. In some embodiments, the heteroaryl group has from 3 to 10 carbon atoms, from 3 to 8 carbon atoms, from 3 to 5 carbon atoms, from 1 to 5 carbon atoms, or from 5 to 10 carbon atoms. In some embodiments, the heteroaryl group contains 3 to 14, 4 to 12, 4 to 8, 9 to 10, or 5 to 6 ring-forming atoms. In some embodiments, the heteroaryl group has 1 to 4, 1 to 3, or 1 to 2 heteroatoms.

As used herein, the term "heteroarylalkyl," employed alone or in combination with other terms, refers to a group of formula heteroaryl-alkyl-. In some embodiments, the alkyl portion has 1 to 4, 1 to 3, 1 to 2, or 1 carbon atom(s). In some embodiments, the alkyl portion is methylene. In some embodiments, the heteroaryl portion is a monocyclic or bicyclic group having 1, 2, 3, or 4 heteroatoms independently selected from nitrogen, sulfur and oxygen. In some embodiments, the heteroaryl portion has 5 to 10 carbon atoms.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention may be isolated as a mixture of isomers or as separated isomeric forms.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention also include all isotopes of atoms occurring in the intermediates or final compounds. Isotopes include those atoms having the same atomic number but different mass numbers. For example, isotopes of hydrogen include tritium and deuterium. In some embodiments, the compounds of the invention include at least one deuterium atom.

The term "compound," as used herein, is meant to include all stereoisomers, geometric isomers, tautomers, and isotopes of the structures depicted, unless otherwise specified.

All compounds, and pharmaceutically acceptable salts thereof, can be found together with other substances such as water and solvents (e.g., in the form of hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared according to numerous preparatory routes known in the literature. Example synthetic methods for preparing compounds of the invention are provided in the Schemes below.

Scheme 1

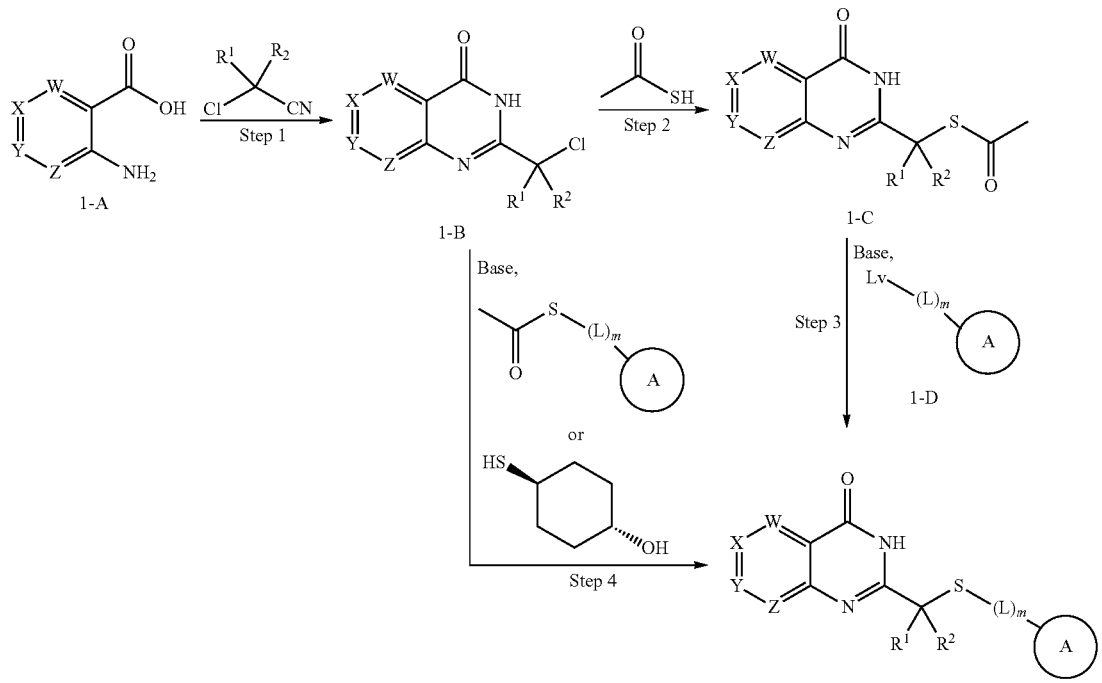

Scheme 1 shows a general synthesis of quinazolinone compounds of the invention. Substituted aminobenzoic acids (1-A), many of which are commercially available or can be made via routes known to one skilled in the art, can be converted to chloromethylquinazolinones (1-B) by treatment with chloroacetonitrile in the presence of a pre-prepared solution of a metal such as sodium in a protic solvent such as methanol at room temperature (Step 1). The chloro group of 1-B can be converted to a thioacetate (1-C) by treatment with thioacetic acid in a polar solvent such as DMF at room temperature (Step 2). Introduction of heterocycles (ring A) can be done by treatment with an appropriate electrophile (1-D), where Lv is an appropriate leaving group such as Br, I, methanesulfonate, or para-toluenesulfonate, in the presence of a base such as aqueous sodium hydroxide in a polar solvent such as DMF at elevated temperature such as 90° C. (Step 3). Alternatively, quinazolinones of the invention can be prepared from chloromethylquinazolinones (1-B) by treatment with a thioacetate-substituted heterocycle or trans-4-mercaptocyclohexanol in the presence of a base such as aqueous sodium hydroxide in a polar solvent such as DMF at room temperature (Step 4).

Scheme 2

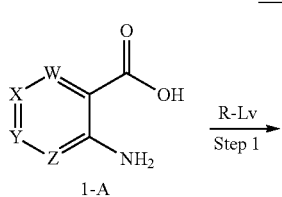

-continued

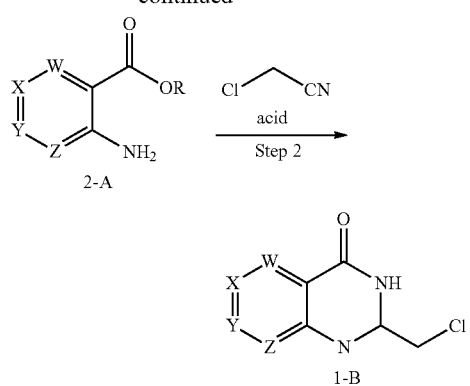

Scheme 2 shows that substituted chloromethylquinazolinone intermediates (1-B) can also be prepared from substituted aminobenzoic acids (1-A) first by conversion to esters (2-A), such as where R is $C_{1-6}$ alkyl such as methyl, by treatment with R-Lv, where Lv is a leaving group such as iodide, in the presence of a base such as potassium carbonate in a polar solvent such as DMF at an appropriate temperature such as 0° C. (Step 1). Many esters (2-A) can also be purchased commercially. Treatment of esters with chloroacetonitrile in the presence of an acid such as hydrochloric acid in a solvent such as dioxane at an appropriate temperature such as 50° C. (Step 2) yields chloromethylquinazolinones (1-B) that can then be further converted to compounds of the invention as depicted in Scheme 1.

Scheme 3

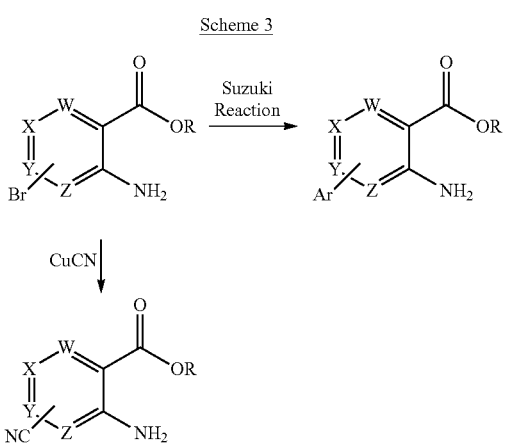

Scheme 3 illustrates that functionalization of the starting brominated ester (e.g., where one of W, X, Y, and Z is C—Br) can be achieved by palladium-mediated couplings such as Suzuki reactions to prepare aromatic ring-substituted derivatives (Ar refers to an aromatic ring which is or may be further derivatized). Alternatively, a nitrile substituent can be introduced via treatment of the starting brominated ester with CuCN in a polar solvent such as NMP at an elevated temperature such as 180° C. Functionalized esters can then be converted to chloromethylquinazolinones as illustrated in Scheme 2.

Scheme 4

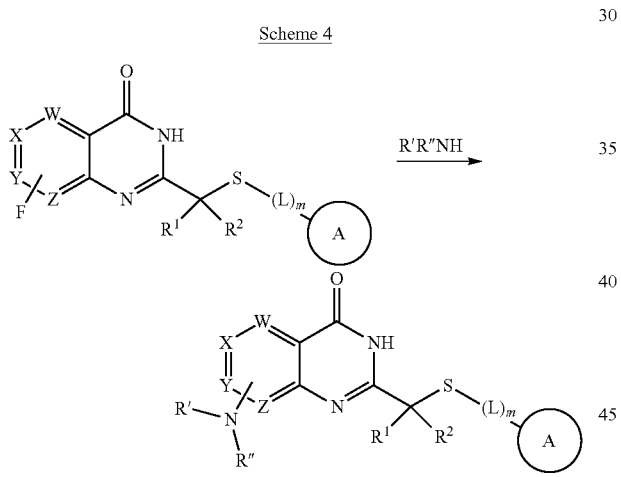

Scheme 4 shows that an amino group can be introduced by treatment of a fluorinated derivative (e.g., where one of W, X, Y, and Z is C—F) with excess amine (R'R"NH, where R' and R" can be, for example, various groups defined by $R^{c2}$ and $R^{d2}$) at an appropriate elevated temperature such as 120° C.

Scheme 5

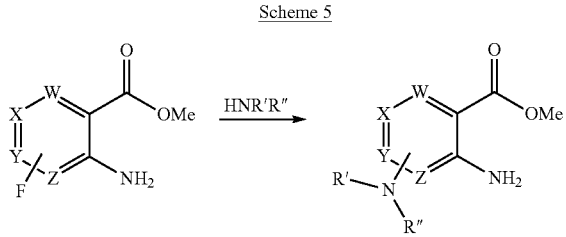

Scheme 5 shows that an amino substituent may also be introduced by treatment of a 2-amino-4-fluorobenzoate (e.g., where one of W, X, Y, and Z is C—F) with an amine in a polar solvent such as DMSO at elevated temperature such as 80° C.

Scheme 6

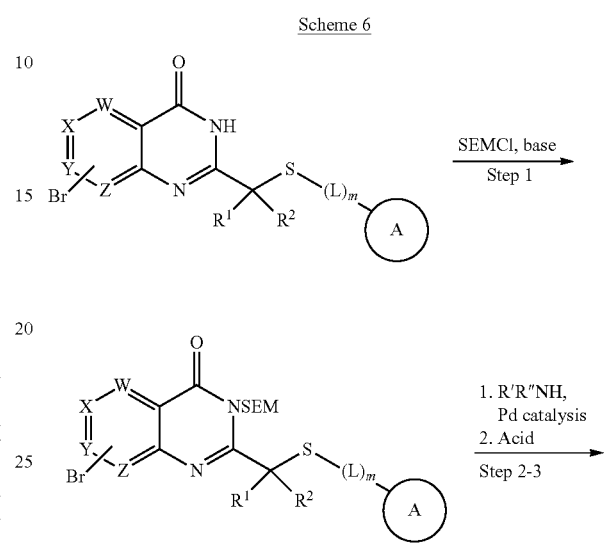

Scheme 6 shows that an amino substituent may be introduced by treatment of a brominated starting material with a base such as LiHMDS and SEMCl in an ethereal solvent such as THF at an appropriate temperature such as 0° C. (Step 1). This reaction can be followed by coupling with amines (R'R"NH), for example, in the presence of a palladium catalyst such as $Pd_2(dba)_3$, a phosphine ligand such as BINAP, a base such as t-BuONa, in a non-polar solvent such as toluene at an elevated temperature such as 110° C. (Step 2). The SEM protecting group can then be removed by treatment with an acid such as HCl in a polar solvent such as dioxane at slightly elevated temperature such as 40° C. (Step 3).

Scheme 7

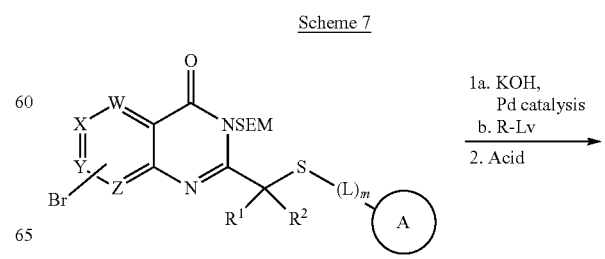

-continued

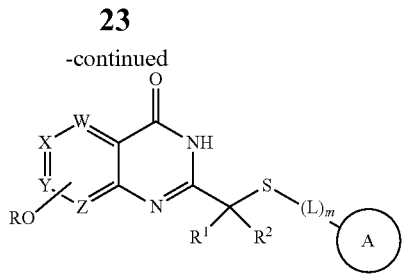

Scheme 7 shows that an alcohol functionality can be introduced to the SEM protected brominated quinazolinone by treatment first with potassium hydroxide in the presence of a palladium catalyst such as $Pd_2(dba)_3$ and a phosphine ligand such as t-BuXPhos in a solvent such as a mixture of dioxane and water at elevated temperature such as 90° C., followed by addition of an electrophile such as an alkyl bromide along with tetrabutylammonium bromide and stirring at room temperature (Step 1, Lv is a leaving group and R is an alkyl group or other group selected from $R^{a2}$). Removal of the SEM group can be achieved by treatment with an acid such as HCl (Step 2).

Scheme 8

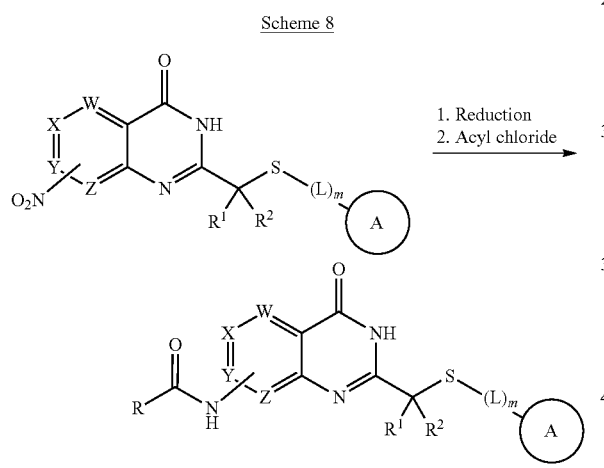

Scheme 8 summarizes preparation of amide compounds (R is, e.g., optionally substituted alkyl or optionally substituted ring structures). Nitro derivatives can be reduced to the amine derivatives by treatment with a reducing agent such as iron in the presence of ammonium chloride in a mixture of water with a protic solvent such as ethanol at elevated temperature such as 80° C. The resulting amine can then be converted to an amide by treatment with an acyl chloride (having the appropriate R group) in the presence of an amine base such as triethylamine in a non-polar solvent such as DCM at room temperature.

Scheme 9

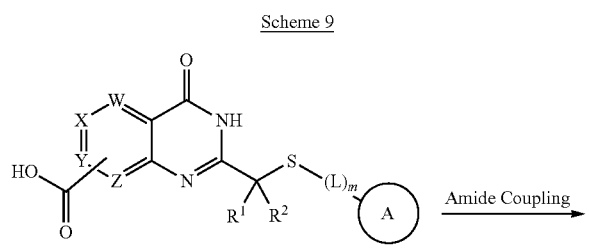

-continued

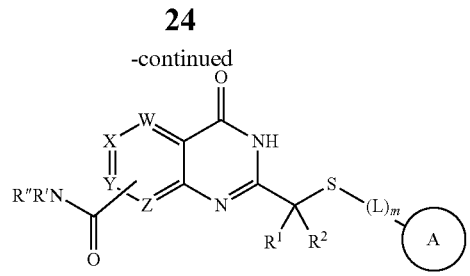

Scheme 9 summarizes preparation of carboxamides by treatment of carboxylic acid derivatives with an amine in the presence of an amide coupling reagent such as EDCI along with HOBt in polar solvent such as DMF at room temperature.

Scheme 10

Non-hydrogen R substituents can be introduced by the two-step procedure in Scheme 10. An appropriately substituted 2-methylaniline (10-1) can be treated with chloral hydrate, sodium sulfate and HCl in water, followed by addition of hydroxylamine and heating at 70° C. to give the methylindoline-2,3-dione intermediate (10-2, Step 1). Conversion to the aminobenzoic acid (10-3) can be achieved by treatment with hydrogen peroxide and NaOH in water at 50° C. (Step 2). The resulting aminobenzoic acids can then be converted to chloromethylquinazolinones using the methods described above.

Scheme 11

Scheme 11 shows that the thioacetate intermediates of Scheme 1, Step 4 can be prepared from suitable electrophiles such as bromides, iodides, methanesulfonates, or para-toluenesulfonates by treatment of the electrophiles with potassium thioacetate in a polar solvent such as DMF at room temperature. In cases where Lv=methanesulfonate or para-toluenesulfonate, the sulfonate group may be installed from the corresponding alcohol by treatment of the alcohols with the appropriate sulfonyl chloride and an amine base such as triethylamine in dichloromethane at 0° C. with warming to ambient temperature.

Scheme 12

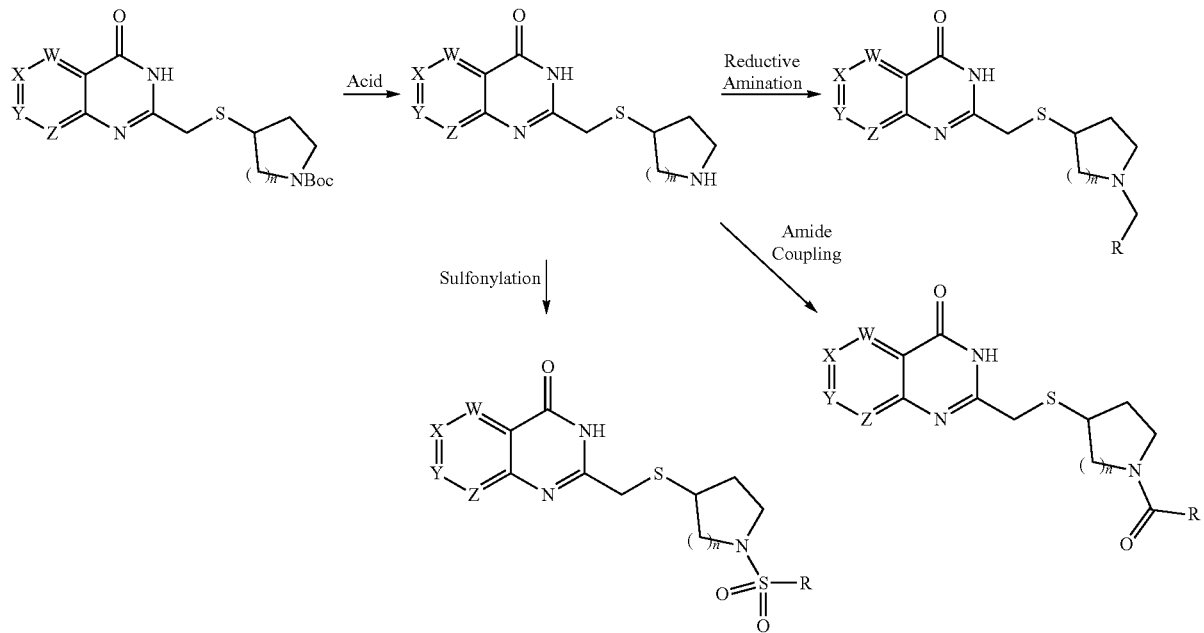

Scheme 12 shows that when Ring A contains a Boc-protected cyclic amine it can first be deprotected by treatment with acid to reveal a free amine, which can then be further functionalized. A representative sampling of such modifications, which includes reductive amination reactions, amide coupling reactions, and sulfonylation reactions, is illustrated.

Scheme 13

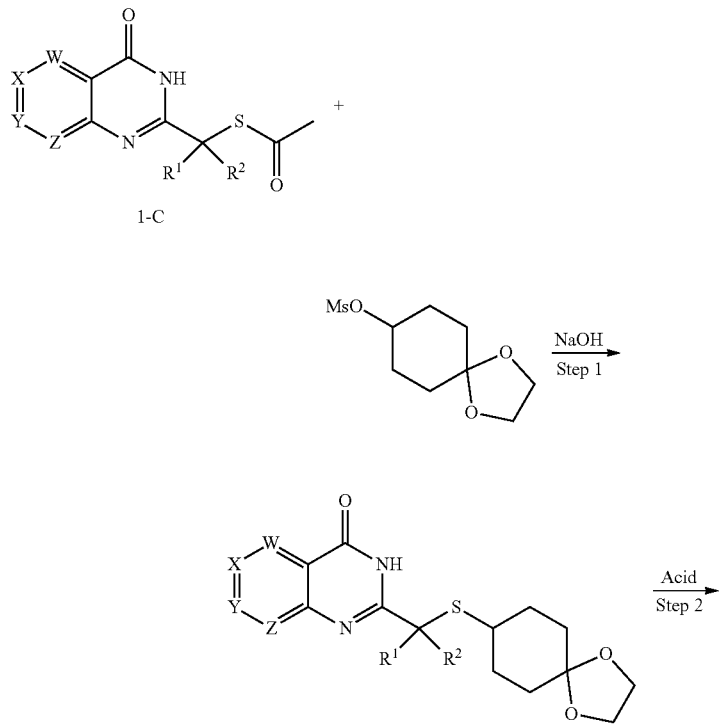

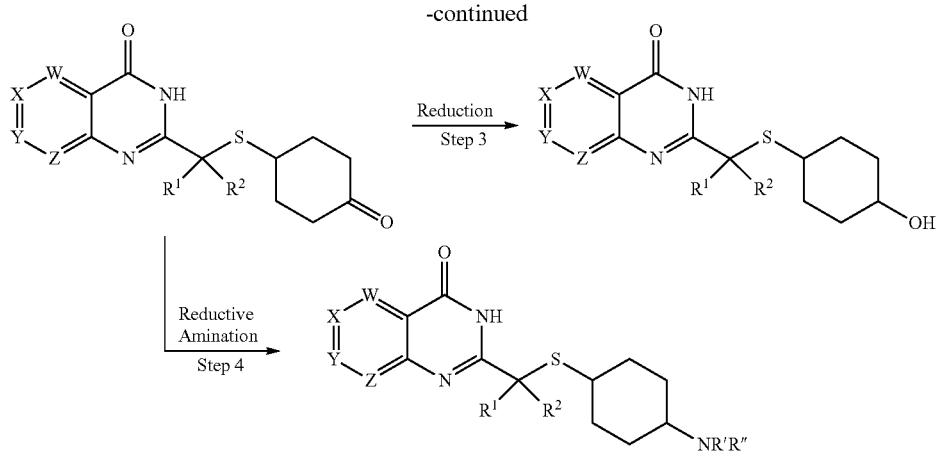

Scheme 13 summarizes methods for preparing substituted cyclohexylthioethers. The thioacetate 1-C from Scheme 1 can be coupled with 1,4-dioxaspiro[4.5]decan-8-yl methanesulfonate in the presence of a base such as sodium hydroxide (Step 1). The acetal can be removed by treatment with an acid such as HCl in a polar solvent such as THF at room temperature (Step 2). The resulting ketone can then be further functionalized by reduction with a hydride source such as sodium borohydride in a protic solvent such as methanol at room temperature (Step 3). Alternatively, the ketone can be converted to an amine via reductive amination, for example by treatment with an amine in the presence of a hydride source such as sodium cyanoborohydride in a polar solvent such as THF at room temperature (Step 4).

Scheme 14

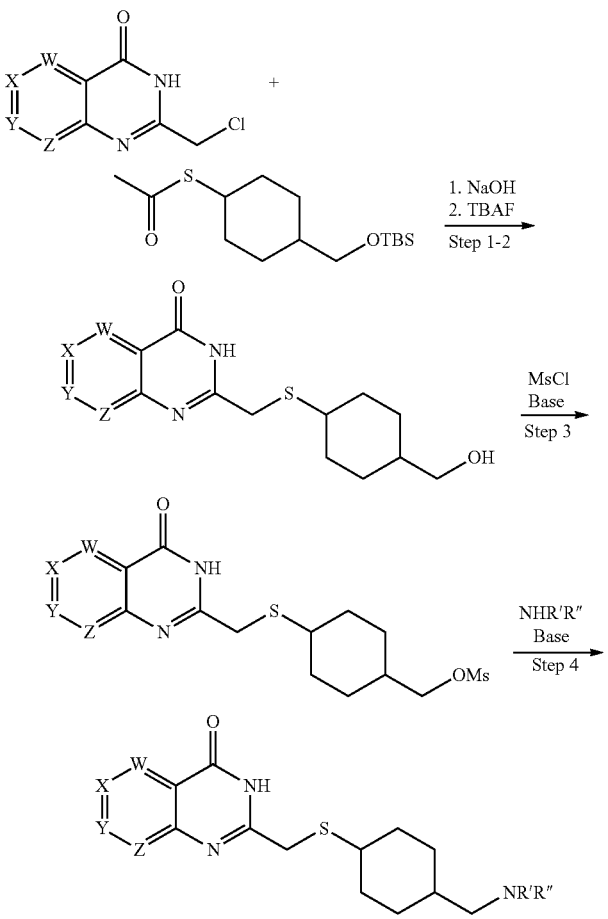

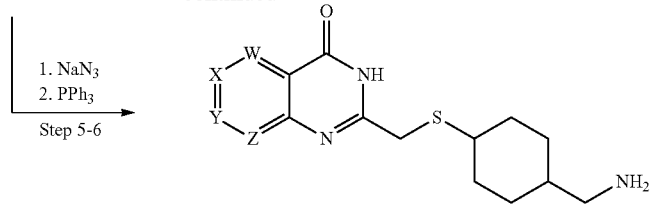

Scheme 14 summarizes methods for preparing substituted cyclohexylthioethers. A chloromethylquinazolinone (Scheme 1) can be coupled with S-(4-(((tert-butyldimethyl-silyl)oxy)methyl)cyclohexyl)ethanethioate in the presence of sodium hydroxide to provide the desired thioether (Step 1). Removal of the TBS group with a fluoride source such as TBAF in a polar solvent such as THF at an elevated temperature such as 50° C. provides the primary alcohol (Step 2). The alcohol can be converted to a methanesulfonate by treating with methanesulfonyl chloride in the presence of an amine base such as triethylamine in a nonpolar solvent such as DCM at room temperature (Step 3). The methanesulfonate can then be replaced with secondary amines in the presence of a tertiary amine base such as triethylamine in a polar solvent such as THF at elevated temperature such as 100° C. (Step 4). Alternatively the mesylate can be converted to a primary amine, first by treatment with sodium azide in a polar solvent such as DMF at 50° C., followed by treatment with triphenylphosphine in a THF/water mixture at room temperature (Steps 5 and 6).

Methods of Use

Compounds of the invention can inhibit the activity of PARP14. For example, the compounds of the invention can be used to inhibit activity of PARP14 in a cell or in an individual or patient in need of inhibition of the enzyme by administering an inhibiting amount of a compound of the invention to the cell, individual, or patient.

The compounds of the invention can further inhibit the production of IL-10 in a cell. For example, the present invention relates to methods of inhibiting or decreasing the production of IL-10 in a cell by contacting the cell with a PARP14 inhibitor of the invention.

As PARP14 inhibitors, the compounds of the invention are useful in the treatment of various diseases associated with abnormal expression or activity of PARP14. For example, the compounds of the invention are useful in the treatment of cancer. In some embodiments, the cancers treatable according to the present invention include hematopoietic malignancies such as leukemia and lymphoma. Example lymphomas include Hodgkin's or non-Hodgkin's lymphoma, multiple myeloma, B-cell lymphoma (e.g., diffuse large B-cell lymphoma (DLBCL)), chronic lymphocytic lymphoma (CLL), T-cell lymphoma, hairy cell lymphoma, and Burkett's lymphoma. Example leukemias include acute lymphocytic leukemia (ALL), acute myelogenous leukemia (AML), chronic lymphocytic leukemia (CLL), and chronic myelogenous leukemia (CML).

Other cancers treatable by the administration of the compounds of the invention include liver cancer (e.g., hepatocellular carcinoma), bladder cancer, bone cancer, glioma, breast cancer, cervical cancer, colon cancer, endometrial cancer, epithelial cancer, esophageal cancer, Ewing's sarcoma, pancreatic cancer, gallbladder cancer, gastric cancer, gastrointestinal tumors, head and neck cancer, intestinal cancers, Kaposi's sarcoma, kidney cancer, laryngeal cancer, liver cancer (e.g., hepatocellular carcinoma), lung cancer, prostate cancer, rectal cancer, skin cancer, stomach cancer, testicular cancer, thyroid cancer, and uterine cancer.

In some embodiments, the cancer treatable by administration of the compounds of the invention is multiple myeloma, DLBCL, hepatocellular carcinoma, bladder cancer, esophageal cancer, head and neck cancer, kidney cancer, prostate cancer, rectal cancer, stomach cancer, thyroid cancer, uterine cancer, breast cancer, glioma, follicular lymphoma, pancreatic cancer, lung cancer, colon cancer, or melanoma.

The PARP14 inhibitors of the invention may also have therapeutic utility in PARP14-related disorders in disease areas such as cardiology, virology, neurodegeneration, inflammation, and pain, particularly where the diseases are characterized by overexpression or increased activity of PARP14.

In some embodiments, the compounds of the invention are useful in the treatment of an inflammatory disease. In some embodiments, the inflammatory diseases treatable according to the present invention include inflammatory bowel diseases (e.g., Crohn's disease or ulcerative colitis), inflammatory arthritis, inflammatory demyelinating disease, psoriasis, allergy and asthma sepsis, allergic airway disease (e.g., asthma), and lupus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" PARP14 or "contacting" a cell with a compound of the invention includes the administration of a compound of the present invention to an individual or patient, such as a human, having PARP14, as well as, for example, introducing a compound of the invention into a sample containing a cellular or purified preparation containing PARP14.

As used herein, the term "individual" or "patient," used interchangeably, refers to mammals, and particularly humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease in an individual who is experiencing or displaying the pathology or symptomatology of the disease (i.e., arresting further development of the pathology and/or symptomatology), or 2) ameliorating the disease in an individual who is experiencing or displaying the pathology or symptomatology of the disease (i.e., reversing the pathology and/or symptomatology).

As used herein the term "preventing" or "prevention" refers to preventing the disease in an individual who may be predisposed to the disease but does not yet experience or display the pathology or symptomatology of the disease.

Combination Therapy

One or more additional pharmaceutical agents or treatment methods such as, for example, chemotherapeutics or other anti-cancer agents, immune enhancers, immunosuppressants, immunotherapies, radiation, anti-tumor and antiviral vaccines, cytokine therapy (e.g., IL2, GM-CSF, etc.), and/or kinase (tyrosine or serine/threonine), epigenetic or signal transduction inhibitors can be used in combination with the compounds of the present invention. The agents can be combined with the present compounds in a single dosage form, or the agents can be administered simultaneously or sequentially as separate dosage forms.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Angiogenesis inhibitors may be efficacious in some tumors in combination with FGFR inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other anti-cancer agent(s) include antibody therapeutics to costimulatory molecules such as CTLA-4, 4-1BB, PD-1, and PD-L1, or antibodies to cytokines (IL-10, TGF-β, etc.). Exemplary cancer immunotherapy antibodies include alemtuzumab, ipilimumab, nivolumab, ofatumumab and rituximab.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

When employed as pharmaceuticals, the compounds of the invention can be administered in the form of pharmaceutical compositions. A pharmaceutical composition refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be oral, topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, or parenteral.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

The compositions can be formulated in a unit dosage form. The term "unit dosage form" refers to a physically discrete unit suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, anti-cancer agents, vaccines, antibodies, immune enhancers, immune suppressants, anti-inflammatory agents and the like.

EXAMPLES

Equipment:

$^1$H NMR Spectra were recorded at 400 MHz using a Bruker AVANCE 400 MHz spectrometer. NMR interpretation was performed using MestReC or MestReNova software to assign chemical shift and multiplicity. In cases where two adjacent peaks of equal or unequal height were observed, these two peaks may be labeled as either a multiplet or as a doublet. In the case of a doublet, a coupling constant using this software may be assigned. In any given example, one or more protons may not be observed due to obscurity by water and/or solvent peaks. LCMS equipment and conditions are as follows:

LC: Agilent Technologies 1290 series, Binary Pump, Diode Array Detector. Agilent Poroshell 120 EC-C18, 2.7 µm, 4.6×50 mm column. Mobile phase: A: 0.05% Formic acid in water (v/v), B: 0.05% Formic acid in ACN (v/v). Flow Rate: 1 mL/min at 25° C. Detector: 214 nm, 254 nm. Gradient stop time, 10 min. Timetable:

| T (min) | A(%) | B(%) |
|---|---|---|
| 0.0 | 90 | 10 |
| 0.5 | 90 | 10 |
| 8.0 | 10 | 90 |
| 10.0 | 0 | 100 |

MS: G6120A, Quadrupole LC/MS, Ion Source: ES-API, TIC: 70~1000 m/z, Fragmentor: 60, Drying gas flow: 10 L/min, Nebulizer pressure: 35 psi, Drying gas temperature: 350° C., Vcap: 3000V.

Sample preparation: samples were dissolved in ACN or methanol at 1~10 mg/mL, then filtered through a 0.22 µm filter membrane. Injection volume: 1~10 µL.

Definitions

AcCl (acetyl chloride); ACN (acetonitrile); Ac$_2$O (acetic anhydride); AcOH (acetic acid); AcSH (thioacetic acid); atm (atmosphere); BINAP (2,2'-bis(diphenylphosphino)-1,1'-binaphthyl); BOP ((benzotriazol-1-yloxy)tris(dimethylamino) phosphonium hexafluorophosphate); BnBr (benzyl bromide); Boc (tert-butoxycarbonyl); Boc$_2$O (di-tert-butyl dicarbonate); CDCl$_3$ (deuterated chloroform); CD$_3$OD (deuterated methanol); conc. (concentrated); CO (carbon monoxide); dba (dibenzylideneacetone); DCM (dichloromethane); DIPEA (N,N-diisopropylethylamine); DMAP (4-dimethylaminopyridine); DME (1,2-dimethoxyethane); DMF (N,N-dimethylformamide); DMSO (dimethylsulfoxide); DMSO-d$_6$ (deuterated dimethylsulfoxide); EDCI (1-ethyl-3-(3-dimethylaminopropyl)carbodiimide); eq (equivalent); ES-API (electrospray atmospheric pressure ionization); Et$_3$N (triethylamine); Et$_2$O (diethyl ether); EtOAc (ethyl acetate); EtOH (ethanol); g (gram); h (hour); HATU (1-[bis(dimethylamino)methylene]-1H-1,2,3-triazolo[4,5-b]pyridinium 3-oxide hexafluorophosphate); HOBt (hydroxybenzotriazole); $^1$H NMR (proton nuclear magnetic resonance); Hz (hertz); KSAc (potassium thioacetate); L (litre); LCMS (liquid chromatography-mass spectrometry); LiHMDS (lithium bis(trimethylsilyl)amide); M (molar); MeOH (methanol); mg (milligrams); MHz (megahertz); min (minutes); mL (millilitres), mmol (millimoles); MsCl (methanesulfonyl chloride); n-BuLi (n-butyllithium); NMP (N-methyl-2-pyrrolidone); PhOH (phenol); prep-HPLC (preparative high-performance liquid chromatography); prep-TLC (preparative thin layer chromatography); ppm (parts per million); psi (pounds per square inch); p-TSA (p-toluenesulfonic acid); pyBOP ((benzotriazol-1-yloxy) tripyrrolidinophosphonium hexafluorophosphate); RT (room temperature); SEM (2-(trimethylsilyl)ethoxymethyl); SEMCl (2-(trimethylsilyl)ethoxymethyl chloride); TBAF (tetra-n-butylammonium fluoride); t-BuXPhos (2-di-tert-butylphosphino-2',4',6'-triisopropylbiphenyl; TFA (trifluoroacetic acid); THF (tetrahydrofuran); TLC (thin layer chromatography); v/v (volume/volume).

Synthesis of Intermediates

Int-A1:
2-(Chloromethyl)-8-methylquinazolin-4(3H)-one

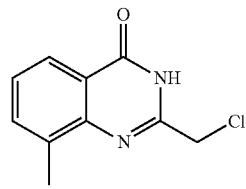

Chloroacetonitrile (75 g, 0.99 mol, 3 eq) was added dropwise to a pre-prepared solution of sodium (1.52 g, 6.6 mmol, 0.2 eq) in methanol (200 mL) over 10 mins at RT under a nitrogen atmosphere. After stirring for 1 h, a solution of 2-amino-3-methylbenzoic acid (50 g, 0.33 mmol, 1.0 eq) in methanol (700 mL) was added and the mixture was stirred at RT for another 2 h. The resulting precipitate was collected by filtration and washed with water then MeOH and dried under vacuum to give the title compound (46.9 g, 68%) as a white solid. LCMS: [M+H]$^+$ 209.0. The following intermediates in Table 1 were similarly prepared from the appropriate amino acid starting material according to the method described for Int-A1.

TABLE 1

| Intermediate | Name | Amino acid | LCMS: [M + H]$^+$ |
|---|---|---|---|
| Int-A2 | 2-(Chloromethyl)-7-methylquinazolin-4(3H)-one | 2-amino-4-methylbenzoic acid | 209.0 |
| Int-A3 | 2-(Chloromethyl)-6-methylquinazolin-4(3H)-one | 2-amino-5-methylbenzoic acid | 209.0 |
| Int-A4 | 2-(Chloromethyl)-8-methoxyquinazolin-4(3H)-one | 2-amino-3-methoxybenzoic acid | 225.0 |
| Int-A5 | 2-(Chloromethyl)-7-methoxyquinazolin-4(3H)-one | 2-amino-4-methoxybenzoic acid | 225.0 |

TABLE 1-continued

| Intermediate | Name | Amino acid | LCMS: [M + H]$^+$ |
|---|---|---|---|
| 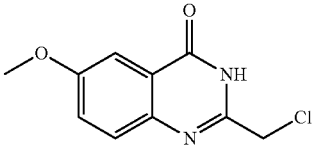 Int-A6 | 2-(Chloromethyl)-6-methoxyquinazolin-4(3H)-one | 2-amino-5-methoxybenzoic acid | 225.0 |
| 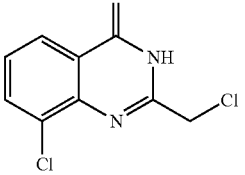 Int-A7 | 8-Chloro-2-(chloromethyl)quinazolin-4(3H)-one | 2-amino-3-chlorobenzoic acid | 229.0 |
| 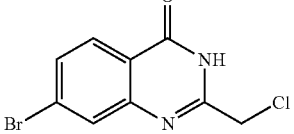 Int-A8 | 7-Bromo-2-(chloromethyl)quinazolin-4(3H)-one | 2-amino-4-bromobenzoic acid | 272.9 |
| 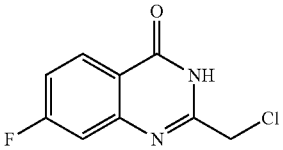 Int-A9 | 2-(Chloromethyl)-7-fluoroquinazolin-4(3H)-one | 2-amino-4-fluorobenzoic acid | 213.0 |
| 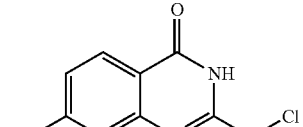 Int-A10 | 2-(Chloromethyl)-7-(trifluoromethyl)quinazolin-4(3H)-one | 2-amino-4-(trifluoromethyl)benzoic acid | 263.0 |
| 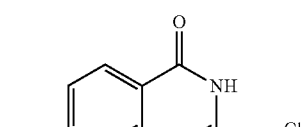 Int-A11 | 2-(Chloromethyl)-7-nitroquinazolin-4(3H)-one | 2-amino-4-nitrobenzoic acid | 240.0 |
| 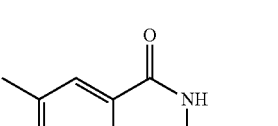 Int-A12 | 2-(Chloromethyl)-6,8-dimethylquinazolin-4(3H)-one | 2-amino-3,5-dimethylbenzoic acid | 223.1 |

TABLE 1-continued

| Intermediate | Name | Amino acid | LCMS: [M + H]+ |
|---|---|---|---|
| 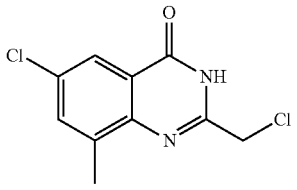<br>Int-A13 | 6-Chloro-2-(chloromethyl)-8-methylquinazolin-4(3H)-one | 2-amino-5-chloro-3-methylbenzoic acid | 243.0 |
| 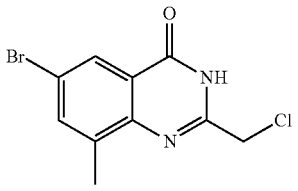<br>Int-A14 | 6-Bromo-2-(chloromethyl)-8-methylquinazolin-4(3H)-one | 2-amino-5-bromo-3-methylbenzoic acid | 287.0 |
| 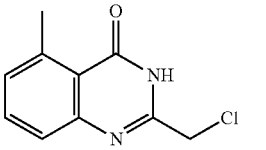<br>Int-A15 | 2-(Chloromethyl)-5-methylquinazolin-4(3H)-one | 2-amino-6-methylbenzoic acid | 209.0 |

Int-A16: Methyl 2-(chloromethyl)-4-oxo-3,4-dihydroquinazoline-7-carboxylate

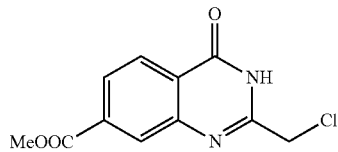 [SMILES: COC(=O)c1ccc2c(=O)[nH]c(CCl)nc2c1]

Chloroacetonitrile (9 g, 120 mmol, 5 eq) and dimethyl 2-aminoterephthalate (5 g, 23.9 mmol, 1.0 eq) were dissolved in a 4.5 M HCl/dioxane solution (80 mL) and the mixture was heated at 50° C. for 3 h under a N₂ atmosphere. The mixture was cooled to RT and the precipitate was collected by filtration, washed with dioxane (10 mL) and dried under vacuum to give the title compound (6 g, 98%) as a white solid. LCMS: [M+H]+ 253.0

Int-A17: 2-(Chloromethyl)-4-oxo-3,4-dihydroquinazoline-8-carbonitrile

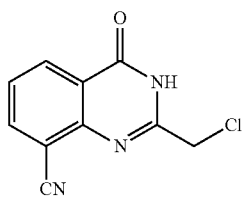 [SMILES: N#Cc1cccc2c(=O)[nH]c(CCl)nc12]

Step 1: Ethyl 2-amino-3-bromobenzoate

To a suspension of 2-amino-3-bromobenzoic acid (1.1 g, 5.1 mmol, 1.0 eq) and Cs₂CO₃ (3.3 g, 10.2 mmol, 2 eq) in DMF (10 mL) at 0° C. was added EtI (0.95 g, 6.1 mmol, 1.2 eq) dropwise. The mixture was then allowed to warm to RT and stirred for 16 h. The mixture was poured into water (20 mL) and extracted with EtOAc (20 mL×3). The organic layers were dried over Na₂SO₄ and concentrated under reduced pressure. The residue was purified by column chromatography (Petroleum ether:EtOAc, 50:1, v/v) to afford the title compound (820 mg, 68%) as a white solid. LCMS: [M+H]+ 244.1.

Step 2: Ethyl 2-amino-3-cyanobenzoate

To a solution of ethyl 2-amino-3-bromobenzoate (340 mg, 1.4 mmol, 1.0 eq) in NMP (4 mL) was added CuCN (251 mg, 2.8 mmol, 2.0 eq) and the mixture was heated at 180° C. for 4 h. After cooling to RT, water (20 mL) was added and the mixture was extracted with EtOAc (20 mL×3). The combined organic layers were dried over Na₂SO₄ and concentrated under reduced pressure. The residue was purified by column chromatography (Petroleum ether:EtOAc, 10:1, v/v) to afford the title compound (170 mg, 64%) as a white solid. LCMS: [M+H]+ 191.3.

Step 3: 2-(Chloromethyl)-4-oxo-3,4-dihydroquinazoline-8-carbonitrile

The title compound was prepared from ethyl 2-amino-3-cyanobenzoate and chloroacetonitrile according to the method described for Int-A16. LCMS: [M+H]+ 220.2.

Int-A18: 2-(Chloromethyl)-4-oxo-3,4-dihydroquinazoline-7-carbonitrile

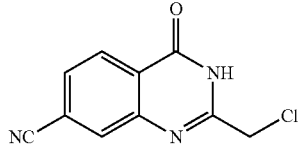 [SMILES: N#Cc1ccc2c(=O)[nH]c(CCl)nc2c1]

The title compound was prepared from 2-amino-4-bromobenzoic acid according to the method described for Int-A17. LCMS: [M+H]+ 220.1.

Int-A19: 2-(Chloromethyl)-7-phenoxyquinazolin-4(3H)-one

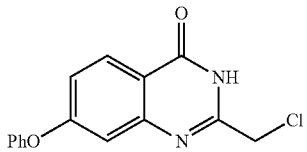 [SMILES: O=c1[nH]c(CCl)nc2cc(Oc3ccccc3)ccc12]

Step 1: Methyl 2-nitro-4-phenoxybenzoate

To a solution of methyl 4-fluoro-2-nitrobenzoate (1.0 g, 5 mmol, 1.0 eq) and PhOH (0.79 g, 7.5 mmol, 1.5 eq) in DMSO (10 mL) was added $K_2CO_3$ (1.38 g, 10 mmol, 2 eq) and the mixture was heated at 90° C. for 2 h. After cooling to RT, water (50 mL) was added and the mixture was extracted with EtOAc (60 mL×3). The combined organic layers were dried over $Na_2SO_4$ and concentrated under reduced pressure. The residue was purified by column chromatography (Petroleum ether:EtOAc, 25:1, v/v) to afford the title compound (1.2 g, 88%) as a white solid, which was used directly in the next step.

Step 2. Methyl 2-amino-4-phenoxybenzoate

To a solution of methyl 2-nitro-4-phenoxybenzoate (1.2 g, 4.4 mmol) in EtOAc (20 mL) was added Pd(OH)$_2$/C (1.2 g, 5% wet) and the mixture was stirred at RT under a H$_2$ atmosphere (1 atm) overnight. The mixture was filtered and the filtrate was concentrated under reduced pressure to give the title compound (1.15 g, 100%), which was used for the next step without further purification. LCMS: [M+H]+ 244.1.

Step 3. 2-(Chloromethyl)-7-phenoxyquinazolin-4(3H)-one

The title compound was prepared from methyl 2-amino-4-phenoxybenzoate and chloroacetonitrile according to the method described for Int-A16. LCMS: [M+H]+ 287.1.

Int-A20: 2-(Chloromethyl)-8-methyl-5-(trifluoromethyl)quinazolin-4(3H)-one

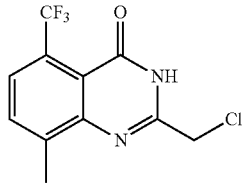

Step 1: 7-Methyl-4-(trifluoromethyl)indoline-2,3-dione

To a solution of chloral hydrate (4.4 g, 26.4 mmol, 1.1 eq) and $Na_2SO_4$ (13.6 g) in water (20 mL) was added a solution of 2-methyl-5-(trifluoromethyl)aniline (4.2 g, 24 mmol, 1.0 eq) in conc. HCl (2.5 mL) dropwise followed by a solution of hydroxylamine hydrochloride (5.46 g) in water (20 mL). The mixture was then heated at 70° C. for 6 h, then allowed to cool to RT and filtered. The filter cake was washed with water (20 mL×3) and dried to give the title compound (2 g, 36%). LCMS: [M+H]+ 247.3.

Step 2: 2-Amino-3-methyl-6-(trifluoromethyl)benzoic Acid

To a solution of 7-methyl-4-(trifluoromethyl)indoline-2,3-dione (500 mg, 2.2 mmol, 1.0 eq) in 2 M NaOH (2.5 mL, 2.3 eq) was added $H_2O_2$ (30%, 0.6 mL) and the mixture was heated at 50° C. overnight. The mixture was cooled to RT, diluted with water (5 mL) and adjusted to pH 6-7 with 1 M HCl. The resulting solid was collected by filtration, washed with water (10 mL×2) and dried to give the title compound (450 mg, 86%) as a brown solid. LCMS: [M+H]+ 220.1.

Step 3: Methyl 2-amino-3-methyl-6-(trifluoromethyl) benzoate

To a suspension of 2-amino-3-methyl-6-(trifluoromethyl)benzoic acid (1.0 g, 4.4 mmol, 1.0 eq) and $K_2CO_3$ (1.2 g, 8.8 mmol, 2 eq) in DMF (20 mL) at 0° C. was added MeI (0.9 g, 6.1 mmol, 1.5 eq) dropwise and the mixture was allowed to warm to RT and stirred for 16 h. The mixture was poured into water (20 mL) and extracted with EtOAc (30 mL×3). The combined organic layers were dried over $Na_2SO_4$ and concentrated under reduced pressure. The residue was purified by column chromatography (Petroleum ether:EtOAc, 50:1, v/v) to afford the title compound (740 mg, 69%) as a brown oil. LCMS: [M+H]+ 234.2.

Step 4: 2-(Chloromethyl)-8-methyl-5-(trifluoromethyl)quinazolin-4(3H)-one

The title compound was prepared from methyl 2-amino-3-methyl-6-(trifluoromethyl)benzoate and chloroacetonitrile according to the method described for Int-A16. LCMS: [M+H]+ 277.1.

Int-A21: 2-(Chloromethyl)-5-fluoro-8-methylquinazolin-4(3H)-one

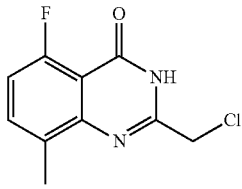

The title compound was prepared from 4-fluoro-7-methylindoline-2,3-dione according to the method described for Int-A20 steps 2, 3, 4. LCMS: [M+H]$^+$ 227.1.

Int-A22: 5-Chloro-2-(chloromethyl)-8-methylquinazolin-4(3H)-one

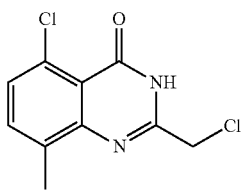

The title compound was prepared from 5-chloro-2-methylaniline according to the methods described for Int-A20. LCMS: [M+H]$^+$ 243.0.

Int-A23: 2-(Chloromethyl)-7-fluoro-8-methylquinazolin-4(3H)-one

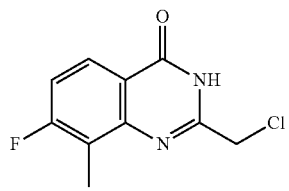

Step 1: Methyl 2-amino-4-fluoro-3-methylbenzoate

The title compound was prepared from 2-amino-4-fluoro-3-methylbenzoic acid according to the method described for Int-A20, step 3. LCMS: [M+H]$^+$ 184.1.

Step 2: 2-(Chloromethyl)-7-fluoro-8-methylquinazolin-4(3H)-one

The title compound was prepared from methyl 2-amino-4-fluoro-3-methylbenzoate and chloroacetonitrile according to the method described for Int-A16. LCMS: [M+H]$^+$ 227.1.

Int-A24: 7-Bromo-2-(chloromethyl)-8-methylquinazolin-4(3H)-one

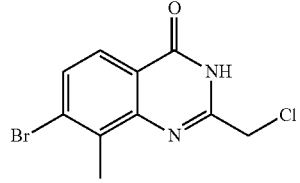

Step 1: Methyl 2-amino-4-bromo-3-methylbenzoate

The title compound was prepared from 2-amino-4-bromo-3-methylbenzoic acid according to the method described for Int-A20, step 3. LCMS: [M+H]$^+$ 229.9.

Step 2: 2-(Chloromethyl)-7-bromo-8-methylquinazolin-4(3H)-one

The title compound was prepared from methyl 2-amino-4-bromo-3-methylbenzoate and chloroacetonitrile according to the method described for Int-A16. LCMS: [M+H]$^+$ 286.9.

Int-A25: 2-(Chloromethyl)-7,8-difluoroquinazolin-4(3H)-one

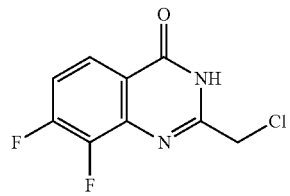 [SMILES: O=c1[nH]c(CCl)nc2c(F)c(F)ccc12]

Step 1: Methyl 2-amino-3,4-difluorobenzoate

The title compound was prepared from 2-amino-3,4-difluorobenzoic acid according to the method described for Int-A20, step 3. LCMS: [M+H]$^+$ 188.1.

Step 2: 2-(Chloromethyl)-7,8-difluoroquinazolin-4(3H)-one

The title compound was prepared from methyl 2-amino-3,4-difluorobenzoate and chloroacetonitrile according to the method described for Int-A16. LCMS: [M+H]$^+$ 231.0.

Int-A26: 7,8-Dichloro-2-(chloromethyl)quinazolin-4(3H)-one

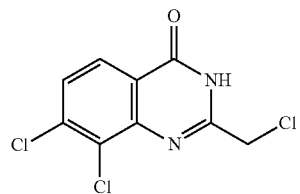 [SMILES: O=c1[nH]c(CCl)nc2c(Cl)c(Cl)ccc12]

Step 1: Methyl 2-amino-3,4-dichlorobenzoate

The title compound was prepared from 2-amino-3,4-dichlorobenzoic acid according to the method described for Int-A20, step 3. LCMS: [M+H]+ 220.0.

Step 2. 7,8-Dichloro-2-(chloromethyl)quinazolin-4(3H)-one

The title compound was prepared from methyl 2-amino-3,4-dichlorobenzoate and chloroacetonitrile according to the method described for Int-A16. LCMS: [M+H]+ 263.0.

Int-A27: 2-(Chloromethyl)pyrido[3,2-d]pyrimidin-4(3H)-one

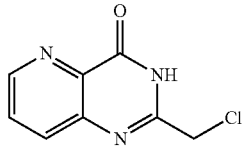 [SMILES: O=c1[nH]c(CCl)nc2cccnc12]

The title compound was prepared from methyl 3-aminopicolinate and chloroacetonitrile according to the method described for Int-A16 but at 120° C. in a microwave for 1 h. LCMS: [M+H]+ 196.0.

Int-A28: 2-(Chloromethyl)pyrido[3,4-d]pyrimidin-4(3H)-one

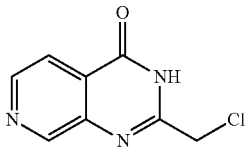 [SMILES: O=c1[nH]c(CCl)nc2cnccc12]

The title compound was prepared from methyl 3-aminoisonicotinate and chloroacetonitrile according to the method described for Int-A16 but at 120° C. in a microwave for 1 h. LCMS: [M+H]+ 196.0.

Int-A29: 2-(Chloromethyl)-8-methylpyrido[3,4-d]pyrimidin-4(3H)-one

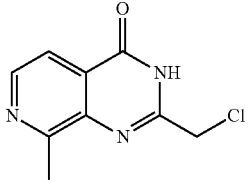

Step 1: Methyl 3-amino-2-methylisonicotinate

To a solution of methyl 3-amino-2-chloroisonicotinate (2.0 g, 10.7 mmol, 1.0 eq) and 2,4,6-trimethyl-1,3,5,2,4,6-trioxatriborinane (4.0 g, 32.2 mmol, 3.0 eq) in 1,4-dioxane (40 mL) under a N2 atmosphere was added Pd(dppf)Cl2 (1.6 g, 2.1 mmol, 0.2 eq) and K2CO3 (3.0 g, 21.4 mmol, 2.0 eq) and the mixture was heated at 100° C. for 1 h in a microwave. The mixture was cooled to RT, diluted with water (50 mL) and extracted with EtOAc (50 mL×3). The combined organic layers were washed with water (40 mL), dried over Na2SO4 and concentrated under reduced pressure. The residue was purified by column chromatography (Petroleum ether:EtOAc, 5:1 to 3:1, v/v) to afford the title compound (1.9 g, 100%) as a yellow solid. LCMS: [M+H]+ 167.1.

Step 2. 2-(Chloromethyl)-8-methylpyrido[3,4-d]pyrimidin-4(3H)-one

The title compound was prepared from methyl 3-amino-2-methylisonicotinate and chloroacetonitrile according to the method described for Int-A16 but heated at 120° C. in a sealed tube for 3 days. LCMS: [M+H]+ 210.1.

Int-A30: 2-(Chloromethyl)-8-methylpyrido[3,2-d]pyrimidin-4(3H)-one

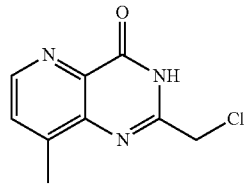

Step 1: Methyl 3-amino-4-methylpicolinate

To a solution of 2-bromo-4-methylpyridin-3-amine (1.0 g, 5.3 mmol) in methanol (20 mL) was added PdCl2(dppf) (390 mg, 5% wet) and the mixture was heated at 70° C. under a CO atmosphere (30 atm) overnight. The mixture was cooled to RT, filtered and concentrated. The residue was purified by column chromatography (Petroleum ether:EtOAc, 3:1, v/v) to afford the title compound (370 mg, 41%) as light yellow solid. LCMS: [M+H]+ 167.1.

Step 2. 2-(Chloromethyl)-8-methylpyrido[3,4-d]pyrimidin-4(3H)-one

The title compound was prepared from methyl 3-amino-4-methylpicolinate and chloroacetonitrile according to the method described for Int-A16 but heated at 100° C. in a sealed tube for 2 days. LCMS: [M+H]+ 210.0.

Int-A31: 2-(Chloromethyl)pyrido[4,3-d]pyrimidin-4(3H)-one

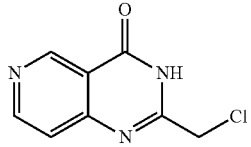 [SMILES: O=c1[nH]c(CCl)nc2ccncc12]

To a mixture of 4-aminopyridine-3-carboxamide (50 mg, 0.36 mmol), DMAP (2 mg, 0.02 mmol) and DIPEA (141 mg, 1.1 mmol) was added 2-chloroacetyl chloride (82 mg, 0.7 mmol, 2 eq) and the mixture was heated at 100° C. in a microwave for 10 min. The mixture was diluted with water (5 mL) and the solid was collected by filtration to give the title compound (66 mg, 93%) as a white solid. LCMS: [M+H]+ 196.0.

Int-A32: 2-(Chloromethyl)pyrido[2,3-d]pyrimidin-4(3H)-one

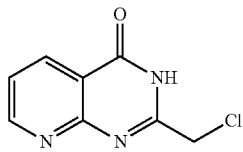 [SMILES: O=c1[nH]c(CCl)nc2ncccc12]

Step 1: 2-[(2-Chloroacetyl)amino]pyridine-3-carboxamide

To a solution of 2-aminopyridine-3-carboxamide (400 mg, 2.9 mmol) and pyridine (0.7 mL, 8.8 mmol) in DCM (20 mL) at 0° C. was added 2-chloroacetyl chloride (362 mg, 3.2 mmol, 1.1 eq) dropwise. The mixture was stirred at 0° C. for 1 h then allowed to warm to RT and stirred overnight. The mixture was poured into water (20 mL) and extracted with DCM (20 mL×3). The combined organic layers were dried over Na₂SO₄ and concentrated under reduced pressure. The residue was purified by column chromatography (Petroleum ether:EtOAc, 2:1, v/v) to afford the title compound (180 mg, 29%) as a black solid. LCMS: [M+H]+ 214.1.

Step 2: 2-(Chloromethyl)-3H-pyrido[2,3-d]pyrimidin-4-one

To a solution of 2-[(2-chloroacetyl)amino]pyridine-3-carboxamide (100 mg, 0.5 mmol) in toluene (10 mL) was added p-TSA (161 mg, 0.9 mmol) and the mixture was heated at reflux for 4 h. The mixture was then concentrated under reduced pressure and the residue was purified by reverse phase column (Biotage, C18 column, 30-80% ACN in water) to afford the title compound (25 mg, 27%) as a gray solid. LCMS: [M+H]+ 196.0.

Int-A33: 2-(1-Chloroethyl)-8-methylquinazolin-4(3H)-one

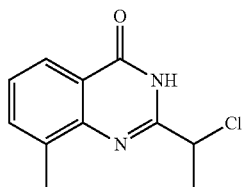

The title compound was prepared from 2-amino-3-methylbenzoic acid and 2-chloropropanenitrile according to the method described for Int-A1. LCMS: [M+H]+ 223.1.

Int-A34: 2-(2-Chloroethyl)-8-methylquinazolin-4(3H)-one

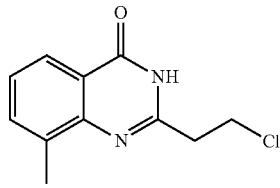

The title compound was prepared from methyl 2-amino-3-methylbenzoate and 3-chloropropanenitrile according to the method described for Int-A16. LCMS: [M+H]+ 223.1.

Int-A35: 8-Benzyl-2-(chloromethyl)quinazolin-4(3H)-one

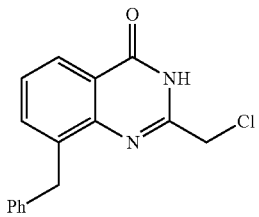 [SMILES: O=c1[nH]c(CCl)nc2c(Cc3ccccc3)cccc12]

Step 1: Ethyl 2-amino-3-benzylbenzoate

To a solution of ethyl 2-amino-3-bromobenzoate (488 mg, 2 mmol, 1.0 eq) in THF/water (24 mL, 5:1) under a N₂ atmosphere was added potassium benzyltrifluoroborate (400 mg, 2.0 mmol, 1.0 eq), PdCl₂(dppf) (80 mg, 0.1 mmol, 0.05 eq) and Cs₂CO₃ (2.0 g, 6.1 mmol, 3.0 eq) and the mixture was heated at 80° C. for 3 days. The mixture was cooled to RT, diluted with water (20 mL) and extracted with EtOAc (40 mL×3). The combined organic layers were washed with water (40 mL), dried over Na₂SO₄ and concentrated under reduced pressure. The residue was purified by column chromatography (Petroleum ether:EtOAc, 10:1, v/v) to afford the title compound (190 mg, 28%) as a brown oil. LCMS: [M+H]+ 256.1.

Step 2: 8-Benzyl-2-(chloromethyl)quinazolin-4(3H)-one

The title compound was prepared from ethyl 2-amino-4-bromobenzoate and chloroacetonitrile according to the method described for Int-A16. LCMS: [M+H]+ 285.2.

Int-A36: 7-Benzyl-2-(chloromethyl)quinazolin-4(3H)-one

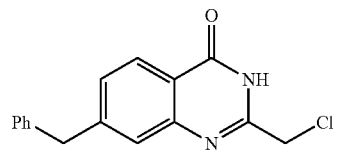 [SMILES: O=c1[nH]c(CCl)nc2cc(Cc3ccccc3)ccc12]

The title compound was prepared from ethyl 2-amino-4-bromobenzoate according to the method described for Int-A35. LCMS: [M+H]+ 285.1.

Int-A37: 2-(Chloromethyl)-7-(cyclopentylamino)-5-fluoroquinazolin-4(3H)-one

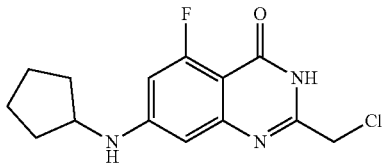 [SMILES: O=c1[nH]c(CCl)nc2cc(NC3CCCC3)cc(F)c12]

Step 1: Methyl 2-amino-4, 6-difluorobenzoate

The title compound was prepared from 4,6-difluoroinoline-2,3-dione according to the method described for Int-A20, steps 2 and 3. LCMS: [M+H]+ 188.0.

Step 2: Methyl 2-amino-4-(cyclopentylamino)-6-fluorobenzoate

To a solution of methyl 2-amino-4,6-difluorobenzoate (3 g, 16.0 mmol, 1.0 eq) in DMSO (5 mL) was added cyclopentanamine (2.73 g, 32.0 mmol, 2.0 eq) and the mixture was heated at 80° C. overnight. The mixture was cooled to RT, diluted with water (5 mL) and extracted with DCM (40 mL×2). The combined organic layers were dried over $Na_2SO_4$ and concentrated under reduced pressure. The residue was purified by column chromatography (Petroleum ether:DCM, 40:1, v/v to Petroleum ether:EtOAc, 30:1 to 20:1, v/v) to afford the title compound (863 mg, 21%) as a red solid. LCMS: [M+H]+ 253.1.

Step 3: 2-(Chloromethyl)-7-(cyclopentylamino)-5-fluoroquinazolin-4(3H)-one

The title compound was prepared from methyl 2-amino-4-(cyclopentylamino)-6-fluorobenzoate and chloroacetonitrile according to the method described for Int-A16. LCMS: [M+H]+ 296.1.

Int-A38: 2-(Chloromethyl)-7-(cyclobutylamino)-5-fluoroquinazolin-4(3H)-one

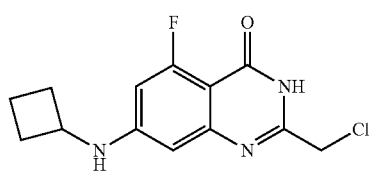 [SMILES: O=c1[nH]c(CCl)nc2cc(NC3CCC3)cc(F)c12]

Step 1: Methyl 2-amino-4-(cyclobutylamino)-6-fluorobenzoate

The title compound was prepared from methyl 2-amino-4,6-difluorobenzoate and cyclobutanamine according to the method described for Int-A37, step 2. LCMS: [M+H]+ 239.1.

Step 2: 2-(Chloromethyl)-7-(cyclobutylamino)-5-fluoroquinazolin-4(3H)-one

The title compounds was prepared from methyl 2-amino-4-(cyclobutylamino)-6-fluorobenzoate and chloroacetonitrile according to the method described for Int-A16. LCMS: [M+H]+ 282.1.

Int-B1: S-(Tetrahydro-2H-pyran-4-yl) ethanethioate

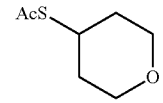

To a solution of 4-bromotetrahydro-2H-pyran (50.0 g, 303 mmol, 1.0 eq) in DMF (300 mL) under a $N_2$ atmosphere was added KSAc (41.5 g, 364 mmol, 1.2 eq) and the mixture was stirred at RT overnight. The mixture was diluted with water (700 mL) and extracted with EtOAc (200 mL×3). The combined organic layers were dried over $Na_2SO_4$ and concentrated under reduced pressure to afford the title compound (41.5 g, 68%) as a brown oil.
$^1$H NMR (400 MHz, CDCl$_3$) δ 3.91-3.87 (m, 2H), 3.71-3.64 (m, 1H), 3.57-3.51 (m, 2H), 2.31 (s, 3H), 1.92-1.88 (m, 2H), 1.71-1.62 (m, 2H).

Int-B2: tert-Butyl 4-(acetylthio)piperidine-1-carboxylate

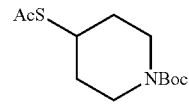

The title compound was prepared from tert-butyl 4-bromopiperidine-1-carboxylate according to the method described for Int-B1.
$^1$H NMR (400 MHz, CDCl$_3$) δ 3.87-3.84 (m, 2H), 3.64-3.57 (m, 1H), 3.08-3.02 (m, 2H), 2.31 (s, 3H), 1.92-1.87 (m, 2H), 1.58-1.45 (m, 2H), 1.45 (s, 9H).

Int-B3: S-(1-Methylpiperidin-3-yl) ethanethioate

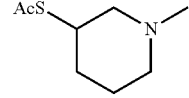

Step 1: 1-Methylpiperidin-3-yl Methanesulfonate

To a solution of 1-methylpiperidin-3-ol (2.0 g, 17.4 mmol, 1.0 eq) and triethylamine (3.5 g, 34.8 mmol, 2.0 eq) in DCM (20 mL) at 0° C. was added methanesulfonyl chloride (2.4 g, 21 mmol, 1.2 eq) dropwise and the mixture was allowed to warm to RT and stirred for 3 h. The mixture was diluted with DCM (120 mL) and washed with 0.5 M HCl (40 mL) and water (40 mL). The organic layer was dried over $Na_2SO_4$ and concentrated under reduced pressure to afford the title compound (3.3 g, 99%) as a light yellow oil, which was used directly in the next step without further purification. LCMS: [M+H]⁺ 194.1.

Step 2: S-(1-Methylpiperidin-3-yl) ethanethioate

To a solution of 1-methylpiperidin-3-yl methanesulfonate (1.6 g, 8.1 mmol, 1.0 eq) in DMF (50 mL) under a $N_2$ atmosphere was added KSAc (1.1 g, 9.7 mmol, 1.2 eq) and the mixture was stirred at RT overnight. The mixture was diluted with water (20 mL) and extracted with EtOAc (40 mL×3). The combined organic layers were dried over $Na_2SO_4$ and concentrated under reduced pressure. The residue was purified by column chromatography (Petroleum ether:EtOAc, 10:1, v/v) to afford the title compound (1 g, 71%) as a brown oil. LCMS: [M+H]⁺ 174.1.

Int-B4: tert-Butyl 3-(acetylthio)piperidine-1-carboxylate

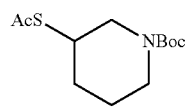

The title compound was prepared from tert-butyl 3-hydroxypiperidine-1-carboxylate according to the method described for Int-B3. LCMS: [M+H−56]⁺ 203.1.

Int-B5-trans: S-(trans-4-((tert-Butoxycarbonyl) amino)cyclohexyl) ethanethioate

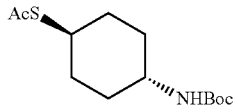

and

Int-B5-cis: S-(cis-4-((tert-Butoxycarbonyl)amino) cyclohexyl) ethanethioate

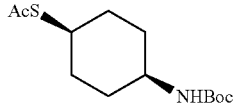

The title compound was prepared from cis/trans-tert-butyl (4-hydroxycyclohexyl)carbamate according to the method described for Int-B3. Purification by column chromatography (Petroleum ether:EtOAc, 1:0 to 10:1, v/v) gave the two separated isomers. Int-B5-trans: LCMS: [M+H−100]⁺ 174.1; Int-B5-cis: LCMS: [M+H−100]⁺ 174.1.

Int-B6: S-1,4-Dioxaspiro[4.5]decan-8-yl ethanethioate

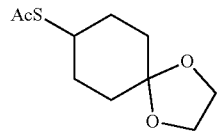

The title compound was prepared from 1,4-dioxaspiro [4.5]decan-8-ol according to the method described for Int-B3.
¹H NMR (400 MHz, $CDCl_3$) δ 3.93 (s, 4H), 3.56-3.51 (m, 1H), 2.32 (s, 3H), 2.00-1.96 (m, 2H), 1.77-1.65 (m, 6H).

Int-B7: S-((trans)-3-(Benzyloxy)cyclobutyl) ethanethioate

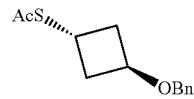

Step 1: cis-3-(Benzyloxy)cyclobutanol

The title compound was prepared from 3-(benzyloxy) cyclobutanone (5.0 g, 28.4 mmol, 1.0 eq) according to the procedure described in *Bioorg. Med. Chem.* 2013, 21, 643 (5.2 g, 100%) as a colorless oil, which was used for the next step without further purification.
¹H NMR (400 MHz, $CDCl_3$) δ 7.36-7.28 (m, 5H), 4.42 (s, 2H), 3.95-3.88 (m, 1H), 3.66-3.60 (m, 1H), 2.75-2.69 (m, 2H), 1.98-1.90 (m, 2H).

Step 2: (cis)-3-(Benzyloxy)cyclobutyl Methanesulfonate

The title compound was prepared from cis-3-(benzyloxy) cyclobutanol according to the procedure described for Int-B3 step 1.
¹H NMR (400 MHz, $CDCl_3$) δ 7.37-7.28 (m, 5H), 4.69-4.61 (m, 1H), 4.43 (s, 2H), 3.77-3.70 (m, 1H), 2.98 (s, 3H), 2.86-2.81 (m, 2H), 2.37-2.30 (m, 2H).

Step 3: S-(trans-3-(Benzyloxy)cyclobutyl) ethanethioate

The title compound was prepared from (cis)-3-(benzyloxy)cyclobutyl methanesulfonate according to the method described for Int-B3 step 2.
¹H NMR (400 MHz, $CDCl_3$) δ 7.37-7.27 (m, 5H), 4.40 (s, 2H), 4.29-4.23 (m, 1H), 4.01-3.95 (m, 1H), 2.64-2.57 (m, 2H), 2.29 (s, 3H), 2.28-2.23 (m, 2H).

Int-B8: S-Oxetan-3-yl ethanethioate

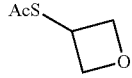

The title compound was prepared from commercially available oxetan-3-yl 4-methylbenzenesulfonate according to the method described for Int-B3 step 2.

$^1$H NMR (400 MHz, CDCl$_3$) δ 5.05 (t, J=7.2 Hz, 2H), 4.69-4.62 (m, 1H), 4.58 (t, J=6.8 Hz, 2H), 2.33 (s, 3H).

Int-B9: S-(trans-3-((tert-Butoxycarbonyl)amino) cyclobutyl) ethanethioate

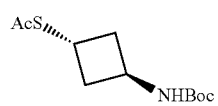

Step 1: tert-Butyl (cis-3-hydroxycyclobutyl)carbamate

To a solution of cis-3-aminocyclobutanol hydrochloride (900 mg, 7.3 mmol, 1.0 eq) in ethanol (5 mL) and Et$_3$N (5 mL) at 0° C. was added Boc$_2$O (800 mg, 3.7 mmol, 0.5 eq) and the mixture was allowed to warm to RT and stirred for 3 h. The mixture was concentrated under reduced pressure, diluted with water (50 mL) and extracted with EtOAc (40 mL×3). The combined organic layers were washed with brine (50 mL), dried over Na$_2$SO$_4$ and concentrated under reduced pressure to afford the title compound (1.2 g, 88%) as a yellow solid, which was used for the next step without further purification. LCMS: [M+H]$^+$ 188.2.

Step 2: (cis)-3-((tert-Butoxycarbonyl)amino)cyclobutyl Methanesulfonate

The title compound was prepared from tert-butyl (cis-3-hydroxycyclobutyl)carbamate according to the procedure described for Int-B3 step 1.

$^1$H NMR (400 MHz, DMSO-d$_6$) δ 7.21 (d, J=8.0 Hz, 1H), 4.70-4.63 (m, 1H), 3.65-3.58 (m, 1H), 3.12 (s, 3H), 2.69-2.63 (m, 2H), 2.16-2.09 (m, 2H), 1.37 (s, 9H).

Step 3: S-(trans-3-((tert-Butoxycarbonyl)amino)cyclobutyl) ethanethioate

The title compound was prepared from cis-3-((tert-butoxycarbonyl)amino)cyclobutyl methanesulfonate according to the method described for Int-B3 step 2.

$^1$H NMR (400 MHz, DMSO-d$_6$) δ 7.29 (d, J=7.6 Hz, 1H), 4.11-4.04 (m, 1H), 3.84-3.79 (m, 1H), 2.46-2.39 (m, 2H), 2.29 (s, 3H), 2.18-2.12 (m, 2H), 1.37 (s, 9H).

Int-B10: S-(4-((tert-Butoxycarbonyl)amino)cycloheptyl) ethanethioate

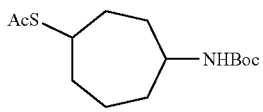

Step 1: tert-Butyl (4-oxocycloheptyl)carbamate

The title compound was prepared from tert-butyl (4-oxocyclohexyl)carbamate according to the procedure described in Liu, H.; et al, *Chem. Eur. J* 2012, 18, 11889: To a solution of n-BuLi (2 M in hexane, 9.76 mL, 24.4 mmol, 1.3 eq) in Et$_2$O (50 mL) at −78° C. under a N$_2$ atmosphere was added TMSCH$_2$N$_2$ (12 mL, 24.4 mmol, 1.3 eq) dropwise and the mixture was allowed to stir at −78° C. for 30 min. A solution of tert-butyl (4-oxocyclohexyl)carbamate (4.0 g, 18.8 mmol, 1.0 eq) in Et$_2$O (50 mL) was then added dropwise and the solution was stirred at −78° C. for a further 30 min. The reaction was quenched with MeOH (1.6 mL) and allowed to warm to RT, diluted with water (50 mL) and extracted with Et$_2$O (50 mL). The combined organic layers were washed with brine (50 mL), dried over Na$_2$SO$_4$ and concentrated under reduced pressure. The residue was purified by column chromatography (Petroleum ether:EtOAc, 8:1 to 6:1, v/v) to afford the title compound as a 2:1 mixture of isomers (1.8 g, 42%) as a white solid.

$^1$H NMR (400 MHz, CDCl$_3$) δ 2.59-2.46 (m, 1H), 2.33-2.12 (m, 4H), 2.01-1.68 (m, 4H), 1.43 (s, 9H), 1.25-1.06 (m, 2H).

Step 2: S-(4-((tert-Butoxycarbonyl)amino)cycloheptyl) ethanethioate

The title compound was prepared from tert-butyl (4-oxocycloheptyl)carbamate according to the methods described for Int-B7 and obtained as a 2:1 mixture of isomers.

$^1$HNMR (400 MHz, CDCl$_3$) δ 3.69-3.52 (m, 2H), 2.32 (s, 1H), 2.04 (s, 2H), 2.12-1.85 (m, 4H), 1.85-1.54 (m, 6H), 1.43 (s, 9H).

Int-B11: trans-4-Mercaptocyclohexanol

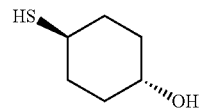

To a solution 7-oxabicyclo[2.2.1]heptane (1 g, 10.2 mmol, 1.0 eq) in ethanol (10 mL) was added p-TSA (2.91 g, 15.3 mmol) and thiourea (1.2 g, 15.8 mmol, 1.5 eq) and the mixture was heated at reflux for 21 h. After cooling to RT, NaOH (1.3 g) and water (3 mL) were added and the solution was heated at reflux for a further 2 h. The mixture was cooled to RT, NaOH (1.3 g) and water (3 mL) were added and the solution was heated at reflux for a further 2 h, then allowed to cool to RT and concentrated under reduced pressure. The residue was diluted with water (15 mL) and adjusted to pH 3-4 with 1 M HCl and extracted with EtOAc (50 mL×3). The combined organic layers were washed with brine (50 mL), dried over Na$_2$SO$_4$ and concentrated under reduced pressure. The residue was purified by column chromatography (Petroleum ether:EtOAc, 10:1, v/v) to afford the title compound (500 mg, 37%) as a yellow oil.

$^1$HNMR (400 MHz, DMSO-d$_6$) δ 6.18 (br s, 1H), 4.51 (br s, 1H), 3.41-3.36 (m, 1H), 2.73-2.64 (m, 1H), 1.96-1.86 (m, 2H), 1.72-1.81 (m, 2H), 1.36-1.26 (m, 2H), 1.23-1.17 (m, 2H).

Int-B12: S-(4-(((tert-Butyldimethylsilyl)oxy)methyl)cyclohexyl) ethanethioate

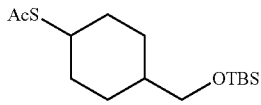

Step 1: 4-(((tert-Butyldimethylsilyl)oxy)methyl)cyclohexyl methanesulfonate

The title compound was prepared from ethyl 4-hydroxycyclohexanecarboxylate (54.3 g, 300 mmol) according to the procedure described in US2005/0054658 yielding a 1:1 mixture of cis/trans isomers (91.0 g, 94%) as a white solid.

$^1$H NMR (400 MHz, CDCl$_3$) δ 5.04-4.94 (m, 1H), 4.64-4.52 (m, 1H), 3.44 (d, J=6.4 Hz, 2H), 3.40 (d, J=6.4 Hz, 2H), 3.01 (s, 3H), 3.00 (s, 3H), 2.21-2.15 (m, 2H), 2.10-2.06 (m, 2H), 1.90-1.83 (m, 2H), 1.69-1.50 (m, 6H), 1.40-1.33 (m, 4H), 1.12-1.01 (m, 2H), 0.89 (s, 9H), 0.88 (s, 9H), 0.04 (s, 6H), 0.03 (s, 6H).

Step 2: S-(4-(((tert-Butyldimethylsilyl)oxy)methyl)cyclohexyl) ethanethioate The title compound was prepared from 4-(((tert-butyldimethylsilyl)oxy)methyl)cyclohexyl methanesulfonate according to the procedure described for Int-B3 step 2.

Ratio of cis/trans isomers=1:2

$^1$H NMR (400 MHz, CDCl$_3$) δ 3.49-3.45 (m, 1H), 3.42-3.38 (m, 2H), 2.30 (s, 2H), 2.29 (s, 1H), 2.12-1.11 (m, 9H), 0.89 (s, 6H), 0.88 (s, 3H), 0.04 (s, 4H), 0.03 (s, 2H).

Int-B13: S-(3-(Hydroxymethyl)cyclohexyl) ethanethioate

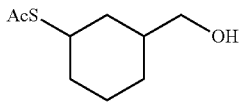

Step 1: Ethyl 3-((methylsulfonyl)oxy)cyclohexanecarboxylate

The title compound was prepared from ethyl 3-hydroxycyclohexanecarboxylate according to the procedure described for Int-B3 step 1.

Ratio of cis/trans isomers=2:3

$^1$H NMR (400 MHz, CDCl$_3$) δ 5.05 (m, 0.4H), 4.66-4.59 (m, 0.6H), 4.14 (q, J=6.8 Hz, 2H), 3.01 (s, 3H), 2.39-2.37 (m, 1H), 2.16-2.14 (m, 1H), 1.94-1.87 (m, 2H), 1.73-1.32 (m, 5H), 1.25 (t, J=6.4 Hz, 3H).

Step 2: 3-(Hydroxymethyl)cyclohexyl Methanesulfonate

To a solution of ethyl 3-((methylsulfonyl)oxy)cyclohexanecarboxylate (7.2 g, 28.8 mmol, 1.0 eq) in DME (20 mL) at 0° C. was added a solution of LiBH$_4$ in THF (14.4 mL, 2 M, 28.8 mmol, 1.0 eq) and the mixture was allowed to warm to RT and stirred overnight. The mixture was concentrated under reduced pressure, diluted with water (80 mL) and extracted with EtOAc (100 mL×3). The combined organic layers were washed with brine (50 mL), dried over Na$_2$SO$_4$ and concentrated under reduced pressure to afford the title compound (4.7 g, 78%) as a colorless oil, which was used for the next step without further purification.

Ratio of cis/trans isomers=3:7

$^1$H NMR (400 MHz, CDCl$_3$) δ 5.05 (m, 0.3H), 4.64-4.59 (m, 0.7H), 3.52-3.44 (m, 2H), 2.99 (s, 3H), 2.23-1.85 (m, 4H), 1.78-1.21 (m, 5H).

Step 3: S-(3-(Hydroxymethyl)cyclohexyl) ethanethioate

The title compound was prepared from 3-(hydroxymethyl)cyclohexyl methanesulfonate according to the procedure described for Int-B3 step 2.

$^1$H NMR (400 MHz, CDCl$_3$) δ 3.98-3.95 (m, 1H), 3.53-3.45 (m, 2H), 2.30 (s, 3H), 1.86-1.46 (m, 9H).

Intermediate C1: ((8-Methyl-4-oxo-3,4-dihydroquinazolin-2-yl)methyl) ethanethioate

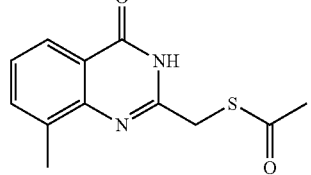

To a solution of Int A1 (5.0 g, 24 mmol, 1 eq) in DMF (50 mL) at RT under a N$_2$ atmosphere was added AcSH (3.7 g, 48 mmol, 2 eq) and the mixture was heated at 80° C. for 16 h. After cooling to RT, the mixture was diluted with petroleum ether and the resulting precipitate was collected by filtration and dried to give the title product (6 g, 100%) as a yellow solid, which was used in the subsequent steps without further purification. LCMS: [M+H]$^+$ 249.1.

The following intermediates in Table 2 were similarly prepared from the appropriate intermediate A precursor and AcSH according to the method described for Intermediate C1.

TABLE 2

| Intermediate | Name | Int. A Precursor | LCMS: [M + H]$^+$ |
|---|---|---|---|
| Int-C2 | S-((6-methyl-4-oxo-3,4-dihydroquinazolin-2-yl)methyl) ethanethioate | A3 | 249.1 |

TABLE 2-continued

| Intermediate | Name | Int. A Precursor | LCMS: [M + H]+ |
|---|---|---|---|
| Int-C3 | S-((6-methoxy-4-oxo-3,4-dihydroquinazolin-2-yl)methyl) ethanethioate | A6 | 265.1 |
| Int-C4 | S-((8-benzyl-4-oxo-3,4-dihydroquinazolin-2-yl)methyl) ethanethioate | A35 | 325.1 |
| Int-C5 | S-(1-(8-methyl-4-oxo-3,4-dihydroquinazolin-2-yl)ethyl) ethanethioate | A33 | 263.1 |
| Int-C6 | S-((5-fluoro-8-methyl-4-oxo-3,4-dihydroquinazolin-2-yl)methyl) ethanethioate | A21 | 267.1 |
| Int-C7 | S-((7-cyano-4-oxo-3,4-dihydroquinazolin-2-yl)methyl) ethanethioate | A18 | 260.0 |
| Int-C8 | S-((5-methyl-4-oxo-3,4-dihydroquinazolin-2-yl)methyl) ethanethioate | A15 | 249.1 |

Int-C9: S-((8-Chloro-4-oxo-3,4-dihydroquinazolin-2-yl)methyl) ethanethioate

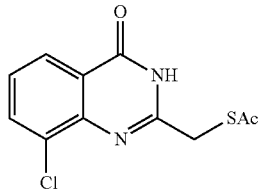

To a solution of Int-A7 (530 mg, 2.3 mmol, 1 eq) in THF (15 mL) and EtOH (5 mL) at RT under a $N_2$ atmosphere was added AcSH (266 mg, 3.5 mmol, 1.5 eq) and the mixture was heated at 70° C. for 3 h. After cooling to RT, the mixture was concentrated under reduced pressure. The residue was purified by column chromatography (Petroleum ether:EtOAc, 15:1, v/v) to afford the title compound (300 mg, 48%) as a white solid. LCMS: [M+H]$^+$ 269.0.

Int-C10: S-((8-Methoxy-4-oxo-3,4-dihydroquinazolin-2-yl)methyl) ethanethioate

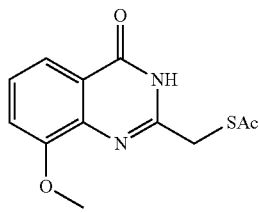

The title compound was prepared from Int-A4 according to the procedure described for Int-C9. LCMS: [M+H]$^+$ 265.1.

Int-C11: S-((7-Benzyl-4-oxo-3,4-dihydroquinazolin-2-yl)methyl) ethanethioate

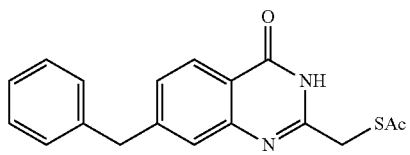

To a suspension of Int A36 (27 mg, 0.1 mmol, 1 eq) and NaHCO$_3$ (10 mg, 0.11 mmol, 1.1 eq) in DMF (3 mL) at RT under a $N_2$ atmosphere was added AcSH (8 mg, 0.12 mmol, 1.2 eq) and the mixture was stirred at RT overnight. The mixture was diluted with water (4 mL) and the resulting precipitate was collected by filtration and dried to give the title product (20 mg, 70%) as a white solid. LCMS: [M+H]$^+$ 325.1.

EXAMPLE COMPOUNDS

Example 1: 4-Oxo-2-(((tetrahydro-2H-pyran-4-yl)thio)methyl)-3,4-dihydroquinazoline-7-carbonitrile

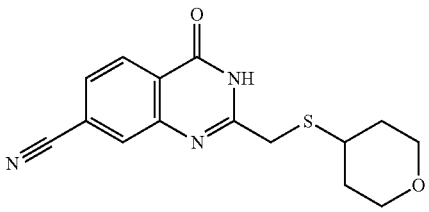 [SMILES: N#Cc1ccc2c(=O)[nH]c(CSC3CCOCC3)nc2c1]

To a solution of Int-C7 (60 mg, 0.23 mmol, 1 eq) and 4-bromotetrahydro-2H-pyran (38 mg, 0.23 mmol, 1.0 e1) in DMF (2 mL) at RT under a $N_2$ atmosphere was added 1 M NaOH (0.5 mL) and the mixture was heated at 90° C. for 16 h. The mixture was poured into water (5 mL), extracted with EtOAc (10 mL×3) and the combined organic layers were washed with water (10 mL), dried over Na$_2$SO$_4$ and concentrated under reduced pressure. The residue was purified by column chromatography (Petroleum ether:EtOAc, 15:1, v/v) to afford the title compound (15 mg, 22%) as a colorless oil. LCMS: [M+H]$^+$ 302.1.

$^1$H NMR (400 MHz, CD$_3$OD) δ 8.32 (d, J=8.0 Hz, 1H), 8.03 (s, 1H), 7.78 (dd, J=8.0, 1.6 Hz, 1H), 3.91 (dt, J=11.6, 3.6 Hz, 2H), 3.75 (s, 2H), 3.43 (td, J=11.6, 2.3 Hz, 2H), 3.09-3.01 (m, 1H), 2.02-1.90 (m, 2H), 1.63-1.53 (m, 2H).

The following examples in Table 3 were similarly prepared from the appropriate intermediate C and 4-bromotetrahydro-2H-pyran according to the method described for Example 1.

TABLE 3

| Example | Name and structure | Int. |
|---|---|---|
| Example 2 | 8-methyl-2-(((tetrahydro-2H-pyran-4-yl)thio)methyl)quinazolin-4(3H)-one | C1 |
| Example 3 | 6-methyl-2-(((tetrahydro-2H-pyran-4-yl)thio)methyl)quinazolin-4(3H)-one | C2 |

TABLE 3-continued

| Example | Name and structure | Int. |
|---|---|---|
| Example 4 | 6-methoxy-2-(((tetrahydro-2H-pyran-4-yl)thio)methyl)quinazolin-4(3H)-one | C3 |
| Example 5 | 8-chloro-2-(((tetrahydro-2H-pyran-4-yl)thio)methyl)quinazolin-4(3H)-one | C9 |
| Example 6 | 8-methoxy-2-(((tetrahydro-2H-pyran-4-yl)thio)methyl)quinazolin-4(3H)-one | C10 |
| Example 7 | 8-methyl-2-(1-((tetrahydro-2H-pyran-4-yl)thio)ethyl)quinazolin-4(3H)-one | C5 |
| Example 8 | 5-fluoro-8-methyl-2-(((tetrahydro-2H-pyran-4-yl)thio)methyl)quinazolin-4(3H)-one | C6 |
| Example 9 | 5-methyl-2-(((tetrahydro-2H-pyran-4-yl)thio)methyl)quinazolin-4(3H)-one | C8 |
| Example 10 | 8-benzyl-2-(((tetrahydro-2H-pyran-4-yl)thio)methyl)quinazolin-4(3H)-one | C4 |
| Example 11 | 7-benzyl-2-(((tetrahydro-2H-pyran-4-yl)thio)methyl)quinazolin-4(3H)-one | C11 |

Example 12: 8-Methyl-2-((((tetrahydro-2H-pyran-4-yl)methyl)thio)methyl)quinazolin-4(3H)-one The title compound was prepared from Int-C1 and 4-(bromomethyl)tetrahydro-2H-pyran according to the method described for Example 1. LCMS: [M+H]$^+$ 305.1.

$^1$H NMR (400 MHz, CDCl$_3$) δ 10.2 (s, 1H), 8.13 (d, J=8.0 Hz, 1H), 7.62 (d, J=7.2 Hz, 1H), 7.37 (t, J=7.6 Hz, 1H), 4.00-3.90 (m, 2H), 3.74 (d, J=2.8 Hz, 2H), 3.33 (td, J=11.6, 2.0 Hz, 2H), 2.60 (d, J=2.8 Hz, 3H), 2.48 (d, J=6.8 Hz, 2H), 1.78-1.69 (m, 3H), 1.35-1.24 (m, 2H).

Example 13: 8-Methyl-2-((piperidin-4-ylthio)methyl)quinazolin-4(3H)-one Trifluoroacetate

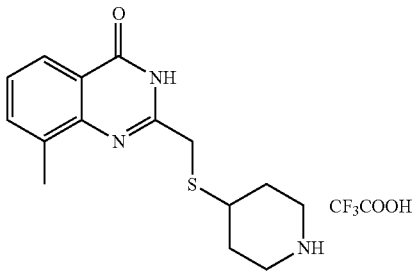 [SMILES: Cc1cccc2c(=O)[nH]c(CSC3CCNCC3)nc12 ; "CF3COOH"]

Step 1: tert-Butyl 4-(((8-methyl-4-oxo-3,4-dihydro-quinazolin-2-yl)methyl)thio)piperidine-1-carboxylate To a solution of Int-C1 (6.6 g, 26.6 mmol, 1.0 eq) and tert-butyl 4-bromopiperidine-1-carboxylate (7.0 g, 26.6 mmol, 1.0 eq) in DMF (130 mL) at RT under a $N_2$ atmosphere was added 1 M NaOH (50 mL) and the mixture was heated at 80° C. for 16 h. The mixture was poured into water (50 mL), extracted with EtOAc (100 mL×3) and the combined organic layers were dried over $Na_2SO_4$ and concentrated under reduced pressure. The residue was purified by column chromatography (Petroleum ether:EtOAc, 4:1, v/v) to afford the title compound (7.2 g, 70%) as a light yellow solid. LCMS: [M+H]$^+$ 390.2.

Step 2: 8-Methyl-2-((piperidin-4-ylthio)methyl)quinazolin-4(3H)-one Trifluoroacetate tert-Butyl 4-(((8-methyl-4-oxo-3,4-dihydroquinazolin-2-yl)methyl)thio)piperidine-1-carboxylate (30 mg, 0.08 mmol, 1.0 eq) was dissolved in TFA (5 mL) and the mixture was stirred at RT for 5 h. The mixture was concentrated under reduced pressure to give the title product (20 mg, 45%) as a yellow solid. LCMS: [M+H]$^+$ 290.2.

$^1$H NMR (400 MHz, CD$_3$OD) δ 8.03 (d, J=8.0 Hz, 1H), 7.75-7.60 (m, 1H), 7.39 (t, J=7.6 Hz, 1H), 3.80 (s, 2H), 3.42-3.36 (m, 2H), 3.26-3.12 (m, 1H), 3.09-2.97 (m, 2H), 2.59 (s, 3H), 2.32-2.28 (m, 2H), 1.83-1.74 (m, 2H).

Example 14: 8-Methyl-2-(((1-methylpiperidin-4-yl)thio)methyl)quinazolin-4(3H)-one

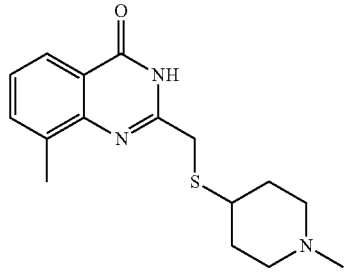 [SMILES: Cc1cccc2c(=O)[nH]c(CSC3CCN(C)CC3)nc12]

To a solution of Example 13 (160 mg, 0.37 mmol, 1.0 eq) and formaldehyde (30% in water, 0.34 mL, 3.7 mmol, 10.0 eq) in MeOH (10 mL) was added AcOH (67 mg, 1.1 mmol, 3.0 eq) and NaCNBH$_3$ (93 mg, 1.5 mmol, 4.0 eq) and the mixture was stirred at RT overnight. The mixture was diluted with water (30 mL), extracted with DCM (30 mL×3) and the combined organic layers were washed with water (20 mL), dried over Na$_2$SO$_4$ and concentrated under reduced pressure. The residue was purified by column chromatography (DCM:MeOH, 10:1, v/v) to afford the title compound (50 mg, 30%) as a light yellow solid. LCMS: [M+H]$^+$ 304.2;

$^1$H NMR (400 MHz, CD$_3$OD) δ 7.94 (d, J=8.0 Hz, 1H), 7.58 (d, J=7.2 Hz, 1H), 7.30 (t, J=7.6 Hz, 1H), 3.74 (s, 2H), 3.28-3.25 (m, 2H), 3.02 (br s, 1H), 2.79 (t, J=11.8 Hz, 2H), 2.60 (s, 3H), 2.50 (s, 3H), 2.25-2.21 (m, 2H), 1.80-1.72 (m, 2H).

Example 15: 8-Methyl-2-((pyrrolidin-3-ylthio)methyl)quinazolin-4(3H)-one trifluoroacetate

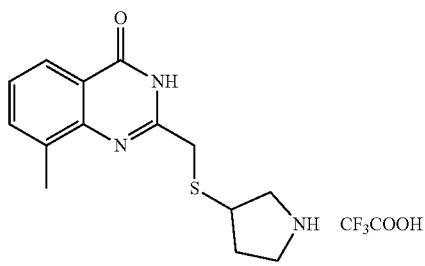 [SMILES: Cc1cccc2c(=O)[nH]c(CSC3CCNC3)nc12 ; "CF3COOH"]

The title compound was prepared from Int-C1 and tert-butyl 3-bromopyrrolidine-1-carboxylate according to the method described for Example 13. LCMS: [M+H]$^+$ 276.1;

$^1$H NMR (400 MHz, DMSO-d$_6$) δ 12.4 (s, 1H), 9.00 (s, 2H), 7.94 (d, J=7.8 Hz, 1H), 7.67 (d, J=7.2 Hz, 1H), 7.38 (t, J=7.4 Hz, 1H), 3.75 (s, 2H), 3.65 (dt, J=12.8, 6.8 Hz, 1H), 3.59-3.49 (m, 1H), 3.31-3.15 (m, 2H), 3.14-3.04 (m, 1H), 2.52 (s, 3H), 2.36-2.35 (m, 1H), 1.90-1.78 (m, 1H).

Example 16: 8-Methyl-2-(((1-methylpyrrolidin-3-yl)thio)methyl)quinazolin-4(3H)-one

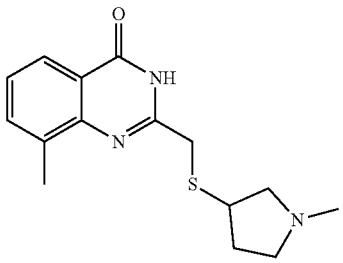 [SMILES: Cc1cccc2c(=O)[nH]c(CSC3CCN(C)C3)nc12]

The title compound was prepared from Example 15 according to the method described for Example 14. LCMS: [M+H]$^+$ 290.1.

$^1$H NMR (400 MHz, DMSO-d$_6$) δ 12.3 (br s, 1H), 7.92 (d, J=7.6 Hz, 1H), 7.65 (d, J=7.2 Hz, 1H), 7.36 (t, J=7.6 Hz, 1H), 3.65 (s, 2H), 3.48-3.38 (m, 1H), 2.87-2.77 (m, 1H), 2.50 (s, 3H), 2.43 (dd, J=13.2, 6.4 Hz, 2H), 2.28 (dd, J=9.6, 5.6 Hz, 1H), 2.22-2.11 (m, 4H), 1.56 (td, J=13.2, 6.4 Hz, 1H).

Example 17: 2-(((1-Acetylpiperidin-4-yl)thio)methyl)-8-methylquinazolin-4(3H)-one

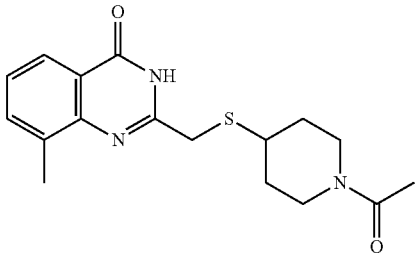 [SMILES: CC(=O)N1CCC(SCc2nc3c(C)cccc3c(=O)[nH]2)CC1]

To a solution of Example 13 (20 mg, 0.07 mmol, 1.0 eq) and Et₃N (14 mg, 0.14 mmol, 2.0 eq) in DCM (10 mL) at 0° C. was added Ac₂O (8 mg, 0.11 mmol, 1.5 eq) dropwise and the mixture was allowed to warm to RT and stirred overnight. The mixture was diluted with DCM (30 mL) and washed with water (30 mL). The organic layer was dried over Na₂SO₄ and concentrated under reduced pressure. The residue was purified by column chromatography (DCM:MeOH, 20:1, v/v) to afford the title compound (10 mg, 43%) as a light yellow solid. LCMS: [M+H]⁺ 332.1.

¹H NMR (400 MHz, CD₃OD) δ 8.04 (d, J=8.0 Hz, 1H), 7.67 (d, J=7.2 Hz, 1H), 7.39 (t, J=7.6 Hz, 1H), 4.28 (d, J=13.6 Hz, 1H), 3.86 (d, J=14.0 Hz, 1H), 3.78 (s, 2H), 3.23-3.06 (m, 2H), 2.59 (s, 3H), 2.87 (t, J=12.4 Hz, 1H), 2.12-2.04 (m, 5H), 1.62-1.41 (m, 2H).

Example 18: 8-Methyl-2-(((1-(pyridin-2-ylmethyl)piperidin-4-yl)thio)methyl)quinazolin-4(3H)-one

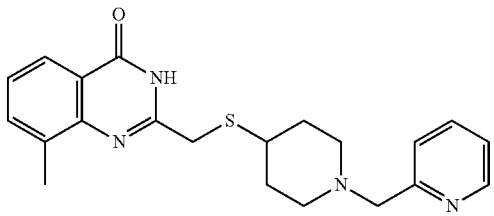 [SMILES: Cc1cccc2c(=O)[nH]c(CSC3CCN(Cc4ccccn4)CC3)nc12]

The title compound was prepared from the compound of Example 13 and picolinaldehyde according to the method described for Example 14. LCMS: [M+H]⁺ 381.2.

¹H NMR (400 MHz, CD₃OD) δ 8.69 (d, J=4.4 Hz, 1H), 8.05 (d, J=7.6 Hz, 1H), 7.91 (td, J=7.6, 1.6 Hz, 1H), 7.69 (d, J=7.2 Hz, 1H), 7.51-7.38 (m, 3H), 4.47 (s, 2H), 3.83 (s, 2H), 3.62-3.53 (m, 2H), 3.21 (t, J=11.6 Hz, 3H), 2.60 (s, 3H), 2.43-2.31 (m, 2H), 2.08-1.91 (m, 2H).

Example 19: 8-Methyl-2-(((tetrahydro-2H-pyran-4-yl)sulfonyl)methyl)quinazolin-4(3H)-one

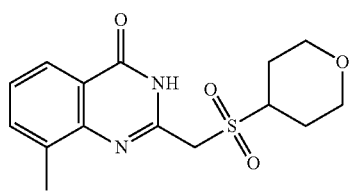 [SMILES: Cc1cccc2c(=O)[nH]c(CS(=O)(=O)C3CCOCC3)nc12]

To a solution of Example 2 (50 mg, 0.17 mmol, 1.0 eq) in AcOH (2 mL) at 0° C. was added H₂O₂ (30% solution in water, 195 mg, 1.7 mmol, 10.0 eq) dropwise and the mixture was allowed to warm to RT and stirred overnight. The mixture was diluted with MeOH (2 mL) and purified by column chromatography (DCM:MeOH, 20:1, v/v) to afford the title compound (6 mg, 11%) as a white solid. LCMS: [M+H]⁺ 323.1.

¹H NMR (400 MHz, DMSO-d₆) δ 12.5 (br s, 1H), 7.97 (d, J=8.0 Hz, 1H), 7.72 (d, J=7.2 Hz, 1H), 7.44 (t, J=7.6 Hz, 1H), 4.55 (s, 2H), 4.02 (dd, J=11.2, 4.0 Hz, 2H), 3.95-3.86 (m, 1H), 3.37 (t, J=10.4 Hz, 2H), 2.54 (s, 3H), 2.13-2.05 (m, 2H), 1.76-1.65 (m, 2H).

Example 20: 2-((Azepan-4-ylthio)methyl)-8-methylquinazolin-4(3H)-one Trifluoroacetate

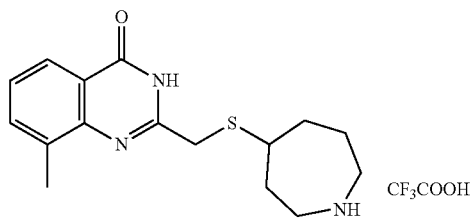

Step 1: tert-Butyl 4-((methylsulfonyl)oxy)azepane-1-carboxylate

The title compound was prepared from tert-butyl 4-hydroxyazepane-1-carboxylate according to the method described for Int-B3, step 1. LCMS: [M+H−56]⁺238.1.

Step 2: tert-Butyl 4-(((8-methyl-4-oxo-3,4-dihydroquinazolin-2-yl)methyl)thio)azepane-1-carboxylate To a solution of Int-C1 (615 mg, 2.5 mmol, 1 eq) and tert-butyl 4-((methylsulfonyl)oxy)azepane-1-carboxylate (800 mg, 2.7 mmol, 1.1 eq) in DMF (20 mL) at RT under a N₂ atmosphere was added 1 M NaOH (5 mL) and the mixture was heated at 80° C. for 6 h. The mixture was poured into water (5 mL), extracted with EtOAc (10 mL×3) and the combined organic layers were washed with water (10 mL), dried over Na₂SO₄ and concentrated under reduced pressure. The residue was purified by column chromatography (Petroleum ether:EtOAc, 5:1, v/v) to afford the title compound (140 mg, 14%) as a white solid. LCMS: [M+H]⁺ 404.2.

Step 3: 2-((Azepan-4-ylthio)methyl)-8-methylquinazolin-4(3H)-one Trifluoroacetate tert-Butyl 4-(((8-methyl-4-oxo-3,4-dihydroquinazolin-2-yl)methyl)thio)azepane-1-carboxylate (140 mg, 0.34 mmol, 1.0 eq) was dissolved in a 3 M HCl/dioxane solution (3 mL) and the mixture was stirred at RT for 3 h. The mixture was concentrated under reduced pressure, diluted with water (10 mL) and adjusted pH to 9-10 with a saturated aqueous Na₂CO₃ solution, then extracted with EtOAc (10 mL×3). The combined organic layers were washed with water (10 mL), dried over Na₂SO₄ and concentrated under reduced pressure. The residue was purified by C18 reverse phase chromatography (Biotage, 30%-70% ACN in water, 0.1% TFA) to afford the title compound (50 mg, 35%) as a white solid. LCMS: [M+H]$^+$ 304.1;

$^1$H NMR (400 MHz, CD$_3$OD) δ 8.03 (d, J=8.0 Hz, 1H), 7.67 (d, J=7.2 Hz, 1H), 7.39 (t, J=7.6 Hz, 1H), 3.79 (s, 2H), 3.41-3.34 (m, 1H), 3.24-3.11 (m, 4H), 2.59 (s, 3H), 2.41-2.30 (m, 1H), 2.27-2.17 (m, 1H), 2.06-1.94 (m, 2H), 1.87-1.70 (m, 2H).

Example 21: 2-(((4-(Dimethylamino)cyclohexyl)thio)methyl)-8-methylquinazolin-4(3H)-one

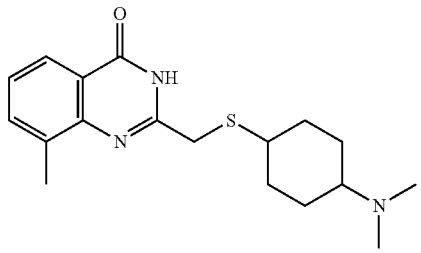 [SMILES: Cc1cccc2c(=O)[nH]c(CSC3CCC(N(C)C)CC3)nc12]

Step 1: 1,4-Dioxaspiro[4.5]decan-8-yl Methanesulfonate

The title compound was prepared from 1,4-dioxaspiro[4.5]decan-8-ol according to the method described for Int-B3, step 1. $^1$H NMR (400 MHz, CDCl$_3$) δ 4.85-4.80 (m, 1H), 3.97-3.90 (m, 4H), 3.00 (s, 3H), 2.01-1.96 (m, 4H), 1.87-1.78 (m, 2H), 1.66-1.60 (m, 2H).

Step 2: 2-(((1,4-Dioxaspiro[4.5]decan-8-yl)thio)methyl)-8-methylquinazolin-4(3H)-one The title compound was prepared from 1,4-dioxaspiro[4.5]decan-8-yl methanesulfonate and Int-C1 according to the method described for Example 20, step 2. LCMS: [M+H]$^+$ 347.1.

Step 3: 8-Methyl-2-(((4-oxocyclohexyl)thio)methyl)quinazolin-4(3H)-one

To a solution of 2-(((1,4-dioxaspiro[4.5]decan-8-yl)thio)methyl)-8-methylquinazolin-4(3H)-one (500 mg, 1.4 mmol, 1.0 eq) in THF (20 mL) was added 1 M HCl (20 mL) and the mixture was stirred at RT overnight. The mixture was diluted with water (20 mL), extracted with DCM (20 mL×3) and the combined organic layers were dried over Na$_2$SO$_4$ and concentrated under reduced pressure to afford the title compound (510 mg, 100%) as a yellow solid, which was used in the subsequent step without further purification. LCMS: [M+H]$^+$ 303.1.

Step 4: 2-(((4-(Dimethylamino)cyclohexyl)thio)methyl)-8-methylquinazolin-4(3H)-one To a solution of 8-methyl-2-(((4-oxocyclohexyl)thio)methyl)quinazolin-4(3H)-one (68 mg, 0.22 mmol, 1.0 eq) in THF (3 mL) was added Me$_2$NH (2 M solution in THF, 2.2 mL, 20.0 eq) and NaBH(OAc)$_3$ (950 mg, 4.5 mmol, 20.0 eq) and the mixture was stirred at RT overnight. The mixture was diluted with a saturated aqueous NaHCO$_3$ solution (20 mL), extracted with EtOAc (30 mL×3) and the combined organic layers were dried over Na$_2$SO$_4$ and concentrated under reduced pressure. The residue was purified by prep-TLC (DCM:MeOH, 10:1, v/v) to afford the title compound (40 mg, 55%) as a light yellow solid. LCMS: [M+H]$^+$ 332.2;

$^1$H NMR (400 MHz, CD$_3$OD) δ 8.03 (d, J=8.0 Hz, 1H), 7.66 (d, J=7.2 Hz, 1H), 7.38 (t, J=7.6 Hz, 1H), 3.75 (d, J=14.0 Hz, 2H), 3.36 (s, 1H), 3.08-2.98 (m, 1H), 2.74 (s, 3H), 2.70 (s, 3H), 2.59 (d, J=9.5 Hz, 3H), 2.32-2.25 (m, 1H), 2.11-2.05 (m, 2H), 1.90-1.84 (m, 3H), 1.53-1.37 (m, 2H).

Example 22: 2-(((4-Hydroxycyclohexyl)thio)methyl)-8-methylquinazolin-4(3H)-one

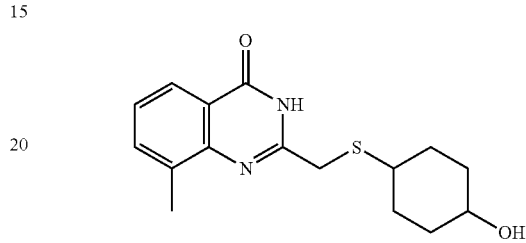

To a solution of 8-methyl-2-((4-oxocyclohexyl)tio)methyl)quinazoin-4(3H)-one (prepared in Example 21, Step 4) (100 mg, 0.33 mmol, 1.0 eq) in MeOH (10 mL) was added NaBH$_4$ (25 mg, 0.66 mmol, 2.0 eq) and the mixture was stirred at RT overnight. The mixture was diluted with water (20 mL), extracted with EtOAc (30 mL×3) and the combined organic layers were dried over Na$_2$SO$_4$ and concentrated under reduced pressure. The residue was purified by prep-TLC (DCM:MeOH, 10:1, v/v) to afford the title compound as a 3:2 mixture of trans/cis isomers (50 mg, 50%) as a white solid. LCMS: [M+H]$^+$ 305.1.

Example 23: 2-((((trans)-4-Hydroxycyclohexyl)thio)methyl)-8-methylquinazolin-4(3H)-one and

Example 24: 2-((((cis)-4-Hydroxycyclohexyl)thio)methyl)-8-methylquinazolin-4(3H)-one Example 23

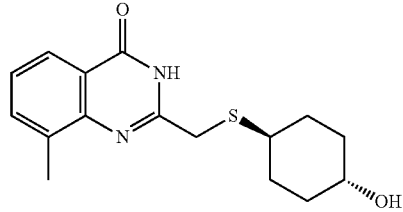

Example 24

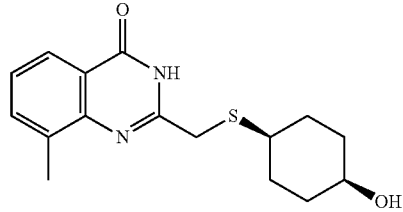

The compound of Example 22 was further purified by prep-HPLC (Agilent 10 prep-C18, 10 μm, 250×21.2 mm column, eluting with a gradient of MeOH in water with 0.1% TFA, at a flow rate of 20 mL/min to afford the title compounds.

Example 23

LCMS: [M+H]+ 305.1;
1H NMR (400 MHz, CD3OD) δ 8.03 (d, J=8.0 Hz, 1H), 7.66 (d, J=7.2 Hz, 1H), 7.38 (t, J=8.0 Hz, 1H), 3.72 (s, 2H), 3.52 (t, J=11.2 Hz, 1H), 2.75 (t, J=11.6 Hz, 1H), 2.59 (s, 3H), 2.11 (d, J=12.8 Hz, 2H), 1.95 (d, J=12.4 Hz, 2H), 1.44-1.15 (m, 4H).

Example 24

LCMS: [M+H]+ 305.1;
1H NMR (400 MHz, CD3OD) δ 8.02 (d, J=8.0 Hz, 1H), 7.65 (d, J=7.2 Hz, 1H), 7.37 (t, J=8.0 Hz, 1H), 3.72 (s, 3H), 2.99 (t, J=6.0 Hz, 1H), 2.58 (s, 3H), 1.82-1.70 (m, 6H), 1.64-1.49 (m, 2H).

Example 25: 2-((Azetidin-3-ylthio)methyl)-8-methylquinazolin-4(3H)-one Trifluoroacetate

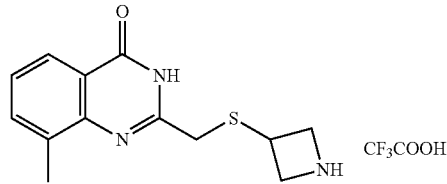 [SMILES: Cc1cccc2c(=O)[nH]c(CSC3CNC3)nc12 ; "CF3COOH"]

Step 1: tert-Butyl 3-(((8-methyl-4-oxo-3,4-dihydroquinazolin-2-yl)methyl)thio)azetidine-1-carboxylate The title compound was prepared from Int-C1 and tert-butyl 3-iodoazetidine-1-carboxylate according to the method described for Example 13, step 1. LCMS: [M+H]+ 362.2.

Step 2: 2-((Azetidin-3-ylthio)methyl)-8-methylquinazolin-4(3H)-one Hydrochloride tert-Butyl 3-(((8-methyl-4-oxo-3,4-dihydroquinazolin-2-yl)methyl)thio)azetidine-1-carboxylate (40 mg, 0.11 mmol, 1.0 eq) was dissolved in a 1.5 M HCl/EtOAc solution (3 mL) and the mixture was stirred at RT overnight. The mixture was diluted with water (10 mL), adjusted to pH 9-10 with a saturated aqueous Na2CO3 solution and extracted with EtOAc (10 mL×3). The combined organic layers were washed with water (10 mL), dried over Na2SO4 and concentrated under reduced pressure. The residue was purified by prep-HPLC (Agilent 10 prep-C18, 10 μm, 250×21.2 mm column, eluting with a gradient of MeOH in water with 0.1% TFA, at a flow rate of 20 mL/min to afford the title compound (1.8 mg, 6%) as a white solid. LCMS: [M+H]+ 262.1.
1H NMR (400 MHz, CD3OD) δ 8.04 (d, J=8.0 Hz, 1H), 7.68 (d, J=7.2 Hz, 1H), 7.41 (t, J=7.6 Hz, 1H), 4.35 (t, J=9.6 Hz, 2H), 4.27-4.21 (m, 1H), 3.89 (t, J=9.2 Hz, 2H), 3.81 (s, 2H), 2.62 (s, 3H); 19F NMR (400 MHz, CD3OD) δ −78.2.

Example 26: 2-((((trans)-4-Methoxycyclohexyl)thio) methyl)-8-methylquinazolin-4(3H)-one and Example 27: 2-((((cis)-4-Methoxycyclohexyl)thio) methyl)-8-methylquinazolin-4(3H)-one

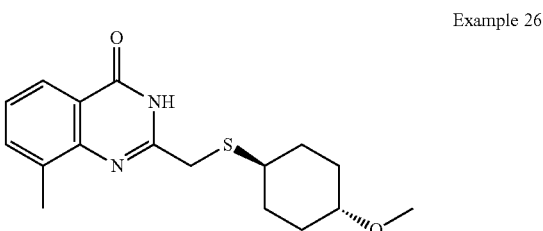

Example 26

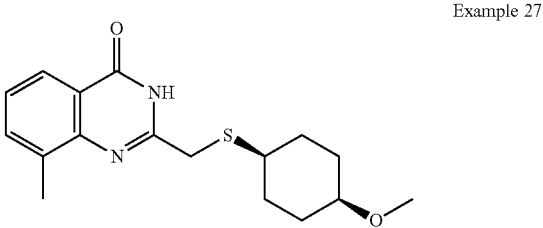

Example 27

Step 1: 4-Methoxycyclohexyl Methanesulfonate

The title compound was prepared from 4-methoxycyclohexanol according to the method described for Int-B3, Step 1.
1H NMR (400 MHz, CDCl3) δ 4.80-4.70 (m, 1H), 3.32 (s, 3H), 3.30-3.25 (m, 1H), 3.01 (s, 3H), 2.12-2.05 (m, 1H), 2.04-1.93 (m, 2H), 1.86-1.65 (m, 4H), 1.55-1.45 (m, 1H).

Step 2: 2-(((4-Methoxycyclohexyl)thio)methyl)-8-methylquinazolin-4(3H)-one

The title compound was prepared from 4-methoxycyclohexyl methanesulfonate and Int-C1 according to the method described for Example 20, Step 2. LCMS: [M+H]+ 319.1.

Step 3: 2-(((trans-4-Methoxycyclohexyl)thio) methyl)-8-methylquinazolin-4(3H)-one and 2-(((cis-4-Methoxycyclohexyl)thio)methyl)-8-methylquinazolin-4(3H)-one 2-(((4-Methoxycyclohexyl)thio)methyl)-8-methylquinazolin-4(3H)-one was purified by prep-HPLC (Agilent 10 prep-C18, 10 μm, 250×21.2 mm column, eluting with a gradient of MeOH in water with 0.1% TFA, at a flow rate of 20 mL/min to afford the title compounds.

Example 26

LCMS: [M+H]+ 319.1;
1H NMR (400 MHz, CDCl3) δ 8.13 (d, J=8.0 Hz, 1H), 7.61 (d, J=7.2 Hz, 1H), 7.37 (t, J=7.6 Hz, 1H), 3.79 (s, 2H), 3.31 (s, 3H), 3.17-3.10 (m, 1H), 2.64-2.71 (m, 1H), 2.59 (s, 3H), 2.14-1.99 (m, 4H), 1.44-1.30 (m, 2H), 1.27-1.17 (m, 2H).

Example 27

LCMS: [M+H]+ 319.1;
1H NMR (400 MHz, CDCl3) δ 8.06 (d, J=7.8 Hz, 1H), 7.55 (d, J=7.2 Hz, 1H), 7.31 (t, J=7.6 Hz, 1H), 3.78 (s, 2H), 3.29-3.23 (m, 1H), 3.22 (s, 3H), 2.72-2.66 (m, 1H), 2.55 (s, 3H), 1.88-1.76 (m, 2H), 1.72-1.64 (m, 4H), 1.46-1.36 (m, 2H).

Example 28: 4-Oxo-2-(((tetrahydro-2H-pyran-4-yl)thio)methyl)-3,4-dihydroquinazoline-8-carbonitrile

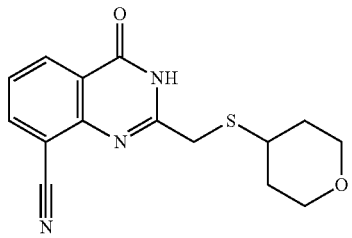 [SMILES: N#Cc1cccc2c(=O)[nH]c(CSC3CCOCC3)nc12]

To a solution of Int-A17 (36 mg, 0.16 mmol, 1.0 eq) and Int-B1 (26 mg, 0.16 mmol, 1.0 eq) in DMF (2 mL) was added 1 M NaOH (2 mL) and the mixture was stirred at RT overnight under a $N_2$ atmosphere. The mixture was diluted with water (5 mL) and extracted with EtOAc (20 mL×3). The combined organic layers were dried over $Na_2SO_4$ and concentrated under reduced pressure. The residue was purified by prep-TLC (Petroleum ether:EtOAc, 1:1, v/v) to afford the title compound (12 mg, 24%) as a white solid. LCMS: [M+H]+ 302.1;

$^1$H NMR (400 MHz, CDCl$_3$) δ 10.4 (s, 1H), 8.48 (d, J=8.0 Hz, 1H), 8.10 (d, J=7.6 Hz, 1H), 7.56 (t, J=7.6 Hz, 1H), 3.97 (dd, J=12.0, 3.6 Hz, 2H), 3.87 (s, 2H), 3.42 (t, J=11.2 Hz, 2H), 2.99 (td, J=10.8, 5.2 Hz, 1H), 1.96 (d, J=12.8 Hz, 2H), 1.72-1.62 (m, 2H).

The following Examples in Table 4 were similarly prepared from the appropriate intermediate A and intermediate B according to the method described for Example 28.

TABLE 4

| Example | Name and structure | Intermediates |
| --- | --- | --- |
| Example 29 | 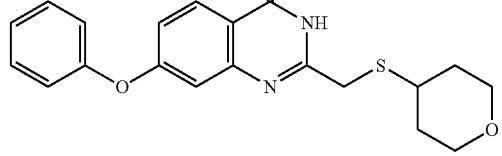<br>7-Phenoxy-2-(((tetrahydro-2H-pyran-4-yl)thio)methyl)quinazolin-4(3H)-one | A19, B1 |
| Example 30 | 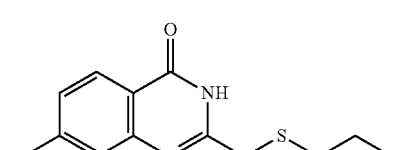<br>7-Fluoro-2-(((tetrahydro-2H-pyran-4-yl)thio)methyl)quinazolin-4(3H)-one | A9, B1 |
| Example 31 | 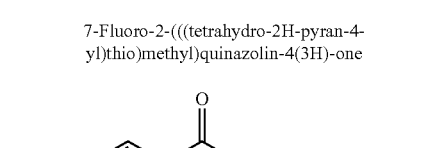<br>7-Methoxy-2-(((tetrahydro-2H-pyran-4-yl)thio)methyl)quinazolin-4(3H)-one | A5, B1 |
| Example 32 | 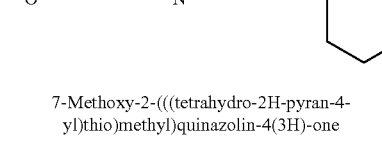<br>8-Methyl-2-(((1-methylpiperidin-3-yl)thio)methyl)quinazolin-4(3H)-one | A1, B3 |

TABLE 4-continued

| Example | Name and structure | Intermediates |
|---|---|---|
| Example 33 | 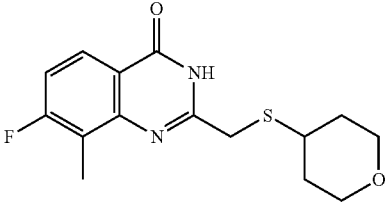 [SMILES: Cc1c(F)ccc2c(=O)[nH]c(CSC3CCOCC3)nc12]<br>7-Fluoro-8-methyl-2-(((tetrahydro-2H-pyran-4-yl)thio)methyl)quinazolin-4(3H)-one | A23, B1 |
| Example 34 | 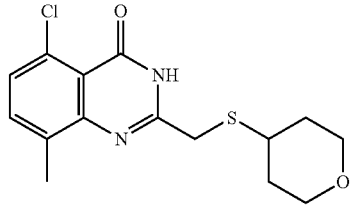 [SMILES: Cc1ccc(Cl)c2c(=O)[nH]c(CSC3CCOCC3)nc12]<br>5-Chloro-8-methyl-2-(((tetrahydro-2H-pyran-4-yl)thio)methyl)quinazolin-4(3H)-one | A22, B1 |
| Example 35 | 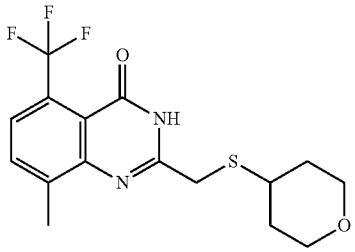 [SMILES: Cc1ccc(C(F)(F)F)c2c(=O)[nH]c(CSC3CCOCC3)nc12]<br>8-Methyl-2-(((tetrahydro-2H-pyran-4-yl)thio)methyl)-5-(trifluoromethyl)quinazolin-4(3H)-one | A20, B1 |
| Example 36 | 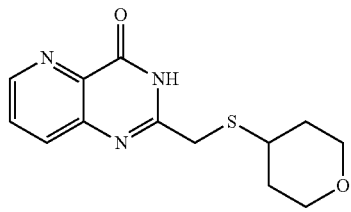 [SMILES: O=c1[nH]c(CSC2CCOCC2)nc2cccnc12]<br>2-(((Tetrahydro-2H-pyran-4-yl)thio)methyl)pyrido[3,2-d]pyrimidin-4(3H)-one | A27, B1 |
| Example 37 | 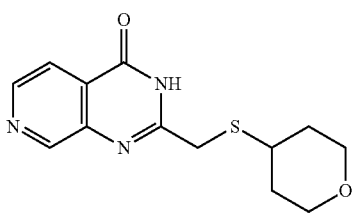 [SMILES: O=c1[nH]c(CSC2CCOCC2)nc2cnccc12]<br>2-(((Tetrahydro-2H-pyran-4-yl)thio)methyl)pyrido[3,4-d]pyrimidin-4(3H)-one | A28, B1 |

TABLE 4-continued

| Example | Name and structure | Intermediates |
|---|---|---|
| Example 38 | 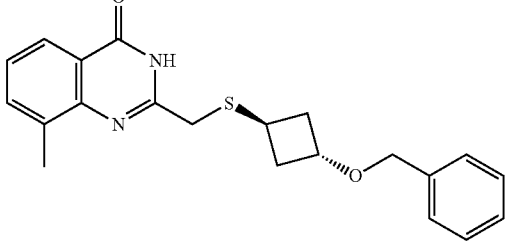<br>2-((((trans)-3-(Benzyloxy)cyclobutyl)thio)methyl)-8-methylquinazolin-4(3H)-one | A1, B7 |
| Example 39 | 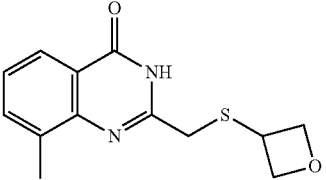 [SMILES: Cc1cccc2c(=O)[nH]c(CSC3COC3)nc12]<br>8-Methyl-2-((oxetan-3-ylthio)methyl)quinazolin-4(3H)-one | A1, B8 |
| Example 40 | 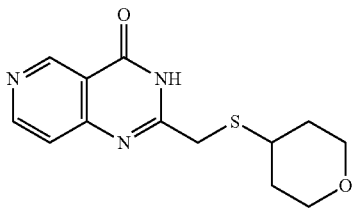 [SMILES: O=c1[nH]c(CSC2CCOCC2)nc2ccncc12]<br>2-(((Tetrahydro-2H-pyran-4-yl)thio)methyl)pyrido[4,3-d]pyrimidin-4(3H)-one | A31, B1 |
| Example 41 | 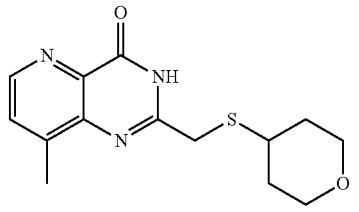 [SMILES: Cc1ccnc2c(=O)[nH]c(CSC3CCOCC3)nc12]<br>8-Methyl-2-(((tetrahydro-2H-pyran-4-yl)thio)methyl)pyrido[3,2-d]pyrimidin-4(3H)-one | A30, B1 |
| Example 42 | 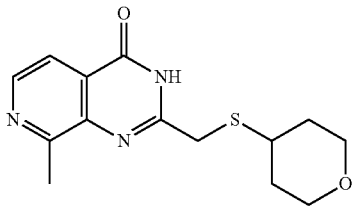 [SMILES: Cc1nccc2c(=O)[nH]c(CSC3CCOCC3)nc12]<br>8-Methyl-2-(((tetrahydro-2H-pyran-4-yl)thio)methyl)pyrido[3,4-d]pyrimidin-4(3H)-one | A29, B1 |

| Example | Name and structure | Intermediates |
|---|---|---|
| Example 43 | 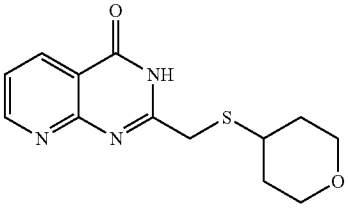 [SMILES: O=c1[nH]c(CSC2CCOCC2)nc2ncccc12]<br>2-(((Tetrahydro-2H-pyran-4-yl)thio)methyl)pyrido[2,3-d]pyrimidin-4(3H)-one | A32, B1 |
| Example 44 | 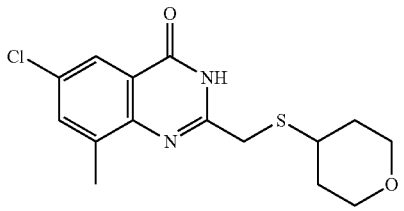 [SMILES: Cc1cc(Cl)cc2c(=O)[nH]c(CSC3CCOCC3)nc12]<br>6-Chloro-8-methyl-2-(((tetrahydro-2H-pyran-4-yl)thio)methyl)quinazolin-4(3H)-one | A13, B1 |
| Example 45 | 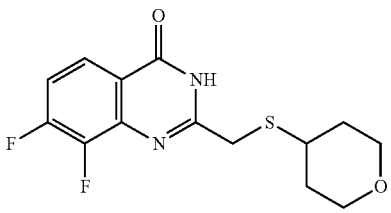 [SMILES: O=c1[nH]c(CSC2CCOCC2)nc2c(F)c(F)ccc12]<br>7,8-Difluoro-2-(((tetrahydro-2H-pyran-4-yl)thio)methyl)quinazolin-4(3H)-one | A25, B1 |

Example 46: 7-Fluoro-2-((((trans)-4-hydroxycyclohexyl)thio)methyl)quinazolin-4(3H)-one

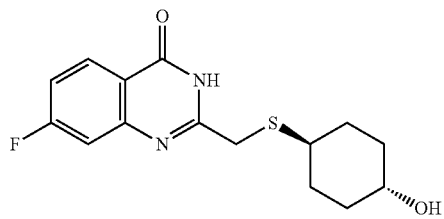 [SMILES: O=c1[nH]c(CS[C@H]2CC[C@H](O)CC2)nc2cc(F)ccc12]

To a solution of Int-A9 (200 mg, 0.94 mmol, 1.0 eq) and Int-B11 (249 mg, 1.13 mmol) in DMF (5 mL) was added 1 M NaOH (3 mL) and the mixture was stirred at RT overnight under a $N_2$ atmosphere. The mixture was diluted with water (50 mL) and extracted with EtOAc (50 mL×3). The combined organic layers were washed with water (100 mL) and brine (100 mL), dried over $Na_2SO_4$ and concentrated under reduced pressure. The residue was purified by prep-TLC (100% EtOAc) to afford the title compound (260 mg, 90%) as a white solid. LCMS: [M+H]+ 309.1.

$^1$H NMR (400 MHz, DMSO-$d_6$) δ 12.4 (s, 1H), 8.15 (dd, J=6.4, 8.8 Hz, 1H), 7.42-7.34 (m, 2H), 4.52 (d, J=4.4 Hz, 1H), 3.63 (s, 2H), 3.41-3.32 (m, 1H), 2.78-2.68 (m, 1H), 2.01-1.92 (m, 2H), 1.85-1.76 (m, 2H), 1.29-1.10 (m, 4H).

Example 47: 2-(((trans-3-Hydroxycyclobutyl)thio)methyl)-8-methylquinazolin-4(3H)-one

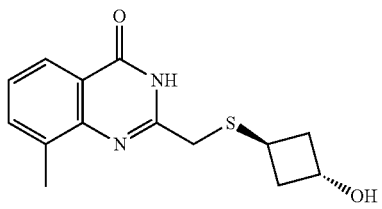 [SMILES: Cc1cccc2c(=O)[nH]c(CS[C@H]3C[C@H](O)C3)nc12]

To a solution of Example 38 (100 mg, 0.27 mmol, 1.0 eq) in DCM (5 mL) was added N,N-dimethylaniline (2 mg, catalytic) and $AlCl_3$ (364 mg, 2.7 mmol, 10.0 eq) and the mixture was stirred at RT for 2 h. The mixture was diluted with water (20 mL), adjusted pH to 3-4 with 1 M HCl and extracted with EtOAc (20 mL×3). The combined organic layers were dried over $Na_2SO_4$ and concentrated under reduced pressure. The residue was washed with hexane (5 mL) to afford the title compound (40 mg, 53%) as a yellow solid. LCMS: [M+H]+ 277.1.

$^1$H NMR (400 MHz, DMSO-$d_6$) δ 12.3 (s, 1H), 7.93 (d, J=7.6 Hz, 1H), 7.66 (d, J=7.2 Hz, 1H), 7.37 (t, J=7.6 Hz, 1H), 4.29 (p, J=6.6 Hz, 1H), 3.60 (s, 2H), 3.54-3.47 (m, 1H), 3.30 (1H (OH) may be obscured by water peak), 2.52 (s, 3H), 2.25-2.15 (m, 2H), 2.13-2.07 (m, 2H).

Example 48: 8-Methyl-2-((piperidin-3-ylthio)methyl)quinazolin-4(3H)-one Hydrochloride

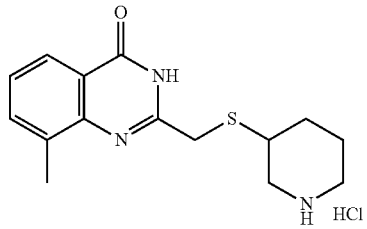 [SMILES: Cc1cccc2c(=O)[nH]c(CSC3CCCNC3)nc12 ; Cl]

Step 1: tert-Butyl 3-(((8-methyl-4-oxo-3,4-dihydroquinazolin-2-yl)methyl)thio)piperidine-1-carboxylate The title compound was prepared from Int-A1 and Int-B4 according to the method described for Example 28. LCMS: [M+H]$^+$ 362.2.

Step 2: 8-Methyl-2-((piperidin-3-ylthio)methyl)quinazolin-4(3H)-one hydrochloride tert-Butyl 3-(((8-methyl-4-oxo-3,4-dihydroquinazolin-2-yl)methyl)thio)piperidine-1-carboxylate (120 mg, 0.31 mmol, 1.0 eq) was dissolved in a 1.5 M HCl/EtOAc solution (10 mL) and the mixture was stirred at RT for 3 h. The mixture was concentrated under reduced pressure to afford the title compound (70 mg, 79%) as a white solid. LCMS: [M+H]$^+$ 290.1.

$^1$H NMR (400 MHz, DMSO-d$_6$) δ 12.4 (br s, 1H), 9.27-9.14 (m, 2H), 7.93 (d, J=7.6 Hz, 1H), 7.67 (d, J=7.2 Hz, 1H), 7.38 (t, J=7.6 Hz, 1H), 3.87-3.72 (m, 2H), 3.52-3.45 (m, 1H), 3.29-3.18 (m, 1H), 3.18-3.09 (m, 1H), 2.89-2.78 (m, 2H), 2.55 (s, 3H), 2.04 (dd, J=18.4, 7.6 Hz, 1H), 1.85-1.63 (m, 2H), 1.56-1.41 (m, 1H).

Example 49: 2-(((trans-4-Aminocyclohexyl)thio)methyl)-8-methylquinazolin-4(3H)-one Hydrochloride

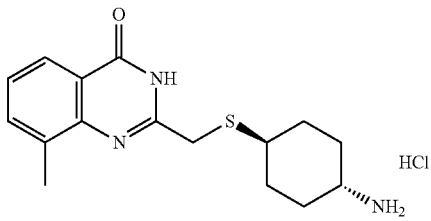 [SMILES: Cc1cccc2c(=O)[nH]c(CS[C@H]3CC[C@H](N)CC3)nc12 ; Cl]

The title compound was prepared from Int-A1 and Int-B5-trans according to the method described for Example 48. LCMS: [M+H]$^+$ 304.1.

$^1$H NMR (400 MHz, DMSO-d$_6$) δ 12.3 (s, 1H), 7.93 (d, J=8.0 Hz, 1H), 7.76 (br s, 3H), 7.66 (d, J=7.2 Hz, 1H), 7.37 (t, J=7.6 Hz, 1H), 3.65 (s, 2H), 3.29-3.25 (m, 1H), 3.05 (br s, 1H), 2.5 (s, 3H), 1.90-1.57 (m, 8H).

Example 50: 2-(((cis-4-Aminocyclohexyl)thio)methyl)-8-methylquinazolin-4(3H)-one Trifluoroacetic Acid

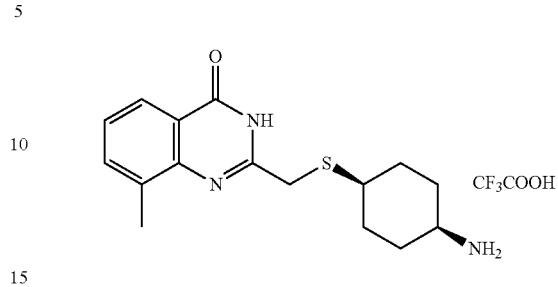

The title compound was prepared from Int-A1 and Int-B5-cis according to the method described for Example 48. LCMS: [M+H]$^+$ 304.1.

$^1$H NMR (400 MHz, DMSO-d$_6$) δ 12.3 (s, 1H), 7.93 (d, J=8.0 Hz, 1H), 7.75 (s, 3H), 7.66 (d, J=7.2 Hz, 1H), 7.37 (t, J=7.6 Hz, 1H), 3.65 (s, 2H), 3.29-3.25 (m, 1H), 3.05 (br s, 1H), 2.50 (s, 3H), 1.90-1.57 (m, 8H).

Example 51: 5-Fluoro-8-methyl-2-((piperidin-4-ylthio)methyl)quinazolin-4(3H)-one Hydrochloride

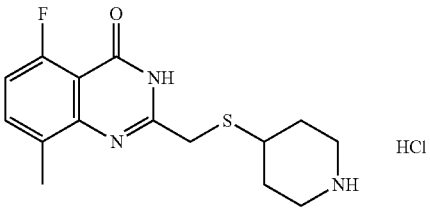 [SMILES: Cc1ccc(F)c2c(=O)[nH]c(CSC3CCNCC3)nc12 ; Cl]

The title compound was prepared from Int-A21 and Int-B2 according to the method described for Example 48. LCMS: [M+H]$^+$ 308.1.

$^1$H NMR (400 MHz, DMSO-d$_6$) δ 12.4 (s, 1H), 9.11-8.83 (m, 2H), 7.64 (t, J=7.2 Hz, 1H), 7.13 (t, J=9.6 Hz, 1H), 3.70 (s, 2H), 3.25-3.11 (m, 3H), 2.88 (q, J=11.2 Hz, 2H), 2.43 (s, 3H), 2.15 (d, J=14.0 Hz, 2H), 1.73-1.64 (m, 2H).

Example 52: 2-(((trans-3-Aminocyclobutyl)thio)methyl)-8-methylquinazolin-4(3H)-one Hydrochloride

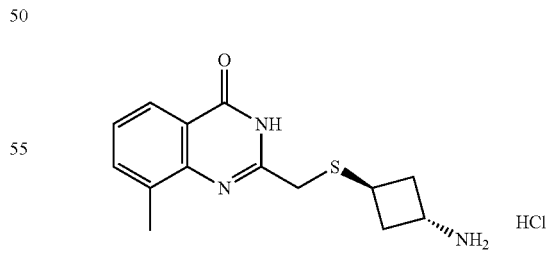

The title compound was prepared from Int-A1 and Int-B9 according to the method described for Example 48. LCMS: [M+H]$^+$ 276.1.

$^1$H NMR (400 MHz, DMSO-d$_6$) δ 12.3 (br s, 1H), 8.38 (br s, 3H), 7.93 (d, J=7.2 Hz, 1H), 7.66 (d, J=7.1 Hz, 1H), 7.37 (t, J=7.6 Hz, 1H), 3.82-3.71 (m, 2H), 3.69 (s, 2H), 2.53 (s, 5H), 2.21-2.11 (m, 2H).

Example 53: 2-(((4-Aminocycloheptyl)thio)methyl)-8-methylquinazolin-4(3H)-one Trifluoroacetate

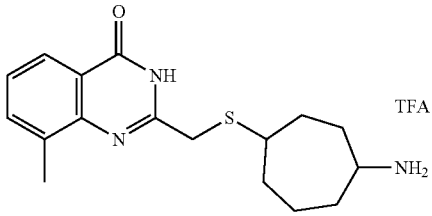 [SMILES: "TFA" ; Cc1cccc2c(=O)[nH]c(CSC3CCCC(N)CC3)nc12]

The title compound was prepared from Int-A1 and Int-B10 according to the method described for Example 48. LCMS: [M+H]+ 318.2.

Example 54: 2-(((trans-4-Aminocycloheptyl)thio)methyl)-8-methylquinazolin-4(3H)-one Trifluoroacetate and Example 55: 2-(((cis-4-Aminocycloheptyl)thio)methyl)-8-methylquinazolin-4(3H)-one Trifluoroacetate Example 54
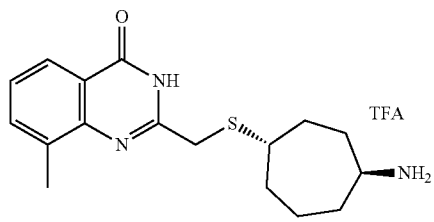

Example 55
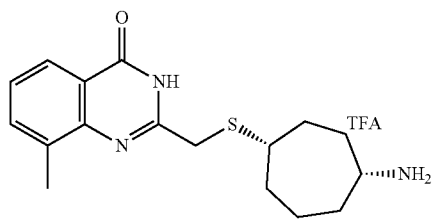

The compound of Example 53 was further purified by prep-HPLC (Agilent 10 prep-C18, 10 μm, 250×21.2 mm column, eluting with a gradient of ACN in water with 0.1% TFA, at a flow rate of 20 mL/min) to afford the title compounds.

Example 54

LCMS: [M+H]+ 318.2.
1H NMR (400 MHz, CD3OD) δ 8.03 (d, J=8.0 Hz, 1H), 7.66 (d, J=7.2 Hz, 1H), 7.39 (t, J=7.6 Hz, 1H), ~3.30 (2H, obscured by solvent peak), 3.29-3.22 (m, 1H), 3.09-3.01 (m, 1H), 2.59 (s, 3H), 2.26-2.16 (m, 1H), 2.11-2.00 (m, 3H), 1.76-1.49 (m, 6H).

Example 55

LCMS: [M+H]+ 318.2.
1H NMR (400 MHz, CD3OD) δ 8.03 (d, J=8.0 Hz, 1H), 7.66 (d, J=7.2 Hz, 1H), 7.39 (t, J=7.6 Hz, 1H), ~3.30 (2H, obscured by solvent peak), 3.28-3.20 (m, 1H), 3.17-3.09 (m, 1H), 2.58 (s, 3H), 2.25-2.15 (m, 1H), 2.12-2.06 (m, 1H), 2.0-1.93 (m, 2H), 1.92-1.80 (m, 3H), 1.57-1.42 (m, 3H).

Example 56: 5-Fluoro-2-(((4-hydroxycyclohexyl)thio)methyl)-8-methylquinazolin-4(3H)-one

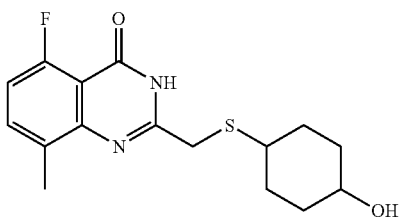 [SMILES: Cc1ccc(F)c2c(=O)[nH]c(CSC3CCC(O)CC3)nc12]

Step 1: 2-((1,4-Dioxaspiro[4.5]decan-8-ylthio)methyl)-5-fluoro-8-methylquinazolin-4(3H)-one The title compound was prepared from Int-A21 and Int-B6 according to the method described for Example 28. LCMS: [M+H]+ 365.1.

Step 2: 5-Fluoro-8-methyl-2-(((4-oxocyclohexyl)thio)methyl)quinazolin-4(3H)-one The title compound was prepared from 2-((1,4-dioxaspiro[4.5]decan-8-ylthio)methyl)-5-fluoro-8-methylquinazolin-4(3H)-one according to the method described for Example 21, step 3. LCMS: [M+H]+ 321.1.

Step 3: 5-Fluoro-2-(((4-hydroxycyclohexyl)thio)methyl)-8-methylquinazolin-4(3H)-one The title compound was prepared from 5-fluoro-8-methyl-2-(((4-oxocyclohexyl)thio)methyl)quinazolin-4(3H)-one according to the procedure described for Example 22. LCMS: [M+H]+ 323.1;

Example 57: 5-Fluoro-2-(((trans-4-hydroxycyclohexyl)thio)methyl)-8-methylquinazolin-4(3H)-one and Example 58: 5-Fluoro-2-(((cis-4-hydroxycyclohexyl)thio)methyl)-8-methylquinazolin-4(3H)-one Example 57
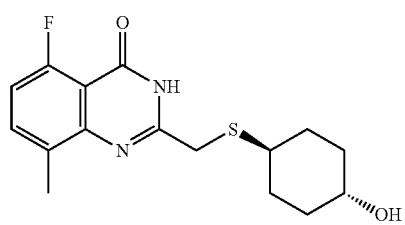

Example 58
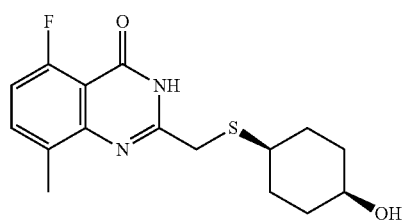

Example 57

LCMS: [M+H]⁺ 323.1.

¹H NMR (400 MHz, CD₃OD) δ 7.62 (dd, J=8.4, 5.6 Hz, 1H), 7.06 (dd, J=11.2, 8.4 Hz, 1H), 3.69 (s, 2H), 3.56-3.49 (m, 1H), 2.80-2.73 (m, 1H), 2.52 (s, 3H), 2.16-2.08 (m, 2H), 2.00-1.91 (m, 2H), 1.42-1.33 (m, 2H), 1.30-1.20 (m, 2H).

Example 58

LCMS: [M+H]⁺ 323.1.

¹H NMR (400 MHz, CD₃OD) δ 7.61 (dd, J=8.4, 5.6 Hz, 1H), 7.06 (dd, J=11.2, 8.4 Hz, 1H), 3.77-3.72 (m, 1H), 3.69 (s, 2H), 3.00 (m, J=6.0 Hz, 1H), 2.51 (s, 3H), 1.83-1.69 (m, 6H), 1.63-1.56 (m, 2H).

Example 59: 2-(((4-Hydroxycyclohexyl)thio) methyl)-8-methyl-5-(trifluoromethyl)quinazolin-4 (3H)-one

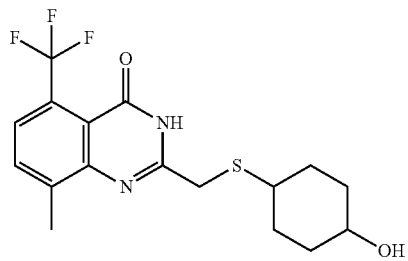 [SMILES: Cc1ccc(C(F)(F)F)c2c(=O)[nH]c(CSC3CCC(O)CC3)nc12]

The title compound was prepared from Int-A20 and Int-B6 according to the method described for Example 56. LCMS: [M+H]⁺ 373.1.

Example 60: 2-(((trans-4-Hydroxycyclohexyl)thio) methyl)-8-methyl-5-(trifluoromethyl) quinazolin-4 (3H)-one and Example 61: 2-(((cis-4-Hydroxycyclohexyl)thio)methyl)-8-methyl-5-(trifluoromethyl) quinazolin-4(3H)-one

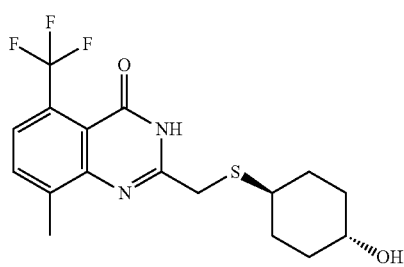
Example 60

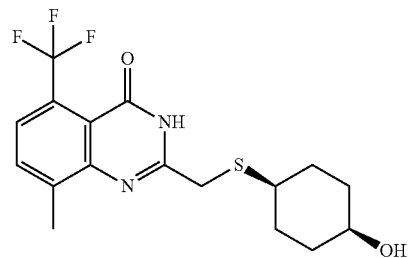
Example 61

The compound of Example 59 was further purified by prep-HPLC (Agilent 10 prep-C18, 10 µm, 250×21.2 mm column, eluting with a gradient of MeOH in water with 0.1% TFA, at a flow rate of 20 mL/min) to afford the title compounds.

Example 60

LCMS: [M+H]⁺ 373.1.

¹H NMR (400 MHz, CD₃OD) δ 7.78-7.73 (m, 2H), 3.71 (s, 2H), 3.58-3.46 (m, 1H), 2.81-2.73 (m, 1H), 2.64 (s, 3H), 2.12 (d, J=12.8 Hz, 2H), 1.96 (d, J=12.8 Hz, 2H), 1.43-1.18 (m, 4H).

Example 61

LCMS: [M+H]⁺ 373.1.

¹H NMR (400 MHz, CD₃OD) δ 7.89-7.58 (m, 2H), 3.77-3.73 (m, 1H), 3.71 (s, 2H), 3.04-2.96 (m, 1H), 2.62 (s, 3H), 1.84-1.79 (m, 4H), 1.77-1.69 (m, 2H), 1.65-1.53 (m, 2H).

Example 62: 2-(((trans-4-(Hydroxymethyl)cyclohexyl)thio)methyl)-8-methylquinazolin-4(3H)-one and Example 63: 2-(((cis-4-(Hydroxymethyl)cyclohexyl)thio)methyl)-8-methylquinazolin-4(3H)-one

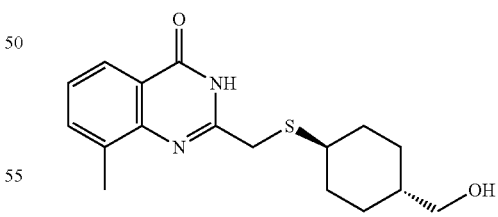
Example 62

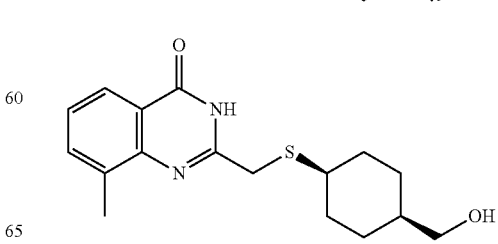
Example 63

Step 1: 2-(((4-(((tert-Butyldimethylsilyl)oxy)methyl)cyclohexyl)thio)methyl)-8-methyl quinazolin-4(3H)-one The title compound was prepared from Int-A1 and Int-B12 according to the method described for Example 28. LCMS: [M+H]+ 433.2.

Step 2: 2-(((trans-4-(Hydroxymethyl)cyclohexyl)thio)methyl)-8-methylquinazolin-4(3H)-one and 2-(((cis-4-(Hydroxymethyl)cyclohexyl)thio)methyl)-8-methylquinazolin-4(3H)-one To a solution of 2-(((4-(((tert-butyldimethylsilyl)oxy)methyl)cyclohexyl)thio)methyl)-8-methylquinazolin-4(3H)-one (1.2 g, 2.7 mmol, 1.0 eq) in THF (10 mL) was added TBAF (913 mg, 3.5 mmol, 1.3 eq) and the mixture was heated at 50° C. for 6 h. The mixture was allowed to cool to RT, diluted with water (50 mL) and extracted with EtOAc (50 mL×3). The combined organic layers were dried over Na₂SO₄ and concentrated under reduced pressure. The residue was purified by column chromatography (DCM:MeOH, 30:1 to 15:1, v/v) to afford Example 62 (100 mg, 12%) and Example 63 (150 mg, 17%) as white solids. Mixed fractions of Example 62/Example 63 in 1:3 ratio (400 mg, 47%) were also obtained.

Example 62

LCMS: [M+H]+ 319.1.

¹H NMR (400 MHz, CDCl₃) δ 8.15 (d, J=7.6 Hz, 1H), 7.66 (d, J=7.2 Hz, 1H), 7.44 (t, J=7.6 Hz, 1H), 4.14 (s, 2H), 3.42 (d, J=6.0 Hz, 2H), 2.71 (s, 3H), 2.70-2.59 (m, 1H), 2.11 (d, J=12.8 Hz, 2H), 1.85 (d, J=13.2 Hz, 2H), 1.56-1.43 (m, 1H), 1.41-1.25 (m, 2H), 1.06-0.92 (m, 2H).

Example 63

LCMS: [M+H]+ 319.1.

¹H NMR (400 MHz, CDCl₃) δ 8.13 (d, J=7.2 Hz, 1H), 7.65 (d, J=7.2 Hz, 1H), 7.42 (t, J=7.6 Hz, 1H), 4.06 (s, 2H), 3.51 (d, J=5.6 Hz, 2H), 3.22-3.11 (m, 1H), 2.70 (s, 3H), 1.91-1.80 (m, 2H), 1.79-1.69 (m, 2H), 1.61-1.54 (m, 3H), 1.47 (t, J=11.6 Hz, 2H).

Example 64: 2-(((4-(Aminomethyl)cyclohexyl)thio)methyl)-8-methylquinazolin-4(3H)-one Trifluoroacetate and Example 65: 2-(((cis-4-(Aminomethyl)cyclohexyl)thio)methyl)-8-methylquinazolin-4(3H)-one Trifluoroacetate Example 64

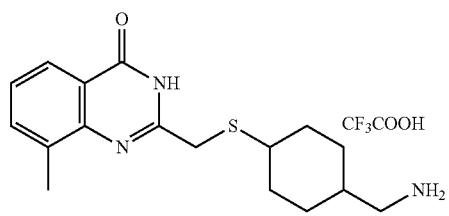

Example 65

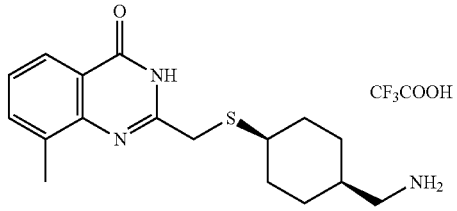

Step 1: (4-(((8-Methyl-4-oxo-3,4-dihydroquinazolin-2-yl)methyl)thio)cyclohexyl)methyl methanesulfonate To a solution of Example 62/Example 63 (1:3 mixture, 400 mg, 1.3 mmol, 1.0 eq) and Et₃N (381 mg, 3.8 mmol, 3.0 eq) in DCM (12 mL) at 0° C. under a N₂ atmosphere was added MsCl (288 mg, 2.6 mmol, 2.0 eq) dropwise and the mixture was allowed to warm to RT and stirred for 3 h. The mixture was diluted with water (20 mL), extracted with DCM (30 mL×3) and the combined organic layers were dried over Na₂SO₄ and concentrated under reduced pressure to afford the title compound (498 mg, 100%) as yellow solid. LCMS: [M+H]+ 397.1

Step 2: 2-(((4-(Azidomethyl)cyclohexyl)thio)methyl)-8-methylquinazolin-4(3H)-one To a solution of (4-(((8-methyl-4-oxo-3,4-dihydroquinazolin-2-yl)methyl)thio)cyclohexyl)methyl methanesulfonate (350 mg, 0.88 mmol, 1.0 eq) in DMF (8 mL) under a N₂ atmosphere was added NaN₃ (172 mg, 2.6 mmol, 3.0 eq) and the mixture was heated at 50° C. for 5 h. The mixture was cooled to RT, diluted with water (20 mL) and extracted with DCM (30 mL×3). The combined organic layers were washed with water (20 mL), dried over Na₂SO₄ and concentrated under reduced pressure. The residue was purified by column chromatography (Petroleum ether:EtOAc, 10:1 to 5:1, v/v) to afford the title compound (200 mg, 75%) as yellow solid. LCMS: [M+H]+ 344.2.

Step 3: 2-(((4-(Aminomethyl)cyclohexyl)thio)methyl)-8-methylquinazolin-4(3H)-one Trifluoroacetate and 2-(((cis-4-(Aminomethyl)cyclohexyl)thio)methyl)-8-methylquinazolin-4(3H)-one Trifluoroacetate To a solution of 2-(((4-(azidomethyl)cyclohexyl)thio)methyl)-8-methylquinazolin-4(3H)-one (190 mg, 0.54 mmol, 1.0 eq) in THF (8 mL) and water (0.1 mL) under a N₂ atmosphere was added PPh₃ (217 mg, 0.84 mmol, 1.5 eq) and the mixture was stirred at RT for 24 h. The mixture was concentrated under reduced pressure and the residue was purified by prep-HPLC (Agilent 10 prep-C18, 10 μm, 250× 21.2 mm column, eluting with a gradient of ACN in water with 0.1% TFA, at a flow rate of 20 mL/min) to afford Example 64 (45.8 mg, 26%) and Example 65 (45.1 mg, 26%) as white solids.

Example 64

LCMS: [M+H]+ 318.2;

Example 65

LCMS: [M+H]+ 318.2; ¹H NMR (400 MHz, DMSO-d₆) δ 12.3 (s, 1H), 7.94 (d, J=7.6 Hz, 1H), 7.67 (d, J=7.6 Hz,

4H), 7.38 (t, J=7.6 Hz, 1H), 3.64 (s, 2H), 3.28-3.24 (m, 1H), 2.71 (t, J=5.2 Hz, 2H), 2.50 (s, 3H), 1.82-1.67 (m, 4H), 1.65-1.60 (m, 1H), 1.55-1.50 (m, 2H), 1.39-1.30 (m, 2H).

Example 66: 2-(((trans-4-(Aminomethyl)cyclohexyl)thio)methyl)-8-methylquinazolin-4(3H)-one Trifluoroacetate

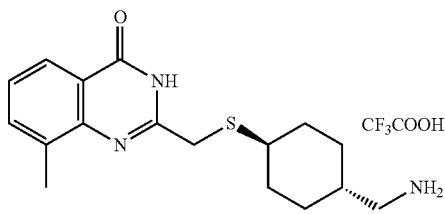 [SMILES: Cc1cccc2c(=O)[nH]c(CS[C@H]3CC[C@H](CN)CC3)nc12 ; "CF3COOH"]

The compound of Example 64 was further purified by prep-HPLC (Agilent 10 prep-C18, 10 μm, 250×21.2 mm column, eluting with a gradient of ACN in water with 0.1% TFA, at a flow rate of 15 mL/min) to afford the title compound. LCMS: [M+H]⁺ 318.2.

¹H NMR (400 MHz, CD₃OD) δ 8.03 (d, J=7.2 Hz, 1H), 7.65 (d, J=7.2 Hz, 1H), 7.38 (t, J=7.6 Hz, 1H), 3.75 (s, 2H), 2.78-2.70 (m, 3H), 2.58 (s, 3H), 2.25-2.08 (m, 2H), 1.92-1.78 (m, 2H), 1.66-1.55 (m, 1H), 1.34 (qd, J=12.8, 3.2 Hz, 2H), 1.05 (qd, J=12.8, 3.2 Hz, 2H).

Example 67: 2-(((4-((Dimethylamino)methyl)cyclohexyl)thio)methyl)-8-methylquinazolin-4(3H)-one trifluoroacetate and Example 68: 2-(((cis-4-((Dimethylamino)methyl)cyclohexyl)thio)methyl)-8-methyl quinazolin-4(3H)-one Trifluoroacetate Example 67

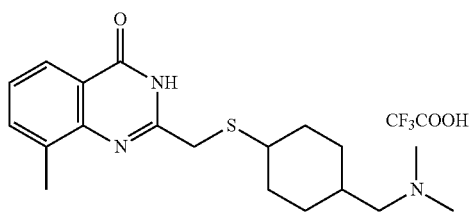

Example 68

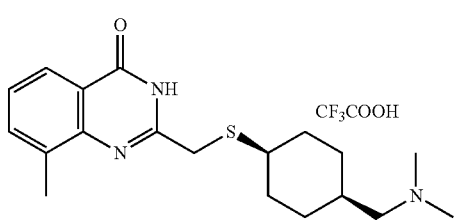

A mixture of (4-(((8-methyl-4-oxo-3,4-dihydroquinazolin-2-yl)methyl)thio)cyclohexyl)methyl methanesulfonate (200 mg, 0.5 mmol, 1.0 eq), Et₃N (101 mg, 1 mmol, 2.0 eq) and dimethylamine (2 M solution in THF, 5 mL, 10 mmol, 20.0 eq) was heated at 100° C. for 24 h. The mixture was cooled to RT and concentrated under reduced pressure. The residue was purified by prep-HPLC (Agilent 10 prep-C18, 10 μm, 250×21.2 mm column, eluting with a gradient of ACN in water with 0.1% TFA, at a flow rate of 20 mL/min) to afford the compounds of Example 67 (65 mg, 37%) and Example 68 (49.3 mg, 28%) as white solids.

Example 67

LCMS: [M+H]⁺ 346.2;

Example 68

LCMS: [M+H]⁺ 346.2; ¹H NMR (400 MHz, DMSO-d₆) δ 12.3 (s, 1H), 9.05 (s, 1H), 7.93 (d, J=8.0 Hz, 1H), 7.66 (d, J=7.2 Hz, 1H), 7.37 (t, J=7.6 Hz, 1H), 3.63 (s, 2H), 3.29-3.22 (m, 1H), 2.97 (d, J=6.4 Hz, 2H), 2.74 (d, J=4.8 Hz, 6H), 2.50 (s, 3H), 1.86-1.78 (m, 1H), 1.78-1.70 (m, 4H), 1.57-1.44 (m, 2H), 1.38-1.29 (m, 2H).

Example 69: 2-(((trans-4-((Dimethylamino)methyl)cyclohexyl)thio)methyl)-8-methyl quinazolin-4(3H)-one Trifluoroacetate

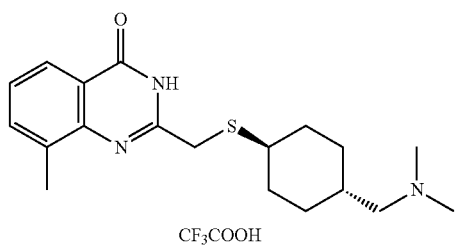 [SMILES: Cc1cccc2c(=O)[nH]c(CS[C@H]3CC[C@H](CN(C)C)CC3)nc12 ; "CF3COOH"]

The compound of Example 67 was further purified by prep-HPLC (Agilent 10 prep-C18, 10 μm, 250×21.2 mm column, eluting with a gradient of ACN in water with 0.1% TFA, at a flow rate of 15 mL/min) to afford the title compound. LCMS: [M+H]⁺ 346.2.

¹H NMR (400 MHz, DMSO-d₆) δ 12.3 (s, 1H), 9.12 (s, 1H), 7.93 (d, J=8.0 Hz, 1H), 7.65 (d, J=7.2 Hz, 1H), 7.36 (t, J=7.6 Hz, 1H), 3.66 (s, 2H), 2.90 (s, 2H), 2.80-2.77 (m, 1H), 2.74 (d, J=4.8 Hz, 6H), 2.51 (s, 3H), 2.08 (d, J=11.6 Hz, 2H), 1.82-1.64 (m, 3H), 1.26 (m, 2H), 0.96 (m, 2H).

Example 70: 2-(((trans-3-(Hydroxymethyl)cyclohexyl)thio)methyl)-8-methylquinazolin-4(3H)-one and Example 71: 2-(((cis-3-(Hydroxymethyl)cyclohexyl)thio)methyl)-8-methylquinazolin-4(3H)-one Example 70

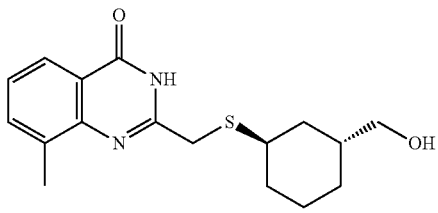

Example 71

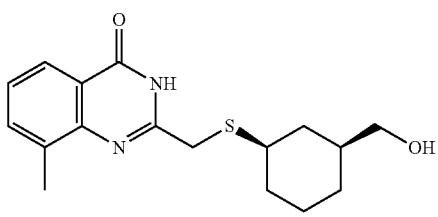

Step 1: 2-(((3-(Hydroxymethyl)cyclohexyl)thio) methyl)-8-methylquinazolin-4(3H)-one To a solution of Int-B13 (316 mg, 1.7 mmol, 1.0 eq) in THF (10 mL) was added 1 M NaOH (4 mL) and the mixture was stirred at RT for 10 min under a $N_2$ atmosphere. Int-A1 (350 mg, 1.7 mmol, 1.0 eq) was then added and the mixture was stirred at RT overnight under a $N_2$ atmosphere. The mixture was diluted with water (5 mL) and extracted with EtOAc (20 mL×3). The combined organic layers were dried over $Na_2SO_4$ and concentrated under reduced pressure. The residue was purified by column chromatography (DCM: MeOH, 10:1, v/v) to afford the title compound as a 5:1 mixture of cis/trans isomers (200 mg, 38%) as a white solid. LCMS: [M+H]$^+$ 319.1.

Step 2: 2-(((trans-3-(Hydroxymethyl)cyclohexyl) thio)methyl)-8-methylquinazolin-4(3H)-one and 2-(((cis-3-(Hydroxymethyl)cyclohexyl)thio)methyl)-8-methylquinazolin-4(3H)-one 2-(((3-(Hydroxymethyl)cyclohexyl)thio)methyl)-8-methylquinazolin-4(3H)-one (100 mg) was further purified by prep-HPLC (Agilent 10 prep-C18, 10 μm, 250×21.2 mm column, eluting with a gradient of MeOH in water with 0.1% TFA, at a flow rate of 20 mL/min) to afford the compounds of Example 70 (2.5 mg) and Example 71 (20 mg).

Example 70

LCMS: [M+H]$^+$ 319.1.
$^1$H NMR (400 MHz, CDCl$_3$) δ 8.13 (d, J=8.0 Hz, 1H), 7.63 (d, J=7.2 Hz, 1H), 7.38 (t, J=7.6 Hz, 1H), 3.83 (s, 2H), 3.45 (t, J=5.2 Hz, 2H), 2.74-2.64 (m, 1H), 2.60 (s, 3H), 2.10 (m, 2H), 1.88-1.69 (m, 2H), 1.51-1.45 (m, 1H), 1.35-1.20 (m, 3H), 0.98-0.84 (m, 1H).

Example 71

LCMS: [M+H]$^+$ 319.1.
$^1$H NMR (400 MHz, CDCl$_3$) δ 8.12 (d, J=8.0 Hz, 1H), 7.60 (d, J=7.2 Hz, 1H), 7.36 (t, J=7.6 Hz, 1H), 3.86-3.70 (m, 2H), 3.55-3.32 (m, 2H), 3.24-3.11 (m, 1H), 2.59 (s, 3H), 2.02-1.91 (m, 1H), 1.89-1.81 (m, 1H), 1.80-1.60 (m, 5H), 1.60-1.48 (m, 2H).

Example 72: 2-((((cis)-3-((Dimethylamino)methyl) cyclohexyl)thio)methyl)-8-methyl quinazolin-4(3H)-one Trifluoroacetate

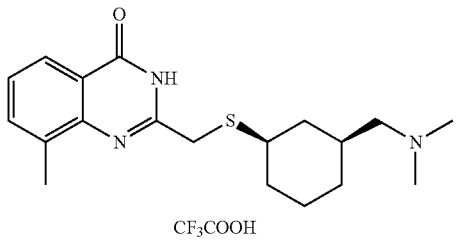 [SMILES: Cc1cccc2c(=O)[nH]c(CS[C@@H]3CCC[C@H](CN(C)C)C3)nc12 ; "CF3COOH"]

Step 1: (3-(((8-Methyl-4-oxo-3,4-dihydroquinazolin-2-yl)methyl)thio)cyclohexyl)methyl methanesulfonate The title compound was prepared from 2-(((3-(hydroxymethyl)cyclohexyl)thio)methyl)-8-methylquinazolin-4(3H)-one according to the method described for Example 64, step 1. LCMS: [M+H]$^+$ 397.1.

Step 2: 2-((((cis)-3-((Dimethylamino)methyl)cyclohexyl)thio)methyl)-8-methylquinazolin-4(3H)-one trifluoroacetate The title compound was prepared from (3-(((8-methyl-4-oxo-3,4-dihydroquinazolin-2-yl)methyl)thio)cyclohexyl) methyl methanesulfonate according to the method described for Example 67 and Example 68. The minor trans isomer was not isolated. LCMS: [M+H]$^+$ 346.2;
$^1$H NMR (400 MHz, CD$_3$OD) δ 8.03 (dd, J=8.0, 1.6 Hz, 1H), 7.67 (d, J=7.2 Hz, 1H), 7.39 (t, J=7.6 Hz, 1H), 3.75-3.71 (m, 2H), 3.46-3.40 (m, 1H), 3.05-2.88 (m, 2H), 2.84 (d, J=5.2 Hz, 6H), 2.58 (s, 3H), 2.25-2.16 (m, 1H), 1.93-1.82 (m, 2H), 1.80-1.69 (m, 3H), 1.65-1.50 (m, 2H), 1.18-1.06 (m, 1H).

Example 73: 8-Methyl-2-(((trans-4-((methylamino) methyl)cyclohexyl)thio)methyl) quinazolin-4(3H)-one

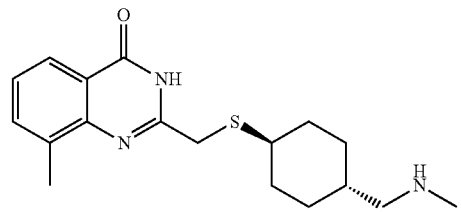 [SMILES: CNC[C@H]1CC[C@H](SCc2nc3c(C)cccc3c(=O)[nH]2)CC1]

Step 1: (trans-4-(((8-Methyl-4-oxo-3,4-dihydroquinazolin-2-yl)methyl)thio)cyclohexyl)methyl methanesulfonate The title compound was prepared from Example 62 according to the method described for Example 64, step 1. LCMS: [M+H]$^+$ 397.1.

Step 2: 8-Methyl-2-(((trans-4-((methylamino) methyl)cyclohexyl)thio)methyl)quinazolin-4(3H)-one A mixture of (trans-4-(((8-methyl-4-oxo-3,4-dihydroquinazolin-2-yl)methyl)thio) cyclohexyl)methyl methanesulfonate (80 mg, 0.2 mmol, 1.0 eq), Et$_3$N (40 mg, 0.2 mmol, 2.0 eq) and methylamine (2 M solution in THF, 5 mL, 10 mmol, 50.0 eq) was heated at 90° C. for 2 days. The mixture was cooled to RT and concentrated under reduced pressure. The residue was purified by prep-TLC (DCM: MeOH, 10:1, v/v) to afford the title compound (10 mg, 15%) as a white solid. LCMS: [M+H]$^+$ 332.2.
$^1$H NMR (400 MHz, CD$_3$OD) δ 8.03 (d, J=8.0 Hz, 1H), 7.66 (d, J=7.2 Hz, 1H), 7.38 (t, J=7.6 Hz, 1H), 3.75 (s, 2H), 2.83 (d, J=7.2 Hz, 2H), 2.77-2.70 (m, 1H), 2.67 (s, 3H), 2.58

(s, 3H), 2.23-2.15 (m, 2H), 1.88-1.81 (m, 2H), 1.73-1.62 (m, 1H), 1.40-1.29 (m, 2H), 1.13-1.01 (m, 2H).

Example 74: 7-Amino-2-(((tetrahydro-2H-pyran-4-yl)thio)methyl)quinazolin-4(3H)-one

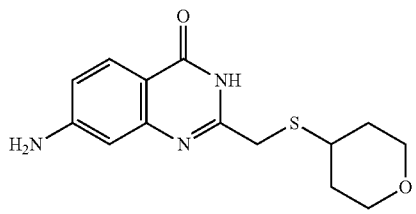 [SMILES: Nc1ccc2c(=O)[nH]c(CSC3CCOCC3)nc2c1]

Step 1: 7-Nitro-2-(((tetrahydro-2H-pyran-4-yl)thio)methyl)quinazolin-4(3H)-one

The title compound was prepared from Int-A11 and Int-B1 according to the method described for Example 28. LCMS: [M+H]$^+$ 322.0.

Step 2: 7-Amino-2-(((tetrahydro-2H-pyran-4-yl)thio)methyl)quinazolin-4(3H)-one

To a solution of 7-nitro-2-(((tetrahydro-2H-pyran-4-yl)thio)methyl)quinazolin-4(3H)-one (100 mg, 0.31 mmol, 1.0 eq) and NH$_4$Cl (100 mg, 1.88 mmol, 6.0 eq) in EtOH (3 mL) and water (2 mL) was added Fe (104 mg, 1.88 mmol, 6.0 eq) and the mixture was heated at 80° C. for 2 h. The mixture was cooled to RT, filtered and concentrated under reduced pressure. The residue was purified by prep-TLC (DCM: MeOH, 60:1, v/v) to afford the title compound (40 mg, 44%) as a white solid. LCMS: [M+H]$^+$ 292.1.

$^1$H NMR (400 MHz, DMSO-d$_6$) δ 11.7 (s, 1H), 7.72 (d, J=8.8 Hz, 1H), 6.68 (dd, J=8.8, 2.4 Hz, 1H), 6.56 (d, J=2.0 Hz, 1H), 6.05 (s, 2H), 3.81 (dt, J=11.6, 3.6 Hz, 2H), 3.57 (s, 2H), 3.33-3.27 (m, 2H), 3.04 (t, J=10.8 Hz, 1H), 1.93-1.85 (m, 2H), 1.49-1.39 (m, 2H).

Example 75: N-(4-Oxo-2-(((tetrahydro-2H-pyran-4-yl)thio)methyl)-3,4-dihydroquinazolin-7-yl)acetamide

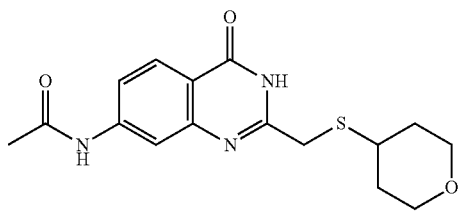 [SMILES: CC(=O)Nc1ccc2c(=O)[nH]c(CSC3CCOCC3)nc2c1]

To a solution of Example 74 (60 mg, 0.21 mmol, 1.0 eq) and Et$_3$N (42 mg, 0.41 mmol, 2.0 eq) in DCM (10 mL) at 0° C. was added AcCl (32 mg, 0.41 mmol, 2.0 eq) dropwise and the mixture was warmed to RT and stirred for 1 h. The mixture was diluted with water (10 mL), extracted with DCM (20 mL×3) and the combined organic layers were washed with water (20 mL), dried over Na$_2$SO$_4$ and concentrated under reduced pressure. The residue was purified by prep-TLC (DCM: MeOH, 60:1, v/v) to afford the title compound (13 mg, 19%) as an off-white solid. LCMS: [M+H]$^+$ 334.1.

$^1$H NMR (400 MHz, CD$_3$OD) δ 8.13-8.09 (m, 2H), 7.59 (dd, J=8.8, 1.6 Hz, 1H), 3.97-3.82 (m, 2H), 3.72 (s, 2H), 3.51-3.37 (m, 2H), 3.09-2.96 (m, 1H), 2.19 (s, 3H), 2.00-1.89 (m, 2H), 1.66-1.50 (m, 2H).

Example 76: N-(4-Oxo-2-(((tetrahydro-2H-pyran-4-yl)thio)methyl)-3,4-dihydroquinazolin-7-yl)benzamide

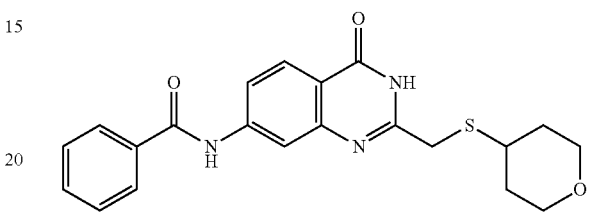

The title compound was prepared from the compound of Example 74 and benzoyl chloride according to the method described for Example 75. LCMS: [M+H]$^+$ 396.1.

$^1$H NMR (400 MHz, DMSO-d$_6$) δ 10.7 (s, 1H), 8.25 (d, J=1.6 Hz, 1H), 8.08 (d, J=8.8 Hz, 1H), 8.04-7.96 (m, 2H), 7.90 (dd, J=8.8, 2.0 Hz, 1H), 7.67-7.60 (m, 1H), 7.60-7.52 (m, 2H), 3.85-3.79 (m, 2H), 3.75 (s, 2H), 3.36-3.29 (m, 2H), 3.15-3.07 (m, 1H), 1.99-1.86 (m, 2H), 1.53-1.38 (m, 2H).

Example 77: N-Methyl-4-oxo-2-(((tetrahydro-2H-pyran-4-yl)thio)methyl)-3,4-dihydro Quinazoline-7-carboxamide

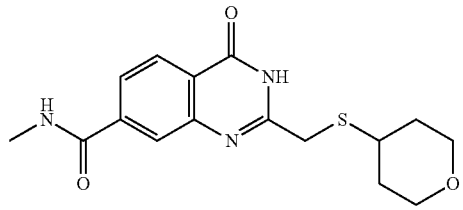 [SMILES: CNC(=O)c1ccc2c(=O)[nH]c(CSC3CCOCC3)nc2c1]

Step 1: 4-Oxo-2-(((tetrahydro-2H-pyran-4-yl)thio)methyl)-3,4-dihydroquinazoline-7-carboxylic acid The title compound was prepared from Int-A16 and Int-B1 according to the method described for Example 28. This coupling reaction proceeded with concomitant hydrolysis of the methyl ester to give the title compound directly. LCMS: [M+H]$^+$ 321.1.

Step 2: N-Methyl-4-oxo-2-(((tetrahydro-2H-pyran-4-yl)thio)methyl)-3,4-dihydroquinazoline-7-carboxamide To a solution of 4-oxo-2-(((tetrahydro-2H-pyran-4-yl)thio)methyl)-3,4-dihydroquinazoline-7-carboxylic acid (150 mg, 0.47 mmol, 1.0 eq) in DMF (5 mL) at RT under a N$_2$ atmosphere was added MeNH$_2$ (2 M solution in THF, 0.94 mL, 1.88 mmol, 4.0 eq), EDCI (180 mg, 0.94 mmol, 2.0 eq) and HOBt (127 mg, 0.94 mmol, 2.0 eq) and the mixture was stirred at RT overnight. The mixture was diluted with water (20 mL), extracted with EtOAc (20 mL×3) and the combined organic layers were washed with water (20 mL), dried over Na₂SO₄ and concentrated under reduced pressure. The residue was purified by prep-TLC (DCM: MeOH, 10:1, v/v) to afford the title compound (100 mg, 64%) as a white solid. LCMS: [M+H]⁺ 334.1.

¹HNMR (400 MHz, DMSO-d₆) δ 12.4 (s, 1H), 8.72 (d, J=4.4 Hz, 1H), 8.15 (d, J=8.0 Hz, 1H), 8.05 (s, 1H), 7.93-7.82 (m, 1H), 3.83-3.80 (m, 2H), 3.69 (s, 2H), 3.32-3.30 (m, 2H), 3.10-3.04 (m, 1H), 2.82 (d, J=4.8 Hz, 3H), 1.90 (d, J=12.2 Hz, 2H), 1.50-1.41 (m, 2H).

Example 78: 4-Oxo-N-phenyl-2-(((tetrahydro-2H-pyran-4-yl)thio)methyl)-3,4-dihydro Quinazoline-7-carboxamide

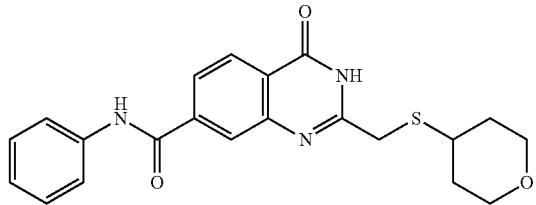 [SMILES: O=C(Nc1ccccc1)c1ccc2c(=O)[nH]c(CSC3CCOCC3)nc2c1]

The title compound was prepared from 4-oxo-2-(((tetrahydro-2H-pyran-4-yl)thio)methyl)-3,4-dihydroquinazoline-7-carboxylic acid and PhNH₂ according to the method described for Example 77, step 2. LCMS: [M+H]⁺ 396.1.

¹H NMR (400 MHz, DMSO-d₆) δ 12.5 (br s, 1H), 10.5 (s, 1H), 8.22-8.20 (m, 2H), 7.98 (d, J=8.4 Hz, 1H), 7.81 (d, J=8.0 Hz, 2H), 7.38 (t, J=8.0 Hz, 2H), 7.13 (t, J=7.2 Hz, 1H), 3.83-3.80 (m, 2H), 3.69 (s, 2H), 3.32-3.30 (m, 2H), 3.10-3.04 (m, 1H), 1.90 (d, J=12.2 Hz, 2H), 1.50-1.41 (m, 2H).

Example 79: 7-(Phenylamino)-2-(((tetrahydro-2H-pyran-4-yl)thio)methyl)quinazolin-4(3H)-one

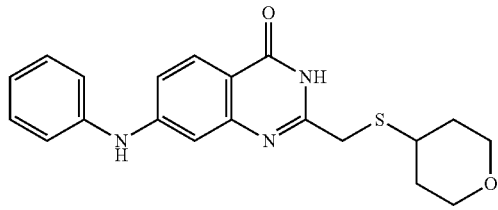 [SMILES: O=c1[nH]c(CSC2CCOCC2)nc2cc(Nc3ccccc3)ccc12]

Step 1: 7-Bromo-2-(((tetrahydro-2H-pyran-4-yl)thio)methyl)quinazolin-4(3H)-one

The title compound was prepared from Int-A8 and Int-B1 according to the method described for Example 28. LCMS: [M+H]⁺ 355.0.

Step 2: 7-Bromo-2-(((tetrahydro-2H-pyran-4-yl)thio)methyl)-3-((2-(trimethylsilyl)ethoxy)methyl)quinazolin-4(3H)-one To a solution of 7-bromo-2-(((tetrahydro-2H-pyran-4-yl)thio)methyl)quinazolin-4(3H)-one (7.5 g, 21.1 mmol, 1.0 eq) in anhydrous THF (100 mL) at 0° C. under a N₂ atmosphere was added LiHMDS (1 M in THF, 42.2 mL, 42.2 mmol, 2.0 eq) dropwise and the mixture was stirred at 0° C. for 1 h. SEMCl (5.3 g, 31.7 mmol, 1.5 eq) was added and the mixture was stirred for a further 1.5 h. The reaction was quenched with water (30 mL) and the mixture was extracted with EtOAc (50 mL×3). The combined organic layers were dried over Na₂SO₄ and concentrated under reduced pressure. The residue was purified by column chromatography (Petroleum ether:EtOAc, 10:1, v/v) to afford the title compound (7.8 g, 76%) as a colorless oil. LCMS: [M+H]⁺ 485.1.

¹H NMR (400 MHz, CD₃OD) δ 8.12 (d, J=8.4 Hz, 1H), 7.80 (d, J=1.2 Hz, 1H), 7.58 (dd, J=8.4, 1.2 Hz, 1H), 5.73 (s, 2H), 3.98-3.94 (m, 4H), 3.66 (t, J=8.0 Hz, 2H), 3.45-3.39 (m, 2H), 3.09-3.02 (m, 1H), 1.93 (d, J=13.2 Hz, 2H), 1.70-1.62 (m, 2H), 0.93 (t, J=8.0 Hz, 2H), 0.02 (s, 9H).

Step 3: 7-(Phenylamino)-2-(((tetrahydro-2H-pyran-4-yl)thio)methyl)-3-((2-(trimethylsilyl)ethoxy)methyl)quinazolin-4(3H)-one To a solution of 7-bromo-2-(((tetrahydro-2H-pyran-4-yl)thio)methyl)-3-((2-(trimethylsilyl)ethoxy) methyl)quinazolin-4(3H)-one (60 mg, 0.12 mmol, 1.0 eq) and PhNH₂ (14 mg, 0.15 mmol, 1.2 eq) in toluene (5 mL) under a N₂ atmosphere was added t-BuONa (35 mg, 0.37 mmol, 3.0 eq), BINAP (15 mg, 0.024 mmol, 0.2 eq) and Pd₂(dba)₃ (11 mg, 0.012 mmol, 0.1 eq) and the mixture was heated at reflux for 3 h. After cooling to RT, the mixture was diluted with water (10 mL) and extracted with EtOAc (15 mL×3). The combined organic layers were dried over Na₂SO₄ and concentrated under reduced pressure. The residue was purified by prep-TLC (Petroleum ether:EtOAc, 3:1, v/v) to afford the title compound (40 mg, 60%) as a yellow solid. LCMS: [M+H]⁺ 498.3.

Step 4: 7-(Phenylamino)-2-(((tetrahydro-2H-pyran-4-yl)thio)methyl)quinazolin-4(3H)-one To a solution of 7-(phenylamino)-2-(((tetrahydro-2H-pyran-4-yl)thio)methyl)-3-((2-(trimethylsilyl)ethoxy) methyl)quinazolin-4(3H)-one (60 mg, 0.12 mmol, 1.0 eq) in dioxane (3 mL) was added a 3 M HCl/dioxane solution (1 mL) and the mixture was heated at 40° C. overnight. The mixture was cooled to RT and concentrated under reduced pressure. The residue was purified by prep-HPLC (Agilent 10 prep-C18, 10 μm, 250×21.2 mm column, eluting with a gradient of ACN in water with 0.1% TFA, at a flow rate of 20 mL/min) to afford the title compound (13 mg, 29%) as a light yellow solid. LCMS: [M+H]⁺ 368.1.

¹H NMR (400 MHz, CD₃OD) δ 7.98 (d, J=8.8 Hz, 1H), 7.39-7.33 (m, 2H), 7.26 (d, J=8.0 Hz, 2H), 7.17-7.05 (m, 3H), 3.89 (dt, J=11.6, 4.0 Hz, 2H), 3.69 (s, 2H), 3.42 (td, J=11.2, 2.4 Hz, 2H), 3.05-2.98 (m, 1H), 1.93 (d, J=13.2 Hz, 2H), 1.62-1.52 (m, 2H).

Example 80: 7-(Pyridin-3-ylamino)-2-(((tetrahydro-2H-pyran-4-yl)thio)methyl)quinazolin-4(3H)-one

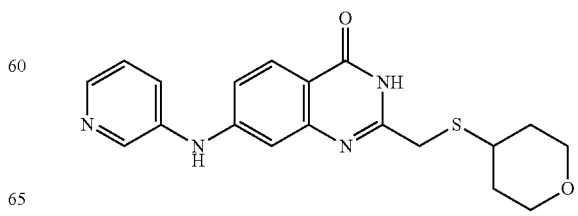

Step 1: 7-(Pyridin-3-ylamino)-2-(((tetrahydro-2H-pyran-4-yl)thio)methyl)-3-((2-(trimethylsilyl)ethoxy)methyl)quinazolin-4(3H)-one The title compound was prepared from 7-bromo-2-(((tetrahydro-2H-pyran-4-yl)thio)methyl)-3-((2-(trimethylsilyl)ethoxy) methyl)quinazolin-4(3H)-one and pyridin-3-amine according to the method described for Example 79, step 3. LCMS: [M+H]+ 499.2.

Step 2: 7-(Pyridin-3-ylamino)-2-(((tetrahydro-2H-pyran-4-yl)thio)methyl)quinazolin-4(3H)-one To a solution of 7-(pyridin-3-ylamino)-2-(((tetrahydro-2H-pyran-4-yl)thio)methyl)-3-((2-(trimethylsilyl)ethoxy) methyl)quinazolin-4(3H)-one (30 mg, 0.06 mmol, 1.0 eq) in THF (1 mL) was added 2 M HCl (1 mL) and the mixture was stirred at RT overnight. The mixture was adjusted pH to 8-9 with a saturated aqueous NaHCO₃ solution and extracted with EtOAc (15 mL×3). The combined organic layers were concentrated under reduced pressure and the residue was purified by prep-TLC (DCM:MeOH, 20:1, v/v) to afford the title compound (10 mg, 45%) as a white solid. LCMS: [M+H]+ 369.1.

¹HNMR (400 HMz, DMSO-$d_6$) δ 12.0 (s, 1H), 9.01 (s, 1H), 8.46 (d, J=4.0 Hz, 1H), 8.22 (dd, J=8.0 Hz, 1H), 7.92 (d, J=8.0 Hz, 1H), 7.66 (d, J=12.0 Hz, 1H), 7.38-7.35 (m, 1H), 7.13 (dd, J=12.0 Hz, 1H), 7.04 (d, J=4.0 Hz, 1H), 3.85-3.76 (m, 2H), 3.61 (s, 2H), 3.31-3.26 (m, 2H), 3.10-3.00 (m, 1H), 1.92-1.84 (m, 2H), 1.49-1.37 (m, 2H).

The following examples in Table 5 were similarly prepared using the two-step procedure in Example 80 beginning with 7-bromo-2-(((tetrahydro-2H-pyran-4-yl)thio)methyl)-3-((2-(trimethylsilyl)ethoxy)methyl)quinazolin-4(3H)-one and the appropriate amine.

TABLE 5

| Example | Name and structure | Amine |
|---|---|---|
| Example 81 | 7-(Pyridin-2-ylamino)-2-(((tetrahydro-2H-pyran-4-yl)thio)methyl)quinazolin-4(3H)-one | pyridin-2-amine |
| Example 82 | 7-((4-Methoxyphenyl)amino)-2-(((tetrahydro-2H-pyran-4-yl)thio)methyl)quinazolin-4(3H)-one | 4-methoxyaniline |
| Example 83 | 7-((3-Methoxyphenyl)amino)-2-(((tetrahydro-2H-pyran-4-yl)thio)methyl)quinazolin-4(3H)-one | 3-methoxyaniline |
| Example 84 | 7-((2-Methoxyphenyl)amino)-2-(((tetrahydro-2H-pyran-4-yl)thio)methyl)quinazolin-4(3H)-one | 2-methoxyaniline |

TABLE 5-continued

| Example | Name and structure | Amine |
|---|---|---|
| Example 85 | 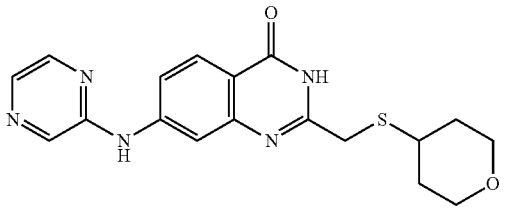 [SMILES: O=c1[nH]c(CSC2CCOCC2)nc2cc(Nc3cccnc3)ccc12]<br>7-(Pyrazin-2-ylamino)-2-(((tetrahydro-2H-pyran-4-yl)thio)methyl)quinazolin-4(3H)-one | pyrazin-2-amine |
| Example 86 | 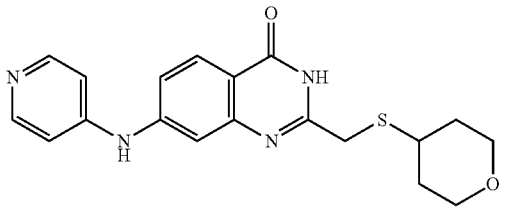<br>7-(Pyridin-4-ylamino)-2-(((tetrahydro-2H-pyran-4-yl)thio)methyl)quinazolin-4(3H)-one | pyridin-4-amine |
| Example 87 | 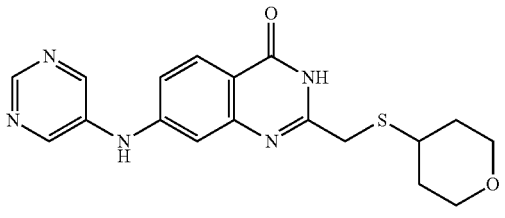 [SMILES: O=c1[nH]c(CSC2CCOCC2)nc2cc(Nc3cncnc3)ccc12]<br>7-(Pyrimidin-5-ylamino)-2-(((tetrahydro-2H-pyran-4-yl)thio)methyl)quinazolin-4(3H)-one | pyrimidin-5-amine |
| Example 88 | 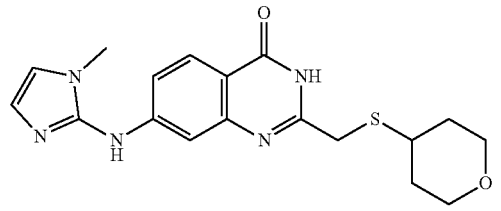 [SMILES: Cn1ccnc1Nc1ccc2c(=O)[nH]c(CSC3CCOCC3)nc2c1]<br>7-((1-Methyl-1H-imidazol-2-yl)amino)-2-(((tetrahydro-2H-pyran-4-yl)thio)methyl)quinazolin-4(3H)-one | 1-methyl-1H-imidazol-2-amine |
| Example 89 | 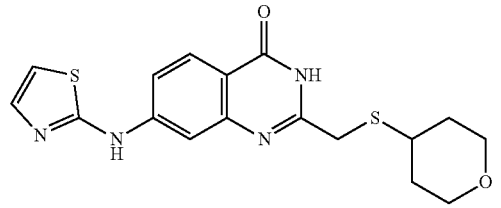 [SMILES: O=c1[nH]c(CSC2CCOCC2)nc2cc(Nc3nccs3)ccc12]<br>2-(((Tetrahydro-2H-pyran-4-yl)thio)methyl)-7-(thiazol-2-ylamino)quinazolin-4(3H)-one | thiazol-2-amine |

TABLE 5-continued

| Example | Name and structure | Amine |
|---|---|---|
| Example 90 | 7-((2-Methylpyridin-3-yl)amino)-2-(((tetrahydro-2H-pyran-4-yl)thio)methyl)quinazolin-4(3H)-one | 2-methylpyridin-3-amine |
| Example 91 | 7-((4-Methylpyridin-3-yl)amino)-2-(((tetrahydro-2H-pyran-4-yl)thio)methyl)quinazolin-4(3H)-one | 4-methylpyridin-3-amine |
| Example 92 | 7-((5-Methylpyridin-3-yl)amino)-2-(((tetrahydro-2H-pyran-4-yl)thio)methyl)quinazolin-4(3H)-one | 5-methylpyridin-3-amine |

Example 93: 7-(4-Amino-1H-pyrazol-1-yl)-2-(((tetrahydro-2H-pyran-4-yl)thio)methyl) quinazolin-4(3H)-one Trifluoroacetate

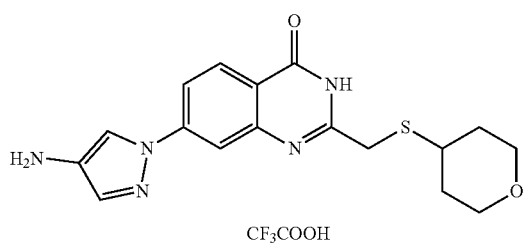 [SMILES: Nc1cnn(-c2ccc3c(=O)[nH]c(CSC4CCOCC4)nc3c2)c1 ; "CF3COOH"]

CF₃COOH

Step 1. 7-(4-Amino-1H-pyrazol-1-yl)-2-(((tetrahydro-2H-pyran-4-yl)thio)methyl)-3-((2-(trimethylsilyl)ethoxy)methyl)quinazolin-4(3H)-one To a solution of 7-bromo-2-(((tetrahydro-2H-pyran-4-yl)thio)methyl)-3-((2-(trimethylsilyl)ethoxy) methyl)quinazolin-4(3H)-one (50 mg, 0.10 mmol, 1.0 eq) and 1H-pyrazol-4-amine (10 mg, 0.12 mmol, 1.2 eq) in toluene (5 mL) under a $N_2$ atmosphere was added t-BuONa (20 mg, 0.20 mmol, 2.0 eq), t-BuXphos (18 mg, 0.04 mmol, 0.4 eq) and Pd₂(dba)₃ (9 mg, 0.01 mmol, 0.1 eq) and the mixture was heated at reflux for 24 h. After cooling to RT, the mixture was diluted with water (10 mL) and extracted with EtOAc (15 mL×3). The combined organic layers were washed with water (10 mL), dried over Na₂SO₄ and concentrated under reduced pressure. The residue was purified by prep-TLC (Petroleum ether:EtOAc, 3:1, v/v) to afford the title compound (19 mg, 40%) as a yellow oil. LCMS: [M+H]⁺ 488.2.

Step 2: 7-(4-Amino-1H-pyrazol-1-yl)-2-(((tetrahydro-2H-pyran-4-yl)thio)methyl)quinazolin-4(3H)-one The title compound was prepared from 7-(4-amino-1H-pyrazol-1-yl)-2-(((tetrahydro-2H-pyran-4-yl)thio)methyl)-3-((2-(trimethylsilyl)ethoxy)methyl)quinazolin-4(3H)-one according to the method described for Example 80, step 2. LCMS: [M+H]⁺ 358.1.

¹H NMR (400 MHz, DMSO-d₆) δ 12.4 (br s, 1H), 8.57 (s, 1H), 8.18 (d, J=9.2 Hz, 1H), 7.99-7.97 (m, 2H), 7.78 (s, 1H), 3.86-3.78 (m, 2H), 3.70 (s, 2H), 3.36-3.30 (m, 2H), 3.12-3.01 (m, 1H), 1.89 (d, J=11.8 Hz, 2H), 1.51-1.42 (m, 2H).

Example 94: 7-(Isoxazol-3-ylamino)-2-(((tetra-hydro-2H-pyran-4-yl)thio)methyl)quinazolin-4(3H)-one

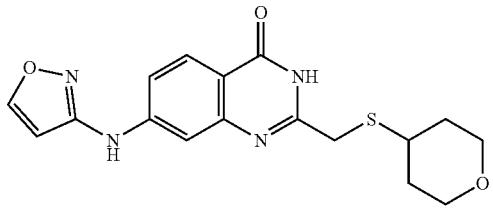 [SMILES: O=c1[nH]c(CSC2CCOCC2)nc2cc(Nc3ccon3)ccc12]

Step 1: 7-(Isoxazol-3-ylamino)-2-(tetrahydropyran-4-ylsulfanylmethyl)-3-(2-trimethylsilyl ethoxymethyl)quinazolin-4-one The title compound was prepared from 7-bromo-2-(((tetrahydro-2H-pyran-4-yl)thio)methyl)-3-((2-(trimethylsilyl)ethoxy)methyl)quinazolin-4(3H)-one and isoxazol-3-amine according to the method described for Example 79, step 3. LCMS: [M+H]$^+$ 489.2

Step 2: 7-(Isoxazol-3-ylamino)-2-(((tetrahydro-2H-pyran-4-yl)thio)methyl)quinazolin-4(3H)-one A mixture of 7-(isoxazol-3-ylamino)-2-(tetrahydropyran-4-ylsulfanylmethyl)-3-(2-trimethylsilylethoxymethyl)quinazolin-4-one (25 mg, 0.05 mmol, 1.0 eq) and formic acid (1.0 mL) was stirred at RT overnight. The mixture was diluted with MeOH (1 mL) and purified by prep-HPLC (Agilent 10 prep-C18, 10 μm, 250×21.2 mm column, eluting with a gradient of ACN in water with 0.1% TFA, at a flow rate of 20 mL/min) to afford the title compound (4 mg, 22%) as a white solid. LCMS: [M+H]$^+$ 359.1.
$^1$H NMR (400 MHz, DMSO-d$_6$) δ 12.0 (s, 1H), 9.80 (s, 1H), 8.70 (d, J=1.8 Hz, 1H), 7.98 (d, J=8.6 Hz, 1H), 7.78 (d, J=2.2 Hz, 1H), 7.38 (dd, J=8.8, 2.4 Hz, 1H), 6.30 (d, J=1.6 Hz, 1H), 3.81 (d, J=11.6 Hz, 2H), 3.65 (s, 2H), 3.40-3.28 (2H obscured by water peak), 3.06 (td, J=10.8, 5.2 Hz, 1H), 1.90 (d, J=13.2 Hz, 2H), 1.61-1.38 (m, 2H).

Example 95: 8-Methyl-7-(phenylamino)-2-(((tetra-hydro-2H-pyran-4-yl)thio)methyl) quinazolin-4(3H)-one

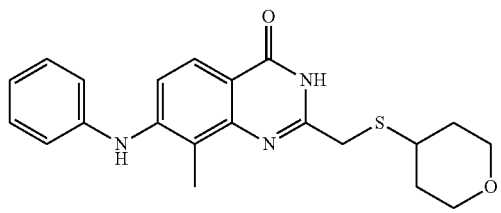 [SMILES: Cc1c(Nc2ccccc2)ccc2c(=O)[nH]c(CSC3CCOCC3)nc12]

Step 1: 7-Bromo-8-methyl-2-(((tetrahydro-2H-pyran-4-yl)thio)methyl)quinazolin-4(3H)-one The title compound was prepared from Int-A24 and Int-B1 according to the method described for Example 28. LCMS: [M+H]$^+$ 369.0.

Step 2: 8-Methyl-7-(phenylamino)-2-(((tetrahydro-2H-pyran-4-yl)thio)methyl)-3-((2-(trimethylsilyl)ethoxy)methyl)quinazolin-4(3H)-one The title compound was prepared from 7-bromo-8-methyl-2-(((tetrahydro-2H-pyran-4-yl)thio)methyl)quinazolin-4(3H)-one according to the method described for Example 79, step 2 and 3. LCMS: [M+H]$^+$ 512.1.

Step 3: 8-Methyl-7-(phenylamino)-2-(((tetrahydro-2H-pyran-4-yl)thio)methyl)quinazolin-4(3H)-one The title compound was prepared from 8-methyl-7-(phenylamino)-2-(((tetrahydro-2H-pyran-4-yl)thio)methyl)-3-((2-(trimethylsilyl)ethoxy)methyl)quinazolin-4(3H)-one according to the method described for Example 80, step 2. LCMS: [M+H]$^+$ 382.2.
$^1$H NMR (400 MHz, CDCl$_3$) δ 9.77 (s, 1H), 8.02 (d, J=8.8 Hz, 1H), 7.40-7.35 (m, 2H), 7.32 (d, J=8.8 Hz, 1H), 7.18 (d, J=7.6 Hz, 2H), 7.14-7.09 (m, 1H), 5.90 (s, 1H), 4.00-3.92 (m, 2H), 3.79 (s, 2H), 3.41-3.33 (m, 2H), 2.99-2.85 (m, 1H), 2.51 (s, 3H), 1.94 (d, J=14.6 Hz, 2H), 1.76-1.61 (m, 2H).

Example 96: 7-(Benzyloxy)-2-(((tetrahydro-2H-pyran-4-yl)thio)methyl)quinazolin-4(3H)-one

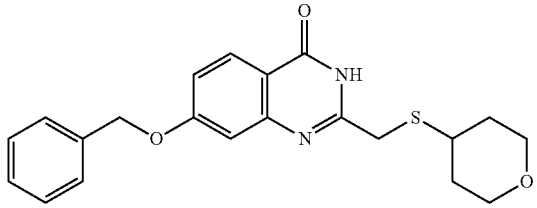 [SMILES: O=c1[nH]c(CSC2CCOCC2)nc2cc(OCc3ccccc3)ccc12]

Step 1: 7-(Benzyloxy)-2-(((tetrahydro-2H-pyran-4-yl)thio)methyl)-3-((2-(trimethylsilyl)ethoxy) methyl) quinazolin-4(3H)-one To a solution of 7-bromo-2-(((tetrahydro-2H-pyran-4-yl)thio)methyl)-3-((2-(trimethylsilyl)ethoxy) methyl)quinazolin-4(3H)-one (80 mg, 0.16 mmol, 1.0 eq) and KOH (28 mg, 0.49 mmol, 3.0 eq) in dioxane (1 mL) and water (1 mL) under a N$_2$ atmosphere was added Pd$_2$(dba)$_3$ (15 mg, 0.016 mmol, 0.1 eq) and t-BuXPhos (25 mg, 0.06 mmol, 0.4 eq) and the mixture was heated at 90° C. overnight. After cooling to RT, BnBr (136 mg, 0.8 mmol, 5.0 eq) and n-Bu$_4$NBr (257 mg, 0.8 mmol, 5.0 eq) was added and the mixture was stirred at RT for 6 h. The mixture was diluted with water (20 mL) and extracted with EtOAc (30 mL×3). The combined organic layers were dried over Na$_2$SO$_4$ and concentrated under reduced pressure. The residue was purified by prep-TLC (Petroleum ether:EtOAc, 3:1 to 1:1, v/v) to afford the title compound (28 mg, 34%) as a gray solid. LCMS: [M+H]$^+$ 513.2.

Step 2: 7-(Benzyloxy)-2-(((tetrahydro-2H-pyran-4-yl)thio)methyl)quinazolin-4(3H)-one To a solution of 7-(benzyloxy)-2-(((tetrahydro-2H-pyran-4-yl)thio)methyl)-3-((2-(trimethylsilyl)ethoxy)methyl)quinazolin-4(3H)-one (45 mg, 0.09 mmol, 1.0 eq) in DCM (1 mL) was added TFA (1 mL) and the mixture was stirred at RT for 2 h. The mixture was concentrated under reduced pressure and the residue was purified by C18 reverse phase column (Biotage, 45%-55% ACN in water) to afford the title compound (6 mg, 18%) as a white solid. LCMS: [M+H]+ 383.1.

$^1$H NMR (400 MHz, CDCl$_3$) δ 8.20 (d, J=8.8 Hz, 1H), 7.46-7.36 (m, 5H), 7.19-7.15 (m, 2H), 5.19 (s, 2H), 3.96-3.92 (m, 2H), 3.82 (s, 2H), 3.37 (t, J=11.2 Hz, 2H), 2.91-2.84 (m, 1H), 1.92-1.88 (m, 2H), 1.71-1.62 (m, 2H).

Example 97: 2-(((4-Hydroxycyclohexyl)thio)methyl)-7-(phenylamino)quinazolin-4(3H)-one

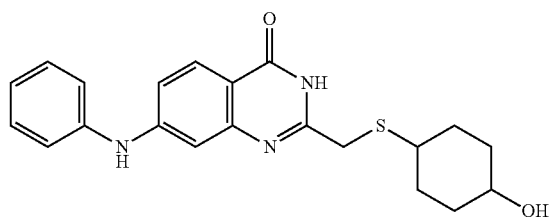 [SMILES: O=c1[nH]c(CSC2CCC(O)CC2)nc2cc(Nc3ccccc3)ccc12]

Step 1: 2-((1,4-Dioxaspiro[4.5]decan-8-ylthio)methyl)-7-bromoquinazolin-4(3H)-one The title compound was prepared from Int-A8 and Int-B6 according to the method described for Example 28. LCMS: [M+H]+ 411.0.

Step 2: 2-((1,4-Dioxaspiro[4.5]decan-8-ylthio)methyl)-7-(phenylamino)-3-((2-(trimethylsilyl)ethoxy)methyl)quinazolin-4(3H)-one The title compound was prepared from 2-((1,4-dioxaspiro[4.5]decan-8-ylthio)methyl)-7-bromoquinazolin-4(3H)-one according to the method described for Example 79, steps 2 and 3.
LCMS: [M+H]+ 541.1.

Step 3: 2-(((4-Oxocyclohexyl)thio)methyl)-7-(phenylamino)quinazolin-4(3H)-one

To a solution of 2-((1,4-dioxaspiro[4.5]decan-8-ylthio)methyl)-7-(phenylamino)-3-((2-(trimethylsilyl)ethoxy)methyl)quinazolin-4(3H)-one (100 mg, 0.18 mmol, 1.0 eq) in THF (5 mL) was added 1 M HCl (5 mL) and the mixture was stirred at RT overnight. The mixture was adjusted pH to 8-9 with a saturated aqueous NaHCO$_3$ solution and extracted with EtOAc (15 mL×3). The combined organic layers were dried over Na$_2$SO$_4$ and concentrated under reduced pressure. The residue was purified by prep-TLC (DCM:MeOH, 10:1, v/v) to afford the title compound (28 mg, 41%) as a white solid. LCMS: [M+H]+ 450.2.

Step 4: 2-(((4-Hydroxycyclohexyl)thio)methyl)-7-(phenylamino)quinazolin-4(3H)-one The title compound was prepared from 2-(((4-oxocyclohexyl)thio)methyl)-7-(phenylamino)quinazolin-4(3H)-one to the method described for Example 22. LCMS: [M+H]+ 382.2.

Example 98: 2-(((trans-4-Hydroxycyclohexyl)thio)methyl)-7-(phenylamino)quinazolin-4(3H)-one and
Example 99: 2-(((cis-4-Hydroxycyclohexyl)thio)methyl)-7-(phenylamino)quinazolin-4(3H)-one Example 98

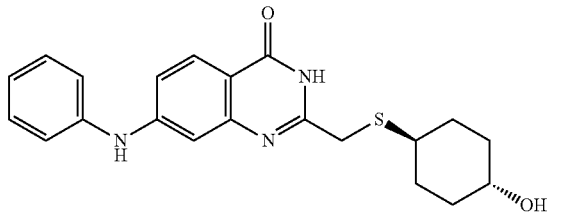

Example 99

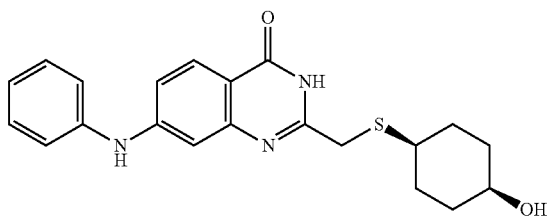

The compound of Example 97 was further purified by prep-HPLC (Agilent 10 prep-C18, 10 μm, 250×21.2 mm column, eluting with a gradient of MeOH in water with 0.1% TFA, at a flow rate of 20 mL/min) to afford the title compounds.

Example 98

LCMS: [M+H]+ 382.2.
$^1$H NMR (400 MHz, CD$_3$OD) δ 7.98 (d, J=8.8 Hz, 1H), 7.36 (t, J=7.6 Hz, 2H), 7.26 (d, J=7.6 Hz, 2H), 7.16 (d, J=2.0 Hz, 1H), 7.14-7.04 (m, 2H), 3.65 (s, 2H), 3.52-2.46 (m, 1H), 2.73-2.65 (m, 1H), 2.05 (d, J=16.0 Hz, 2H), 1.94 (d, J=10.4 Hz, 2H), 1.38-1.32 (m, 2H), 1.26-1.22 (m, 2H).

Example 99

LCMS: [M+H]+ 382.2.
$^1$H NMR (400 MHz, CD$_3$OD) δ 7.97 (d, J=8.4 Hz, 1H), 7.36 (t, J=8.0 Hz, 2H), 7.26 (d, J=8.0 Hz, 2H), 7.16 (d, J=2.0 Hz, 1H), 7.14-7.04 (m, 2H), 3.72 (s, 1H), 3.64 (s, 2H), 2.97-2.89 (m, 1H), 1.81-1.72 (m, 4H), 1.72-1.55 (m, 4H).

Example 100: 2-(((cis-4-Hydroxycyclohexyl)thio)methyl)-7-(pyridin-3-ylamino)quinazolin-4(3H)-one and Example 101: 2-(((trans-4-Hydroxycyclohexyl)thio)methyl)-7-(pyridin-3-ylamino)quinazolin-4(3H)-one Example 100

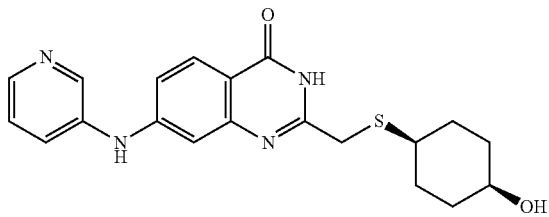

Example 101

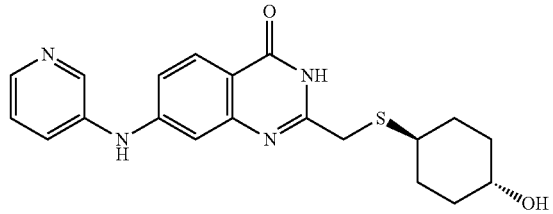

Step 1: 2-((1,4-Dioxaspiro[4.5]decan-8-ylthio) methyl)-7-(pyridin-3-ylamino)-3-((2-(trimethylsilyl)ethoxy)methyl)quinazolin-4(3H)-one The title compound was prepared from 2-((1,4-dioxaspiro[4.5]decan-8-ylthio)methyl)-7-bromoquinazolin-4(3H)-one according to the method described for Example 79, steps 2 and 3, using pyridin-3-amine. LCMS: [M+H]⁺ 425.2.

Step 2: 2-(((4-Oxocyclohexyl)thio)methyl)-7-(pyridin-3-ylamino)quinazolin-4(3H)-one The title compound was prepared from 2-((1,4-dioxaspiro[4.5]decan-8-ylthio)methyl)-7-(pyridin-3-ylamino)-3-((2-(trimethylsilyl)ethoxy)methyl)quinazolin-4(3H)-one according to the method described for Example 97, step 3. LCMS: [M+H]⁺ 381.2.

Step 3: 2-(((4-Hydroxycyclohexyl)thio)methyl)-7-(pyridin-3-ylamino)quinazolin-4(3H)-one The title compound was prepared from 2-(((4-oxocyclohexyl)thio)methyl)-7-(pyridin-3-ylamino)quinazolin-4(3H)-one according to the method described for Example 22. LCMS: [M+H]⁺ 383.2.

Step 4: 2-(((cis-4-Hydroxycyclohexyl)thio)methyl)-7-(pyridin-3-ylamino)quinazolin-4(3H)-one and 2-(((trans-4-Hydroxycyclohexyl)thio)methyl)-7-(pyridin-3-ylamino)quinazolin-4(3H)-one 2-(((4-Hydroxycyclohexyl)thio)methyl)-7-(pyridin-3-ylamino)quinazolin-4(3H)-one was further purified by prep-HPLC (Agilent 10 prep-C18, 10 μm, 250×21.2 mm column, eluting with a gradient of ACN in water with 0.1% TFA, at a flow rate of 20 mL/min) to afford the title compounds.

Example 100

LCMS: [M+H]⁺ 383.2.
¹H NMR (400 MHz, CD₃OD) δ 8.45 (d, J=2.8 Hz, 1H), 8.18 (dd, J=4.8, 1.2 Hz, 1H), 8.04 (d, J=8.8 Hz, 1H), 7.82-7.75 (m, 1H), 7.41 (dd, J=8.4, 4.8 Hz, 1H), 7.21 (d, J=2.4 Hz, 1H), 7.16 (dd, J=8.8, 2.4 Hz, 1H), 3.72 (d, J=3.2 Hz, 1H), 3.35 (s, 2H), 2.95 (d, J=4.4 Hz, 1H), 1.97-1.45 (m, 8H).

Example 101

LCMS: [M+H]⁺ 383.2.
¹H NMR (400 MHz, CD₃OD) δ 8.45 (d, J=2.4 Hz, 1H), 8.22-8.17 (m, 1H), 8.05 (d, J=8.8 Hz, 1H), 7.81-7.75 (m, 1H), 7.42 (dd, J=8.4, 4.8 Hz, 1H), 7.22 (d, J=2.0 Hz, 1H), 7.17 (dd, J=8.8, 2.2 Hz, 1H), 3.52 (td, J=10.4, 5.2 Hz, 1H), 3.35 (s, 2H), 2.70 (td, J=11.2, 3.6 Hz, 1H), 2.06 (d, J=12.4 Hz, 2H), 1.93 (d, J=11.6 Hz, 2H), 1.40-1.22 (m, 4H).

Example 102: 7-(Cyclopentylamino)-2-(((trans-4-hydroxycyclohexyl)thio)methyl) quinazolin-4(3H)-one and Example 103: 7-(Cyclopentylamino)-2-(((cis-4-hydroxycyclohexyl)thio)methyl) quinazolin-4(3H)-one Example 102

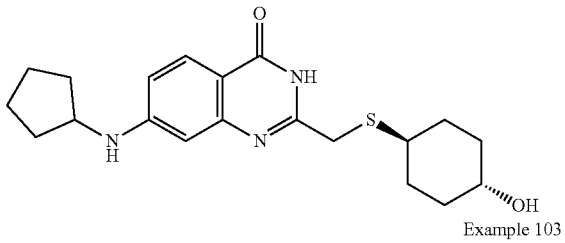

Example 103

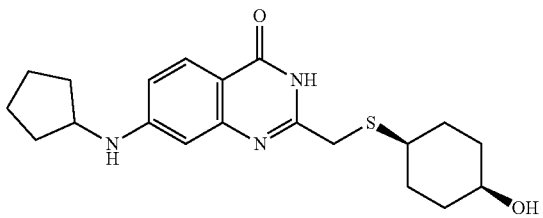

Step 1: 2-((1,4-Dioxaspiro[4.5]decan-8-ylthio) methyl)-7-(cyclopentylamino)-3-((2-(trimethylsilyl)ethoxy)methyl)quinazolin-4(3H)-one The title compound was prepared from 2-((1,4-dioxaspiro[4.5]decan-8-ylthio)methyl)-7-bromoquinazolin-4(3H)-one and cyclopentanamine amine according to the method described for Example 79, step 2, 3. LCMS: [M+H]⁺ 446.3.

Step 2: 7-(Cyclopentylamino)-2-(((4-oxocyclohexyl)thio)methyl)quinazolin-4(3H)-one The title compound was prepared from 2-((1,4-dioxaspiro[4.5]decan-8-ylthio)methyl)-7-(cyclopentylamino)-3-((2-(trimethylsilyl)ethoxy)methyl)quinazolin-4(3H)-one according to the method described for Example 97, step 3. LCMS: [M+H]⁺ 372.2.

Step 3: 7-(Cyclopentylamino)-2-(((4-hydroxycyclohexyl)thio)methyl)quinazolin-4(3H)-one The title compound was prepared from 7-(cyclopentylamino)-2-(((4-oxocyclohexyl)thio)methyl)quinazolin-4(3H)-one according to the method described for Example 22. LCMS: [M+H]⁺ 374.2.

Step 4: 7-(Cyclopentylamino)-2-(((trans-4-hydroxycyclohexyl)thio)methyl)quinazolin-4(3H)-one and 7-(Cyclopentylamino)-2-(((cis-4-hydroxycyclohexyl)thio)methyl) quinazolin-4(3H)-one 7-(Cyclopentylamino)-2-(((4-hydroxycyclohexyl)thio)methyl)quinazolin-4(3H)-one was further purified by prep-HPLC (Agilent 10 prep-C18, 10 μm, 250×21.2 mm column, eluting with a gradient of ACN in water, at a flow rate of 20 mL/min) to afford the title compounds.

Example 102

LCMS: [M+H]⁺ 374.2.

¹HNMR (400 MHz, DMSO-d$_6$) δ ppm: 11.6 (br s, 1H), 7.70 (d, J=8.0 Hz, 1H), 6.69 (dd, J=8.0, 2.0 Hz, 1H), 6.50 (m, 1H), 6.45 (d, J=2.0 Hz, 1H), 4.52 (br s, 1H), 3.74-3.82 (m, 1H), 3.52 (s, 2H), 3.39-3.35 (m, 1H), 2.76-2.64 (m, 1H), 2.03-1.90 (m, 4H), 1.82-1.76 (m, 2H), 1.73-1.63 (m, 2H), 1.62-1.53 (m, 2H), 1.52-1.42 (m, 2H), 1.24-1.13 (m, 4H).

Example 103

LCMS: [M+H]⁺ 374.2.

¹HNMR (400 MHz, DMSO-d$_6$) δ ppm: 11.6 (br s, 1H), 7.70 (d, J=8.0 Hz, 1H), 6.69 (d, J=8.0, 2.0 Hz, 1H), 6.50 (m, 1H), 6.45 (s, 1H), 4.41 (br s, 1H), 3.80-3.75 (m, 1H), 3.59-3.56 (m, 1H), 3.51 (s, 2H), 2.97-2.90 (m, 1H), 1.97-1.90 (m, 2H), 1.72-1.61 (m, 6H), 1.62-1.42 (m, 8H).

Example 104: 2-(((trans-4-(Hydroxymethyl)cyclohexyl)thio)methyl)-7-(phenylamino) quinazolin-4(3H)-one and Example 105: 2-(((cis-4-(Hydroxymethyl)cyclohexyl)thio)methyl)-7-(phenylamino) quinazolin-4(3H)-one

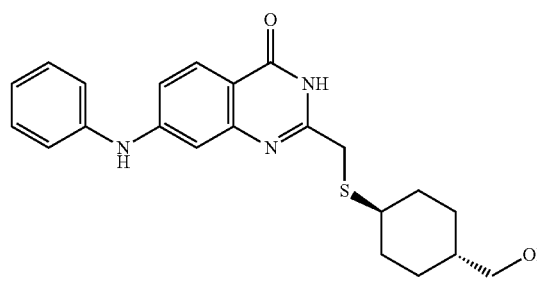
Example 104

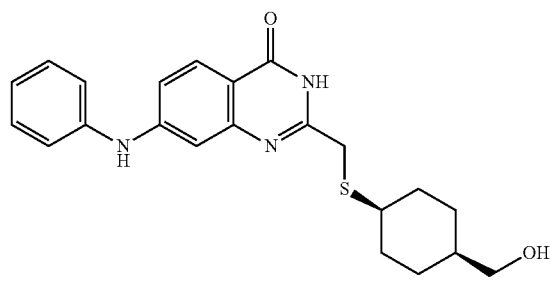
Example 105

Step 1: 7-Bromo-2-(((4-(((tert-butyldimethylsilyl)oxy)methyl)cyclohexyl)thio)methyl)quinazolin-4(3H)-one The title compound were prepared from Int-A8 and Int-B12 according to the method described in Example 70 and Example 71, step 1, as a 1:1 mixture of cis/trans isomers, which was used directly in the next step.

Step 2: 2-(((4-(((tert-Butyldimethylsilyl)oxy)methyl)cyclohexyl)thio)methyl)-7-(phenylamino)-3-((2-(trimethylsilyl)ethoxy)methyl)quinazolin-4(3H)-one The title compound was prepared from 7-bromo-2-(((4-(((tert-butyldimethylsilyl)oxy)methyl)cyclohexyl)thio)methyl)quinazolin-4(3H)-one according to the method described for Example 79, step 2 and 3. LCMS: [M+H]⁺ 640.3.

Step 3: 2-(((4-(Hydroxymethyl)cyclohexyl)thio)methyl)-7-(phenylamino)quinazolin-4(3H)-one To a solution of 2-(((4-(((tert-butyldimethylsilyl)oxy)methyl)cyclohexyl)thio)methyl)-7-(phenylamino)-3-((2-(trimethylsilyl)ethoxy)methyl)quinazolin-4(3H)-one (600 mg, 0.94 mmol, 1.0 eq) in THF (4 mL) was added 2 M HCl (4 mL) and the mixture was stirred at RT overnight. The mixture was adjusted to pH 8-9 with a saturated aqueous NaHCO$_3$ solution and extracted with EtOAc (15 mL×3). The combined organic layers were dried over Na$_2$SO$_4$ and concentrated under reduced pressure. The residue was purified by prep-TLC (DCM:MeOH, 50:1, v/v) to afford the title compound (90 mg, trans/cis=3:1, 24%) as a white solid. LCMS: [M+H]⁺ 396.2.

Step 4: 2-(((trans-4-(Hydroxymethyl)cyclohexyl)thio)methyl)-7-(phenylamino) quinazolin-4(3H)-one and 2-(((cis-4-(Hydroxymethyl)cyclohexyl)thio)methyl)-7-(phenylamino)quinazolin-4(3H)-one 2-(((4-(Hydroxymethyl)cyclohexyl)thio)methyl)-7-(phenylamino)quinazolin-4(3H)-one was further purified by prep-HPLC (Agilent 10 prep-C18, 10 μm, 250×21.2 mm column, eluting with a gradient of ACN in water with 0.1% TFA, at a flow rate of 20 mL/min) to afford the title compounds.

Example 104

LCMS: [M+H]⁺ 396.2.

¹H NMR (400 MHz, DMSO-d$_6$) δ 11.9 (br s, 1H), 8.87 (s, 1H), 7.88 (d, J=8.8 Hz, 1H), 7.35 (t, J=7.6 Hz, 2H), 7.22 (d, J=7.6 Hz, 2H), 7.10-6.99 (m, 3H), 3.51 (s, 2H), 3.30 (1H (OH) may be obscured by water peak), 3.17 (d, J=5.2 Hz, 2H), 2.67 (t, J=6.8 Hz, 1H), 2.00 (d, J=10.8 Hz, 2H), 1.73 (d, J=11.2 Hz, 2H), 1.35-1.31 (m, 1H), 1.21-1.11 (m, 2H), 0.94-0.85 (m, 2H).

Example 105

LCMS: [M+H]⁺ 396.2.

¹H NMR (400 MHz, DMSO-d$_6$) δ 12.1 (br s, 1H), 8.89 (s, 1H), 7.89 (d, J=8.8 Hz, 1H), 7.36 (t, J=7.6 Hz, 2H), 7.23 (d, J=8.0 Hz, 2H), 7.10-7.00 (m, 3H), 3.55 (t, J=6.0 Hz, 2H), 3.30 (1H (OH) may be obscured by water peak), 3.22-3.17 (m, 3H), 1.75-1.65 (m, 4H), 1.48-1.37 (m, 3H), 1.32-1.23 (m, 2H).

Example 106: 2-(((cis-4-(Hydroxymethyl)cyclohexyl)thio)methyl)-7-(pyridin-3-ylamino) quinazolin-4(3H)-one and Example 107: 2-(((trans-4-(Hydroxymethyl)cyclohexyl)thio)methyl)-7-(pyridin-3-ylamino) quinazolin-4(3H)-one Example 106

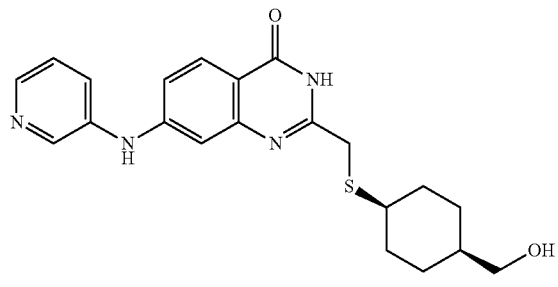

Example 107

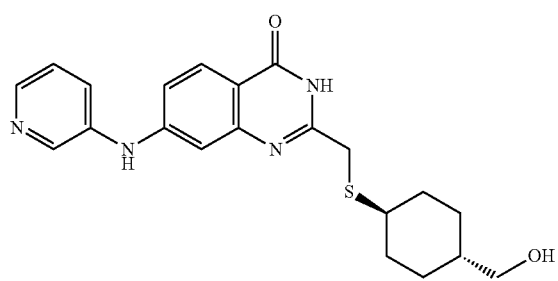

Step 1: 2-(((4-(((tert-Butyldimethylsilyl)oxy)methyl)cyclohexyl)thio)methyl)-7-(pyridin-3-ylamino)-3-((2-(trimethylsilyl)ethoxy)methyl)quinazolin-4(3H)-one The title compound was prepared from 7-bromo-2-(((4-(((tert-butyldimethylsilyl)oxy)methyl)cyclohexyl)thio) methyl) quinazolin-4(3H)-one and pyridin-3-amine according to the method described for Example 79, step 2 and 3. LCMS: [M+H]$^+$ 641.3.

Step 2: 2-(((4-(Hydroxymethyl)cyclohexyl)thio)methyl)-7-(pyridin-3-ylamino)quinazolin-4(3H)-one The title compound was prepared from 2-(((4-(((tert-butyldimethylsilyl)oxy)methyl)cyclohexyl)thio)methyl)-7-(pyridin-3-ylamino)-3-((2-(trimethylsilyl)ethoxy)methyl) quinazolin-4(3H)-one according to the method described for Example 104 and Example 105, step 3. LCMS: [M+H]$^+$ 397.2.

Step 3: 2-(((cis-4-(Hydroxymethyl)cyclohexyl)thio)methyl)-7-(pyridin-3-ylamino) quinazolin-4(3H)-one and 2-(((trans-4-(Hydroxymethyl)cyclohexyl)thio)methyl)-7-(pyridin-3-ylamino) quinazolin-4(3H)-one 2-(((4-(Hydroxymethyl)cyclohexyl)thio)methyl)-7-(pyridin-3-ylamino)quinazolin-4(3H)-one was further purified by prep-HPLC (Agilent 10 prep-C18, 10 μm, 250×21.2 mm column, eluting with a gradient of ACN in water with 0.1% TFA, at a flow rate of 20 mL/min) to afford the title compounds.

Example 106

LCMS: [M+H]$^+$ 397.2.
$^1$HNMR (400 MHz, CD$_3$OD) δ 8.45 (d, J=4.0 Hz, 1H), 8.20 (d, J=4.0 Hz, 1H), 8.04 (d, J=8.0 Hz, 1H), 7.78 (d, J=8.0 Hz, 1H), 7.44-7.40 (m, 1H), 7.21 (s, 1H), 7.17 (d, J=8.0 Hz, 1H), 3.63 (s, 2H), 3.37 (d, J=4.0 Hz, 2H), 3.20-3.16 (m, 1H), 2.05-2.00 (m, 1H), 1.84-1.70 (m, 4H), 1.45-1.29 (m, 4H).

Example 107

LCMS: [M+H]$^+$ 397.2.
$^1$HNMR (400 MHz, CD$_3$OD) δ 8.46 (d, J=2.4 Hz, 1H), 8.21 (dd, J=4.8, 1.2 Hz, 1H), 8.05 (d, J=8.8 Hz, 1H), 7.79 (d, J=10.0 Hz, 1H), 7.42 (m, 1H), 7.22 (s, 1H), 7.18 (dd, J=8.8, 2.4 Hz, 1H), 3.70 (s, 2H), 3.32 (m, 2H), 2.66 (m, 1H), 2.07 (d, J=12.4 Hz, 2H), 1.82 (d, J=13.2 Hz, 2H), 1.59 (m, 1H), 1.33-1.24 (m, 2H), 1.06-0.94 (m, 2H).

Example 108: 7-(Cyclohexylamino)-2-(((tetrahydro-2H-pyran-4-yl)thio)methyl)quinazolin-4(3H)-one

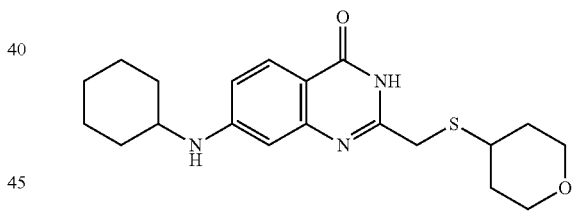

A mixture of the compound of Example 30 (100 mg, 0.34 mmol, 1.0 eq) and cyclohexanamine (2 mL) was heated at 120° C. for 2 days in a sealed tube. The mixture was allowed to cool to RT and concentrated under reduced pressure. The residue was diluted with water (20 mL) and extracted with EtOAc (30 mL×3). The combined organic layers were dried over Na$_2$SO$_4$ and concentrated under reduced pressure. The residue was purified by prep-TLC (Petroleum ether:EtOAc, 3:1 to 1:1, v/v) to afford the title compound (35 mg, 28%) as a gray solid. LCMS: [M+H]$^+$ 374.2.
$^1$HNMR (400 MHz, DMSO-d$_6$) δ 11.7 (s, 1H), 7.72 (d, J=8.8 Hz, 1H), 6.72 (d, J=8.8 Hz, 1H), 6.49 (s, 1H), 6.46 (d, J=7.6 Hz, 1H), 3.83-3.79 (m, 2H), 3.58 (s, 2H), 3.34-3.29 (m, 3H), 3.08-3.00 (m, 1H), 1.95-1.86 (m, 4H), 1.76-1.71 (m, 2H), 1.63-1.59 (m, 1H), 1.49-1.33 (m, 4H), 1.23-1.14 (m, 3H).

The following examples in Table 6 were similarly prepared from Example 30 and the appropriate amine according to the method described for Example 108.

TABLE 6

| Example | Name and structure | Amine |
|---|---|---|
| Example 109 | 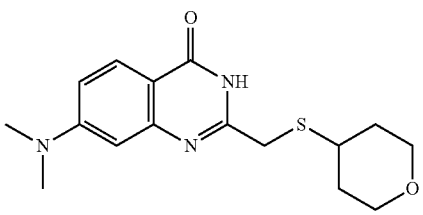 [SMILES: CN(C)c1ccc2c(=O)[nH]c(CSC3CCOCC3)nc2c1]<br>7-(Dimethylamino)-2-(((tetrahydro-2H-pyran-4-yl)thio)methyl)quinazolin-4(3H)-one | dimethylamine |
| Example 110 | 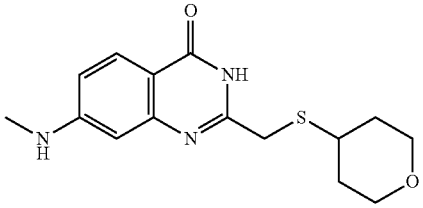 [SMILES: CNc1ccc2c(=O)[nH]c(CSC3CCOCC3)nc2c1]<br>7-(Methylamino)-2-(((tetrahydro-2H-pyran-4-yl)thio)methyl)quinazolin-4(3H)-one | methylamine |
| Example 111 | 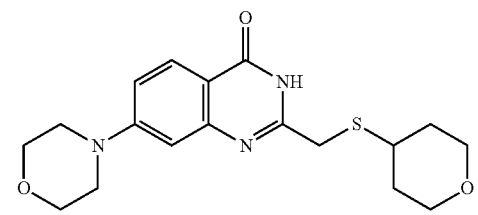 [SMILES: O=c1[nH]c(CSC2CCOCC2)nc2cc(N3CCOCC3)ccc12]<br>7-Morpholino-2-(((tetrahydro-2H-pyran-4-yl)thio)methyl)quinazolin-4(3H)-one | morpholine |
| Example 112 | 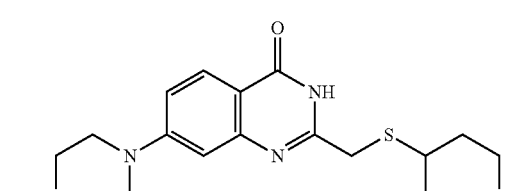<br>7-(4-Methylpiperazin-1-yl)-2-(((tetrahydro-2H-pyran-4-yl)thio)methyl)quinazolin-4(3H)-one | 1-methylpiperazine |
| Example 113 | 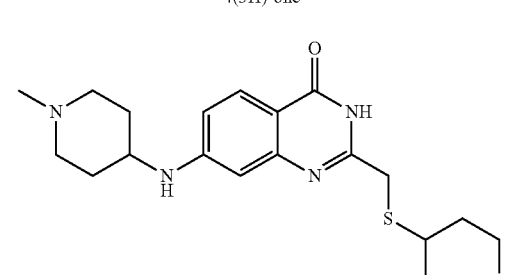<br>7-((1-Methylpiperidin-4-yl)amino)-2-(((tetrahydro-2H-pyran-4-yl)thio)methyl)quinazolin-4(3H)-one | 1-methylpiperidin-4-amine |

TABLE 6-continued

| Example | Name and structure | Amine |
|---|---|---|
| Example 114 | 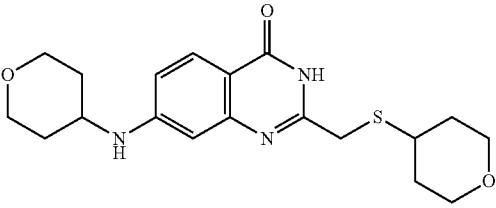 [SMILES: O=c1[nH]c(CSC2CCOCC2)nc2cc(NC3CCOCC3)ccc12] 7-((Tetrahydro-2H-pyran-4-yl)amino)-2-(((tetrahydro-2H-pyran-4-yl)thio)methyl)quinazolin-4(3H)-one | tetrahydro-2H-pyran-4-amine |
| Example 115 | 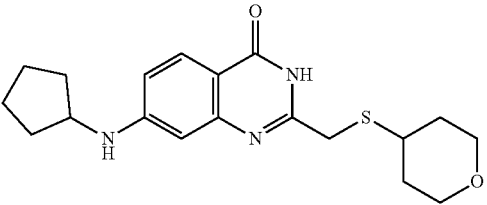 7-(Cyclopentylamino)-2-(((tetrahydro-2H-pyran-4-yl)thio)methyl)quinazolin-4(3H)-one | cyclopentanamine |
| Example 116 | 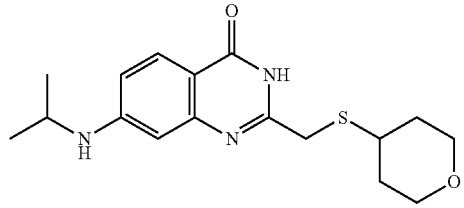 [SMILES: CC(C)Nc1ccc2c(=O)[nH]c(CSC3CCOCC3)nc2c1] 7-(Isopropylamino)-2-(((tetrahydro-2H-pyran-4-yl)thio)methyl)quinazolin-4(3H)-one | propan-2-amine |
| Example 117 | 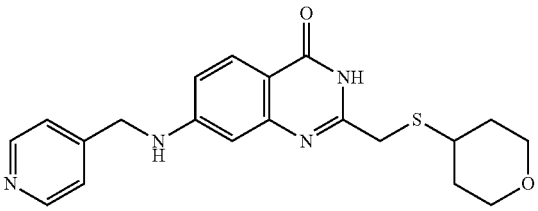 [SMILES: O=c1[nH]c(CSC2CCOCC2)nc2cc(NCc3ccncc3)ccc12] 7-((Pyridin-4-ylmethyl)amino)-2-(((tetrahydro-2H-pyran-4-yl)thio)methyl)quinazolin-4(3H)-one | pyridin-4-ylmethanamine |
| Example 118 | 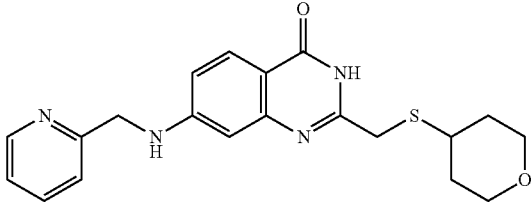 [SMILES: O=c1[nH]c(CSC2CCOCC2)nc2cc(NCc3ccccn3)ccc12] 7-((Pyridin-2-ylmethyl)amino)-2-(((tetrahydro-2H-pyran-4-yl)thio)methyl)quinazolin-4(3H)-one | pyridin-3-ylmethanamine |

TABLE 6-continued

| Example | Name and structure | Amine |
|---|---|---|
| Example 119 | 7-(Benzylamino)-2-(((tetrahydro-2H-pyran-4-yl)thio)methyl)quinazolin-4(3H)-one | phenylmethanamine |
| Example 120 | 7-((1-Phenylethyl)amino)-2-(((tetrahydro-2H-pyran-4-yl)thio)methyl)quinazolin-4(3H)-one | 1-phenylethan-1-amine |
| Example 121 | 2-(((Tetrahydro-2H-pyran-4-yl)thio)methyl)-7-((tetrahydrofuran-3-yl)amino)quinazolin-4(3H)-one | tetrahydrofuran-3-amine |
| Example 122 | 7-(Cyclobutylamino)-2-(((tetrahydro-2H-pyran-4-yl)thio)methyl)quinazolin-4(3H)-one | cyclobutanamine |
| Example 123 | 7-((Pyridin-3-ylmethyl)amino)-2-(((tetrahydro-2H-pyran-4-yl)thio)methyl)quinazolin-4(3H)-one | pyridin-3-ylmethanamine |

TABLE 6-continued

| Example | Name and structure | Amine |
|---|---|---|
| Example 124 | 7-(Cyclopropylamino)-2-(((tetrahydro-2H-pyran-4-yl)thio)methyl)quinazolin-4(3H)-one | cyclopropanamine |
| Example 125 | 7-(Cyclohexyl(methyl)amino)-2-(((tetrahydro-2H-pyran-4-yl)thio)methyl)quinazolin-4(3H)-one | N-methylcyclohexanamine |

Example 126: 7-[(1-Benzyl-3-piperidyl)amino]-2-(tetrahydropyran-4-ylsulfanylmethyl)-3H-quinazolin-4-one

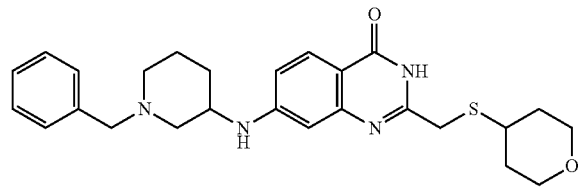 [SMILES: O=c1[nH]c(CSC2CCOCC2)nc2cc(NC3CCCN(Cc4ccccc4)C3)ccc12]

A mixture of the compound of Example 30 (150 mg, 0.5 mmol, 1.0 eq) and 1-benzylpiperidin-3-amine (1 mL) was heated at 120° C. in a sealed tube for 2 days. The mixture was allowed to cool to RT, diluted with water (20 mL) and extracted with EtOAc (30 mL×3). The combined organic layers were dried over Na$_2$SO$_4$ and concentrated under reduced pressure. The residue was purified by prep-TLC (DCM:MeOH, 10/1, v/v) to afford the title compound (70 mg, 30%) as yellow solid. LCMS: [M+H]$^+$ 465.2.

$^1$H-NMR: (400 MHz, CD$_3$OD) δ 7.85 (d, J=4.8 Hz, 1H), 7.40-7.23 (m, 5H), 6.86 (dd, J=2.4 Hz, 9.2 Hz, 1H), 6.32 (s, 1H), 3.94-3.85 (m, 2H), 3.67 (s, 2H), 3.66-3.54 (m, 3H), 3.46-3.37 (m, 2H), 3.09-2.96 (m, 2H), 2.84-2.74 (m, 1H), 2.27-2.17 (m, 1H), 2.16-2.06 (m, 1H), 2.05-1.97 (m, 1H), 1.97-1.90 (m, 2H), 1.85-1.76 (m, 1H), 1.75-1.65 (m, 1H), 1.63-1.51 (m, 2H), 1.45-1.33 (m, 1H).

Example 127: 7-(3-Piperidylamino)-2-(tetrahydropyran-4-ylsulfanylmethyl)-3H-quinazolin-4-one

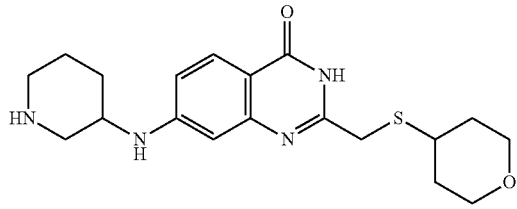 [SMILES: O=c1[nH]c(CSC2CCOCC2)nc2cc(NC3CCCNC3)ccc12]

To a solution of the compound of Example 126 (65 mg, 0.14 mmol, 1.0 eq) in DCE (3 mL) was added 1-chloroethyl carbonochloridate (80 mg, 0.56 mmol, 4.0 eq) and DIPEA (0.1 mL, 0.56 mmol, 4.0 eq). The mixture was stirred at 25° C. for 48 h and then concentrated under reduced pressure. Methanol (5 mL) was added and the mixture was heated at reflux for 2 h, then allowed to cool to RT and concentrated under reduced pressure. The residue was purified by prep-TLC (DCM/MeOH=10/1, v/v) to afford the title compound (10 mg, 19%) as a yellow solid. LCMS: [M+H]$^+$ 375.2.

$^1$H-NMR: (400 MHz, DMSO-d$_6$) δ 11.7 (br s, 1H), 7.78 (d, J=8.8 Hz, 1H), 6.78 (dd, J=2.0 Hz, 8.8 Hz, 1H), 6.73 (d, J=8.0 Hz, 1H), 6.62 (d, J=1.6 Hz, 1H), 3.86-3.76 (m, 2H), 3.75-3.67 (m, 1H), 3.60 (s, 2H), 3.19-3.11 (m, 2H), 3.07-2.98 (m, 2H), 2.85-2.76 (m, 2H), 2.68-2.57 (m, 2H), 2.01-1.92 (m, 1H), 1.87 (d, J=12.0 Hz, 3H), 1.77-1.64 (m, 1H), 1.57-1.38 (m, 3H).

Example 128: 7-((1-Benzylpiperidin-4-yl)amino)-2-((((tetrahydro-2H-pyran-4-yl)thio)methyl) quinazolin-4(3H)-one

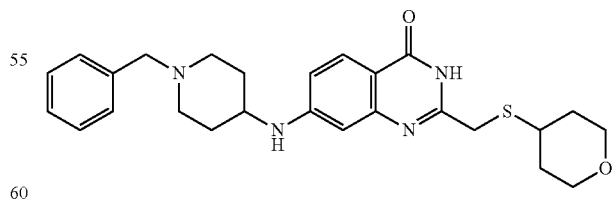

The title compound was prepared from the compound of Example 30 and 1-benzylpiperidin-4-amine according to the method described for Example 126. LCMS: [M+H]$^+$ 465.2.

$^1$H NMR (400 MHz, CD$_3$OD) δ 7.88 (d, J=8.8 Hz, 1H), 7.49-7.35 (m, 5H), 6.82 (dd, J=8.9, 2.0 Hz, 1H), 6.65 (d, J=1.6 Hz, 1H), 3.99-3.86 (m, 4H), 3.68 (s, 2H), 3.65-3.54

(m, 1H), 3.47-3.37 (m, 2H), 3.27-3.16 (m, 2H), 3.07-2.97 (m, 1H), 2.81-2.64 (m, 2H), 2.23-2.10 (m, 2H), 1.99-1.89 (m, 2H), 1.79-1.64 (m, 2H), 1.66-1.50 (m, 2H).

Example 129: 7-(Piperidin-4-ylamino)-2-(((tetrahydro-2H-pyran-4-yl)thio)methyl) quinazolin-4(3H)-one

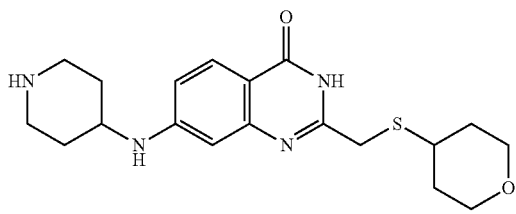 [SMILES: O=c1[nH]c(CSC2CCOCC2)nc2cc(NC3CCNCC3)ccc12]

The title compound was prepared from Example 128 according to the method described for Example 127. LCMS: [M+H]$^+$ 375.1.

$^1$H NMR (400 MHz, CD$_3$OD) δ 7.91 (d, J=4.8 Hz 1H), 6.87-6.85 (m, 1H), 6.71-6.68 (m, 1H), 3.93-3.86 (m, 2H), 3.83-3.74 (m, 1H), 3.70 (s, 2H), 3.56-3.39 (m, 4H), 3.24-3.17 (m, 2H), 3.08-2.95 (m, 1H), 2.30-2.26 (m, 2H), 1.93 (d, J=6.8 Hz, 2H), 1.79-1.69 (m, 2H), 1.63-1.55 (m, 2H).

Example 130: 7-(Pyrrolidin-3-ylamino)-2-(((tetrahydro-2H-pyran-4-yl)thio)methyl) quinazolin-4(3H)-one

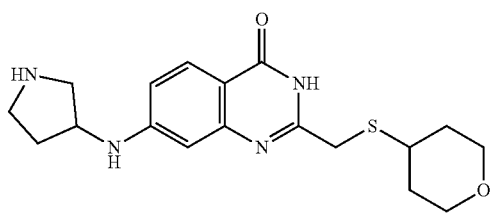 [SMILES: O=c1[nH]c(CSC2CCOCC2)nc2cc(NC3CCNC3)ccc12]

Step 1: 7-((1-Benzylpyrrolidin-3-yl)amino)-2-(((tetrahydro-2H-pyran-4-yl)thio)methyl) quinazolin-4(3H)-one The title compound was prepared from Example 30 and 1-benzylpyrrolidin-3-amine according to the method described for Example 126. LCMS: [M+H]$^+$ 451.2.

Step 2: 7-(Pyrrolidin-3-ylamino)-2-(((tetrahydro-2H-pyran-4-yl)thio)methyl)quinazolin-4(3H)-one The title compound was prepared from 7-((1-benzylpyrrolidin-3-yl)amino)-2-(((tetrahydro-2H-pyran-4-yl)thio) methyl) quinazolin-4(3H)-one according to the method described for Example 127. LCMS: [M+H]$^+$ 361.2.

$^1$H NMR (400 MHz, CDCl$_3$) δ 7.98-7.91 (m, 1H), 6.91-6.85 (m, 1H), 6.69 (d, J=10.4 Hz, 1H), 4.39-4.32 (m, 1H), 3.93-3.86 (m, 2H), 3.72 (s, 2H), 3.60-3.54 (m, 1H), 3.45-3.31 (m, 4H), 3.31-3.22 (m, 1H), 3.07-2.97 (m, 1H), 2.39-2.25 (m, 1H), 2.21-2.09 (m, 1H), 1.90 (d, J=6.4 Hz, 2H), 1.64-1.52 (m, 2H).

Example 131: 7-((1-Acetylpiperidin-4-yl)amino)-2-(((tetrahydro-2H-pyran-4-yl)thio)methyl) quinazolin-4(3H)-one

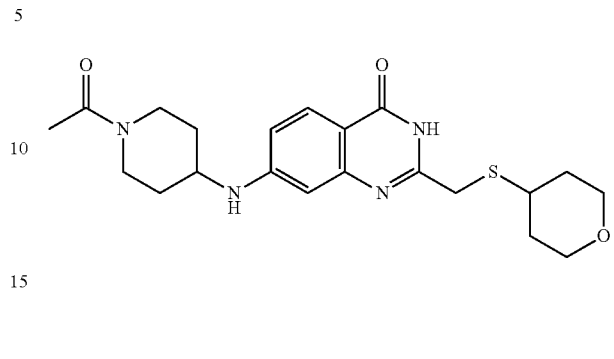

A solution of Example 30 (110 mg, 0.37 mmol, 1.0 eq) and 1-(4-aminopiperidin-1-yl)ethanone (53 mg, 0.37 mmol, 1.0 eq) in THF (10 mL) was heated at 120° C. in a sealed tube for 2 days. The mixture was allowed to cool to RT, diluted with water (20 mL) and extracted with EtOAc (30 mL×3). The combined organic layers were dried over Na$_2$SO$_4$ and concentrated under reduced pressure. The residue was purified by prep-TLC (DCM:MeOH, 10/1, v/v) to afford the title compound (20 mg, 12%) as a white solid. LCMS: [M+H]$^+$ 417.2.

$^1$H NMR (400 MHz, DMSO-d$_6$) δ 11.9 (s, 1H), 7.93-7.72 (m, 2H), 7.13 (dd, J=9.2, 2.4 Hz, 1H), 6.90-6.85 (m, 1H), 3.95-3.85 (m, 2H), 3.85-3.75 (m, 3H), 3.61 (s, 2H), 3.36-3.34 (m, 1H), 3.31-3.27 (m, 1H), 3.10-2.95 (m, 3H), 1.94-1.84 (m, 2H), 1.84-1.81 (m, 2H), 1.79 (s, 3H), 1.35-1.51 (m, 4H).

Example 132: 7-((1-Acetylpiperidin-3-yl)amino)-2-(((tetrahydro-2H-pyran-4-yl)thio) methyl)quinazolin-4(3H)-one

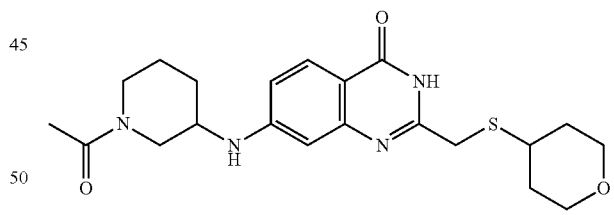

The title compound was prepared from the compound of Example 30 and 1-(3-aminopiperidin-1-yl)ethanone according to the method described for Example 131. LCMS: [M+H]$^+$ 417.2.

$^1$H NMR (400 MHz, DMSO-d$_6$) δ 11.8 (s, 1H), 7.90 (d, J=7.2 Hz, 1H), 7.84 (d, J=9.2 Hz, 1H), 7.09 (dd, J=9.2, 2.4 Hz, 1H), 6.86 (d, J=2.4 Hz, 1H), 3.86-3.72 (m, 4H), 3.72-3.65 (m, 1H), 3.60 (s, 2H), 3.34-3.27 (m, 2H), 3.09-2.96 (m, 2H), 2.86-2.76 (m, 1H), 1.93-1.81 (m, 3H), 1.87 (s, 3H), 1.79-1.72 (m, 1H), 1.56-1.38 (m, 4H).

Example 133: 7-((1-Methylpiperidin-3-yl)amino)-2-(((tetrahydro-2H-pyran-4-yl)thio) methyl)quinazolin-4(3H)-one

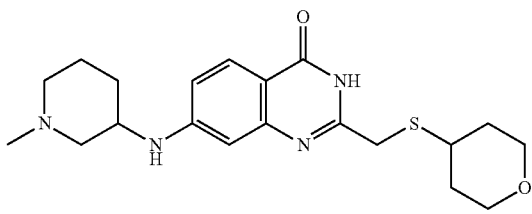 [SMILES: CN1CCCC(Nc2ccc3c(=O)[nH]c(CSC4CCOCC4)nc3c2)C1]

The title compound was prepared from the compound of Example 127 and formaldehyde according to the method described for Example 14. LCMS: [M+H]+ 389.2.

$^1$H NMR (400 MHz, CDCl$_3$) δ 9.85 (s, 1H), 7.59 (d, J=8.8 Hz, 1H), 6.68 (d, J=7.6 Hz, 1H), 6.64 (s, 1H), 3.92 (d, J=10.4 Hz, 2H), 3.85-3.78 (m, 1H), 3.75 (s, 2H), 3.36 (t, J=10.8 Hz, 2H), 2.93-2.83 (m, 2H), 2.80-2.63 (m, 2H), 2.44-2.25 (m, 4H), 1.97-1.85 (m, 4H), 1.66-1.54 (m, 4H).

Example 134: 7-((1-Acetylpyrrolidin-3-yl)amino)-2-(((tetrahydro-2H-pyran-4-yl)thio) methyl)quinazolin-4(3H)-one

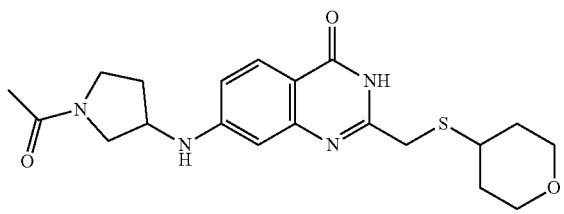 [SMILES: CC(=O)N1CCC(Nc2ccc3c(=O)[nH]c(CSC4CCOCC4)nc3c2)C1]

The title compound was prepared from the compound of Example 130 according to the method described for Example 17. LCMS: [M+H]+ 403.2.

$^1$H NMR (400 MHz, CD$_3$OD) δ 7.97-7.87 (m, 1H), 6.90-6.81 (m, 1H), 6.68 (s, 1H), 4.58 (s, 2H), 4.23 (m, 1H), 3.91 (m, 2H), 3.69 (s, 3H), 3.58 (t, J=7.2 Hz, 1H), 3.44 (m, 3H), 3.07-2.97 (m, 1H), 2.31 (m, 1H), 2.15-1.98 (m, 3H), 1.94 (m, 2H), 1.58 (m, 2H).

Example 135: 8-Methyl-7-phenoxy-2-(((tetrahydro-2H-pyran-4-yl)thio)methyl)quinazolin-4(3H)-one

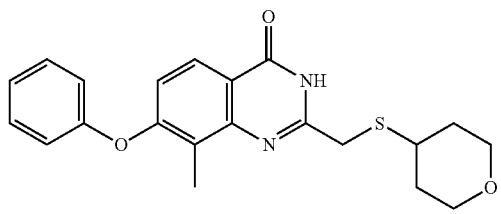 [SMILES: Cc1c(Oc2ccccc2)ccc2c(=O)[nH]c(CSC3CCOCC3)nc12]

To a solution of the compound of Example 33 (108 mg, 0.35 mmol, 1.0 eq) and PhOH (70 mg, 0.74 mmol, 2.1 eq) in DMSO (1 mL) under a N$_2$ atmosphere was added K$_2$CO$_3$ (99 mg, 0.72 mmol, 2.0 eq) and the mixture was heated at 120° C. overnight. The mixture was allowed to cool to RT, diluted with water (20 mL) and extracted with EtOAc (20 mL×3). The combined organic layers were dried over Na$_2$SO$_4$ and concentrated under reduced pressure. The residue was purified by prep-TLC (Petroleum ether:EtOAc, 5:1, v/v) followed by prep-HPLC (Agilent 10 prep-C18, 10 μm, 250×21.2 mm column, eluting with a gradient of ACN in water, at a flow rate of 20 mL/min) to afford the title compound (1 mg, 1%) as a white solid. LCMS: [M+H]+ 383.2.

$^1$H NMR (400 MHz, CD$_3$OD) δ 8.01 (d, J=8.8 Hz, 1H), 7.43-7.36 (m, 2H), 7.17 (t, J=7.2 Hz, 1H), 7.03-6.96 (m, 3H), 3.97-3.89 (m, 2H), 3.77 (s, 2H), 3.51-3.38 (m, 2H), 3.15-3.13 (m, 1H), 2.51 (s, 3H), 2.01 (d, J=11.6 Hz, 2H), 1.68-1.55 (m, 2H).

Example 136: 7-(Cyclohexylamino)-2-(((trans-4-(hydroxymethyl)cyclohexyl)thio)methyl) quinazolin-4(3H)-one and Example 137: 7-(Cyclohexylamino)-2-(((cis-4-(hydroxymethyl)cyclohexyl)thio) methyl) quinazolin-4(3H)-one Example 136

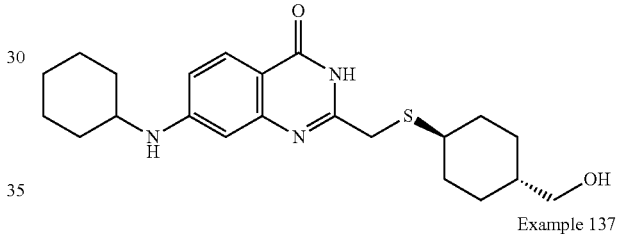

Example 137

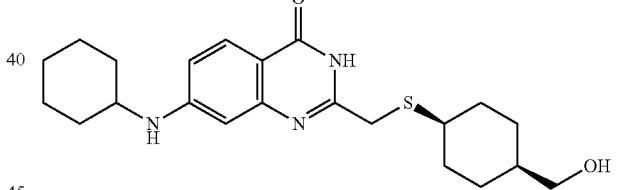

Step 1: 2-(((4-(((tert-Butyldimethylsilyl)oxy)methyl)cyclohexyl)thio)methyl)-7-fluoroquinazolin-4(3H)-one The title compound was prepared from Int-A9 and Int-B12 according to the method described for Example 28. LCMS: [M+H]+ 437.2.

Step 2: 7-(Cyclohexylamino)-2-(((4-(hydroxymethyl)cyclohexyl)thio)methyl)quinazolin-4(3H)-one The title compound was prepared from 2-(((4-(((tert-butyldimethylsilyl)oxy)methyl)cyclohexyl)thio)methyl)-7-fluoroquinazolin-4(3H)-one and cyclohexanamine according to the method described for Example 108. Loss of the TBS protecting group occurred in this reaction. LCMS: [M+H]+ 437.2.

Step 3: 7-(Cyclohexylamino)-2-(((trans-4-(hydroxymethyl)cyclohexyl)thio)methyl)quinazolin-4(3H)-one and 7-(Cyclohexylamino)-2-(((cis-4-(hydroxymethyl)cyclohexyl)thio)methyl)quinazolin-4(3H)-one 7-(Cyclohexylamino)-2-(((4-(hydroxymethyl)cyclohexyl)thio)methyl)quinazolin-4(3H)-one was purified by prep-HPLC (Agilent 10 prep-C18, 10 μm, 250×21.2 mm column, eluting with a gradient of MeOH in water with 0.1% TFA, at a flow rate of 20 mL/min) to afford the title compounds.

Example 136

LCMS: [M+H]$^+$ 402.2.
$^1$H NMR (400 MHz, CD$_3$OD) δ 7.84 (d, J=8.8 Hz, 1H), 6.78 (dd, J=8.8, 2.0 Hz, 1H), 6.60 (s, 1H), 3.66 (s, 2H), 3.39-3.32 (m, 3H), 2.71-2.61 (m, 1H), 2.12-2.01 (m, 4H), 1.87-1.77 (m, 4H), 1.74-1.66 (m, 1H), 1.49-1.37 (m, 3H), 1.31-1.21 (m, 5H), 1.05-0.96 (m, 2H).

Example 137

LCMS: [M+H]$^+$ 402.2.
$^1$H NMR (400 MHz, CD$_3$OD) δ 7.84 (d, J=8.8 Hz, 1H), 6.78 (dd, J=8.8, 2.4 Hz, 1H), 6.60 (s, 1H), 3.61 (s, 2H), 3.38 (m, 3H), 3.21-3.15 (m, 1H), 2.10-2.04 (m, 2H), 1.88-1.63 (m, 7H), 1.61-1.38 (m, 7H), 1.26-1.21 (m, 3H).

Example 138: 8-Methyl-2-(((1-((1-methyl-1H-imidazol-2-yl)methyl)piperidin-4-yl)thio) methyl)quinazolin-4(3H)-one bistrifluoroacetate

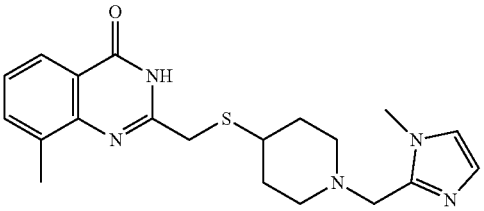

2 CF$_3$COOH

To a solution of Example 13 (53 mg, 0.17 mmol, 1.0 eq) and 1-methyl-1H-imidazole-2-carbaldehyde (28 mg, 0.25 mmol, 1.5 eq) in THF (2 mL) under a N$_2$ atmosphere was added NaBH(OAc)$_3$ (72 mg, 0.34 mmol, 2.0 eq) and the mixture was stirred at RT overnight. The mixture was purified by C18 reverse phase column (Biotage, 30% to 70% ACN in water, 0.1% TFA) to afford the title compound (22 mg, 34%) as a white solid. LCMS: [M+H]$^+$ 384.2.
$^1$H NMR (400 MHz, CDCl$_3$) δ 8.10 (d, J=8.4 Hz, 1H), 7.65 (d, J=7.2 Hz, 1H), 7.41 (s, 2H), 7.20 (s, 1H), 4.78 (s, 2H), 3.98 (s, 3H), 3.80 (s, 2H), 3.40 (m, 2H), 3.17-3.00 (m, 3H), 2.59 (s, 3H), 2.24 (m, 2H), 1.95 (m, 2H).

The following examples in Table 7 were similarly prepared from Example 13 and the appropriate aldehyde according to the method described for Example 138.

TABLE 7

| Example | Name and structure | Aldehyde |
|---|---|---|
| Example 139 | N-(4-((4-(((8-Methyl-4-oxo-3,4-dihydroquinazolin-2-yl)methyl)thio)piperidin-1-yl)methyl)phenyl)acetamide trifluoroacetate | N-(4-formylphenyl)acetamide |
| Example 140 | 2-(((1-(4-(Dimethylamino)benzyl)piperidin-4-yl)thio)methyl)-8-methylquinazolin-4(3H)-one trifluoroacetate | 4-(dimethylamino)benzaldehyde |

TABLE 7-continued

| Example | Name and structure | Aldehyde |
|---|---|---|
| Example 141 | 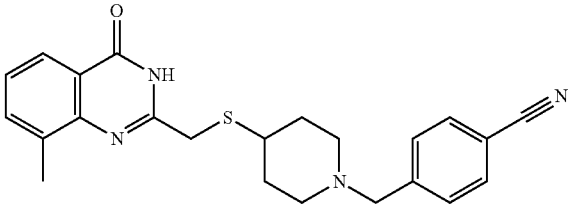<br>CF₃COOH<br><br>4-((4-(((8-Methyl-4-oxo-3,4-dihydroquinazolin-2-yl)methyl)thio)piperidin-1-yl)methyl)benzonitrile trifluoroacetate | 4-formylbenzonitrile |
| Example 142 | 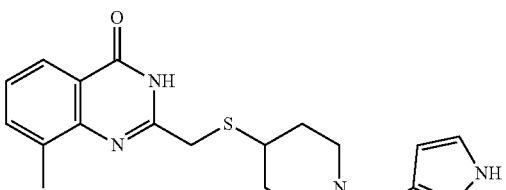<br>CF₃COOH<br><br>2-(((1-((1H-Pyrazol-3-yl)methyl)piperidin-4-yl)thio)methyl)-8-methylquinazolin-4(3H)-one trifluoroacetate | 1H-pyrazole-3-carbaldehyde |
| Example 143 | 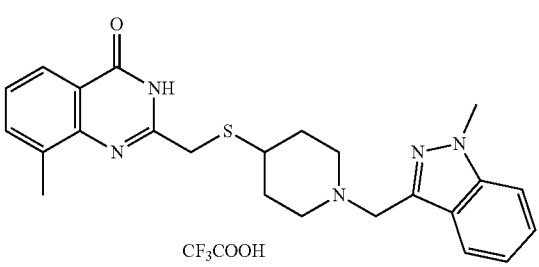 [SMILES: Cc1cccc2c(=O)[nH]c(CSC3CCN(Cc4nn(C)c5ccccc45)CC3)nc12 ; "CF3COOH"]<br>CF₃COOH<br><br>8-Methyl-2-(((1-((1-methyl-1H-indazol-3-yl)methyl)piperidin-4-yl)thio)methyl)quinazolin-4(3H)-one trifluoroacetate | 1-methyl-1H-indazole-3-carbaldehyde |
| Example 144 | 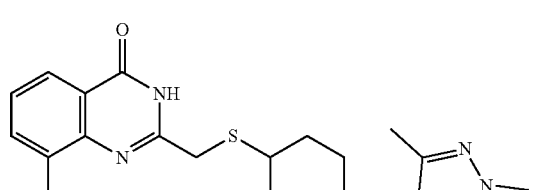<br>CF₃COOH<br><br>2-(((1-((1,3-Dimethyl-1H-pyrazol-4-yl)methyl)piperidin-4-yl)thio)methyl)-8-methylquinazolin-4(3H)-one trifluoroacetate | 1,3-dimethyl-1H-pyrazole-4-carbaldehyde |

TABLE 7-continued

| Example | Name and structure | Aldehyde |
|---|---|---|
| Example 145 | 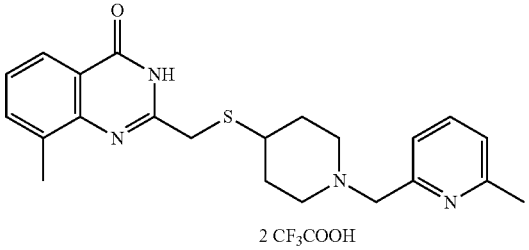 [SMILES: Cc1cccc(CN2CCC(SCc3nc4c(C)cccc4c(=O)[nH]3)CC2)n1]<br>2 CF₃COOH<br>8-Methyl-2-(((1-((6-methylpyridin-2-yl)methyl)piperidin-4-yl)thio)methyl)quinazolin-4(3H)-one bistrifluoroacetate | 6-methylpicolinaldehyde |
| Example 146 | 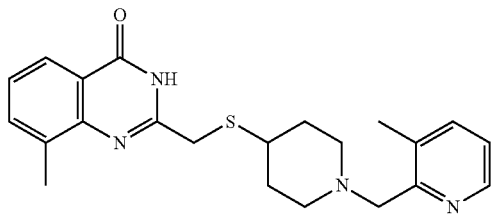<br>2 CF₃COOH<br>8-Methyl-2-(((1-((3-methylpyridin-2-yl)methyl)piperidin-4-yl)thio)methyl)quinazolin-4(3H)-one bistrifluoroacetate | 3-methylpicolinaldehyde |
| Example 147 | 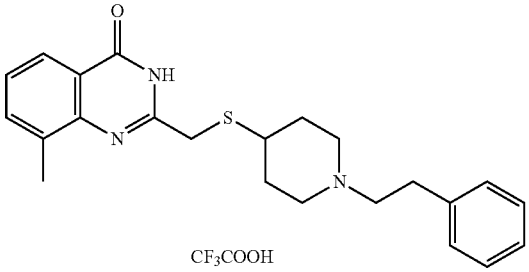 [SMILES: Cc1cccc2c(=O)[nH]c(CSC3CCN(CCc4ccccc4)CC3)nc12 ; "CF3COOH"]<br>CF₃COOH<br>8-Methyl-2-(((1-phenethylpiperidin-4-yl)thio)methyl)quinazolin-4(3H)-one trifluoroacetate | 2-phenylacetaldehyde |
| Example 148 | 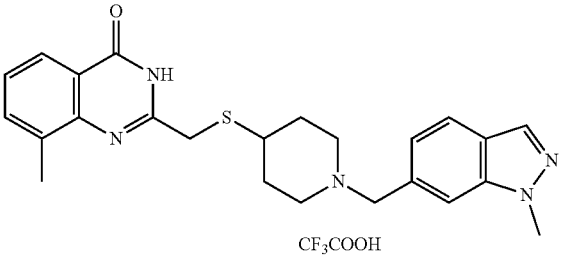 [SMILES: Cc1cccc2c(=O)[nH]c(CSC3CCN(Cc4ccc5cnn(C)c5c4)CC3)nc12 ; "CF3COOH"]<br>CF₃COOH<br>8-Methyl-2-(((1-((1-methyl-1H-indazol-6-yl)methyl)piperidin-4-yl)thio)methyl)quinazolin-4(3H)-one trifluoroacetate | 1-methyl-1H-indazole-5-carbaldehyde |

TABLE 7-continued

| Example | Name and structure | Aldehyde |
|---|---|---|
| Example 149 | 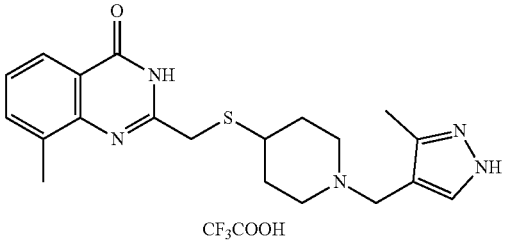 [SMILES: Cc1n[nH]cc1CN1CCC(SCc2nc3c(C)cccc3c(=O)[nH]2)CC1 ; "CF3COOH"]<br>CF₃COOH<br><br>8-Methyl-2-(((1-((3-methyl-1H-pyrazol-4-yl)methyl)piperidin-4-yl)thio)methyl)quinazolin-4(3H)-one trifluoroacetate | 3-methyl-1H-pyrazole-4-carbaldehyde |
| Example 150 | 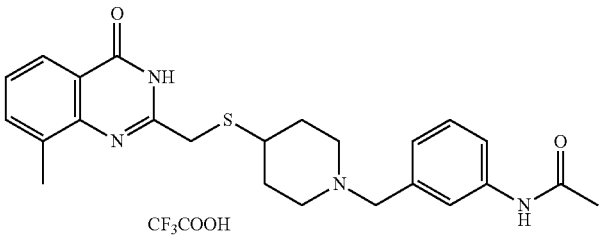 [SMILES: CC(=O)Nc1cccc(CN2CCC(SCc3nc4c(C)cccc4c(=O)[nH]3)CC2)c1 ; "CF3COOH"]<br>CF₃COOH<br><br>N-(3-((4-(((8-Methyl-4-oxo-3,4-dihydroquinazolin-2-yl)methyl)thio)piperidin-1-yl)methyl)phenyl)acetamide trifluoroacetate | N-(3-formylphenyl)acetamide |
| Example 151 | 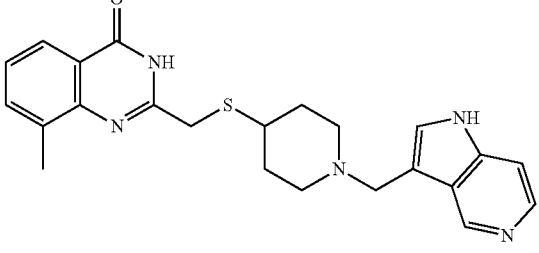<br>2 CF₃COOH<br><br>2-(((1-((1H-Pyrrolo[3,2-c]pyridin-3-yl)methyl)piperidin-4-yl)thio)methyl)-8-methylquinazolin-4(3H)-one bistrifluoroacetate | 1H-pyrrolo[3,2-c]pyridine-3-carbaldehyde |
| Example 152 | 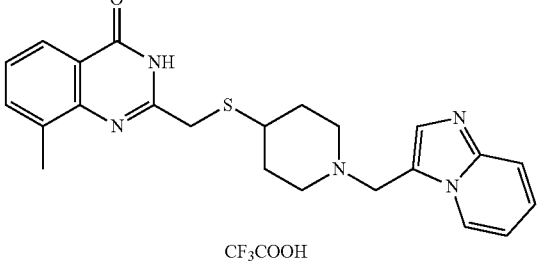<br>CF₃COOH<br><br>2-(((1-(Imidazo[1,2-a]pyridin-3-ylmethyl)piperidin-4-yl)thio)methyl)-8-methylquinazolin-4(3H)-one trifluoroacetate | imidazo[1,2-a]pyridine-3-carbaldehyde |

TABLE 7-continued

| Example | Name and structure | Aldehyde |
|---|---|---|
| Example 153 | 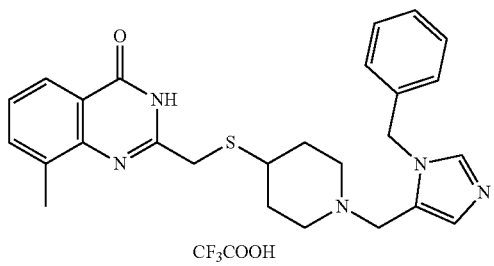 [SMILES: Cc1cccc2c(=O)[nH]c(CSC3CCN(Cc4cncn4Cc4ccccc4)CC3)nc12 ; "CF3COOH"]<br>CF₃COOH<br>2-(((1-((1-Benzyl-1H-imidazol-5-yl)methyl)piperidin-4-yl)thio)methyl)-8-methylquinazolin-4(3H)-one trifluoroacetate | 1-benzyl-1H-imidazole-5-carbaldehyde |
| Example 154 | 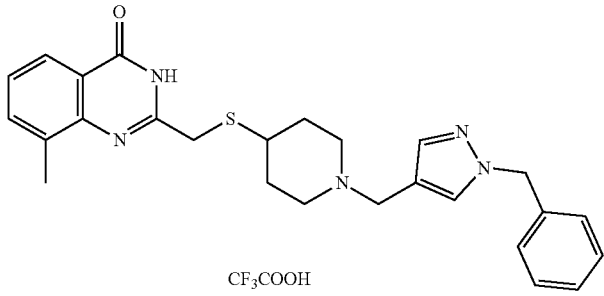 [SMILES: Cc1cccc2c(=O)[nH]c(CSC3CCN(Cc4cnn(Cc5ccccc5)c4)CC3)nc12 ; "CF3COOH"]<br>CF₃COOH<br>2-(((1-((1-Benzyl-1H-pyrazol-4-yl)methyl)piperidin-4-yl)thio)methyl)-8-methylquinazolin-4(3H)-one trifluoroacetate | 1-benzyl-1H-pyrazole-4-carbaldehyde |
| Example 155 | 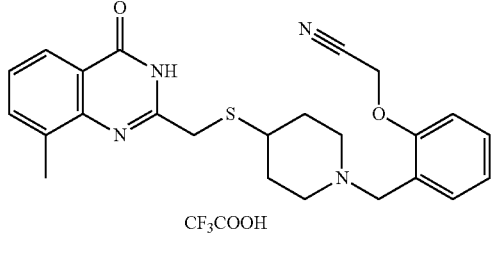 [SMILES: Cc1cccc2c(=O)[nH]c(CSC3CCN(Cc4ccccc4OCC#N)CC3)nc12 ; "CF3COOH"]<br>CF₃COOH<br>2-(2-((4-(((8-Methyl-4-oxo-3,4-dihydroquinazolin-2-yl)methyl)thio)piperidin-1-yl)methyl)phenoxy)acetonitrile trifluoroacetate | 2-(2-formyl-phenoxy)acetonitrile |
| Example 156 | 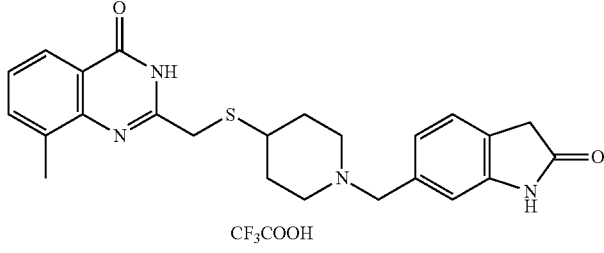 [SMILES: Cc1cccc2c(=O)[nH]c(CSC3CCN(Cc4ccc5c(c4)NC(=O)C5)CC3)nc12 ; "CF3COOH"]<br>CF₃COOH<br>8-Methyl-2-(((1-((2-oxoindolin-6-yl)methyl)piperidin-4-yl)thio)methyl)quinazolin-4(3H)-one trifluoroacetate | 2-oxoindoline-6-carbaldehyde |

TABLE 7-continued

| Example | Name and structure | Aldehyde |
|---|---|---|
| Example 157 | 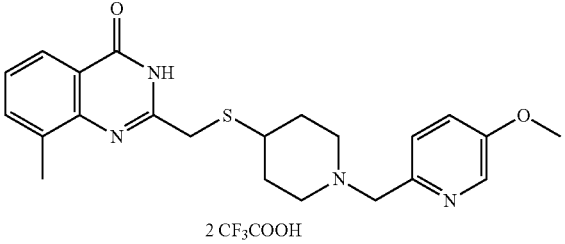 [SMILES: COc1ccc(CN2CCC(SCc3nc4c(C)cccc4c(=O)[nH]3)CC2)nc1 ; "2 CF3COOH"]<br>2 CF$_3$COOH<br>2-(((1-((5-Methoxypyridin-2-yl)methyl)piperidin-4-yl)thio)methyl)-8-methylquinazolin-4(3H)-one bistrifluoroacetate | 5-methoxypicolinaldehyde |
| Example 158 | 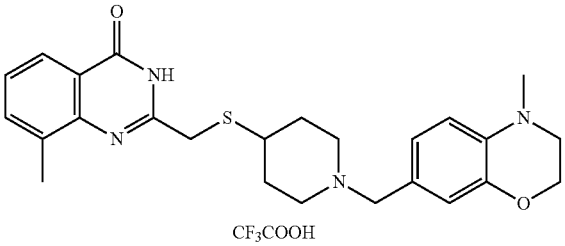 [SMILES: Cc1cccc2c(=O)[nH]c(CSC3CCN(Cc4ccc5c(c4)OCCN5C)CC3)nc12 ; "CF3COOH"]<br>CF$_3$COOH<br>8-Methyl-2-(((1-((4-methyl-3,4-dihydro-2H-benzo[b][1,4]oxazin-7-yl)methyl)piperidin-4-yl)thio)methyl)quinazolin-4(3H)-one trifluoroacetate | 4-methyl-3,4-dihydro-2H-benzo[b][1,4]oxazine-7-carbaldehyde |

Example 159: (S)-2-(((1-(2,3-Dihydroxypropyl)piperidin-4-yl)thio)methyl)-8-methyl quinazolin-4(3H)-one Trifluoroacetate

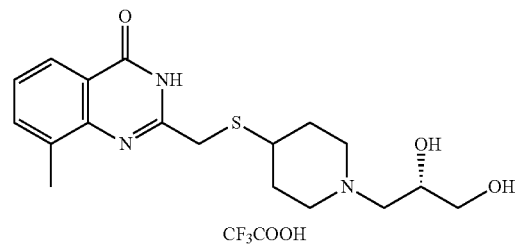 [SMILES: Cc1cccc2c(=O)[nH]c(CSC3CCN(C[C@H](O)CO)CC3)nc12 ; "CF3COOH"]

CF$_3$COOH

The title compound was prepared from the compound of Example 13 and (R)-2,2-dimethyl-1,3-dioxolane-4-carbaldehyde according to the method described for Example 138. Purification by C18 reverse phase column (Biotage, 40% to 60% ACN in water, 0.1% TFA) resulted in loss of the protecting group and gave the title compound directly. LCMS: [M+H]$^+$ 364.2.

$^1$H NMR (400 MHz, CD$_3$OD) δ 8.04 (d, J=8.0 Hz, 1H), 7.67 (d, J=7.2 Hz, 1H), 7.40 (t, J=7.6 Hz, 1H), 4.06-3.97 (m, 1H), 3.85-3.77 (m, 2H), 3.74-3.61 (m, 2H), 3.59-3.38 (m, 3H), 3.22-2.94 (m, 4H), 2.60 (s, 3H), 2.45-1.99 (m, 2H), 1.92-1.75 (m, 2H).

Example 160: (R)-2-(((1-(2,3-Dihydroxypropyl)piperidin-4-yl)thio)methyl)-8-methyl quinazolin-4(3H)-one Trifluoroacetate

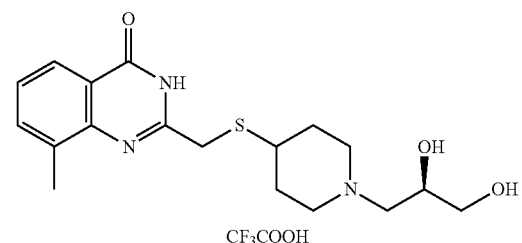

CF$_3$COOH

The title compound was prepared from Example 13 and (S)-2,2-dimethyl-1,3-dioxolane-4-carbaldehyde according to the method described for Example 138. Purification by C$_{18}$ reverse phase column (Biotage, 40% to 60% ACN in water, 0.1% TFA) resulted in loss of the protecting group and gave the title compound directly. LCMS: [M+H]$^+$ 364.2;

$^1$H NMR (400 MHz, CD$_3$OD) δ 8.04 (d, J=8.0 Hz, 1H), 7.67 (d, J=7.2 Hz, 1H), 7.40 (t, J=7.6 Hz, 1H), 4.06-3.97 (m, 1H), 3.85-3.77 (m, 2H), 3.74-3.61 (m, 2H), 3.59-3.38 (m, 3H), 3.22-2.94 (m, 4H), 2.60 (s, 3H), 2.45-1.99 (m, 2H), 1.92-1.75 (m, 2H).

Example 161: (S)-8-Methyl-2-(((1-(pyrrolidin-2-ylmethyl)piperidin-4-yl)thio)methyl) quinazolin-4(3H)-one Hydrochloride

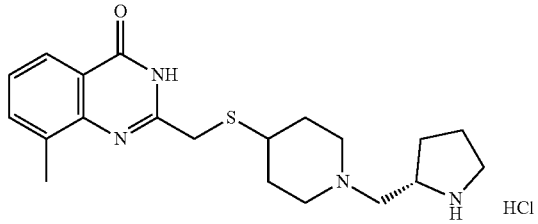 [SMILES: Cc1cccc2c(=O)[nH]c(CSC3CCN(C[C@@H]4CCCN4)CC3)nc12 ; Cl]

Step 1: (S)-tert-Butyl 2-((4-(((8-methyl-4-oxo-3,4-dihydroquinazolin-2-yl)methyl)thio)piperidin-1-yl)methyl)pyrrolidine-1-carboxylate The title compound was prepared from the compound of Example 13 and (S)-tert-butyl 2-formylpyrrolidine-1-carboxylate according to the method described for Example 138. LCMS: [M+H−56]$^+$417.3.

Step 2: (S)-8-Methyl-2-(((1-(pyrrolidin-2-ylmethyl)piperidin-4-yl)thio)methyl)quinazolin-4(3H)-one Hydrochloride The title compound was prepared from (S)-tert-butyl 2-((4-(((8-methyl-4-oxo-3,4-dihydroquinazolin-2-yl)methyl)thio) piperidin-1-yl)methyl)pyrrolidine-1-carboxylate according to the method described for Example 48, step 2. LCMS: [M+H]$^+$ 373.2.
$^1$H NMR (400 MHz, CD$_3$OD) δ 8.09 (d, J=7.6 Hz, 1H), 7.65 (d, J=7.2 Hz, 1H), 7.50 (t, J=7.2 Hz, 1H), 4.16 (m, 1H), 3.83 (m, 1H), 3.68 (t, J=4.8 Hz, 2H), 3.63 (m, 2H), 3.56 (t, J=4.8 Hz, 2H), 3.42 (m, 2H), 3.20 (m, 2H), 2.65 (s, 3H), 2.40 (m, 3H), 2.14-1.90 (m, 4H), 1.82 (m, 1H).

Example 162: 2-(((1-(2-Hydroxyethyl)piperidin-4-yl)thio)methyl)-8-methylquinazolin-4(3H)-one

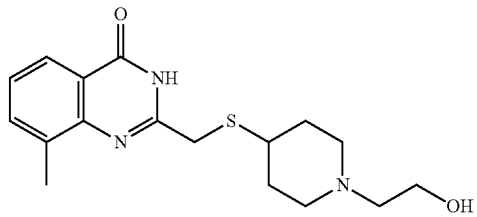 [SMILES: Cc1cccc2c(=O)[nH]c(CSC3CCN(CCO)CC3)nc12]

The title compound was prepared from the compound of Example 13 and 2-((tert-butyldimethylsilyl)oxy)acetaldehyde according to the method described for Example 138. Purification by prep-TLC (DCM:MeOH, 10:1, v/v) resulted in loss of the protecting group and gave the title compound directly. LCMS: [M+H]$^+$ 334.2.
$^1$H NMR (400 MHz, CD$_3$OD) δ 8.02 (d, J=8.0 Hz, 1H), 7.65 (d, J=7.2 Hz, 1H), 7.37 (t, J=7.6 Hz, 1H), 3.75 (s, 2H), 3.71 (t, J=5.6 Hz, 2H), 3.10 (d, J=12.0 Hz, 2H), 3.00-2.89 (m, 1H), 2.70 (t, J=5.6 Hz, 2H), 2.58 (s, 3H), 2.49-2.36 (m, 2H), 2.18-2.08 (m, 2H), 1.78-1.63 (m, 2H).

Example 163: 2-(((1-(2-Aminoethyl)piperidin-4-yl)thio)methyl)-8-methylquinazolin-4(3H)-one dihydrochloride

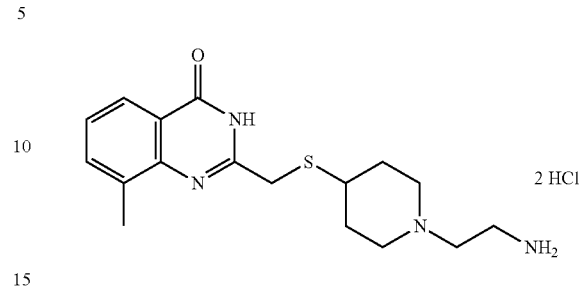

Step 1: tert-Butyl (2-(4-(((8-methyl-4-oxo-3,4-dihydroquinazolin-2-yl)methyl)thio)piperidin-1-yl) ethyl)carbamate The title compound was prepared from the compound of Example 13 and tert-butyl (2-oxoethyl)carbamate according to the method described for Example 138. LCMS: [M+H]$^+$ 433.2

Step 2: 2-(((1-(2-Aminoethyl)piperidin-4-yl)thio)methyl)-8-methylquinazolin-4(3H)-one dihydrochloride The title compound was prepared from tert-butyl (2-(4-(((8-methyl-4-oxo-3,4-dihydroquinazolin-2-yl)methyl)thio)piperidin-1-yl)ethyl)carbamate according to the method described for Example 48, step 2. LCMS: [M+H]$^+$ 333.2.
$^1$H NMR (400 MHz, CD$_3$OD) δ 8.11 (d, J=7.6 Hz, 1H), 7.77 (d, J=6.8 Hz, 1H), 7.53 (t, J=7.6 Hz, 1H), 3.71 (d, J=11.2 Hz, 2H), 3.58-3.42 (m, 6H), 3.27-3.08 (m, 3H), 2.65 (s, 3H), 2.47-2.34 (m, 2H), 2.12-1.92 (m, 2H).

Example 164: N-(2-(4-(((8-Methyl-4-oxo-3,4-dihydroquinazolin-2-yl)methyl)thio)piperidin-1-yl)ethyl) picolinamide

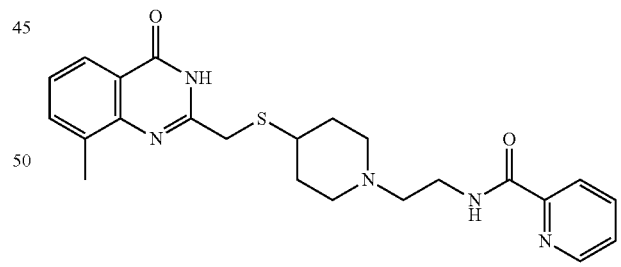

To a solution of the compound of Example 163 (40 mg, 0.12 mmol, 1.0 eq), picolinic acid (16 mg, 0.13 mmol, 1.1 eq) and DIPEA (47 mg, 0.36 mmol, 3.0 eq) in DCM (3 mL) at RT under a N$_2$ atmosphere was added EDCI (25 mg, 0.13 mmol, 1.1 eq) and HOBt (18 mg, 0.13 mmol, 1.1 eq) and the mixture was stirred overnight. The mixture was diluted with water (40 mL), extracted with EtOAc (20 mL×3) and the combined organic layers were washed with water (15 mL), dried over Na$_2$SO$_4$ and concentrated under reduced pressure. The residue was purified by prep-TLC (DCM: MeOH, 10:1, v/v) to afford the title compound (10 mg, 17%) as a white solid. LCMS: [M+H]$^+$ 438.2.

$^1$H NMR (400 MHz, CD$_3$OD) δ 8.62 (d, J=4.0 Hz, 1H), 8.08 (d, J=7.6 Hz, 1H), 8.03 (d, J=7.6 Hz, 1H), 7.98-7.92 (m, 1H), 7.65 (d, J=7.2 Hz, 1H), 7.57-7.51 (m, 1H), 7.38 (t, J=7.6 Hz, 1H), 3.75 (s, 2H), 3.58 (t, J=6.4 Hz, 2H), 3.10-3.00 (m, 2H), 2.96-2.85 (m, 1H), 2.69 (t, J=6.4 Hz, 2H), 2.57 (s, 3H), 2.29 (m, 2H), 2.11 (m, 2H), 1.72-1.60 (m, 2H).

Example 165: 2-(((1-(3-Aminopropyl)piperidin-4-yl)thio)methyl)-8-methylquinazolin-4(3H)-one dihydrochloride

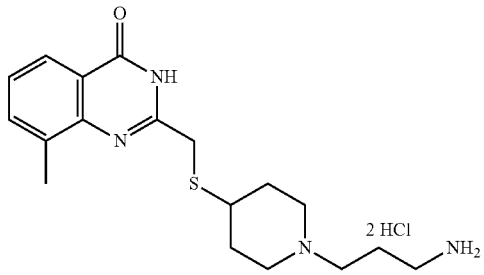 [SMILES: Cc1cccc2c(=O)[nH]c(CSC3CCN(CCCN)CC3)nc12]

Step 1: tert-Butyl (3-(4-(((8-methyl-4-oxo-3,4-dihydroquinazolin-2-yl)methyl)thio)piperidin-1-yl) propyl)carbamate The title compound was prepared from the compound of Example 13 and tert-butyl (3-oxopropyl)carbamate according to the method described for Example 138. LCMS: [M+H]$^+$ 447.2.

Step 2: 2-(((1-(3-Aminopropyl)piperidin-4-yl)thio)methyl)-8-methylquinazolin-4(3H)-one dihydrochloride The title compound was prepared from tert-butyl (3-(4-(((8-methyl-4-oxo-3,4-dihydroquinazolin-2-yl)methyl)thio)piperidin-1-yl)propyl)carbamate according to the method described for Example 48, step 2. LCMS: [M+H]$^+$ 347.2.

$^1$H NMR (400 MHz, CD$_3$OD) δ 8.01 (d, J=7.6 Hz, 1H), 7.63 (d, J=7.2 Hz, 1H), 7.36 (t, J=8.0 Hz, 1H), 3.73 (s, 2H), 2.97-2.69 (m, 5H), 2.56 (s, 3H), 2.39 (t, J=8.0 Hz, 2H), 2.12-1.99 (m, 4H), 1.76-1.52 (m, 4H).

Example 166: 2-(((1-Glycylpiperidin-4-yl)thio)methyl)-8-methylquinazolin-4(3H)-one Hydrochloride

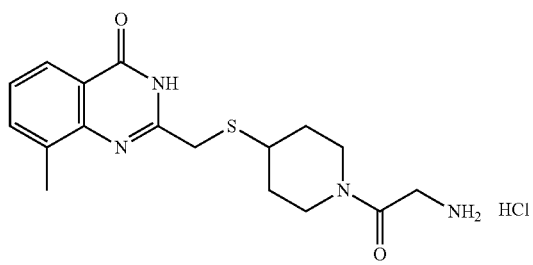 [SMILES: Cc1cccc2c(=O)[nH]c(CSC3CCN(C(=O)CN)CC3)nc12 ; Cl]

Step 1: tert-Butyl (2-(4-(((8-Methyl-4-oxo-3,4-dihydroquinazolin-2-yl)methyl)thio)piperidin-1-yl)-2-oxoethyl)carbamate To a solution of 2-((tert-butoxycarbonyl)amino)acetic acid (36 mg, 0.20 mmol, 1.1 eq) and DIPEA (72 mg, 0.55 mmol, 3.0 eq) in NMP (5 mL) at RT under a N$_2$ atmosphere was added HATU (105 mg, 0.28 mmol, 1.5 eq) and the mixture was stirred for 1 h before adding Example 13 (60 mg, 0.19 mmol, 1.0 eq). The mixture was stirred at RT overnight and then diluted with water (10 mL) and extracted with EtOAc (30 mL×3). The combined organic layers were dried over Na$_2$SO$_4$ and concentrated under reduced pressure. The residue was purified by column chromatography (Petroleum ether:EtOAc, 3:1, v/v) to afford the title compound (50 mg, 61%) as a yellow solid. LCMS: [M+H]$^+$ 447.2.

Step 2: 2-(((1-Glycylpiperidin-4-yl)thio)methyl)-8-methylquinazolin-4(3H)-one Hydrochloride The title compound was prepared from tert-butyl (2-(4-(((8-methyl-4-oxo-3,4-dihydroquinazolin-2-yl)methyl)thio)piperidin-1-yl)-2-oxoethyl)carbamate according to the method described for Example 48, step 2. LCMS: [M+H]$^+$ 347.2.

$^1$H NMR (400 MHz, CD$_3$OD) δ 8.11 (d, J=8.0 Hz, 1H), 7.77 (s, 1H), 7.56-7.48 (m, 1H), 4.29 (m, 1H), 4.04-3.85 (m, 3H), 3.71 (m, 1H), 3.36-3.34 (m, 1H), 3.26-3.16 (m, 2H), 3.02 (t, J=12.1 Hz, 1H), 2.65 (s, 3H), 2.18-2.16 (m, 2H), 1.69-1.46 (m, 2H).

Example 167: 2-(((1-(3-Aminopropanoyl)piperidin-4-yl)thio)methyl)-8-methylquinazolin-4(3H)-one Hydrochloride

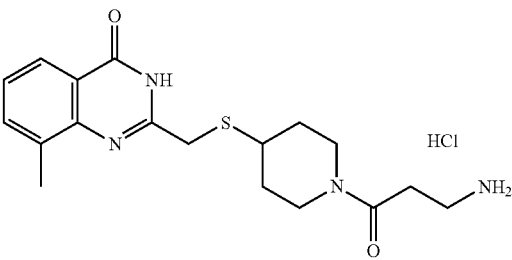 [SMILES: Cc1cccc2c(=O)[nH]c(CSC3CCN(C(=O)CCN)CC3)nc12 ; Cl]

The title compound was prepared from the compound of Example 13 and 3-((tert-butoxycarbonyl)amino)propanoic acid according to the method described for Example 166. LCMS: [M+H]$^+$ 361.2.

$^1$H NMR (400 MHz, CD$_3$OD) δ 8.03 (d, J=7.6 Hz, 1H), 7.66 (d, J=7.2 Hz, 1H), 7.39 (t, J=7.6 Hz, 1H), 4.34-4.26 (m, 1H), 3.87-3.75 (m, 3H), 3.22-3.10 (m, 4H), 2.97-2.88 (m, 1H), 2.74 (t, J=12.4 Hz, 2H), 2.59 (s, 3H), 2.16-2.05 (m, 2H), 1.61-1.44 (m, 2H).

Example 168: 2-(((1-(3-(Dimethylamino)propanoyl) piperidin-4-yl)thio)methyl)-8-methyl quinazolin-4 (3H)-one

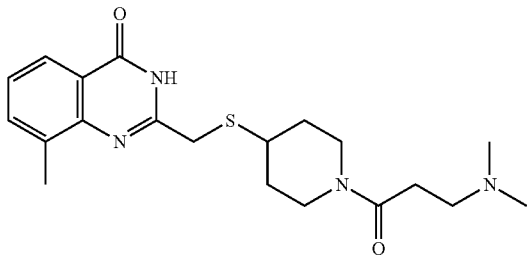 [SMILES: Cc1cccc2c(=O)[nH]c(CSC3CCN(C(=O)CCN(C)C)CC3)nc12]

The title compound was prepared from the compound of Example 167 and formaldehyde according to the method described for Example 14. LCMS: [M+H]⁺ 389.2.

¹H NMR (400 MHz, CDCl₃) δ 8.12 (d, J=7.6 Hz, 1H), 7.64 (d, J=7.2 Hz, 1H), 7.40 (t, J=7.6 Hz, 1H), 4.26 (m, 1H), 3.82 (s, 2H), 3.77 (m, 1H), 3.22-3.05 (m, 2H), 3.04-2.90 (m, 5H), 2.88 (s, 6H), 2.59 (s, 3H), 2.14-1.95 (m, 2H), 1.69-1.47 (m, 2H).

Example 169: (R)-1-(4-Amino-5-(4-(((8-methyl-4-oxo-3,4-dihydroquinazolin-2-yl) methyl)thio)piperidin-1-yl)-5-oxopentyl)guanidine Trihydrochloride

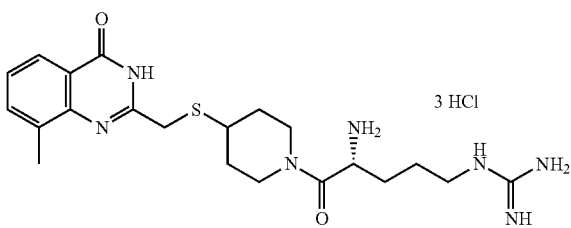 [SMILES: Cc1cccc2c(=O)[nH]c(CSC3CCN(C(=O)[C@H](N)CCCNC(=N)N)CC3)nc12]

Step 1: (R)-tert-Butyl (5-guanidino-1-(4-(((8-methyl-4-oxo-3,4-dihydroquinazolin-2-yl)methyl) thio) piperidin-1-yl)-1-oxopentan-2-yl)carbamate To a solution of the compound of Example 13 (100 mg, 0.33 mmol, 1.0 eq), (R)-2-((tert-butoxycarbonyl)amino)-5-guanidinopentanoic acid (93 mg, 0.33 mmol, 1.0 eq) and DIPEA (213 mg, 1.65 mmol, 5.0 eq) in DMF (4 mL) at RT under a N₂ atmosphere was added BOP (146 mg, 0.36 mmol, 1.1 eq) and the mixture was stirred for 5 h. The mixture was diluted with water (40 mL), extracted with EtOAc (30 mL×3) and the combined organic layers were dried over Na₂SO₄ and concentrated under reduced pressure. The residue was purified by prep-TLC (DCM: MeOH, 10:1, v/v) to afford the title compound (85 mg, 52%) as a white solid. LCMS: [M+H]⁺ 546.3.

Step 2: (R)-1-(4-Amino-5-(4-(((8-methyl-4-oxo-3,4-dihydroquinazolin-2-yl)methyl)thio) piperidin-1-yl)-5-oxopentyl)guanidine Trihydrochloride The title compound was prepared from (R)-tert-butyl (5-guanidino-1-(4-(((8-methyl-4-oxo-3,4-dihydroquinazolin-2-yl) methyl)thio)piperidin-1-yl)-1-oxopentan-2-yl)carbamate according to the method described for Example 48, step 2. LCMS: [M+H]⁺ 446.3;

¹H NMR (400 MHz, CD₃OD) δ 8.12 (d, J=8.0 Hz, 1H), 7.81-7.76 (m, 1H), 7.58-7.50 (m, 1H), 4.55-4.45 (m, 1H), 4.42-4.17 (m, 1H), 3.92 (m, 1H), 3.34-3.18 (m, 6H), 3.23-2.96 (m, 1H), 2.66 (d, J=4.0 Hz, 3H), 2.25-2.11 (m, 2H), 1.89 (m, 2H), 1.77-1.46 (m, 4H).

Example 170: (S)-1-(4-Amino-5-(4-(((8-methyl-4-oxo-3,4-dihydroquinazolin-2-yl)methyl) thio)piperidin-1-yl)-5-oxopentyl)guanidine Trihydrochloride

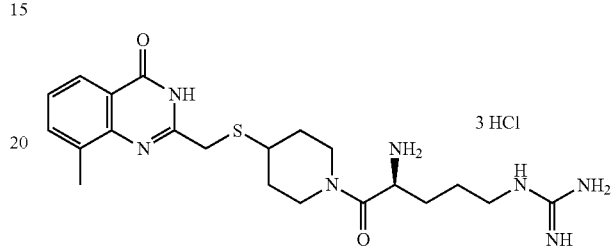

The title compound was prepared from the compound of Example 13 and (S)-2-((tert-butoxycarbonyl)amino)-5-guanidinopentanoic acid according to the method described for Example 169. LCMS: [M+H]⁺ 446.3.

¹H NMR (400 MHz, CD₃OD) δ 8.12-8.04 (m, 1H), 7.78-7.70 (m, 1H), 7.54-7.43 (m, 1H), 4.55-4.45 (m, 1H), 4.42-4.17 (m, 1H), 3.92 (m, 1H), 3.34-3.18 (m, 6H), 3.23-2.96 (m, 1H), 2.66 (br s, 3H), 2.26-2.07 (m, 2H), 1.85 (m, 2H), 1.75-1.45 (m, 4H).

Example 171: 2-(((1-(L-Lysyl)piperidin-4-yl)thio) methyl)-8-methylquinazolin-4(3H)-one Dihydrochloride

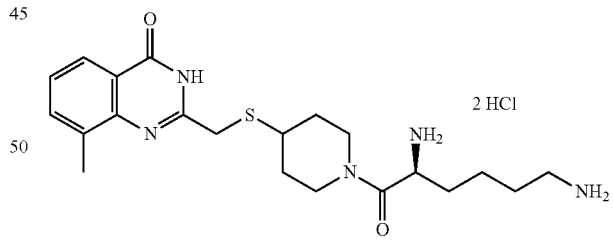

The title compound was prepared from the compound of Example 13 and (S)-2,6-bis((tert-butoxycarbonyl)amino) hexanoic acid according to the method described for Example 166.

LCMS: [M+H]⁺ 418.2.

¹H NMR (400 MHz, DMSO-d₆) δ 12.5 (br s, 1H), 8.30 (s, 3H), 8.17 (s, 3H), 7.93 (d, J=7.6 Hz, 1H), 7.66 (d, J=7.2 Hz, 1H), 7.38 (t, J=7.6 Hz, 1H), 4.41-4.27 (m, 1H)), 4.27-4.05 (m, 1H), 3.91-3.78 (m, 1H), 3.76 (s, 2H), 3.25-3.11 (m, 2H), 3.03-2.77 (m, 1H), 2.80-2.66 (m, 2H), 2.51 (s, 3H), 2.13-1.99 (m, 2H), 1.73-1.61 (m, 2H), 1.57-1.27 (m, 6H).

Example 172: 2-(((1-(D-Lysyl)piperidin-4-yl)thio)methyl)-8-methylquinazolin-4(3H)-one Dihydrochloride

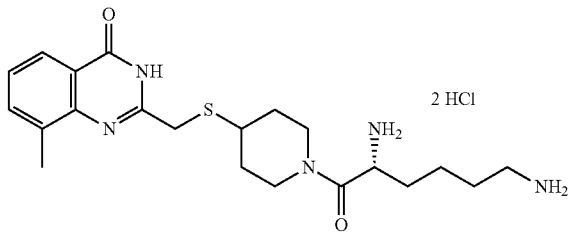 [SMILES: Cc1cccc2c(=O)[nH]c(CSC3CCN(C(=O)[C@H](N)CCCCN)CC3)nc12]

The title compound was prepared from the compound of Example 13 and (R)-2,6-bis((tert-butoxycarbonyl)amino)hexanoic acid according to the method described for Example 166. LCMS: [M+H]+ 418.2.

$^1$H NMR (400 MHz, CD$_3$OD) δ 8.14 (d, J=7.6 Hz, 1H), 7.83 (dd, J=3.2, 1.2 Hz, 1H), 7.66-7.53 (m, 1H), 4.57-4.11 (m, 3H), 4.03-3.82 (m, 1H), 3.35 (s, 2H), 3.22-2.90 (m, 3H), 2.70 (s, 3H), 2.32-2.09 (m, 2H), 1.96-1.42 (m, 9H);

$^1$H NMR (400 MHz, DMSO-d$_6$) δ 12.5 (br s, 1H), 8.30 (s, 3H), 8.17 (s, 3H), 7.93 (d, J=7.6 Hz, 1H), 7.66 (d, J=7.2 Hz, 1H), 7.38 (t, J=7.6 Hz, 1H), 4.41-4.27 (m, 1H)), 4.27-4.05 (m, 1H), 3.91-3.78 (1H, obscured by water peak), 3.76 (2H, obscured by water peak), 3.25-3.11 (m, 2H), 3.03-2.77 (m, 1H), 2.80-2.66 (m, 2H), 2.51 (s, 3H), 2.13-1.99 (m, 2H), 1.73-1.61 (m, 2H), 1.57-1.27 (m, 6H).

Example 173: 8-Methyl-2-(((1-(3-(pyridin-2-yl)propanoyl)piperidin-4-yl)thio)methyl) quinazolin-4(3H)-one

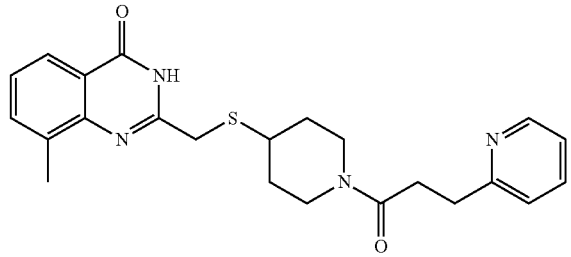 [SMILES: Cc1cccc2c(=O)[nH]c(CSC3CCN(C(=O)CCc4ccccn4)CC3)nc12]

To a solution of the compound of Example 13 (50 mg, 0.15 mmol, 1.0 eq), 3-(pyridin-2-yl)propanoic acid (23 mg, 0.15 mmol, 1.0 eq) and Et$_3$N (46 mg, 0.46 mmol, 3.0 eq) in DMF (3 mL) at RT under a N$_2$ atmosphere was added PyBOP (96 mg, 0.18 mmol, 1.2 eq) and the mixture was stirred for 4 h. The mixture was diluted with water (40 mL), extracted with EtOAc (30 mL×3) and the combined organic layers were dried over Na$_2$SO$_4$ and concentrated under reduced pressure. The residue was purified by prep-TLC (DCM:MeOH, 10:1, v/v) to afford the title compound (16 mg, 25%) as a white solid. LCMS: [M+H]+ 423.2.

$^1$H NMR (400 MHz, CDCl$_3$) δ 10.2 (br s, 1H), 8.52 (d, J=4.8 Hz, 1H), 8.12 (d, J=8.0 Hz, 1H), 7.71-7.63 (m, 1H), 7.61 (d, J=7.2 Hz, 1H), 7.37 (t, J=7.6 Hz, 1H), 7.30 (d, J=8.0 Hz, 1H), 7.18 (dd, J=7.6, 5.2 Hz, 1H), 4.33 (m, 1H), 3.85 (m, 1H), 3.79 (s, 2H), 3.20-3.13 (m, 2H), 3.07 (m, 1H), 2.96-2.77 (m, 4H), 2.58 (s, 3H), 2.03-1.95 (m, 2H), 1.56-1.43 (m, 2H).

Example 174: 8-Methyl-2-(((1-(methylsulfonyl)piperidin-4-yl)thio)methyl)quinazolin-4(3H)-one

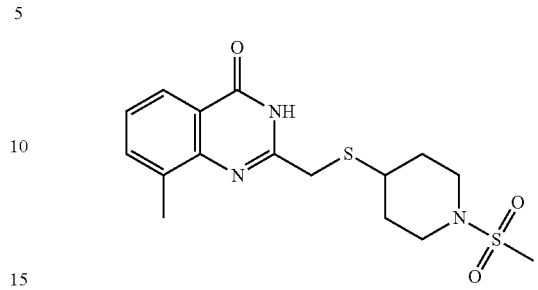

To a solution of Example 13 (100 mg, 0.31 mmol, 1.0 eq) and Et$_3$N (94 mg, 0.93 mmol, 3.0 eq) in DCM (5 mL) at RT under a N$_2$ atmosphere was added MsCl (42 mg, 0.37 mmol, 1.2 eq) and the mixture was stirred for 2 h. The mixture was diluted with water (20 mL), extracted with EtOAc (30 mL×3) and the combined organic layers were dried over Na$_2$SO$_4$ and concentrated under reduced pressure. The residue was purified by prep-TLC (DCM:MeOH, 15:1, v/v) to afford the title compound (12 mg, 11%) as a white solid. LCMS: [M+H]+ 368.2;

$^1$H NMR (400 MHz, CDCl$_3$) δ 8.14 (d, J=7.6 Hz, 1H), 7.65 (d, J=7.6 Hz, 1H), 7.42 (t, J=8.0 Hz, 1H), 3.98 (s, 2H), 3.65 (d, J=11.8 Hz, 2H), 2.99-2.79 (m, 3H), 2.76 (s, 3H), 2.65 (s, 3H), 2.18-2.06 (m, 2H), 1.80-1.70 (m, 2H).

Example 175: 8-Methyl-2-(((1-(pyridin-2-ylsulfonyl)piperidin-4-yl)thio)methyl)quinazolin-4(3H)-one

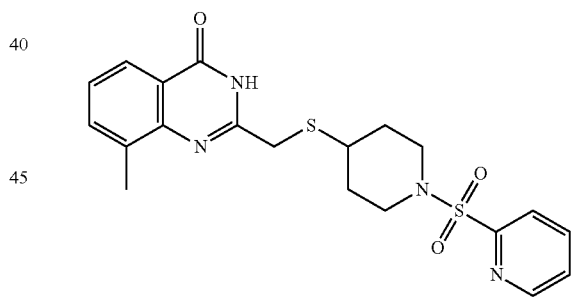

To a solution of Example 13 (50 mg, 0.15 mmol, 1.0 eq) and Et$_3$N (47 mg, 0.47 mmol, 3.0 eq) in DMF (3 mL) at RT under a N$_2$ atmosphere was added pyridine-2-sulfonyl chloride hydrochloride (41 mg, 0.23 mmol, 1.5 eq) and the mixture was stirred for 3 h. The mixture was diluted with water (20 mL) and extracted with EtOAc (30 mL×3) and the combined organic layers were dried over Na$_2$SO$_4$ and concentrated under reduced pressure. The residue was purified by prep-TLC (DCM:MeOH, 15:1, v/v) to afford the title compound (12 mg, 18%) as a white solid. LCMS: [M+H]+ 431.1.

$^1$H NMR (400 MHz, CD$_3$OD) δ 8.69 (d, J=4.8 Hz, 1H), 8.08-7.99 (m, 2H), 7.94 (d, J=7.9 Hz, 1H), 7.67-7.59 (m, 2H), 7.38 (t, J=7.6 Hz, 1H), 3.79-3.69 (m, 4H), 2.98-2.83 (m, 3H), 2.53 (s, 3H), 2.12-2.03 (m, 2H), 1.68-1.55 (m, 2H).

Example 176: 7-(Cyclopentylamino)-5-fluoro-2-((piperidin-4-ylthio)methyl)quinazolin-4(3H)-one Hydrochloride

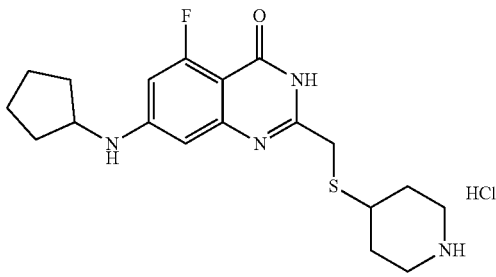 [SMILES: O=c1[nH]c(CSC2CCNCC2)nc2cc(NC3CCCC3)cc(F)c12 ; Cl]

Step 1: tert-Butyl 4-(((7-(cyclopentylamino)-5-fluoro-4-oxo-3,4-dihydroquinazolin-2-yl)methyl)thio)piperidine-1-carboxylate To a solution of Int-B2 (44 mg, 0.17 mmol, 1.0 eq) and Int-A37 (50 mg, 0.17 mmol, 1.0 eq) in THF (4 mL) was added 1 M NaOH (2 mL) and the mixture was stirred at RT overnight under a $N_2$ atmosphere. The mixture was diluted with water (5 mL) and extracted with EtOAc (20 mL×3). The combined organic layers were dried over $Na_2SO_4$ and concentrated under reduced pressure. The residue was purified by column chromatography (DCM:MeOH, 10:1, v/v) to afford the title compound (25 mg, 31%) as a white solid. LCMS: $[M+H]^+$ 477.2.

Step 2: 7-(Cyclopentylamino)-5-fluoro-2-((piperidin-4-ylthio)methyl)quinazolin-4(3H)-one hydrochloride The title compound was prepared from tert-butyl 4-(((7-(cyclopentylamino)-5-fluoro-4-oxo-3,4-dihydroquinazolin-2-yl) methyl)thio)piperidine-1-carboxylate according to the method described for Example 48, step 2. LCMS: $[M+H]^+$ 377.2.

$^1$H NMR (400 MHz, DMSO-$d_6$) δ 8.90 (br s, 1H), 8.77 (br s, 1H), 6.53 (s, 1H), 6.51 (d, J=14.0 Hz, 1H), 3.80-3.77 (m, 1H), 3.73 (s, 2H), 3.25-3.22 (m, 2H), 3.17-3.11 (m, 1H), 2.94-2.86 (m, 2H), 2.16-2.13 (m, 2H), 2.02-1.93 (m, 2H), 1.78-1.66 (m, 4H), 1.63-1.52 (m, 2H), 1.50-1.42 (m, 2H).

Example 177: 7-(Cyclobutylamino)-5-fluoro-2-((piperidin-4-ylthio)methyl)quinazolin-4(3H)-one Hydrochloride

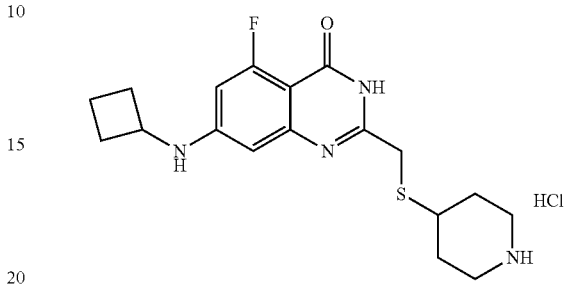

Step 1: tert-Butyl 4-(((7-(cyclobutylamino)-5-fluoro-4-oxo-3,4-dihydroquinazolin-2-yl)methyl)thio)piperidine-1-carboxylate The title compound was prepared from Int-A38 and Int-B2 according to the method described for Example 176, step 1. LCMS: $[M+H]^+$ 463.2.

Step 2: 7-(Cyclobutylamino)-5-fluoro-2-((piperidin-4-ylthio)methyl)quinazolin-4(3H)-one hydrochloride The title compound was prepared from tert-butyl 4-(((7-(cyclobutylamino)-5-fluoro-4-oxo-3,4-dihydroquinazolin-2-yl) methyl)thio)piperidine-1-carboxylate according to the method described for Example 48, step 2. LCMS: $[M+H]^+$ 363.2.

$^1$H NMR (400 MHz, DMSO-$d_6$) δ 9.01 (br s, 1H), 8.88 (br s, 1H), 6.52 (s, 1H), 6.47 (d, J=13.6 Hz, 1H), 3.96-3.88 (m, 1H), 3.77 (s, 2H), 3.24-3.15 (m, 3H), 2.93-2.85 (m, 2H), 2.38-2.33 (m, 2H), 2.19-2.14 (m, 2H), 1.92-1.85 (m, 2H), 1.78-1.61 (m, 4H).

Table 8 lists analytical data for the Examples.

TABLE 8

| Example | Analytical Data |
|---|---|
| Example 2 | LCMS: $[M + H]^+$ 291.1; $^1$H NMR (400 MHz, CDCl$_3$) δ 10.1 (s, 1H), 8.13 (dd, J = 8.0, 1.6 Hz, 1H), 7.62 (d, J = 7.2 Hz, 1H), 7.38 (t, J = 7.6 Hz, 1H), 3.95 (dt, J = 11.6, 4.0 Hz, 2H), 3.81 (s, 2H), 3.37 (td, J = 11.6, 2.4 Hz, 2H), 2.92 (tt, J = 10.8, 4.0 Hz, 1H), 2.59 (s, 3H), 1.98-1.81 (m, 2H), 1.75-1.60 (m, 2H). |
| Example 3 | LCMS: $[M + H]^+$ 291.1; $^1$H NMR (400 MHz, CDCl$_3$) δ 9.88 (br s, 1H), 8.08 (s, 1H), 7.59 (s, 2H), 3.93 (d, J = 11.6 Hz, 2H), 3.81 (s, 2H), 3.36 (t, J = 11.2 Hz, 2H), 2.93-2.78 (m, 1H), 2.50 (s, 3H), 1.94-1.85 (m, 2H), 1.67 (dd, J = 18.4, 8.0 Hz, 2H). |
| Example 4 | LCMS: $[M + H]^+$ 307.1; $^1$H NMR (400 MHz, CDCl$_3$) δ 9.80 (br s, 1H), 7.65 (s, 1H), 7.61 (d, J = 9.2 Hz, 1H), 7.37 (d, J = 10.4 Hz, 1H), 3.93-3.89 (m, 5H), 3.80 (s, 2H), 3.36 (t, J = 11.2 Hz, 2H), 2.92-2.79 (m, 1H), 1.95-1.85 (m, 2H), 1.70-1.60 (m, 2H). |
| Example 5 | LCMS: $[M + H]^+$ 311.1; $^1$H NMR (400 MHz, DMSO-$d_6$) δ 12.6 (br s, 1H), 8.05 (d, J = 7.6 Hz, 1H), 7.95 (d, J = 7.6 Hz, 1H), 7.46 (t, J = 8.0 Hz, 1H), 3.88-3.78 (m, 2H), 3.70 (s, 2H), 3.33-3.17 (m, 2H), 3.20-3.12 (m, 1H), 2.00-1.90 (m, 2H), 1.50-1.40 (m, 2H). |

TABLE 8-continued

| Example | Analytical Data |
|---|---|
| Example 6 | LCMS: [M + H]$^+$ 307.1;<br>$^1$H NMR (400 MHz, DMSO-d$_6$) δ 12.3 (br s, 1H), 7.64 (d, J = 7.8 Hz, 1H), 7.41 (t, J = 7.8 Hz, 1H), 7.34 (d, J = 7.8 Hz, 1H), 3.89 (s, 3H), 3.88-3.78 (m, 2H), 3.68 (s, 2H), 3.33-3.17 (m, 2H), 3.16-3.03 (m, 1H), 1.94-1.85 (m, 2H), 1.50-1.40 (m, 2H). |
| Example 7 | LCMS: [M + H]$^+$ 305.1;<br>$^1$H NMR (400 MHz, DMSO-d$_6$) δ 12.2 (br s, 1H), 7.92 (d, J = 7.6 Hz, 1H), 7.65 (d, J = 7.2 Hz, 1H), 7.37 (t, J = 7.6 Hz, 1H), 4.00 (q, J = 7.2 Hz, 1H), 3.80-3.77 (m, 2H), 3.32-3.23 (m, 2H), 3.12-3.00 (m, 1H), 2.51 (s, 3H), 1.90-1.82 (m, 1H), 1.79-1.69 (m, 1H), 1.63 (d, J = 7.2 Hz, 3H), 1.43 (m, 2H). |
| Example 8 | LCMS: [M + H]$^+$ 309.1;<br>$^1$H NMR (400 MHz, CD$_3$OD) δ 7.62 (dd, J = 8.0, 5.6 Hz, 1H), 7.06 (dd, J = 10.8, 8.4 Hz, 1H), 3.92 (dt, J = 11.6, 3.6 Hz, 2H), 3.72 (s, 2H), 3.41 (td, J = 11.2, 2.0 Hz, 2H), 3.13-3.05 (m, 1H), 2.51 (s, 3H), 2.05-1.95 (m, 2H), 1.71-1.61 (m, 2H). |
| Example 9 | LCMS: [M + H]$^+$ 291.1;<br>$^1$H NMR (400 MHz, CDCl$_3$) δ 10.1 (s, 1H), 7.60 (t, J = 7.6 Hz, 1H), 7.50 (d, J = 8.0 Hz, 1H), 7.24 (d, J = 7.2 Hz, 1H), 3.93 (dt, J = 12.0, 3.6 Hz, 2H), 3.76 (s, 2H), 3.37 (t, J = 11.2 Hz, 2H), 2.93-2.89 (m, 4H), 1.91 (d, J = 12.4 Hz, 2H), 1.71-1.61 (m, 2H). |
| Example 10 | LCMS: [M + H]$^+$ 367.1;<br>$^1$H NMR (400 MHz, CDCl$_3$) δ 9.80 (br s, 1H), 8.17 (d, J = 8.0 Hz, 1H), 7.58 (d, J = 12 Hz, 1H), 7.44-7.37 (m, 1H), 7.25-7.12 (m, 5H), 4.40 (s, 2H), 3.94-3.84 (m, 2H), 3.78 (s, 2H), 3.28 (t, J = 11.2 Hz, 2H), 2.89-2.77 (m, 1H), 1.91-1.80 (m, 2H), 1.70-1.60 (m, 2H). |
| Example 11 | LCMS: [M + H]$^+$ 367.1;<br>$^1$H NMR (400 MHz, CDCl$_3$) δ 9.75 (br s, 1H), 8.19 (d, J = 8.0 Hz, 1H), 7.47 (s, 1H), 7.30-7.14 (m, 6H), 4.11 (s, 2H), 3.93 (dt, J = 11.8, 3.6 Hz, 2H), 3.77 (s, 2H), 3.36 (t, J = 11.4 Hz, 2H), 2.80 (m, 1H), 1.83 (d, J = 13.2 Hz, 2H), 1.74-1.60 (m, 2H). |
| Example 29 | LCMS: [M + H]$^+$ 369.1;<br>$^1$H NMR (400 MHz, DMSO-d$_6$) δ 12.3 (s, 1H), 8.08 (d, J = 8.8 Hz, 1H), 7.53-7.45 (m, 2H), 7.29 (td, J = 7.3, 1.1 Hz, 1H), 7.22-7.16 (m, 2H), 7.13 (dd, J = 8.8, 2.4 Hz, 1H), 6.91 (d, J = 2.4 Hz, 1H), 3.79 (dt, J = 11.6, 4.0 Hz, 2H), 3.63 (s, 2H), 3.28 (dd, J = 11.2, 2.4 Hz, 2H), 3.08-2.96 (m, 1H), 1.86 (d, J = 13.2 Hz, 2H), 1.47-1.37 (m, 2H). |
| Example 30 | LCMS: [M + H]$^+$ 295.1;<br>$^1$H NMR (400 MHz, DMSO-d$_6$) δ 12.4 (s, 1H), 8.14 (dd, J = 8.8, 6.4 Hz, 1H), 7.47-7.30 (m, 2H), 3.80 (dt, J = 11.6, 3.6 Hz, 2H), 3.67 (s, 2H), 3.37-3.26 (m, 2H), 3.06 (tt, J = 10.8, 4.0 Hz, 1H), 1.88 (dd, J = 13.2, 3.6 Hz, 2H), 1.51-1.40 (m, 2H). |
| Example 31 | LCMS: [M + H]$^+$ 307.1;<br>$^1$H NMR (400 MHz, DMSO-d$_6$) δ 12.2 (s, 1H), 7.98 (d, J = 8.4 Hz, 1H), 7.06 (d, J = 8.0 Hz, 2H), 3.88 (s, 3H), 3.83-3.76 (m, 2H), 3.65 (s, 2H), 3.30-3.00 (m, 2H), 3.05 (td, J = 10.8, 5.2 Hz, 1H), 1.93-1.84 (m, 2H), 1.52-1.38 (m, 2H). |
| Example 32 | LCMS: [M + H]$^+$ 304.1;<br>$^1$H NMR (400 MHz, CDCl$_3$) δ 14.1 (br s, 1H), 8.10 (d, J = 12 Hz, 1H), 7.55 (d, J = 6.8 Hz, 1H), 7.31 (t, J = 7.6 Hz, 1H), 4.07 (d, J = 15.2 Hz, 1H), 3.82-3.73 (m, 1H), 3.43 (d, J = 15.2 Hz, 1H), 3.05 (dd, J = 15.2, 3.2 Hz, 1H), 2.92 (dd, J = 15.2, 3.2 Hz, 1H), 2.76-2.68 (m, 1H), 2.57 (s, 3H), 2.43 (s, 3H), 2.35 (dd, J = 16.4, 9.2 Hz, 1H), 1.99-1.76 (m, 4H). |
| Example 33 | LCMS: [M + H]$^+$ 309.1;<br>$^1$H NMR (400 MHz, CDCl$_3$) δ 10.5 (s, 1H), 8.14 (t, J = 7.6 Hz, 1H), 7.18 (t, J = 8.8 Hz, 1H), 3.96 (d, J = 12.0 Hz, 2H), 3.81 (s, 2H), 3.38 (t, J = 11.2 Hz, 2H), 3.00-2.82 (m, 1H), 2.49 (s, 3H), 1.94 (d, J = 13.2 Hz, 2H), 1.72-1.62 (m, 2H). |
| Example 34 | LCMS: [M + H]$^+$ 325.1;<br>$^1$H NMR (400 MHz, CDCl$_3$) δ 9.77 (s, 1H), 7.47 (d, J = 8.0 Hz, 1H), 7.36 (d, J = 8.0 Hz, 1H), 3.95 (d, J = 12.0 Hz, 2H), 3.76 (s, 2H), 3.37 (t, J = 11.2 Hz, 2H), 2.95-2.83 (m, 1H), 2.52 (s, 3H), 1.94-1.90 (m, 2H), 1.74-1.60 (m, 2H). |
| Example 35 | LCMS: [M + H]$^+$ 359.1;<br>$^1$H NMR (400 MHz, CDCl$_3$) δ 10.8 (s, 1H), 7.77-7.67 (m, 2H), 3.98-3.95 (m, 2H), 3.80 (s, 2H), 3.57-3.30 (m, 2H), 3.01-2.94 (m, 1H), 2.63 (s, 3H), 1.97-1.94 (m, 2H), 1.70-1.67 (m, 2H). |
| Example 36 | LCMS: [M + H]$^+$ 278.1;<br>$^1$H NMR (400 MHz, DMSO-d$_6$) δ 12.6 (s, 1H), 8.76 (s, 1H), 8.03 (d, J = 8.4 Hz, 1H), 7.78 (dd, J = 8.4, 4.2 Hz, 1H), 3.80 (d, J = 11.6 Hz, 2H), 3.70 (s, 2H), 3.31-3.28 (m, 2H), 3.07 (t, J = 10.4 Hz, 1H), 1.88 (d, J = 12.8 Hz, 2H), 1.45 (q, J = 12.0, 11.0 Hz, 2H). |
| Example 37 | LCMS: [M + H]$^+$ 278.1;<br>$^1$H NMR (400 MHz, CD$_3$OD) δ 8.99 (s, 1H), 8.62 (d, J = 5.2 Hz, 1H), 8.05 (d, J = 5.2 Hz, 1H), 3.91 (dt, J = 11.6, 3.6 Hz, 2H), 3.77 (s, 2H), 3.43 (dt, J = 11.2, 2.4 Hz, 2H), 3.09-3.02 (m, 1H), 1.97 (d, J = 13.6 Hz, 2H), 1.63-1.54 (m, 2H). |

TABLE 8-continued

| Example | Analytical Data |
|---|---|
| Example 38 | LCMS: [M + H]$^+$ 367.1;<br>$^1$H NMR (400 MHz, CDCl$_3$) δ 8.13 (d, J = 7.4 Hz, 1H), 7.62 (d, J = 6.8 Hz, 1H), 7.38 (t, J = 7.6 Hz, 1H), 7.35-7.26 (m, 5H), 4.37 (s, 2H), 4.35-4.27 (m, 1H), 3.84 (s, 2H), 3.58-3.52 (m, 1H), 2.62 (s, 3H), 2.47-2.40 (m, 2H), 2.31-2.17 (m, 2H). |
| Example 39 | LCMS: [M + H]$^+$ 263.1;<br>$^1$H NMR (400 MHz, CD$_3$OD) δ 8.03 (dd, J = 8.0, 1.6 Hz, 1H), 7.67 (d, J = 7.2 Hz, 1H), 7.39 (t, J = 7.6 Hz, 1H), 4.89 (t, J = 12 Hz, 2H), 4.42 (t, J = 6.4 Hz, 2H), 4.36-4.30 (m, 1H), 3.73 (s, 2H), 2.60 (s, 3H). |
| Example 40 | LCMS: [M + H]$^+$ 278.1;<br>$^1$H NMR (400 MHz, CD$_3$OD) δ 8.83 (s, 1H), 8.67 (d, J = 6.0 Hz, 1H), 8.19 (d, J = 6.0 Hz, 1H), 4.00-3.90 (m, 2H), 3.56 (s, 2H), 3.46 (td, J = 11.2, 2.4 Hz, 2H), 3.17-3.04 (m, 1H), 2.07-1.95 (m, 2H), 1.69-1.55 (m, 2H). |
| Example 41 | LCMS: [M + H]$^+$ 292.1;<br>$^1$H NMR (400 MHz, CD$_3$OD) δ 8.56 (d, J = 4.4 Hz, 1H), 7.69 (d, J = 4.4 Hz, 1H), 3.92 (dt, J = 11.8, 3.6 Hz, 2H), 3.78 (s, 2H), 3.41 (td, J = 11.6, 2.4 Hz, 2H), 3.13-3.06 (m, 1H), 2.64 (s, 3H), 2.06-1.88 (m, 2H), 1.64-1.55 (m, 2H). |
| Example 42 | LCMS: [M + H]$^+$ 292.1;<br>$^1$H NMR (400 MHz, CD$_3$OD) δ 8.44 (d, J = 5.4 Hz, 1H), 7.90 (d, J = 5.4 Hz, 1H), 3.92 (dt, J = 11.8, 3.6 Hz, 2H), 3.77 (s, 2H), 3.42 (td, J = 11.2, 2.4 Hz, 2H), 3.13-3.06 (m, 1H), 2.82 (s, 3H), 2.06-1.94 (m, 2H), 1.65-1.55 (m, 2H). |
| Example 43 | LCMS: [M + H]$^+$ 278.1;<br>$^1$H NMR (400 MHz, CD$_3$OD) δ 8.95 (s, 1H), 8.71 (dd, J = 8.0, 1.6 Hz, 1H), 7.64 (dd, J = 8.0, 4.8 Hz, 1H), 3.91 (dt, J = 11.6, 3.6 Hz, 2H), 3.72 (s, 2H), 3.43 (td, J = 11.2, 2.4 Hz, 2H), 3.16-3.09 (m, 1H), 2.02-1.91 (m, 2H), 1.63-1.54 (m, 2H). |
| Example 44 | LCMS: [M + H]$^+$ 325.1;<br>$^1$H NMR (400 MHz, CD$_3$OD) δ 7.98-7.95 (m, 1H), 7.67-7.62 (m, 1H), 3.95-3.88 (m, 2H), 3.74 (s, 2H), 3.45-3.36 (m, 2H), 3.15-3.01 (m, 1H), 2.56 (s, 3H), 2.03-1.95 (m, 2H), 1.65-1.54 (m, 2H). |
| Example 45 | LCMS: [M + H]$^+$ 313.1;<br>$^1$H NMR (400 MHz, DMSO-d$_6$) δ 12.6 (s, 1H), 8.02-7.84 (m, 1H), 7.64-7.42 (m, 1H), 3.87-3.78 (m, 2H), 3.71 (s, 2H), 3.34-3.25 (m, 2H), 3.15-3.02 (m, 1H), 1.95-1.85 (m, 2H), 1.53-1.38 (m, 2H). |
| Example 81 | LCMS: [M + H]$^+$ 369.1;<br>$^1$H NMR (400 MHz, DMSO-d$_6$) δ 9.76 (s, 1H), 8.34-8.20 (m, 2H), 7.96 (d, J = 8.8 Hz, 1H), 7.74-7.56 (m, 2H), 7.04-6.85 (m, 2H), 3.81 (d, J = 11.2 Hz, 2H), 3.69 (d, J = 6.0 Hz, 2H), 3.33 (q, J = 11.2 Hz, 2H), 3.08 (t, J = 10.8 Hz, 1H), 1.90 (d, J = 13.2 Hz, 2H), 1.46 (q, J = 11.6, 10.0 Hz, 2H). |
| Example 82 | LCMS: [M + H]$^+$ 398.2;<br>$^1$H NMR (400 MHz, CD$_3$OD) δ 7.95 (d, J = 8.8 Hz, 1H), 7.20 (d, J = 8.4 Hz, 2H), 7.03-6.91 (m, 4H), 3.89 (dt, J = 11.6, 4.0 Hz, 2H), 3.81 (s, 3H), 3.70 (d, J = 6.0 Hz, 2H), 3.42 (td, J = 11.2, 2.4 Hz, 2H), 3.05-2.98 (m, 1H), 1.93 (d, J = 13.6 Hz, 2H), 1.61-1.52 (m, 2H). |
| Example 83 | LCMS: [M + H]$^+$ 398.2;<br>$^1$H NMR (400 MHz, DMSO-d$_6$) δ 11.9 (s, 1H), 8.88 (s, 1H), 7.89 (d, J = 8.8 Hz, 1H), 7.25 (t, J = 8.0 Hz, 1H), 7.15-7.04 (m, 2H), 6.85-6.77 (m, 1H), 6.74 (t, J = 2.4 Hz, 1H), 6.60 (dd, J = 8.0, 2.4 Hz, 1H), 3.80 (d, J = 12.0 Hz, 2H), 3.75 (s, 3H), 3.61 (s, 2H), 3.30-3.27 (m, 2H), 3.09-3.00 (m, 1H), 1.88 (d, J = 12.4 Hz, 2H), 1.49-1.38 (m, 2H). |
| Example 84 | LCMS: [M + H]$^+$ 398.2;<br>$^1$H NMR (400 MHz, DMSO-d$_6$) δ 8.61 (s, 1H), 7.87 (d, J = 8.8 Hz, 1H), 7.30 (dd, J = 7.6, 1.6 Hz, 1H), 7.21-7.13 (m, 2H), 7.05 (dd, J = 8.8, 2.4 Hz, 1H), 6.99 (td, J = 7.6, 1.6 Hz, 1H), 6.85 (d, J = 2.4 Hz, 1H), 3.85-3.75 (m, 7H), 3.31 (m, 2H), 3.13-3.07 (m, 1H), 1.93-1.84 (m, 2H), 1.49-1.36 (m, 2H). |
| Example 85 | LCMS: [M + H]$^+$ 370.1;<br>$^1$H NMR (400 MHz, DMSO-d$_6$) δ 12.1 (s, 1H), 10.0 (s, 1H), 8.34 (s, 1H), 8.27 (br s, 1H), 8.19 (d, J = 2.0 Hz, 1H), 8.06 (d, J = 2.8 Hz, 1H), 7.99 (d, J = 8.8 Hz, 1H), 7.61 (dd, J = 8.8, 2.0 Hz, 1H), 3.92-3.80 (m, 2H), 3.66 (s, 2H), 3.37-3.29 (m, 2H), 3.09-3.04 (m, 1H), 1.90 (d, J = 12.8 Hz, 2H), 1.50-1.41 (m, 2H). |
| Example 86 | LCMS: [M + H]$^+$ 369.1;<br>$^1$H NMR (400 MHz, CD$_3$OD) δ 8.32-8.25 (m, 2H), 8.14 (d, J = 8.8 Hz, 1H), 7.45 (d, J = 2.4 Hz, 1H), 7.36 (dd, J = 8.8, 2.4 Hz, 1H), 7.24-7.16 (m, 2H), 3.90 (dt, J = 11.6, 3.6 Hz, 2H), 3.73 (s, 2H), 3.43 (td, J = 11.2, 2.4 Hz, 2H), 3.08-2.99 (m, 1H), 1.96 (d, J = 13.2 Hz, 2H), 1.59 (m, 2H). |
| Example 87 | LCMS: [M + H]$^+$ 370.1;<br>$^1$H NMR (400 MHz, DMSO-d$_6$) δ 12.0 (s, 1H), 9.15 (s, 1H), 8.82 (s, 1H), 8.73 (s, 2H), 7.97 (d, J = 8.8 Hz, 1H), 7.19 (dd, J = 8.8, 2.0 Hz, 1H), 7.10 (s, 1H), 3.82-3.80 (m, 2H), 3.63 (s, 2H), 3.32-3.28 (m, 2H), 3.08-3.03 (m, 1H), 1.88 (d, J = 13.2 Hz, 2H), 1.49-1.42 (m, 2H). |

TABLE 8-continued

| Example | Analytical Data |
|---|---|
| Example 88 | LCMS: [M + H]+ 372.1;<br>$^1$H NMR (400 MHz, CD$_3$OD) δ 8.01 (d, J = 8.8 Hz, 1H), 7.10-7.05 (m, 1H), 7.04-6.99 (m, 2H), 6.89 (d, J = 1.6 Hz, 1H), 3.92-3.86 (m, 2H), 3.68 (s, 2H), 3.70 (s, 3H), 3.45-3.37 (m, 2H), 3.06-2.95 (m, 1H), 1.97-1.89 (m, 2H), 1.62-1.50 (m, 2H). |
| Example 89 | LCMS: [M + H]+ 375.1;<br>$^1$H NMR (400 MHz, CD$_3$OD) δ 8.23 (d, J = 2.0 Hz, 1H), 8.09 (d, J = 8.8 Hz, 1H), 7.51 (dd, J = 8.8, 2.4 Hz, 1H), 7.36 (d, J = 3.6 Hz, 1H), 6.96 (d, J = 3.6 Hz, 1H), 3.93-3.88 (m, 2H), 3.75 (s, 2H), 3.47-3.41 (m, 2H), 3.09-3.02 (m, 1H), 1.98-1.94 (m, 2H), 1.64-1.54 (m, 2H). |
| Example 90 | LCMS: [M + H]+ 383.2;<br>$^1$H NMR (400 MHz, DMSO-d$_6$) δ 11.9 (s, 1H), 8.40 (d, J = 8.0 Hz, 1H), 8.26 (d, J = 9.2 Hz, 1H), 7.88 (d, J = 8.4 Hz, 1H), 7.67 (d, J = 8.0 Hz, 1H), 7.28-7.25 (m, 1H), 6.95 (d, J = 12.4 Hz, 1H), 6.69 (s, 1H), 3.82-3.76 (m, 2H), 3.59 (s, 2H), 3.30-3.26 (m, 2H), 3.06-2.97 (m, 1H), 2.42 (s, 3H), 1.87 (d, J = 12.8 Hz, 2H), 1.49-1.38 (m, 2H). |
| Example 91 | LCMS: [M + H]+ 383.2;<br>$^1$H NMR (400 MHz, DMSO-d$_6$) δ 11.9 (s, 1H), 8.45 (d, J = 8.0 Hz, 2H), 8.29 (d, J = 4.0 Hz, 1H), 7.87 (d, J = 8.0 Hz, 1H), 7.35 (d, J = 4.0 Hz, 1H), 6.91 (dd, J = 8.0 Hz, 1H), 6.59 (d, J = 4.0 Hz, 1H), 3.83-3.76 (m, 2H), 3.58 (s, 2H), 3.28 (d, J = 4.0 Hz, 2H), 3.06-2.97 (m, 1H), 2.21 (s, 3H), 1.87 (d, J = 12.0 Hz, 2H), 1.49-1.37 (m, 2H). |
| Example 92 | LCMS: [M + H]+ 383.2;<br>$^1$H NMR (400 MHz, DMSO-d$_6$) δ 12.0 (s, 1H), 8.98 (s, 1H), 8.28 (s, 1H), 8.08 (s, 1H), 7.93 (d, J = 8.8 Hz, 1H), 7.50 (s, 1H), 7.13 (dd, J = 8.8, 2.0 Hz, 1H), 7.09-7.01 (m, 1H), 3.86-3.75 (m, 2H), 3.62 (s, 2H), 3.30-3.24 (m, 2H), 3.12-3.01 (m, 1H), 2.31 (s, 3H), 1.89 (d, J = 11.8 Hz, 2H), 1.50-1.36 (m, 2H). |
| Example 109 | LCMS: [M + H]+ 320.1;<br>$^1$H NMR (400 MHz, DMSO-d$_6$) δ 11.8 (s, 1H), 7.84 (d, J = 8.8 Hz, 1H), 6.90 (dd, J = 8.8, 1.6 Hz, 1H), 6.63 (d, J = 1.6 Hz, 1H), 3.81 (dt, J = 11.6, 3.6 Hz, 2H), 3.60 (s, 2H), 3.37-3.32 (m, 1H), 3.31-3.26 (m, 1H), 3.03 (s, 6H), 3.02-2.99 (m, 1H), 1.88 (d, J = 12.4 Hz, 2H), 1.52-1.37 (m, 2H). |
| Example 110 | LCMS: [M + H]+ 306.1;<br>$^1$H NMR (400 MHz, DMSO-d$_6$) δ 11.7 (s, 1H), 7.74 (d, J = 8.8 Hz, 1H), 6.71 (dd, J = 8.8, 2.0 Hz, 1H), 6.65 (d, J = 4.8 Hz, 1H), 6.45 (d, J = 2.0 Hz, 1H), 3.87-3.76 (m, 2H), 3.59 (s, 2H), 3.37-3.33 (m, 1H), 3.29 (d, J = 2.0 Hz, 1H), 3.11-2.99 (m, 1H), 2.76 (d, J = 4.8 Hz, 3H), 1.94-1.83 (m, 2H), 1.51-1.39 (m, 2H). |
| Example 111 | LCMS: [M + H]+ 362.2;<br>$^1$H NMR (400 MHz, DMSO-d$_6$) δ 11.9 (s, 1H), 7.88 (d, J = 8.8 Hz, 1H), 7.15 (dd, J = 8.8, 2.4 Hz, 1H), 6.93-6.88 (m, 1H), 3.87-3.77 (m, 2H), 3.78-3.71 (m, 4H), 3.62 (s, 2H), 3.11-2.99 (m, 1H), 2.07-1.94 (m, 1H), 1.93-1.84 (m, 2H), 1.52-1.38 (m, 2H), 1.35-1.14 (m, 5H). |
| Example 112 | LCMS: [M + H]+ 375.2;<br>$^1$H NMR (400 MHz, DMSO-d$_6$) δ 11.9 (s, 1H), 7.86 (d, J = 8.8 Hz, 1H), 7.14 (dd, J = 8.8, 2.4 Hz, 1H), 6.88 (d, J = 2.4 Hz, 1H), 3.81 (dt, J = 11.6, 3.6 Hz, 2H), 3.61 (s, 2H), 3.37-3.32 (m, 5H), 3.32-3.27 (m, 1H), 3.10-3.00 (m, 1H), 2.44 (t, J = 5.0 Hz, 4H), 2.22 (s, 3H), 1.89 (d, J = 12.8 Hz, 2H), 1.52-1.39 (m, 2H). |
| Example 113 | LCMS: [M + H]+ 389.2;<br>$^1$H NMR (400 MHz, DMSO-d$_6$) δ 11.7 (s, 1H), 7.75 (d, J = 8.8 Hz, 1H), 6.76 (dd, J = 8.8, 2.0 Hz, 1H), 6.62 (d, J = 7.6 Hz, 1H), 6.57 (s, 1H), 3.81 (d, J = 11.2 Hz, 2H), 3.59 (s, 2H), 3.56-3.47 (m, 1H), 3.30-2.99 (m, 10H), 2.07-1.98 (m, 2H), 1.92-1.84 (m, 2H), 1.67-1.55 (m, 2H), 1.49-1.40 (m, 2H). |
| Example 114 | LCMS: [M + H]+ 376.2;<br>$^1$H NMR (400 MHz, DMSO-d$_6$) δ 11.7 (s, 1H), 7.73 (d, J = 8.8 Hz, 1H), 6.77-6.74 (m, 1H), 6.56-6.54 (m, 2H), 3.88-3.79 (m, 4H), 3.58 (s, 3H), 3.45 (t, J = 10.4 Hz, 2H), 3.32-3.28 (m, 2H), 3.07-2.99 (m, 1H), 1.88 (d, J = 12.8 Hz, 4H), 1.49-1.36 (m, 4H). |
| Example 115 | LCMS: [M + H]+ 360.2;<br>$^1$H NMR (400 MHz, DMSO-d$_6$) δ 11.7 (s, 1H), 7.72 (d, J = 8.8 Hz, 1H), 6.74-6.71 (m, 1H), 6.60 (d, J = 8.8 Hz, 1H), 6.48 (d, J = 1.6 Hz, 1H), 3.82-3.76 (m, 3H), 3.59 (s, 2H), 3.32-3.28 (m, 2H), 3.00-3.07 (m, 1H), 1.98-1.87 (m, 4H), 1.69-1.55 (m, 4H), 1.51-1.49 (m, 4H). |
| Example 116 | LCMS: [M + H]+ 334.2;<br>$^1$H NMR (400 MHz, DMSO-d$_6$) δ 11.7 (s, 1H), 7.76-7.71 (m, 1H), 6.71 (dd, J = 2.0 Hz, 8.4 Hz, 1H), 6.50-6.43 (m, 2H), 3.85-3.77 (m, 2H), 3.70-3.61 (m, 1H), 3.59 (s, 2H), 3.36-3.26 (m, 2H), 3.09-3.00 (m, 1H), 1.93-1.83 (m, 2H), 1.50-1.38 (m, 2H), 1.17 (d, J = 6.4 Hz, 6H). |
| Example 117 | LCMS: [M + H]+ 383.2;<br>$^1$H NMR (400 MHz, DMSO-d$_6$) δ 11.7 (s, 1H), 8.51 (d, J = 6.0 Hz, 2H), 7.76 (d, J = 8.8 Hz, 1H), 7.36 (d, J = 5.6 Hz, 2H), 7.32 (t, J = 6.0 Hz, 1H), 6.81 (dd, J = 8.8, 2.4 Hz, 1H), 6.40 (d, J = 2.0 Hz, 1H), 4.45 (d, J = 6.0 Hz, 2H), 3.79 (dt, J = 11.6, 3.6 Hz, 2H), 3.55 (s, 2H), 3.25 (td, J = |

TABLE 8-continued

| Example | Analytical Data |
|---|---|
| | 11.6, 2.4 Hz, 2H), 3.02-2.95 (m, 1H), 1.85 (d, J = 12.4 Hz, 2H), 1.47-1.35 (m, 2H). |
| Example 118 | LCMS: [M + H]$^+$ 383.2;<br>$^1$H NMR (400 MHz, DMSO-d$_6$) δ 11.7 (s, 1H), 8.54 (d, J = 4.8 Hz, 1H), 7.72-7.78 (m, 2H), 7.36-7.25 (m, 3H), 6.83 (dd, J = 8.8, 2.0 Hz, 1H), 6.44 (d, J = 4.0 Hz, 1H), 4.47 (d, J = 6.8 Hz, 2H), 3.76-3.83 (m, 2H), 3.56 (s, 2H), 3.22-3.30 (m, 2H), 3.03-2.95 (m, 1H), 1.85 (d, J = 12.0 Hz, 2H), 1.46-1.36 (m, 2H). |
| Example 119 | LCMS: [M + H]$^+$ 382.2;<br>$^1$H NMR (400 MHz, DMSO-d$_6$) δ 11.7 (s, 1H), 7.73 (d, J = 8.0 Hz, 1H), 7.31-7.37 (m, 4H), 7.21-7.26 (m, 2H), 6.79 (d, J = 12.0 Hz, 1H), 6.45 (d, J = 2.4 Hz, 1H), 4.37 (d, J = 4.0 Hz, 2H), 3.76-3.81 (m, 2H), 3.55 (s, 2H), 3.26 (t, J = 9.2 Hz, 2H), 2.95-3.05 (m, 1H), 1.85 (d, J = 12.0 Hz, 2H), 1.35-1.47 (m, 2H). |
| Example 120 | LCMS: [M + H]$^+$ 396.2;<br>$^1$H NMR (400 MHz, DMSO-d$_6$) δ 11.7 (s, 1H), 7.69 (d, J = 8.0 Hz, 1H), 7.38 (d, J = 4.0 Hz, 2H), 7.30 (t, J = 7.6 Hz, 2H), 7.19 (t, J = 7.2 Hz, 1H), 7.14 (d, J = 8.0 Hz, 1H), 6.78 (d, J = 8.0 Hz, 1H), 6.32 (s, 1H), 4.55-4.63 (m, 1H), 3.75-3.81 (m, 2H), 3.52 (s, 2H), 3.20-3.27 (m, 2H), 2.93-3.00 (m, 1H), 1.78-1.87 (m, 2H), 1.45 (d, J = 8.0 Hz, 3H), 1.34-1.40 (m, 2H). |
| Example 121 | LCMS: [M + H]$^+$ 362.1;<br>$^1$H NMR (400 MHz, DMSO-d$_6$) δ 11.7 (s, 1H), 7.75 (d, J = 8.8 Hz, 1H), 6.81 (d, J = 6.4 Hz, 1H), 6.76 (dd, J = 8.8, 2.0 Hz, 1H), 6.51 (d, J = 2.0 Hz, 1H), 4.10 (s, 1H), 3.91-3.86 (m, 1H), 3.81 (dt, J = 7.6, 5.6 Hz, 3H), 3.74 (td, J = 8.0, 5.6 Hz, 1H), 3.62-3.56 (m, 3H), 3.30 (d, J = 11.6 Hz, 2H), 3.09-3.00 (m, 1H), 2.22 (dq, J = 14.9, 7.5 Hz, 1H), 1.88 (d, J = 12.4 Hz, 2H), 1.80 (dd, J = 16.0, 12.6 Hz, 1H), 1.44 (qd, J = 10.9, 4.2 Hz, 2H). |
| Example 122 | LCMS: [M + H]$^+$ 346.2;<br>$^1$H NMR (400 MHz, DMSO-d$_6$) δ 11.7 (s, 1H), 7.73 (d, J = 8.8 Hz, 1H), 6.87 (d, J = 6.4 Hz, 1H), 6.68 (dd, J = 8.8, 2.0 Hz, 1H), 6.40 (d, J = 2.0 Hz, 1H), 3.93 (d, J = 7.2 Hz, 1H), 3.80 (dd, J = 13.2, 9.8 Hz, 2H), 3.58 (s, 2H), 3.35 (d, J = 6.8 Hz, 1H), 3.28 (d, J = 7.2 Hz, 1H), 3.08-2.98 (m, 1H), 2.41-2.31 (m, 2H), 1.95-1.81 (m, 4H), 1.79-1.71 (m, 2H), 1.51-1.38 (m, 2H) |
| Example 123 | LCMS: [M + H]$^+$ 383.2;<br>$^1$H NMR (400 MHz, DMSO-d$_6$) δ 11.7 (br s, 1H), 8.60 (d, J = 1.6 Hz, 1H), 8.46 (dd, J = 4.4, 0.8 Hz, 1H), 7.75 (d, J = 8.8 Hz, 2H), 7.36 (m, 1H), 7.24 (t, J = 6.0 Hz, 1H), 6.81 (dd, J = 8.8, 2.0 Hz, 1H), 6.49 (d, J = 2.0 Hz, 1H), 4.43 (d, J = 6.0 Hz, 2H), 3.82-3.76 (m, 2H), 3.56 (s, 2H), 3.24-3.31 (m, 2H), 3.03-2.96 (m, 1H), 1.86 (d, J = 12.0 Hz, 2H), 1.46-1.36 (m, 2H). |
| Example 124 | LCMS: [M + H]$^+$ 332.1;<br>$^1$H NMR (400 MHz, DMSO-d$_6$) δ 11.7 (s, 1H), 7.76 (d, J = 8.8 Hz, 1H), 6.98 (s, 1H), 6.78 (dd, J = 8.8, 2.0 Hz, 1H), 6.72 (d, J = 2.0 Hz, 1H), 3.85-3.79 (m, 2H), 3.60 (s, 2H), 3.33-3.29 (m, 2H), 3.07-3.02 (m, 1H), 2.43 (br s, 1H), 1.91-1.87 (m, 2H), 1.49-1.41 (m, 2H), 0.78-0.74 (m, 2H), 0.44-0.40 (m, 2H). |
| Example 125 | LCMS: [M + H]$^+$ 388.2;<br>$^1$H NMR (400 MHz, CD$_3$OD) δ 7.96 (d, J = 92 Hz, 1H), 7.03 (dd, J = 9.2, 2.4 Hz, 1H), 6.78 (d, J = 2.4 Hz, 1H), 3.92-3.87 (m, 2H), 3.85-3.78 (m, 1H), 3.69 (s, 2H), 3.43 (td, J = 11.6, 2.0 Hz, 2H), 3.07-2.97 (m, 1H), 2.93 (s, 3H), 1.96-1.88 (m, 4H), 1.81-1.72 (m, 3H), 1.67-1.44 (m, 6H), 1.27-1.21 (m, 1H). |
| Example 139 | LCMS: [M + H]$^+$ 437.2;<br>$^1$H NMR (400 MHz, CD$_3$OD) δ 8.03 (d, J = 8.0 Hz, 1H), 7.67 (d, J = 8.0 Hz, 3H), 7.41 (d, J = 8.0 Hz, 3H), 4.24 (s, 2H), 3.79 (s, 2H), 3.51 (d, J = 13.6 Hz, 2H), 3.33 (m, 1H), 2.99 (t, J = 13.6 Hz, 2H), 2.58 (s, 3H), 2.38 (d, J = 14.4 Hz, 2H), 2.14 (s, 3H), 1.73 (m, 2H). |
| Example 140 | LCMS: [M + H]$^+$ 423.2;<br>$^1$H NMR (400 MHz, CD$_3$OD) δ 7.88 (d, J = 8.0 Hz, 1H), 7.52 (d, J = 7.6 Hz, 1H), 7.30 (d, J = 8.4 Hz, 2H), 7.25 (t, J = 7.2 Hz, 1H), 7.00 (d, J = 8.0 Hz, 2H), 4.01 (s, 2H), 3.38 (s, 2H), 3.18-3.13 (m, 3H), 2.96 (s, 6H), 2.91-2.80 (m, 2H), 2.44 (s, 3H), 2.27-2.14 (m, 2H), 1.70-1.55 (m, 2H). |
| Example 141 | LCMS: [M + H]$^+$ 405.2;<br>$^1$H NMR (400 MHz, CDCl$_3$) δ 8.10 (d, J = 8.0 Hz, 1H), 7.72 (d, J = 7.6 Hz, 2H), 7.67 (d, J = 7.2 Hz, 1H), 7.56 (d, J = 8.0 Hz, 2H), 7.43 (t, J = 7.6 Hz, 1H), 4.24 (s, 2H), 3.84 (m, 2H), 3.62 (m, 1H), 3.42 (s, 2H), 3.11 (s, 1H), 2.81 (m, 1H), 2.57 (s, 3H), 2.41-2.23 (m, 2H), 2.09-2.01 (m, 2H). |
| Example 142 | LCMS: [M + H]$^+$ 370.2;<br>$^1$H NMR (400 MHz, DMSO-d$_6$) δ 12.4 (s, 1H), 9.93 (s, 1H), 7.93 (d, J = 8.0 Hz, 1H), 7.81 (s, 1H), 7.66 (d, J = 7.2 Hz, 1H), 7.37 (t, J = 7.6 Hz, 1H), 6.41 (s, 1H), 4.29 (s, 2H), 3.71 (s, 2H), 3.45 (d, J = 13.1 Hz, 2H), 3.31-3.11 (m, 1H), 2.98 (m, 2H), 2.50 (3H, obscured by solvent peak), 2.24 (d, J = 14.0 Hz, 2H), 1.70-1.64 (m, 2H). |

TABLE 8-continued

| Example | Analytical Data |
|---|---|
| Example 143 | LCMS: [M + H]$^+$ 434.2;<br>$^1$H NMR (400 MHz, CD$_3$OD) δ 8.03 (d, J = 8.0 Hz, 1H), 7.84 (d, J = 8.4 Hz, 1H), 7.64 (dd, J = 14.0, 8.0 Hz, 2H), 7.50 (t, J = 8.0 Hz, 1H), 7.39 (t, J = 8.0 Hz, 1H), 7.29 (t, J = 7.6 Hz, 1H), 4.66 (s, 2H), 4.12 (s, 3H), 3.79 (s, 2H), 3.69 (d, J = 12.4 Hz, 2H), 3.19-2.97 (m, 3H), 2.55 (s, 3H), 2.41-2.36 (m, 2H), 1.75 (m, 2H). |
| Example 144 | LCMS: [M + H]$^+$ 398.2;<br>$^1$H NMR (400 MHz, DMSO-d$_6$) δ 12.3 (s, 1H), 9.43 (s, 1H), 7.93 (d, J = 8.0 Hz, 1H), 7.76-7.56 (m, 2H), 7.37 (t, J = 7.6 Hz, 1H), 4.08 (s, 2H), 3.76 (s, 3H), 3.71 (s, 2H), 3.42 (d, J = 11.6 Hz, 2H), 3.26-3.05 (m, 1H), 2.98-2.85 (m, 2H), 2.50 (3H, obscured by solvent peak), 2.25 (m, 2H), 2.15 (s, 3H), 1.67-1.57 (m, 2H). |
| Example 145 | LCMS: [M + H]$^+$ 395.2;<br>$^1$H NMR (400 MHz, CD$_3$OD) δ 8.03 (d, J = 8.0 Hz, 1H), 7.77 (t, J = 8.0 Hz, 1H), 7.67 (d, J = 7.2 Hz, 1H), 7.39 (t, J = 7.6 Hz, 1H), 7.32 (d, J = 8.0 Hz, 1H), 7.27 (d, J = 7.6 Hz, 1H), 4.39 (s, 2H), 3.81 (s, 2H), 3.55 (d, J = 12.4 Hz, 2H), 3.19 (m, 3H), 2.58 (s, 6H), 2.38-2.34 (m, 2H), 1.97-1.91 (m, 2H). |
| Example 146 | LCMS: [M + H]$^+$ 395.2;<br>$^1$H NMR (400 MHz, CD$_3$OD) δ 8.48 (s, 1H), 8.04 (d, J = 8.0 Hz, 1H), 7.68 (t, J = 9.2 Hz, 2H), 7.41 (d, J = 7.2 Hz, 1H), 7.33 (s, 1H), 4.49 (s, 2H), 3.83 (s, 2H), 3.63 (d, J = 12.8 Hz, 2H), 3.24 (m, 3H), 2.60 (s, 3H), 2.41-2.37 (m, 2H), 2.32 (s, 3H), 2.06-2.00 (m, 2H). |
| Example 147 | LCMS: [M + H]$^+$ 394.2;<br>$^1$H NMR (400 MHz, CD$_3$OD) δ 8.03 (d, J = 8.0 Hz, 1H), 7.67 (d, J = 7.2 Hz, 1H), 7.39 (t, J = 7.6 Hz, 1H), 7.36-7.31 (m, 2H), 7.29-7.24 (m, 3H), 3.83 (s, 2H), 3.69 (d, J = 12.6 Hz, 2H), 3.49 (m, 1H), 3.42-3.33 (m, 2H), 3.10-2.99 (m, 4H), 2.59 (s, 3H), 2.43-2.39 (m, 2H), 1.84-1.74 (m, 2H). |
| Example 148 | LCMS: [M + H]$^+$ 434.2;<br>$^1$H NMR (400 MHz, CD$_3$OD) δ 8.05 (s, 1H), 8.02 (dd, J = 8.0, 1.6 Hz, 1H), 7.86 (d, J = 8.4 Hz, 1H), 7.71 (s, 1H), 7.65 (d, J = 7.2 Hz, 1H), 7.38 (t, J = 7.6 Hz, 1H), 7.24 (d, J = 8.4 Hz, 1H), 4.45 (s, 2H), 4.09 (s, 3H), 3.56 (m, 2H), 3.37 (s, 2H), 3.06 (m, 3H), 2.57 (s, 3H), 2.38-2.35 (m, 2H), 1.82-1.72 (m, 2H). |
| Example 149 | LCMS: [M + H]$^+$ 384.2;<br>$^1$H NMR (400 MHz, CD$_3$OD) δ 8.03 (d, J = 8.0 Hz, 1H), 7.67 (d, J = 9.6 Hz, 2H), 7.39 (t, J = 7.6 Hz, 1H), 4.18 (s, 2H), 3.63-3.50 (m, 2H), 3.49-3.23 (m, 2H), 3.04-2.89 (m, 3H), 2.58 (s, 3H), 2.38 (d, J = 14.2 Hz, 2H), 2.32 (s, 3H), 1.81-1.69 (m, 2H). |
| Example 150 | LCMS: [M + H]$^+$ 437.2;<br>$^1$H NMR (400 MHz, CD$_3$OD) δ 7.92 (d, J = 8.0 Hz, 1H), 7.78 (s, 1H), 7.56 (d, J = 7.2 Hz, 1H), 7.36-7.28 (m, 3H), 7.09 (d, J = 6.8 Hz, 1H), 4.21 (s, 2H), 3.44-3.41 (m, 2H), 3.25 (s, 2H), 2.95-2.89 (m, 3H), 2.46 (s, 3H), 2.27 (d, J = 14.4 Hz, 2H), 2.04 (s, 3H), 1.69-1.63 (m, 2H). |
| Example 151 | LCMS: [M + H]$^+$ 420.2;<br>$^1$H NMR (400 MHz, CD$_3$OD) δ 9.38 (s, 1H), 8.44 (d, J = 6.8 Hz, 1H), 8.11 (s, 1H), 8.03 (d, J = 7.2 Hz, 2H), 7.66 (d, J = 7.2 Hz, 1H), 7.39 (t, J = 7.6 Hz, 1H), 4.65 (s, 2H), 3.79 (s, 2H), 3.72-3.36 (m, 3H), 3.05 (m, 2H), 2.58 (s, 3H), 2.37 (m, 2H), 1.78 (m, 2H). |
| Example 152 | LCMS: [M + H]$^+$ 420.2;<br>$^1$H NMR (400 MHz, CD$_3$OD) δ 8.96 (d, J = 6.8 Hz, 1H), 8.29 (s, 1H), 8.06-7.97 (m, 3H), 7.67 (d, J = 7.2 Hz, 1H), 7.57 (t, J = 6.4 Hz, 1H), 7.40 (t, J = 7.6 Hz, 1H), 3.62-3.59 (m, 2H), 3.31 (4H, obscured by solvent peak), 3.18 (m, 3H), 2.59 (s, 3H), 2.31 (d, J = 16.4 Hz, 2H), 1.92-1.88 (m, 2H). |
| Example 153 | LCMS: [M + H]$^+$ 460.2;<br>$^1$H NMR (400 MHz, CD$_3$OD) δ 8.94 (s, 1H), 8.03 (d, J = 8.0 Hz, 1H), 7.91 (s, 1H), 7.67 (d, J = 12 Hz, 1H), 7.46-7.33 (m, 6H), 5.55 (s, 2H), 4.46 (s, 2H), 3.47 (m, 2H), 3.31 (2H obscured by solvent peak), 3.13-3.04 (m, 3H), 2.59 (s, 3H), 2.31 (m, 2H), 1.94-1.87 (m, 2H). |
| Example 154 | LCMS: [M + H]$^+$ 460.2;<br>$^1$H NMR (400 MHz, CD$_3$OD) δ 8.03 (d, J = 8.0 Hz, 1H), 7.87 (d, J = 4.0 Hz, 1H), 7.70-7.61 (m, 2H), 7.43-7.23 (m, 6H), 5.36 (s, 2H), 4.22 (s, 2H), 3.51-3.48 (m, 2H), 3.31 (2H, obscured by solvent peak), 3.05-2.90 (m, 3H), 2.57 (s, 3H), 2.38 (m, 2H), 1.70 (m, 2H). |
| Example 155 | LCMS: [M + H]$^+$ 435.2;<br>$^1$H NMR (400 MHz, CD$_3$OD) δ 8.03 (d, J = 7.6 Hz, 1H), 7.67 (d, J = 7.2 Hz, 1H), 7.56 (t, J = 8.0 Hz, 1H), 7.49 (d, J = 7.6 Hz, 1H), 7.39 (t, J = 7.6 Hz, 1H), 7.26 (d, J = 8.4 Hz, 1H), 7.20 (t, J = 7.6 Hz, 1H), 5.12 (s, 2H), 4.37 (s, 2H), 3.54 (m, 2H), 3.35 (s, 2H), 3.07-3.04 (m, 3H), 2.59 (s, 3H), 2.38 (m, 2H), 1.77-1.74 (m, 2H). |
| Example 156 | LCMS: [M + H]$^+$ 435.2;<br>$^1$H NMR (400 MHz, CD$_3$OD) δ 8.03 (d, J = 8.0 Hz, 1H), 7.67 (d, J = 7.2 Hz, 1H), 7.43-7.30 (m, 2H), 7.10 (d, J = 7.6 Hz, 1H), 7.02 (s, 1H), 4.29 (s, 2H), 3.61-3.46 (m, 3H), 3.01 (m, 3H), 2.57 (s, 3H), 2.37 (m, 2H), 1.77 (m, 2H). Note: 3H obscured by water and/or solvent peak. |

TABLE 8-continued

| Example | Analytical Data |
|---|---|
| Example 157 | LCMS: [M + H]+ 411.2;<br>¹H NMR (400 MHz, CD₃OD) δ 8.27 (d, J = 2.4 Hz, 1H), 8.03 (dd, J = 8.0, 1.6 Hz, 1H), 7.66 (d, J = 7.2 Hz, 1H), 7.46-7.36 (m, 3H), 4.04 (m, 2H), 3.88 (s, 3H), 3.77 (s, 2H), 3.24 (m, 2H), 3.05 (m, 1H), 2.75 (m, 2H), 2.58 (s, 3H), 2.22 (d, J = 14.0 Hz, 2H), 1.80 (d, J = 12.0 Hz, 2H). |
| Example 158 | LCMS: [M + H]+ 451.2;<br>¹H NMR (400 MHz, CD₃OD) δ 8.03 (d, J = 8.0 Hz, 1H), 7.66 (d, J = 7.2 Hz, 1H), 7.39 (t, J = 7.6 Hz, 1H), 6.82 (dd, J = 8.0, 2.0 Hz, 1H), 6.75 (d, J = 2.0 Hz, 1H), 6.69 (d, J = 8.0 Hz, 1H), 4.58-4.56 (m, 1H), 4.25 (t, J = 4.4 Hz, 2H), 3.87 (s, 1H), 3.81-3.75 (m, 2H), 3.28-3.22 (m, 4H), 3.04 (q, J = 7.2 Hz, 1H), 2.89 (s, 3H), 2.72-2.67 (m, 2H), 2.57 (s, 3H), 2.24-2.20 (m, 2H), 1.78-1.75 (m, 2H). |

Further example compounds of the invention prepared by the methods described herein are provided in Table 9.

TABLE 9

| Example | Name and structure | LCMS: [M + H]+ |
|---|---|---|
| Example 178 | 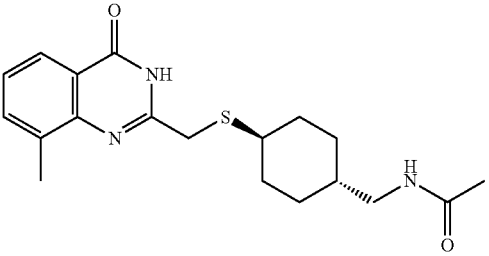 [SMILES: CC(=O)NC[C@H]1CC[C@H](SCc2nc3c(C)cccc3c(=O)[nH]2)CC1]<br>N-(((trans)-4-(((8-methyl-4-oxo-3,4-dihydroquinazolin-2-yl)methyl)thio)cyclohexyl)methyl)acetamide | 360.2 |
| Example 179 | 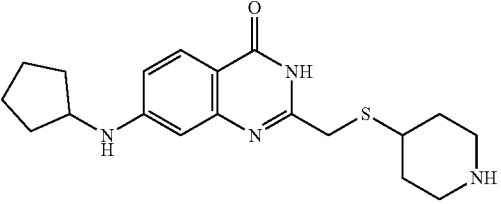 [SMILES: O=c1[nH]c(CSC2CCNCC2)nc2cc(NC3CCCC3)ccc12]<br>7-(cyclopentylamino)-2-((piperidin-4-ylthio)methyl)quinazolin-4(3H)-one | 359.2 |
| Example 180 | 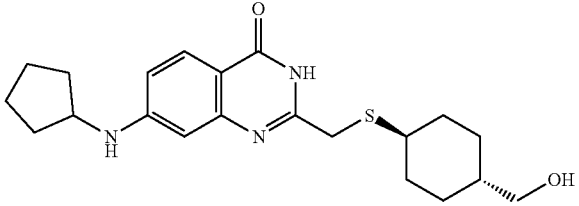 [SMILES: O=c1[nH]c(CS[C@H]2CC[C@H](CO)CC2)nc2cc(NC3CCCC3)ccc12]<br>7-(cyclopentylamino)-2-(((((1R,4R)-4-(hydroxymethyl)cyclohexyl)thio)methyl)quinazolin-4(3H)-one | 388.2 |

TABLE 9-continued

| Example | Name and structure | LCMS: [M + H]+ |
|---|---|---|
| Example 181 | 2-((((trans)-4-(2-aminoethyl)cyclohexyl)thio)methyl)-8-methylquinazolin-4(3H)-one | 332.2 |
| Example 182 | 2-(((3-(aminomethyl)cyclobutyl)thio)methyl)-8-methylquinazolin-4(3H)-one | 290.1 |
| Example 183 | 2-((((trans)-3-(2-aminoethyl)cyclopentyl)thio)methyl)-8-methylquinazolin-4(3H)-one | 318.1 |
| Example 184 | 7-(cyclopentylamino)-5-fluoro-2-(((tetrahydro-2H-pyran-4-yl)thio)methyl)quinazolin-4(3H)-one | 378.2 |
| Example 185 | 7-(cyclopentylamino)-5-fluoro-2-(((((1R,4R)-4-hydroxycyclohexyl)thio)methyl)quinazolin-4(3H)-one | 392.2 |

TABLE 9-continued

| Example | Name and structure | LCMS: [M + H]+ |
|---|---|---|
| Example 186 | 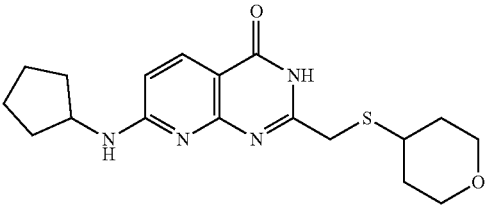 [SMILES: O=c1[nH]c(CSC2CCOCC2)nc2nc(NC3CCCC3)ccc12]<br>7-(cyclopentylamino)-2-(((tetrahydro-2H-pyran-4-yl)thio)methyl)pyrido[2,3-d]pyrimidin-4(3H)-one | 361.2 |
| Example 187 | 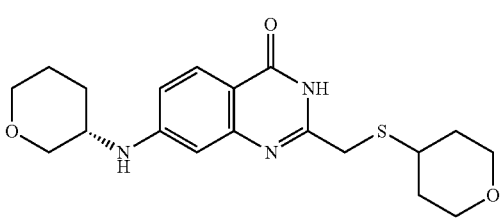 [SMILES: O=c1[nH]c(CSC2CCOCC2)nc2cc(N[C@H]3CCCOC3)ccc12]<br>(S)-7-((tetrahydro-2H-pyran-3-yl)amino)-2-(((tetrahydro-2H-pyran-4-yl)thio)methyl)quinazolin-4(3H)-one | 376.2 |
| Example 188 | 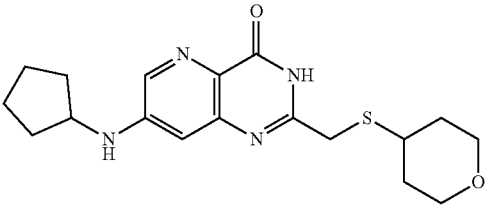 [SMILES: O=c1[nH]c(CSC2CCOCC2)nc2cc(NC3CCCC3)cnc12]<br>7-(cyclopentylamino)-2-(((tetrahydro-2H-pyran-4-yl)thio)methyl)pyrido[3,2-d]pyrimidin-4(3H)-one | 361.2 |
| Example 189 | 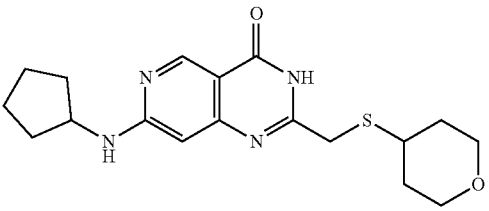 [SMILES: O=c1[nH]c(CSC2CCOCC2)nc2cc(NC3CCCC3)ncc12]<br>7-(cyclopentylamino)-2-(((tetrahydro-2H-pyran-4-yl)thio)methyl)pyrido[4,3-d]pyrimidin-4(3H)-one | 361.2 |
| Example 190 | 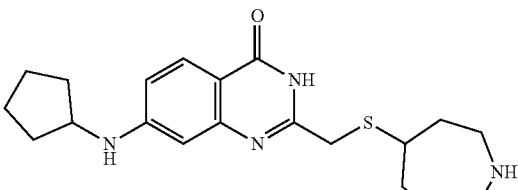<br>2-((azepan-4-ylthio)methyl)-7-(cyclopentylamino)quinazolin-4(3H)-one | 373.2 |

TABLE 9-continued

| Example | Name and structure | LCMS: [M + H]+ |
|---|---|---|
| Example 191 | 2-(((3-(aminomethyl)cyclopentyl)thio)methyl)-8-methylquinazolin-4(3H)-one | 304.1 |
| Example 192 | 7-((3-methylisoxazol-5-yl)amino)-2-(((tetrahydro-2H-pyran-4-yl)thio)methyl)quinazolin-4(3H)-one | 373.2 |
| Example 193 | (R)-7-((1-(methylsulfonyl)piperidin-3-yl)amino)-2-(((tetrahydro-2H-pyran-4-yl)thio)methyl)quinazolin-4(3H)-one | 453.2 |
| Example 194 | 7-(cyclobutylamino)-2-(((((1R,4R)-4-hydroxycyclohexyl)thio)methyl)quinazolin-4(3H)-one | 360.2 |
| Example 195 | 7-((1-(methylsulfonyl)azetidin-3-yl)amino)-2-(((tetrahydro-2H-pyran-4-yl)thio)methyl)quinazolin-4(3H)-one | 425.1 |

TABLE 9-continued

| Example | Name and structure | LCMS: [M + H]+ |
|---|---|---|
| Example 196 | 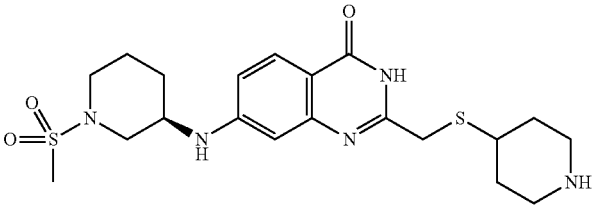 [SMILES: CS(=O)(=O)N1CCC[C@@H](Nc2ccc3c(=O)[nH]c(CSC4CCNCC4)nc3c2)C1]<br>(R)-7-((1-(methylsulfonyl)piperidin-3-yl)amino)-2-((piperidin-4-ylthio)methyl)quinazolin-4(3H)-one | 452.2 |
| Example 197 | 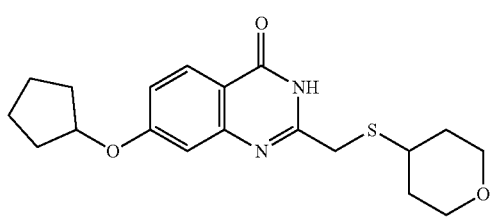 [SMILES: O=c1[nH]c(CSC2CCOCC2)nc2cc(OC3CCCC3)ccc12]<br>7-(cyclopentyloxy)-2-(((tetrahydro-2H-pyran-4-yl)thio)methyl)quinazolin-4(3H)-one | 361.1 |
| Example 198 | 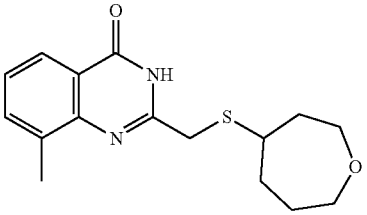 [SMILES: Cc1cccc2c(=O)[nH]c(CSC3CCCOCC3)nc12]<br>8-methyl-2-((oxepan-4-ylthio)methyl)quinazolin-4(3H)-one | 305.1 |
| Example 199 | 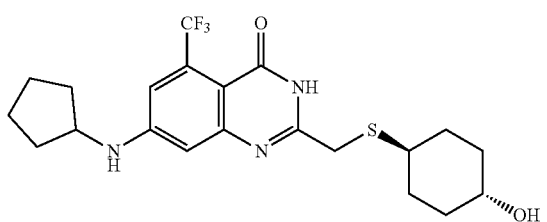 [SMILES: O=c1[nH]c(CS[C@H]2CC[C@H](O)CC2)nc2cc(NC3CCCC3)cc(C(F)(F)F)c12]<br>7-(cyclopentylamino)-2-(((((1R,4R)-4-hydroxycyclohexyl)thio)methyl)-5-(trifluoromethyl)quinazolin-4(3H)-one | 442.1 |
| Example 200 | 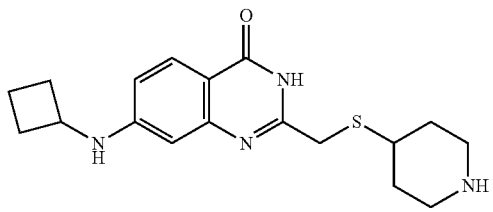 [SMILES: O=c1[nH]c(CSC2CCNCC2)nc2cc(NC3CCC3)ccc12]<br>7-(cyclobutylamino)-2-((piperidin-4-ylthio)methyl)quinazolin-4(3H)-one | 345.2 |

TABLE 9-continued

| Example | Name and structure | LCMS: [M + H]+ |
|---|---|---|
| Example 201 | 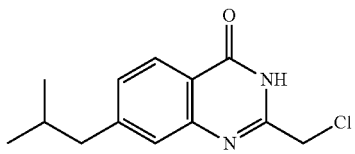 [SMILES: CC(C)Cc1ccc2c(=O)[nH]c(CCl)nc2c1]<br>(R)-7-((1-(methylsulfonyl)piperidin-3-yl)amino)-2-(((tetrahydro-2H-pyran-4-yl)thio)methyl)pyrido[2,3-d]pyrimidin-4(3H)-one | 454.1 |

Int-A39: 2-(Chloromethyl)-7-isobutylquinazolin-4(3H)-one

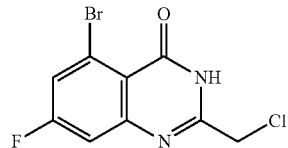 [SMILES: O=c1[nH]c(CCl)nc2cc(F)cc(Br)c12]

Step 1: 2-Amino-4-(2-methylprop-1-en-1-yl)benzoic Acid

To a solution of 2-amino-4-bromo-benzoic acid (500 mg, 2.31 mmol, 1.0 eq) in 1,4-dioxane/water (4:1, 20 mL) under a $N_2$ atmosphere was added 4,4,5,5-tetramethyl-2-(2-methylprop-1-enyl)-1,3,2-dioxaborolane (548 mg, 3.01 mmol, 1.3 eq), Pd(dppf)Cl$_2$ (169 mg, 0.23 mmol, 0.1 eq) and potassium carbonate (640 mg, 4.63 mmol, 2.0 eq) and the mixture was heated at 100° C. for 6 h. After cooling to RT, the mixture was diluted with water (20 mL) and extracted with EtOAc (40 mL×3). The combined organic layers were washed with water (40 mL), dried over $Na_2SO_4$ and concentrated under reduced pressure to afford the title compound (400 mg, 90%) as a brown oil. LCMS: [M+H]+ 192.2.

Step 2: Methyl 2-amino-4-(2-methylprop-1-en-1-yl)benzoate

Prepared from 2-amino-4-(2-methylprop-1-en-1-yl) benzoic acid according to the method described for Int-A20, step 3. LCMS: [M+H]+ 206.2.

Step 3: Methyl 2-amino-4-isobutylbenzoate

A solution of methyl 2-amino-4-(2-methylprop-1-enyl) benzoate (200 mg, 0.97 mmol) and Pt/C (10% wet, 20 mg) in EtOAc (20 mL) was stirred at RT under a $H_2$ atmosphere overnight. The mixture was filtered and the filtrate was concentrated under reduced pressure to afford the title compound (200 mg, 99%) as a colorless oil. LCMS: [M+H]+ 208.2.

Step 4: 2-(Chloromethyl)-7-isobutylquinazolin-4(3H)-one

Prepared from methyl 2-amino-4-isobutylbenzoate and chloroacetonitrile according to the method described for Int-A16. LCMS: [M+H]+ 251.1.

Int-A40: 5-Bromo-2-(chloromethyl)-7-fluoroquinazolin-4(3H)-one

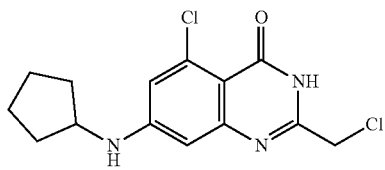 [SMILES: O=c1[nH]c(CCl)nc2cc(NC3CCCC3)cc(Cl)c12]

Prepared from 3-bromo-5-fluoroaniline according to the method described for Int-A20. LCMS: [M+H]+ 290.9; $^1$HNMR (400 MHz, DMSO-d$_6$) δ 7.76 (dd, J=8.8, 2.8 Hz, 1H), 7.51 (dd, J=9.2, 2.4 Hz, 1H), 4.52 (s, 2H).

Int-A41: 5-Chloro-2-(chloromethyl)-7-(cyclopentylamino)quinazolin-4(3H)-one

Step 1: Methyl 4-bromo-2-chloro-6-fluorobenzoate

Prepared from 4-bromo-2-chloro-6-fluorobenzoic acid according to the method described for Int-A20, step 3. $^1$HNMR (400 MHz, CDCl$_3$) δ 7.41 (s, 1H), 7.26-7.24 (m, 1H), 3.96 (s, 3H).

Step 2: Methyl 2-chloro-4-(cyclopentylamino)-6-fluorobenzoate

To a solution of methyl 4-bromo-2-chloro-6-fluorobenzoate (2.0 g, 7.48 mmol, 1.0 eq) and cyclopentane amine (0.76 g, 8.97 mmol, 1.2 eq) in toluene (5 mL) under a $N_2$ atmosphere were added $Cs_2CO_3$ (4.87 g, 15.0 mmol, 2.0 eq), BINAP (931 mg, 1.5 mmol, 0.2 eq) and Pd(OAc)$_2$ (168 mg, 0.75 mmol, 0.1 eq) and the mixture was heated at reflux for 30 min. After cooling to RT, the mixture was filtered and the filtrate was concentrated under reduced pressure. The residue was purified by column chromatography (petroleum ether:EtOAc, 10:1, v/v) to afford the title compound (2.0 g, 98%) as a colorless oil. LCMS: [M+H]$^+$ 272.1.

Step 3: Methyl 2-chloro-4-(cyclopentylamino)-6-((2,4-dimethoxybenzyl)amino)benzoate To a solution of methyl 2-chloro-4-(cyclopentylamino)-6-fluorobenzoate (2.0 g, 7.36 mmol, 1.0 eq) and (2,4-dimethoxyphenyl)methanamine (3.69 g, 22.1 mmol, 3.0 eq) in NMP (30 mL) under a $N_2$ atmosphere was added $K_2CO_3$ (2.03 g, 14.7 mmol, 2.0 eq) and the mixture was heated at 100° C. overnight. After cooling to RT, the mixture was diluted with water (90 mL) and extracted with EtOAc (30 mL×3). The combined organic layers were dried over $Na_2SO_4$ and concentrated under reduced pressure. The residue was purified by column chromatography (petroleum ether:EtOAc, 8:1 to 5:1, v/v) to afford the title compound (1.6 g, 56%) as a white solid. LCMS: [M+H]$^+$ 419.1.

Step 4: Methyl 2-amino-6-chloro-4-(cyclopentylamino)benzoate

To a solution of methyl 2-chloro-4-(cyclopentylamino)-6-((2,4-dimethoxybenzyl)amino)benzoate (1.6 g, 3.82 mmol, 1.0 eq) in DCM (10 mL) was added TFA (5 mL) and the mixture was stirred at RT for 30 min. The mixture was concentrated under reduced pressure and the residue was diluted with a saturated aqueous $Na_2CO_3$ solution (30 mL) and extracted with EtOAc (30 mL×3). The combined organic layers were dried over $Na_2SO_4$ and concentrated under reduced pressure. The residue was purified by column chromatography (petroleum ether:EtOAc, 5:1, v/v) to afford the title compound (610 mg, 59%) as a yellow solid. LCMS: [M+H]$^+$ 269.1.

Step 5: 5-Chloro-2-(chloromethyl)-7-(cyclopentylamino)quinazolin-4(3H)-one

Prepared from methyl 2-amino-6-chloro-4-(cyclopentylamino)benzoate and chloroacetonitrile according to the method described for Int-A16. LCMS: [M+H]$^+$ 312.1.

Int-A42: 2-(Chloromethyl)-7-(cyclopentylamino)-5-methoxyquinazolin-4(3H)-one

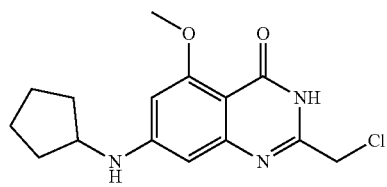 [SMILES: COc1cc(NC2CCCC2)cc2nc(CCl)[nH]c(=O)c12]

Step 1: Methyl 4-bromo-2-((2,4-dimethoxybenzyl)amino)-6-fluorobenzoate

Prepared from methyl 4-bromo-2,6-difluorobenzoate according to the method described for Int-A41, step 3. LCMS: [M+H]$^+$ 398.0.

Step 2: 4-Bromo-2-((2,4-dimethoxybenzyl)amino)-6-methoxybenzoic Acid

To a solution of methyl 4-bromo-2-((2,4-dimethoxybenzyl)amino)-6-fluorobenzoate (3.98 g, 9.99 mmol, 1.0 eq) in methanol (20 mL) and NMP (20 mL) was added NaH (60% w/w suspension in oil, 2.0 g, 50.0 mmol, 5.0 eq) and the mixture was heated at 120° C. overnight. After cooling to RT, the mixture was adjusted to pH 4 with 6 M HCl and the resulting precipitate was collected by filtration to afford the title compound (1.4 g, 35%) as a white solid. LCMS: [M+H]$^+$ 396.0.

Step 3: Methyl 4-bromo-2-((2,4-dimethoxybenzyl)amino)-6-methoxybenzoate

Prepared from 4-bromo-2-((2,4-dimethoxybenzyl)amino)-6-methoxybenzoic acid according to the method described for Int-A20 step 3. LCMS: [M+H]$^+$ 410.1.

Step 4: Methyl 4-(cyclopentylamino)-2-((2,4-dimethoxybenzyl)amino)-6-methoxybenzoate To a solution of methyl 4-bromo-2-((2,4-dimethoxybenzyl)amino)-6-methoxybenzoate (820 mg, 2.0 mmol, 1.0 eq) and cyclopentanamine (255 mg, 3.0 mmol, 1.5 eq) in toluene (15 mL) under a $N_2$ atmosphere was added $Cs_2CO_3$ (1.95 g, 6.0 mmol, 3.0 eq), Xantphos (231 mg, 0.4 mmol, 0.2 eq) and Pd(OAc)$_2$ (45 mg, 0.20 mmol, 0.1 eq) and the mixture was heated at reflux for 8 h. After cooling to RT, the mixture was filtered and the filtrate was concentrated under reduced pressure. The residue was purified by column chromatography (petroleum ether:EtOAc, 7:1, v/v) to afford the title compound (680 mg, 82%) as a white solid. LCMS: [M+H]$^+$ 415.2.

Step 5: Methyl 2-amino-4-(cyclopentylamino)-6-methoxy-benzoate

Prepared from methyl 4-(cyclopentylamino)-2-((2,4-dimethoxybenzyl)amino)-6-methoxybenzoate according to the method described for Int-A41, step 4. LCMS: [M+H]$^+$ 265.2.

Step 6: 2-(Chloromethyl)-7-(cyclopentylamino)-5-methoxyquinazolin-4(3H)-one

Prepared from methyl 2-amino-4-(cyclopentylamino)-6-methoxy-benzoate and chloroacetonitrile according to the method described for Int-A16. LCMS: [M+H]$^+$ 308.1.

Int-A43: 2-(Chloromethyl)-7-(cyclopentylamino)-5-fluoroquinazolin-4(3H)-one

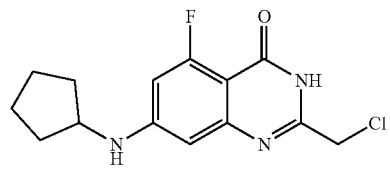 [SMILES: O=c1[nH]c(CCl)nc2cc(NC3CCCC3)cc(F)c12]

Step 1: Methyl 2-amino-4-(cyclopentylamino)-6-fluorobenzoate

Prepared from methyl 4-bromo-2,6-difluorobenzoate according to the method described for Int 39, step 2, 3 and 4. LCMS: [M+H]$^+$ 253.1.

Step 2: 2-(Chloromethyl)-7-(cyclopentylamino)-5-fluoroquinazolin-4(3H)-one

Prepared from methyl 2-amino-4-(cyclopentylamino)-6-fluorobenzoate and chloroacetonitrile according to the method described for Int-A16. LCMS: [M+H]$^+$ 296.1.

Int-A44: 7-Chloro-2-(chloromethyl)pyrido[2,3-d]pyrimidin-4(3H)-one

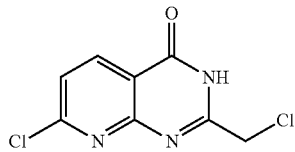 [SMILES: O=c1[nH]c(CCl)nc2nc(Cl)ccc12]

A solution of 2-amino-6-chloro-pyridine-3-carboxamide (500 mg, 2.91 mmol, 1.0 eq) in 2-chloro-1,1,1-trimethoxyethane (5 mL) was heated at 120° C. under a N$_2$ atmosphere for 3 h. The mixture was then filtered and the filter cake was washed with EtOAc/petroleum ether (1:3, 20 mL) then dried under reduced pressure to afford the title compound (450 mg, ~50% purity, 33%) as a brown solid, which was used without further purification. LCMS: [M+H]$^+$ 230.0.

Int-A45: 7-Bromo-2-(chloromethyl)-6-methoxyquinazolin-4(3H)-one

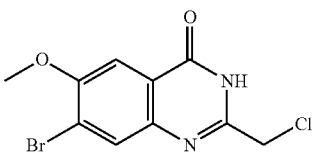 [SMILES: COc1cc2c(=O)[nH]c(CCl)nc2cc1Br]

Step 1: Ethyl 2-amino-4-bromo-5-methoxybenzoate

Prepared from 4-bromo-5-fluoro-2-nitrobenzoic acid according to the procedure described in WO2014128655.

Step 2: 7-Bromo-2-(chloromethyl)-6-methoxyquinazolin-4(3H)-one

Prepared from ethyl 2-amino-4-bromo-5-methoxybenzoate and chloroacetonitrile according to the method described for Int-A16. LCMS: [M+H]$^+$ 303.0.

Int-A46: 7-Bromo-2-(chloromethyl)-5-fluoroquinazolin-4(3H)-one

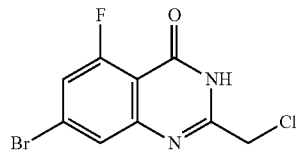 [SMILES: O=c1[nH]c(CCl)nc2cc(Br)cc(F)c12]

Step 1: Methyl 4-bromo-2-((2,4-dimethoxybenzyl)amino)-6-fluorobenzoate

Prepared from methyl 4-bromo-2,6-difluorobenzoate and (2,4-dimethoxyphenyl)methanamine according to the method described for Int-A41, step 3. LCMS: [M+H]$^+$ 398.0.

Step 2: 7-Bromo-2-(chloromethyl)-5-fluoroquinazolin-4(3H)-one

A mixture of methyl 4-bromo-2-[(2,4-dimethoxyphenyl)methylamino]-6-fluoro-benzoate (100 g, 251 mmol, 1.0 eq), 2-chloroacetonitrile (47.7 mL, 753 mmol, 3.0 eq) and a 4 M HCl in dioxane solution (300 mL) was heated at 100° C. overnight. After cooling to RT, the mixture was filtered and the collected solid was purified by column chromatography (DCM:MeOH, 50:1 to 10:1, v/v) to afford the title compound (84 g, >100%) as a light-yellow solid, which was used in subsequent steps without further purification LCMS: [M+H]$^+$ 290.9.

Int-A47: 2-(Chloromethyl)-7-(cyclopentylamino)-5,6-difluoroquinazolin-4(3H)-one

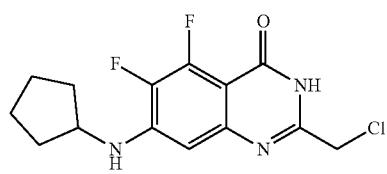 [SMILES: O=c1[nH]c(CCl)nc2cc(NC3CCCC3)c(F)c(F)c12]

Step 1: Methyl 6-amino-2,3,4-trifluorobenzoate

Prepared from 3,4,5-trifluoroaniline according to the method described for Int-A20, step 1, 2 and 3. LCMS: [M+H]$^+$ 206.0.

Step 2: Methyl 6-amino-4-(cyclopentylamino)-2,3-difluorobenzoate

A mixture of methyl 6-amino-2,3,4-trifluoro-benzoate (2.05 g, 9.99 mmol, 1.0 eq), cyclopentanamine (1.18 mL, 12.0 mmol) and K$_2$CO$_3$ (1.38 g, 9.99 mmol, 1.0 eq) in DMSO (20 mL) was heated at 55° C. for 16 h. After cooling to RT, the mixture was diluted with EtOAc (100 mL), washed with brine (20 mL×3) and the organic layer was concentrated under reduced pressure. The residue was purified by C18 reverse phase column (Biotage, 40% to 80%

ACN in water) to afford the title compound (1.1 g, 41%) as a pale green solid. LCMS: [M+H]+ 271.1.

Step 3: 2-(Chloromethyl)-7-(cyclopentylamino)-5,6-difluoroquinazolin-4(3H)-one

Prepared from methyl 6-amino-4-(cyclopentylamino)-2,3-difluorobenzoate and chloroacetonitrile according to the method described for Int-A16. LCMS: [M+H]+ 314.1.

Int-A48: 7-Bromo-2-(chloromethyl)-6-fluoroquinazolin-4(3H)-one

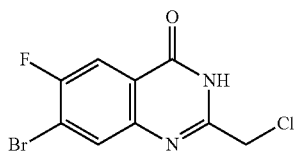 [SMILES: O=c1[nH]c(CCl)nc2cc(Br)c(F)cc12]

Step 1: Methyl 4-bromo-5-fluoro-2-nitrobenzoate

Prepared from 4-bromo-5-fluoro-2-nitrobenzoic acid according to the method described for Int-A20, step 3.

$^1$HNMR (400 MHz, CDCl$_3$) δ 8.20 (d, J=5.6 Hz, 1H), 7.47 (d, J=7.6 Hz, 1H), 3.94 (s, 3H).

Step 2: Methyl 2-amino-4-bromo-5-fluorobenzoate

To a solution of methyl 4-bromo-5-fluoro-2-nitrobenzoate (2.0 g, 7.19 mmol, 1.0 eq) in ethanol (20 mL) and water (10 mL) was added NH$_4$Cl (1.15 g, 21.6 mmol, 3.0 eq) and zinc (1.41 g, 21.6 mmol, 3.0 eq) and the mixture was heated at 40° C. for 2 h. After cooling to RT, the mixture was filtered and the filtrate was concentrated under reduce pressure. The residue was diluted with water (50 mL) and extracted with EtOAc (50 mL×3). The combined organic layers were dried over Na$_2$SO$_4$ and concentrated under reduced pressure. The residue was purified by column chromatography (petroleum ether:EtOAc, 20:1, v/v) to afford the title compound (390 mg, 22%) as a white solid. LCMS: [M+H]+ 248.0.

Step 3: 7-Bromo-2-(chloromethyl)-6-fluoroquinazolin-4(3H)-one

Prepared from methyl 2-amino-4-bromo-5-fluorobenzoate and chloroacetonitrile according to the method described for Int-A16. LCMS: [M+H]+ 291.0.

Int-A49: 2-(Chloromethyl)-7-(cyclopropylmethoxy)-5-fluoroquinazolin-4(3H)-one

Step 1: Methyl 2-((2,4-dimethoxybenzyl)amino)-6-fluoro-4-hydroxybenzoate

To a solution of methyl 4-bromo-2-((2,4-dimethoxybenzyl)amino)-6-fluorobenzoate (50 g, 126 mmol, 1.0 eq; see Int-A42, step 1) in 1,4-dioxane (150 mL) and water (150 mL) was added NaOH (12.6 g, 314 mmol, 3.0 eq), Pd$_2$(dba)$_3$ (2.3 g, 2.51 mmol, 0.01 eq) and t-BuXphos (1.06 g, 2.51 mmol, 0.01 eq) and the mixture was heated at 90° C. under a N$_2$ atmosphere for 3 h. After cooling to RT, the mixture was filtered and the filtrate was adjusted to pH 5 with 0.5 M HCl and extracted with EtOAc (300 mL×3). The combined organic layers were dried over Na$_2$SO$_4$ and concentrated under reduced pressure. The residue was purified by column chromatography (petroleum ether:EtOAc, 5:1, v/v) to afford the title compound (25 g, 48%) as a yellow solid. LCMS: [M+H]+ 336.1.

Step 2: Methyl 4-(cyclopropylmethoxy)-2-((2,4-dimethoxybenzyl)amino)-6-fluorobenzoate To a solution of methyl 2-((2,4-dimethoxybenzyl)amino)-6-fluoro-4-hydroxybenzoate (3.2 g, 8.11 mmol, 1.0 eq) in DMF (20 mL) was added bromomethylcyclopropane (1.31 g, 9.73 mmol, 1.2 eq) and K$_2$CO$_3$ (2.24 g, 16.2 mmol, 2.0 eq) and the mixture was heated at 80° C. for 3 h. After cooling to RT, the mixture was diluted with water (100 mL) and extracted with EtOAc (100 mL×3). The combined organic layers were dried over Na$_2$SO$_4$ and concentrated under reduced pressure. The residue was purified by column chromatography (petroleum ether:EtOAc, 10/1, v/v) to afford the title compound (2.4 g, 76%) as a white solid. LCMS: [M+H]+ 390.2.

Step 3: Methyl 2-amino-4-(cyclopropylmethoxy)-6-fluorobenzoate

To a solution of methyl 4-(cyclopropylmethoxy)-2-((2,4-dimethoxybenzyl)amino)-6-fluorobenzoate (1.6 g, 4.11 mmol, 1.0 eq) in DCM (8.0 mL) was added TFA (4.0 mL) and the mixture was stirred at RT for 2 h. The mixture was concentrated under reduced pressure and the residue was purified by column chromatography (DCM:MeOH, 20/1, v/v) to afford the title compound (0.9 g, 91%) as a brown solid. LCMS: [M+H]+ 240.1.

Step 4: 2-(Chloromethyl)-7-(cyclopropylmethoxy)-5-fluoroquinazolin-4(3H)-one

Prepared from methyl 2-amino-4-(cyclopropylmethoxy)-6-fluorobenzoate and chloroacetonitrile according to the method described for Int-A16. LCMS: [M+H]+ 283.1.

Alternative Synthesis of Int-A49: 2-(Chloromethyl)-7-(cyclopropylmethoxy)-5-fluoroquinazolin-4(3H)-one

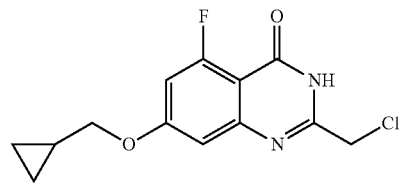 [SMILES: O=c1[nH]c(CCl)nc2cc(OCC3CC3)cc(F)c12]

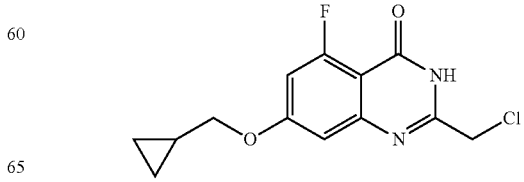

Step 1: Methyl 4-(cyclopropylmethoxy)-2,6-difluorobenzoate

A mixture of methyl 2,6-difluoro-4-hydroxybenzoate, preparation of which is described in Example 333, Step 4 (180 g, 957 mmol), (bromomethyl)cyclopropane (102 mL, 1.05 mol) and K$_2$CO$_3$ (330 g, 2.39 mol) in DMSO (1 L) was heated at 80° C. overnight. The mixture was diluted with water (5 L) and extracted with EtOAc (1 L×3). The combined organic extracts were washed with water (800 mL), brine (800 mL), dried over Na$_2$SO$_4$ and concentrated under reduced pressure to afford the title compound (214 g, 92%) as a brown oil. LCMS: [M+H]$^+$ 243.1.

Step 2: Methyl 4-(cyclopropylmethoxy)-2-((2,4-dimethoxybenzyl)amino)-6-fluorobenzoate A mixture of methyl 4-(cyclopropylmethoxy)-2,6-difluorobenzoate (214 g, 881 mmol), (2,4-dimethoxyphenyl)methanamine (139 mL, 926 mmol) and K$_2$CO$_3$ (243 g, 1.76 mol) in NMP (1 L) was heated at 80° C. overnight. The mixture was poured into water (5 L) and the resulting precipitate was collected by filtration and washed with water (800 mL). The filter cake was dissolved in DCM (2.5 L) and washed with brine (800 mL). The organic layer was dried over Na$_2$SO$_4$ and concentrated under reduced pressure to give the title compound (343 g, 99%) as an off-white solid. LCMS: [M+Na]$^+$ 412.1.

Step 3: Methyl 2-amino-4-(cyclopropylmethoxy)-6-fluorobenzoate

To a solution of methyl 4-(cyclopropylmethoxy)-2-((2,4-dimethoxybenzyl)amino)-6-fluorobenzoate (1.6 g, 4.11 mmol, 1.0 eq) in DCM (8.0 mL) was added TFA (4.0 mL) and the mixture was stirred at RT for 2 h. The mixture was concentrated under reduced pressure and the residue was purified by column chromatography (DCM:MeOH, 20/1, v/v) to afford the title compound (0.9 g, 91%) as a brown solid. LCMS: [M+H]$^+$ 240.1.

Step 4: 2-(Chloromethyl)-7-(cyclopropylmethoxy)-5-fluoroquinazolin-4(3H)-one Prepared from methyl 2-amino-4-(cyclopropylmethoxy)-6-fluorobenzoate and chloroacetonitrile according to the method described for Int-A16. LCMS: [M+H]$^+$ 283.1.

Int-A50: 2-(Chloromethyl)-5-fluoro-7-((tetrahydro-2H-pyran-4-yl)methoxy)quinazolin-4(3H)-one

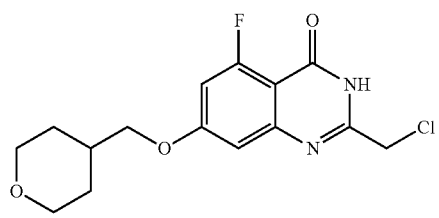 [SMILES: O=c1[nH]c(CCl)nc2cc(OCC3CCOCC3)cc(F)c12]

Step 1: Methyl 2-amino-6-fluoro-4-((tetrahydro-2H-pyran-4-yl)methoxy) benzoate Prepared from methyl 2-((2,4-dimethoxybenzyl)amino)-6-fluoro-4-hydroxybenzoate and 4-(bromomethyl)tetrahydro-2H-pyran according to the method described for Int-A49, step 2 and 3. LCMS: [M+H]$^+$ 284.1.

Step 2: 2-(Chloromethyl)-5-fluoro-7-((tetrahydro-2H-pyran-4-yl) methoxy) quinazolin-4(3H)-one Prepared from methyl 2-amino-6-fluoro-4-((tetrahydro-2H-pyran-4-yl)methoxy) benzoate and chloroacetonitrile according to the method described for Int-A16. LCMS: [M+H]$^+$ 327.1.

Int-A51: 2-(Chloromethyl)-7-(cyclobutylmethoxy)-5-methylquinazolin-4(3H)-one

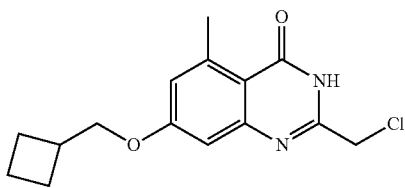 [SMILES: Cc1cc(OCC2CCC2)cc2nc(CCl)[nH]c(=O)c12]

Step 1: Methyl 4-bromo-2-fluoro-6-methylbenzoate

Prepared from 4-bromo-2-fluoro-6-methylbenzoic acid according to the method described for Int-A20 step 3.

Step 2: Methyl 4-bromo-2-((2,4-dimethoxybenzyl)amino)-6-methylbenzoate

Prepared from methyl 4-bromo-2-fluoro-6-methylbenzoate and (2,4-dimethoxyphenyl)methanamine according to the method described for Int-A41, step 3. LCMS: [M+H]$^+$ 394.1.

Step 3: Methyl 2-amino-4-(cyclobutylmethoxy)-6-methylbenzoate

Prepared from methyl 4-bromo-2-((2,4-dimethoxybenzyl)amino)-6-methylbenzoate and (bromomethyl)cyclobutane according to the method described for Int-A49, step 1, 2 and 3. LCMS: [M+H]$^+$ 250.1.

Step 4: 2-(Chloromethyl)-7-(cyclobutylmethoxy)-5-methylquinazolin-4(3H)-one

Prepared from methyl 2-amino-4-(cyclobutylmethoxy)-6-methylbenzoate and chloroacetonitrile according to the method described for Int-A16. LCMS: [M+H]$^+$ 293.1.

Int-A52: 2-(Chloromethyl)-5-fluoro-7-((tetrahydrofuran-3-yl)methoxy)quinazolin-4(3H)-one

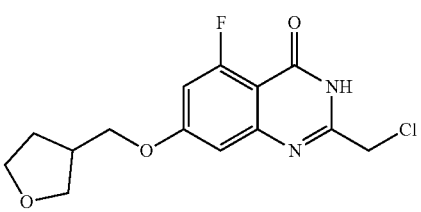 [SMILES: O=c1[nH]c(CCl)nc2cc(OCC3CCOC3)cc(F)c12]

Step 1: (Tetrahydrofuran-3-yl)methyl Methanesulfonate

Prepared from (tetrahydrofuran-3-yl)methanol according to the method described for Int-B3, step 1 and used directly in the next step.

Step 2: Methyl 2-amino-6-fluoro-4-((tetrahydrofuran-3-yl)methoxy) benzoate

Prepared from methyl 2-((2,4-dimethoxybenzyl)amino)-6-fluoro-4-hydroxybenzoate and (tetrahydrofuran-3-yl)methyl methanesulfonate according to the method described for Int-A47, step 2 and 3. LCMS: [M+H]+ 270.1.

Step 3: 2-(Chloromethyl)-5-fluoro-7-((tetrahydrofuran-3-yl)methoxy) quinazolin-4(3H)-one Prepared from methyl 2-amino-6-fluoro-4-((tetrahydrofuran-3-yl)methoxy) benzoate and chloroacetonitrile according to the method described for Int-A16. LCMS: [M+H]+ 313.0.

Int-A53: 2-(Chloromethyl)-5-fluoro-7-hydroxyquinazolin-4(3H)-one

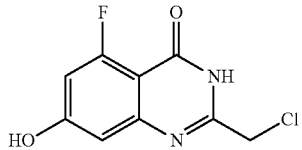 [SMILES: O=c1[nH]c(CCl)nc2cc(O)cc(F)c12]

Step 1: Methyl 2-((2,4-dimethoxybenzyl)amino)-6-fluoro-4-hydroxybenzoate

To a solution of methyl 4-bromo-2-((2,4-dimethoxybenzyl)amino)-6-fluorobenzoate (50.0 g, 125 mmol) in 1,4-dioxane (150 mL) and water (150 mL) was added KOH (14.1 g, 251.1 mmol), Pd$_2$(dba)$_3$ (1.15 g, 1.26 mmol) and t-BuXphos (1.06 g, 2.51 mmol) and the mixture was heated at 90° C. under a N$_2$ atmosphere for 3 h. After cooling to RT, the mixture was extracted with EtOAc (300 mL). The organic layer was washed with brine (100 mL×3), dried over Na$_2$SO$_4$ and concentrated under reduced pressure. The residue was purified by column chromatography (Petroleum ether:EtOAc, 5:1, v/v) to afford the title compound (29.0 g, 55%) as a yellow solid. LCMS: [M+H]+ 336.0.

Step 2: 2-(Chloromethyl)-5-fluoro-7-hydroxyquinazolin-4(3H)-one

Prepared from methyl 2-((2,4-dimethoxybenzyl)amino)-6-fluoro-4-hydroxybenzoate and chloroacetonitrile according to the method described for Int-A16. LCMS: [M+H]+ 229.0.

Int-B14: Ethyl 4-(acetylthio) cyclohexane-1-carboxylate

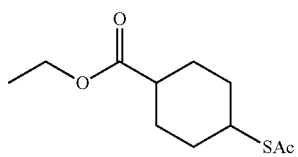

Prepared from ethyl 4-hydroxycyclohexane-1-carboxylate according to the method described for Int-B3, step 1 and 2 and obtained as a 2:1 mixture of cis and trans isomers.

$^1$H NMR (400 MHz, CDCl$_3$) 4.10-4.02 (m, 2H), 3.70 (m, 0.67H), 3.31 (m, 0.33H), 2.51-2.44 (m, 1H), 2.24 (s, 2H), 2.23 (s, 1H), 2.19-2.17 (m, 2H), 2.04-1.91 (m, 4H), 1.66-1.46 (m, 2H), 1.20-1.17 (m, 3H).

Int-B15: Ethyl 2-(trans-4-(acetylthio)cyclohexyl)acetate

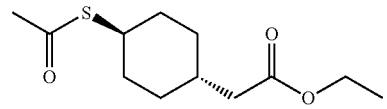 [SMILES: CCOC(=O)C[C@H]1CC[C@H](SC(C)=O)CC1]

Step 1: Ethyl 2-(cis-4-hydroxycyclohexyl)acetate

Prepared from ethyl 2-(4-hydroxyphenyl)acetate according to the procedure described in WO2006/044524.

Step 2: Ethyl 2-(trans-4-(acetylthio)cyclohexyl)acetate

Prepared from ethyl 2-(cis-4-hydroxycyclohexyl)acetate according to the method described for Int-B3, step 1 and 2.

$^1$H NMR (400 MHz, CDCl$_3$) δ 4.06 (q, J=7.2 Hz, 2H), 3.26 (m, 1H), 2.29 (s, 3H), 2.18 (d, J=6.8 Hz, 2H), 1.99-1.96 (m, 2H), 1.83-1.79 (m, 3H), 1.43-1.33 (m, 2H), 1.18 (t, J=7.2 Hz, 3H), 1.13-1.03 (m, 2H)

Int-B16: S-((cis)-4-Hydroxy-4-methylcyclohexyl) ethanethioate

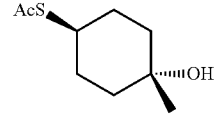

Step 1: (trans)-4-Hydroxy-4-methylcyclohexyl Methanesulfonate

Prepared from (cis)-1-methylcyclohexane-1,4-diol according to the method described for Int-B3, step 1 $^1$H NMR (400 MHz, DMSO-d$_6$) δ 4.60-4.49 (m, 1H), 3.15 (s, 3H), 1.86-1.70 (m, 4H), 1.63-1.51 (m, 2H), 1.45-1.32 (m, 2H), 1.09 (s, 3H). One signal (OH) not observed.

Step 2: S-((cis)-4-Hydroxy-4-methylcyclohexyl) ethanethioate

Prepared from (trans)-4-hydroxy-4-methylcyclohexyl methanesulfonate according to the method described for Int-B3, step 2. $^1$H NMR (400 MHz, DMSO-d$_6$) δ 3.60-3.50 (m, 1H), 2.29 (s, 3H), 2.02-1.89 (m, 2H), 1.49-1.37 (m, 6H), 1.08 (s, 3H). One signal (OH) not observed.

Int-C12: S-((7-(cyclopentylamino)-5-fluoro-4-oxo-3,4-dihydroquinazolin-2-yl) methyl) ethanethioate

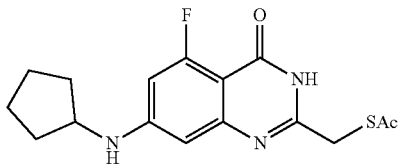

Prepared from Int-A41 and KSAc according to the method described for Int-C1. LCMS: [M+H]$^+$ 336.1.

Example 202: 7-Isobutyl-2-(((tetrahydro-2H-pyran-4-yl)thio)methyl)quinazolin-4(3H)-one

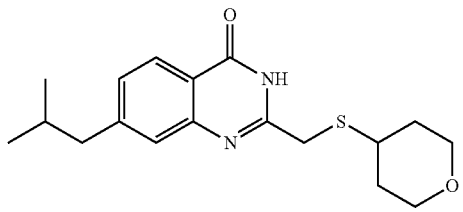 [SMILES: CC(C)Cc1ccc2c(=O)[nH]c(CSC3CCOCC3)nc2c1]

To a solution of Int-A39 (100 mg, 0.40 mmol, 1.0 eq) and Int-B1 (64 mg, 0.40 mmol, 1.0 eq) in THF (2 mL) was added 2 M NaOH (0.8 mL) and the mixture was stirred under a N$_2$ atmosphere at RT overnight. The mixture was diluted with water (5 mL) and extracted with EtOAc (20 mL×3). The combined organic layers were dried over Na$_2$SO$_4$ and concentrated under reduced pressure. The residue was purified by prep-TLC (DCM:MeOH, 20:1, v/v) to afford the title compound (45 mg, 34%) as a yellow solid. LCMS: [M+H]$^+$ 333.2;
$^1$H NMR (400 MHz, DMSO-d$_6$) δ 12.2 (s, 1H), 7.99 (d, J=8.0 Hz, 1H), 7.39 (s, 1H), 7.31 (d, J=8.0 Hz, 1H), 3.81 (m, 2H), 3.66 (s, 2H), 3.34-3.28 (m, 2H), 3.06 (m, 1H), 2.60 (d, J=7.2 Hz, 2H), 1.91 (m, 3H), 1.45 (m, 2H), 0.88 (d, J=6.4 Hz, 6H).

Example 203: 7-(Cyclopentylamino)-5-methyl-2-(((tetrahydro-2H-pyran-4-yl)thio)methyl) quinazolin-4(3H)-one

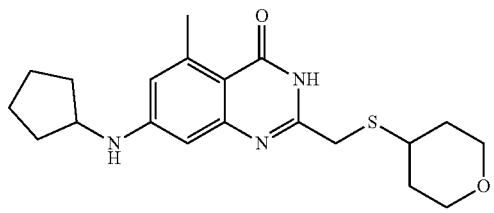 [SMILES: Cc1cc(NC2CCCC2)cc2nc(CSC3CCOCC3)[nH]c(=O)c12]

Step 1: 5-Bromo-7-fluoro-2-(((tetrahydro-2H-pyran-4-yl)thio)methyl)quinazolin-4(3H)-one Prepared from Int-A40 and Int-B1 according to the method described for Example 202. LCMS: [M+H]$^+$ 373.0.

Step 2: 7-Fluoro-5-methyl-2-(((tetrahydro-2H-pyran-4-yl)thio)methyl)quinazolin-4(3H)-one To a solution of 5-bromo-7-fluoro-2-((((tetrahydro-2H-pyran-4-yl)thio)methyl) quinazolin-4(3H)-one (373 mg, 1.0 mmol, 1.0 eq) and 2,4,6-trimethyl-1,3,5,2,4,6-trioxatriborinane (376 mg, 3.0 mmol, 3.0 eq) in dioxane/water (10:1, 22 mL) under a N$_2$ atmosphere was added K$_2$CO$_3$ (276 mg, 2.0 mmol, 2.0 eq) and PdCl$_2$(dppf) (82 mg, 0.1 mmol, 0.1 eq) and the mixture was heated at 100° C. overnight. After cooling to RT, the mixture was filtered and the filtrate was concentrated under reduced pressure. The residue was purified by column chromatography (DCM:MeOH, 100:1, v/v) to afford the title compound (230 mg, 75%) as a pink solid. LCMS: [M+H]$^+$ 309.1.

Step 3: 7-(Cyclopentylamino)-5-methyl-2-(((tetrahydro-2H-pyran-4-yl)thio)methyl)quinazolin-4(3H)-one Prepared from 7-fluoro-5-methyl-2-(((tetrahydro-2H-pyran-4-yl)thio)methyl) quinazolin-4(3H)-one and cyclopentanamine according to the method described for Example 126. LCMS: [M+H]$^+$ 374.2;
$^1$H NMR (400 MHz, CD$_3$OD) δ 6.54 (s, 1H), 6.49 (s, 1H), 3.95-3.80 (m, 3H), 3.63 (s, 2H), 3.42 (t, J=10.4 Hz, 2H), 3.06-2.95 (m, 1H), 2.69 (s, 3H), 2.09-1.98 (m, 2H), 1.95-1.89 (m, 2H), 1.81-1.75 (m, 2H), 1.72-1.63 (m, 2H), 1.63-1.50 (m, 4H).

Example 204: cis-4-(((8-Methyl-4-oxo-3,4-dihydroquinazolin-2-yl)methyl)thio)cyclohexane-1-carboxamide

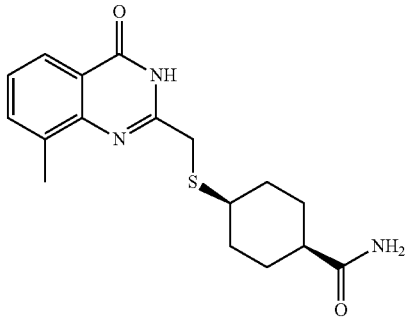 [SMILES: Cc1cccc2c(=O)[nH]c(CS[C@H]3CC[C@@H](C(N)=O)CC3)nc12]

Step 1: 4-(((8-Methyl-4-oxo-3,4-dihydroquinazolin-2-yl)methyl)thio)cyclohexane-1-carboxylic acid Prepared from Int-A1 and Int-B14 according to the method described for Example 202. This coupling reaction proceeded with concomitant hydrolysis of the ester to give the title compound directly. LCMS: [M+H]$^+$ 333.1.

Step 2: cis-4-(((8-Methyl-4-oxo-3,4-dihydroquinazolin-2-yl)methyl)thio)cyclohexane-1-carboxylic acid and trans-4-(((8-Methyl-4-oxo-3,4-dihydroquinazolin-2-yl)methyl)thio)cyclohexane-1-carboxylic Acid 4-(((8-Methyl-4-oxo-3,4-dihydroquinazolin-2-yl)methyl)thio)cyclohexane-1-carboxylic acid was further purified by prep-HPLC (Agilent 10 prep-C18, 10 μm, 250×21.2 mm column, eluting with a gradient of MeOH in water with 0.1% TFA, at a flow rate of 20 mL/min to afford the trans isomer as the first eluting isomer, LCMS: [M+H]$^+$ 333.1 and the cis isomer as the second eluting isomer, LCMS: [M+H]$^+$ 333.1

Step 3: cis-4-(((8-Methyl-4-oxo-3,4-dihydroquinazolin-2-yl)methyl)thio)cyclohexane-1-carboxamide Prepared from cis-4-(((8-methyl-4-oxo-3,4-dihydroquinazolin-2-yl)methyl)thio)cyclohexane-1-carboxylic acid and NH$_4$Cl according to the method described for Example 77, step 2. LCMS: [M+H]$^+$ 332.2;
$^1$H NMR (400 MHz, CD$_3$OD) δ 8.03 (d, J=8.0 Hz, 1H), 7.66 (d, J=7.2 Hz, 1H), 7.39 (t, J=8.0 Hz, 1H), 3.72 (s, 2H), 3.26-3.22 (m, 1H), 2.58 (s, 3H), 2.31-2.23 (m, 1H), 1.95-1.76 (m, 6H), 1.66-1.56 (m, 2H).

Example 205: trans-4-(((8-Methyl-4-oxo-3,4-dihydroquinazolin-2-yl)methyl)thio)cyclohexane-1-carboxamide

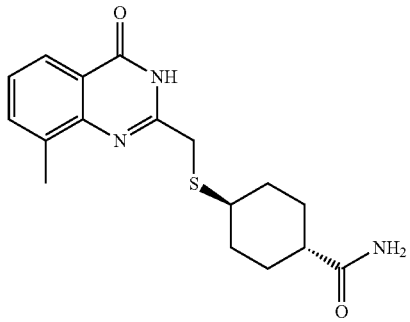 [SMILES: Cc1cccc2c(=O)[nH]c(CS[C@H]3CC[C@H](C(N)=O)CC3)nc12]

Prepared from trans-4-(((8-methyl-4-oxo-3,4-dihydroquinazolin-2-yl)methyl)thio)cyclohexane-1-carboxylic acid and NH$_4$Cl according to the method described for Example 77, step 2. LCMS: [M+H]$^+$ 332.2;
$^1$H NMR (400 MHz, CD$_3$OD) δ 8.03 (d, J=7.6 Hz, 1H), 7.66 (d, J=6.8 Hz, 1H), 7.38 (t, J=7.6 Hz, 1H), 3.75 (s, 2H), 2.74-2.81 (m, 1H), 2.60 (s, 3H), 2.25-2.14 (m, 3H), 1.90-1.87 (m, 2H), 1.53-1.43 (m, 2H), 1.38-1.29 (m, 2H).

Example 206: 5-Chloro-7-(cyclopentylamino)-2-((piperidin-4-ylthio)methyl)quinazolin-4(3H)-one Hydrochloride

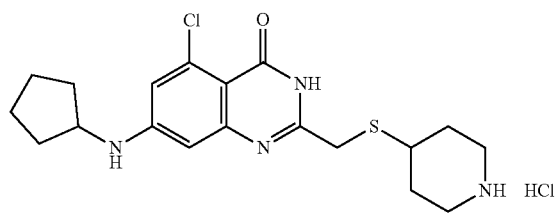 [SMILES: O=c1[nH]c(CSC2CCNCC2)nc2cc(NC3CCCC3)cc(Cl)c12 ; Cl]

Step 1: tert-Butyl 4-(((5-chloro-7-(cyclopentylamino)-4-oxo-3,4-dihydroquinazolin-2-yl)methyl)thio)piperidine-1-carboxylate Prepared from Int-A41 and Int-B2 according to the method described for Example 202. LCMS: [M+H]$^+$ 493.2.

Step 2: 5-Chloro-7-(cyclopentylamino)-2-((piperidin-4-ylthio)methyl)quinazolin-4(3H)-one hydrochloride Prepared from tert-butyl 4-(((5-chloro-7-(cyclopentylamino)-4-oxo-3,4-dihydroquinazolin-2-yl)methyl)thio)piperidine-1-carboxylate according to the method described for Example 48, step 2. LCMS: [M+H]$^+$ 393.2;
$^1$H NMR (400 MHz, CD$_3$OD) δ 6.91 (d, J=2.0 Hz, 1H), 6.73 (d, J=2.0 Hz, 1H), 4.00-3.96 (m, 2H), 3.90-3.84 (m, 1H), 3.46-3.37 (m, 2H), 3.35-3.26 (m, 1H), 3.16-3.10 (m, 2H), 2.37-2.28 (m, 2H), 2.12-2.04 (m, 2H), 1.84-1.64 (m, 6H), 1.62-1.53 (m, 2H).

Example 207: 7-(Cyclopentylamino)-5-methoxy-2-(((tetrahydro-2H-pyran-4-yl)thio)methyl)quinazolin-4(3H)-one

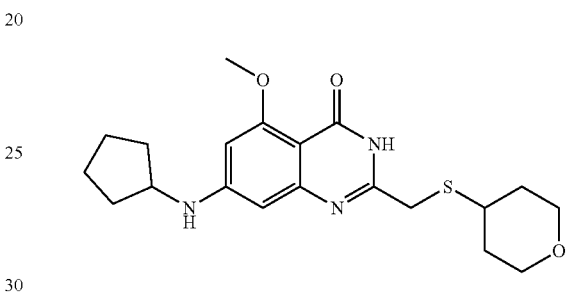

Prepared from Int-A42 and Int-B1 according to the method described for Example 202. LCMS: [M+H]$^+$ 390.1.
$^1$H NMR (400 MHz, DMSO-d$_6$) δ 11.3 (s, 1H), 6.52 (d, J=6.0 Hz, 1H), 6.19 (s, 1H), 6.12 (s, 1H), 3.87-3.76 (m, 3H), 3.73 (s, 3H), 3.51 (s, 2H), 3.33-3.27 (m, 2H), 3.10-2.97 (m, 1H), 2.01-1.82 (m, 4H), 1.76-1.63 (m, 2H), 1.60-1.52 (m, 2H), 1.52-1.36 (m, 4H).

Example 208: Methyl 4-(((7-(cyclopentylamino)-4-oxo-3,4-dihydroquinazolin-2-yl)methyl)thio)piperidine-1-carboxylate

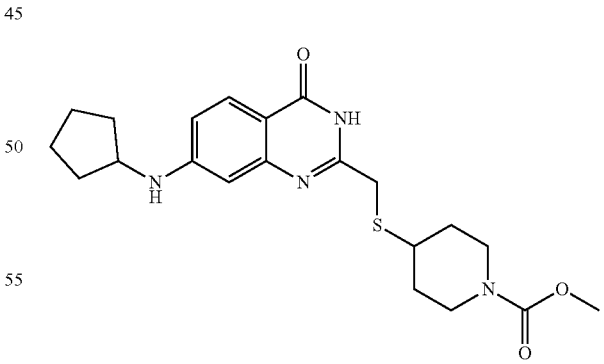

Step 1: tert-Butyl 4-(((7-fluoro-4-oxo-3,4-dihydroquinazolin-2-yl)methyl)thio)piperidine-1-carboxylate Prepared from Int-A9 and Int-B2 according to the method described for Example 202. LCMS: [M+H]$^+$ 394.1.

Step 2: tert-Butyl 4-(((7-(cyclopentylamino)-4-oxo-3,4-dihydroquinazolin-2-yl)methyl)thio)piperidine-1-carboxylate Prepared from tert-butyl 4-(((7-fluoro-4-oxo-3,4-dihydroquinazolin-2-yl)methyl)thio)piperidine-1-carboxylate and cyclopentanamine according to the method described for Example 126. LCMS: [M+H]+ 459.2.

Step 3: 7-(Cyclopentylamino)-2-((piperidin-4-ylthio)methyl)quinazolin-4(3H)-one Hydrochloride Prepared from tert-butyl 4-(((7-(cyclopentylamino)-4-oxo-3,4-dihydroquinazolin-2-yl)methyl)thio)piperidine-1-carboxylate according to the method described for Example 48, step 2. LCMS: [M+H]+ 359.2.

Step 4: Methyl 4-(((7-(cyclopentylamino)-4-oxo-3,4-dihydroquinazolin-2-yl)methyl)thio)piperidine-1-carboxylate To a solution of 7-(cyclopentylamino)-2-((piperidin-4-ylthio)methyl)quinazolin-4(3H)-one hydrochloride (110 mg, 0.28 mmol, 1.0 eq) in NMP (4 mL) was added K$_2$CO$_3$ (85 mg, 0.61 mmol, 2.2 eq) followed by methyl carbonochloridate (32 mg, 0.33 mmol, 1.2 eq) dropwise and the mixture was heated at 40° C. overnight. After cooling to RT, the mixture was diluted with water (30 mL) and extracted with EtOAc (30 mL×3). The combined organic layers were washed with water (20 mL), dried over Na$_2$SO$_4$ and concentrated under reduced pressure. The residue was purified by prep-TLC (DCM:MeOH, 20:1, v/v) to afford the title compound (5 mg, 4%) as a yellow solid. LCMS: [M+H]+ 417.2;
$^1$H NMR (400 MHz, CD$_3$OD) δ 7.85 (d, J=8.8 Hz, 1H), 6.80 (dd, J=8.8, 2.4 Hz, 1H), 6.62 (s, 1H), 4.00-3.90 (m, 2H), 3.91-3.82 (m, 1H), 3.68 (s, 2H), 3.66 (s, 3H), 3.05-2.94 (m, 3H), 2.11-1.93 (m, 4H), 1.84-1.73 (m, 2H), 1.73-1.64 (m, 2H), 1.64-1.54 (m, 2H), 1.52-1.39 (m, 2H).

Example 209: 2-((trans)-4-(((8-Methyl-4-oxo-3,4-dihydroquinazolin-2-yl)methyl)thio)cyclohexyl)acetamide

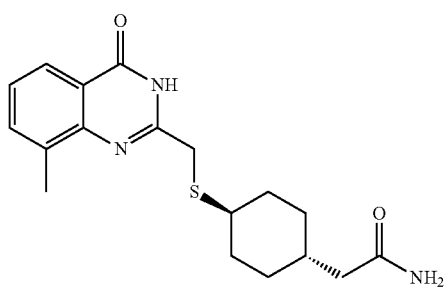 [SMILES: Cc1cccc2c(=O)[nH]c(CS[C@H]3CC[C@H](CC(N)=O)CC3)nc12]

Step 1: 2-(trans-4-(((8-Methyl-4-oxo-3,4-dihydroquinazolin-2-yl)methyl)thio)cyclohexyl)acetic acid Prepared from Int-A1 and Int-B15 according to the method described for Example 202. This coupling reaction proceeded with concomitant hydrolysis of the ester to give the title compound directly. LCMS: [M+H]+ 347.1.

Step 2: 2-((trans)-4-(((8-Methyl-4-oxo-3,4-dihydroquinazolin-2-yl)methyl)thio)cyclohexyl)acetamide Prepared from 2-(trans-4-(((8-methyl-4-oxo-3,4-dihydroquinazolin-2-yl)methyl)thio)cyclohexyl)acetic acid and NH$_4$Cl according to the method described for Example 77, step 2. LCMS: [M+H]+ 346.2;
$^1$H NMR (400 MHz, DMSO-d$_6$) δ 12.3 (s, 1H), 7.93 (d, J=8.0 Hz, 1H), 7.66 (d, J=6.8 Hz, 1H), 7.37 (t, J=8.0 Hz, 1H), 7.20 (br s, 1H), 6.89 (br s, 1H), 3.65 (s, 2H), 2.72-2.80 (m, 1H), 2.50 (3H, obscured by solvent peak), 2.00-2.09 (m, 2H), 1.89 (d, J=7.6 Hz, 2H), 1.70-1.73 (m, 2H), 1.65-1.59 (m, 1H), 1.26-1.18 (m, 2H), 0.98-0.88 (m, 2H).

Example 210: 7-(Cyclopentylamino)-5-fluoro-2-(((trans-3-fluoropiperidin-4-yl)thio)methyl)quinazolin-4(3H)-one Hydrochloride

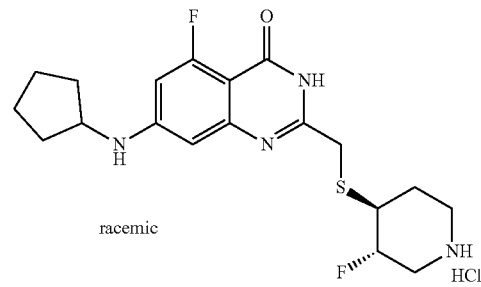 [SMILES: O=c1[nH]c(CS[C@H]2CCNC[C@@H]2F)nc2cc(NC3CCCC3)cc(F)c12 ; Cl]

racemic

Step 1: tert-butyl cis-3-fluoro-4-hydroxypiperidine-1-carboxylate

Prepared from tert-butyl 3-fluoro-4-oxopiperidine-1-carboxylate according to literature WO2011036576.

Step 2: tert-Butyl cis-3-fluoro-4-((methylsulfonyl)oxy)piperidine-1-carboxylate Prepared from tert-butyl cis-3-fluoro-4-hydroxypiperidine-1-carboxylate according to the method described for Int B3, step 1. LCMS: [M+H]+ 298.1.

Step 3: tert-Butyl trans-4-(((7-(cyclopentylamino)-5-fluoro-4-oxo-3,4-dihydroquinazolin-2-yl)methyl)thio)-3-fluoropiperidine-1-carboxylate To a solution of Int-C12 (100 mg, 0.30 mmol, 1.0 eq) and tert-butyl cis-3-fluoro-4-((methylsulfonyl)oxy)piperidine-1-carboxylate (177 mg, 0.90 mmol, 3.0 eq) in DMF (2 mL) at RT under a N$_2$ atmosphere was added 2 M NaOH (0.6 mL) and the mixture was heated at 100° C. for 3 h. The mixture was poured into water (5 mL), extracted with EtOAc (10 mL×3) and the combined organic layers were washed with water (10 mL), dried over Na$_2$SO$_4$ and concentrated under reduced pressure. The residue was purified by prep-TLC (petroleum ether:EtOAc, 1:2, v/v) to afford the title compound (30 mg, 20%) as a yellow solid. LCMS: [M+H]+ 495.2.

Step 4: 7-(Cyclopentylamino)-5-fluoro-2-(((trans-3-fluoropiperidin-4-yl)thio)methyl)quinazolin-4(3H)-one Hydrochloride Prepared from tert-butyl trans-4-(((7-(cyclopentylamino)-5-fluoro-4-oxo-3,4-dihydroquinazolin-2-yl)methyl)thio)-3- fluoropiperidine-1-carboxylate according to the method described for Example 48, step 2. LCMS: [M+H]+ 395.1;

¹HNMR (400 MHz, DMSO-d₆) δ 12.0 (br s, 1H), 9.37 (br s, 1H), 9.09 (br s, 1H), 6.50-6.46 (m, 2H), 4.96-4.84 (m, 1H), 3.83-3.74 (m, 3H), 3.53-3.34 (m, 2H), 3.28-3.18 (m, 1H), 3.12-2.97 (m, 2H), 2.34-2.22 (m, 1H), 1.99-1.93 (m, 2H), 1.85-1.77 (m, 1H), 1.42-1.73 (m, 6H).

Example 211: 7-(Cyclopentylamino)-5-fluoro-2-((((3S,4S)-3-fluoropiperidin-4-yl)thio)methyl)quinazolin-4(3H)-one and 7-(Cyclopentylamino)-5-fluoro-2-((((3R,4R)-3-fluoropiperidin-4-yl)thio)methyl)quinazolin-4(3H)-one

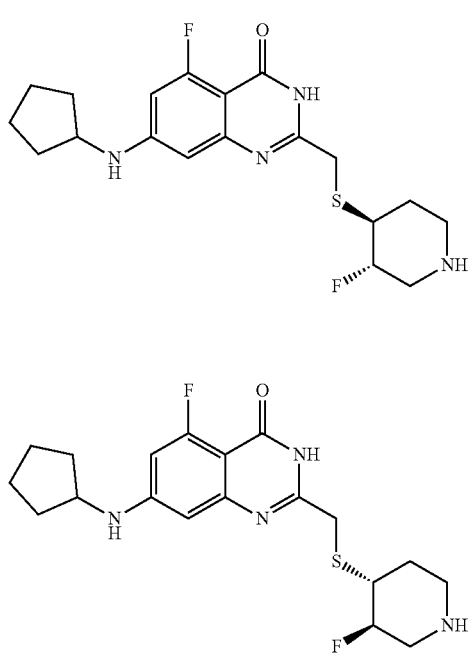

Example 210 was further purified by chiral prep-HPLC (Chiralpak IE-3, 3 μm, 0.46×5 cm column, eluting with a gradient of MTBE (0.1% DEA):IPA 50:50 at a flow rate of 1.0 mL/min), to afford the title compounds with retention times of 1.99 minutes (211a) and 2.72 minutes (211b).

Example 211a

LCMS: [M+H]+ 395.2;

¹H NMR (400 MHz, CD₃OD) δ 6.48-6.43 (m, 2H), 4.84-4.80 (m, 1H), 3.86-3.70 (m, 3H), 3.45-3.30 (m, 2H), 3.15-2.96 (m, 3H), 2.40-2.28 (m, 1H), 2.07-2.02 (m, 2H), 1.80-1.52 (m, 7H).

Example 211b

LCMS: [M+H]+ 395.2;

¹H NMR (400 MHz, CD₃OD) δ 6.48-6.42 (m, 2H), 4.84-4.80 (m, 1H), 3.86-3.72 (m, 3H), 3.31-3.20 (m, 2H), 2.96-2.74 (m, 3H), 2.20-2.17 (m, 1H), 2.07-2.00 (m, 2H), 1.80-1.52 (m, 7H).

Example 212: 7-(Cyclopentylamino)-5-fluoro-2-((((cis)-3-fluoropiperidin-4-yl)thio)methyl)quinazolin-4(3H)-one Hydrochloride

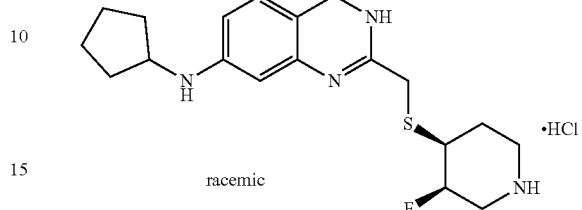

racemic

Step 1: tert-Butyl trans-3-fluoro-4-hydroxypiperidine-1-carboxylate

Prepared from tert-butyl 3-fluoro-4-oxopiperidine-1-carboxylate according to literature WO2011036576.

Step 2: tert-Butyl trans-3-fluoro-4-((methylsulfonyl)oxy)piperidine-1-carboxylate Prepared from tert-butyl trans-3-fluoro-4-hydroxypiperidine-1-carboxylate according to the method described for Int B3, step 1. LCMS: [M+H]+ 298.1.

Step 3: tert-Butyl cis-4-(((7-(cyclopentylamino)-5-fluoro-4-oxo-3,4-dihydroquinazolin-2-yl)methyl)thio)-3-fluoropiperidine-1-carboxylate Prepared from Int-C12 and tert-butyl trans-3-fluoro-4-((methylsulfonyl)oxy)piperidine-1-carboxylate according to the method described for Example 210, step 3. LCMS: [M+H]+ 495.2.

Step 4: 7-(Cyclopentylamino)-5-fluoro-2-(((cis-3-fluoropiperidin-4-yl)thio)methyl)quinazolin-4(3H)-one Hydrochloride Prepared from tert-butyl cis-4-(((7-(cyclopentylamino)-5-fluoro-4-oxo-3,4-dihydroquinazolin-2-yl)methyl)thio)-3-fluoropiperidine-1-carboxylate according to the method described for Example 48, step 2. LCMS: [M+H]+ 395.2;

¹H NMR (400 MHz, DMSO-d₆) δ 11.9 (br s, 1H), 9.28 (br s, 1H), 8.67 (br s, 1H), 7.00 (br s, 1H), 6.48-6.42 (m, 2H), 5.09 (d, J=44.8 Hz, 1H), 3.84-3.65 (m, 3H), 3.57 (m, 1H), 3.43-3.16 (m, 3H), 2.96 (m, 1H), 2.09-1.82 (m, 4H), 1.72-1.64 (m, 2H), 1.63-1.52 (m, 2H), 1.52-1.41 (m, 2H).

Example 213: 7-(Cyclopentylamino)-5-fluoro-2-((((3R,4S)-3-fluoropiperidin-4-yl)thio)methyl)quinazolin-4(3H)-one and 7-(cyclopentylamino)-5-fluoro-2-((((3S,4R)-3-fluoropiperidin-4-yl)thio)methyl)quinazolin-4(3H)-one

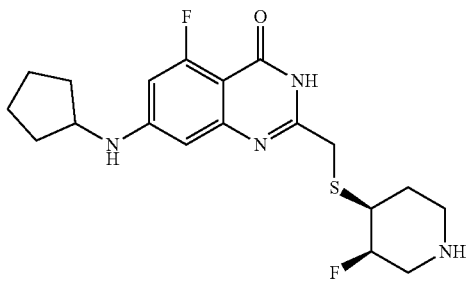

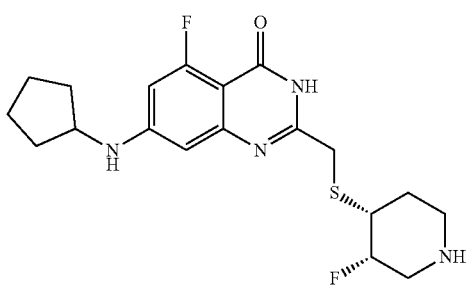

Example 212 was further purified by chiral prep-HPLC (Chiralpak IG-3, 3 μm, 0.46×10 cm column, eluting with a gradient of MTBE (0.1% DEA):EtOH 70:30 at a flow rate of 1.0 mL/min) to afford the title compounds with retention times of 3.79 minutes (213a) and 4.87 minutes (213b).

Example 213a

LCMS: [M+H]$^+$ 395.2;

$^1$H NMR (400 MHz, DMSO-d$_6$) δ 11.66 (br s, 1H), 6.84-6.83 (m, 1H), 6.43-6.36 (m, 2H), 4.69-4.57 (m, 1H), 3.81-3.77 (m, 1H), 3.60-3.51 (m, 2H), 3.37-3.02 (m, 2H), 2.87-2.83 (m, 1H), 2.70-2.51 (m, 2H), 2.50-2.43 (m, 1H), 1.97-1.94 (m, 2H), 1.65-1.48 (m, 8H).

Example 213b

LCMS: [M+H]$^+$ 395.2;

$^1$H NMR (400 MHz, DMSO-d$_6$) δ 11.66 (br s, 1H), 6.84-6.83 (m, 1H), 6.43-6.36 (m, 2H), 4.69-4.57 (m, 1H), 3.81-3.77 (m, 1H), 3.60-3.51 (m, 2H), 3.37-3.02 (m, 2H), 2.87-2.83 (m, 1H), 2.70-2.51 (m, 2H), 2.50-2.43 (m, 1H), 1.97-1.94 (m, 2H), 1.65-1.48 (m, 8H).

Example 214: 7-(Cyclopentylamino)-5-fluoro-2-(((1-(2-hydroxyacetyl)piperidin-4-yl)thio)methyl)quinazolin-4(3H)-one

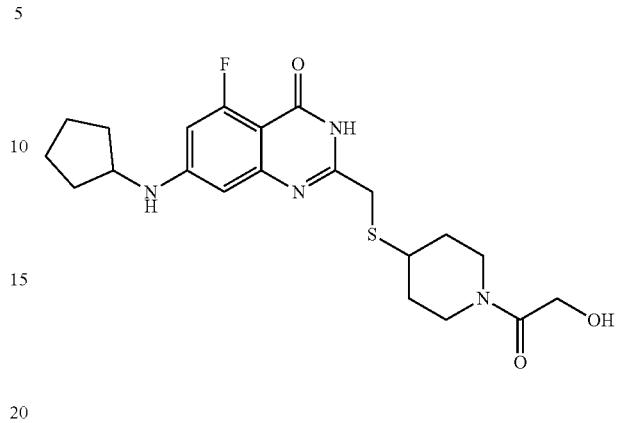

Step 1: tert-Butyl 4-(((7-(cyclopentylamino)-5-fluoro-4-oxo-3,4-dihydroquinazolin-2-yl)methyl)thio)piperidine-1-carboxylate Prepared from Int-A43 and Int-B2 according to the method described for Example 202. LCMS: [M+H]$^+$ 477.1.

Step 2: 7-(Cyclopentylamino)-5-fluoro-2-((piperidin-4-ylthio)methyl)quinazolin-4(3H)-one hydrochloride Prepared from tert-butyl 4-(((7-(cyclopentylamino)-5-fluoro-4-oxo-3,4-dihydroquinazolin-2-yl)methyl)thio)piperidine-1-carboxylate according to the method described for Example 48, step 2. LCMS: [M+H]$^+$ 377.1.

Step 3: 7-(Cyclopentylamino)-5-fluoro-2-(((1-(2-hydroxyacetyl)piperidin-4-yl)thio)methyl)quinazolin-4(3H)-one To a solution 7-(cyclopentylamino)-5-fluoro-2-((piperidin-4-ylthio)methyl)quinazolin-4(3H)-one hydrochloride (100 mg, 0.24 mmol, 1.0 eq) and Et$_3$N (75 mg, 0.72 mmol, 3.0 eq) in DMF (3 mL) were added 2-hydroxyacetic acid (37 mg, 0.48 mmol, 2.0 eq), EDCI (98 mg, 0.51 mmol, 2.1 eq) and HOBt (68 mg, 0.51 mmol, 2.1 eq) and the mixture was stirred at RT overnight. The mixture was diluted with water (10 mL) and extracted with EtOAc (10 mL×3). The combined organic layers were dried over Na$_2$SO$_4$ and concentrated under reduced pressure. The residue was purified by prep-TLC (DCM:MeOH, 10:1, v/v) to afford the title compound (35 mg, 33%) as a white solid. LCMS: [M+H]$^+$ 435.2;

$^1$H NMR (400 MHz, DMSO-d$_6$) δ 11.7 (s, 1H), 6.82 (d, J=6.4 Hz, 1H), 6.41 (d, J=14.0 Hz, 1H), 6.36 (s, 1H), 4.47 (t, J=5.6 Hz, 1H), 4.11-4.03 (m, 3H), 3.78 (m, 1H), 3.62-3.58 (m, 1H), 3.56 (s, 2H), 3.05-3.03 (m, 2H), 2.90-2.80 (m, 1H), 2.02-1.86 (m, 4H), 1.67-1.65 (m, 2H), 1.57-1.56 (m, 2H) 1.50-1.29 (m, 4H).

Example 215: 2-(((Cyclohexylthio)methyl)-7-(cyclopentylamino)-5-fluoroquinazolin-4(3H)-one

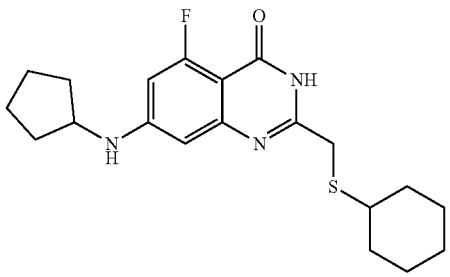 [SMILES: O=c1[nH]c(CSC2CCCCC2)nc2cc(NC3CCCC3)cc(F)c12]

Prepared from Int-A43 and cyclohexanethiol according to the method described for Example 202. LCMS: [M+H]+ 376.1;
$^1$H NMR (400 MHz, DMSO-d$_6$) δ 11.6 (s, 1H), 6.81 (d, J=6.8 Hz, 1H), 6.41 (dd, J=13.6, 2.4 Hz, 1H), 6.35 (d, J=2.4 Hz, 1H), 3.83-3.75 (m, 1H), 3.51 (s, 2H), 2.87-2.74 (m, 1H), 2.02-1.87 (m, 4H), 1.75-1.60 (m, 4H), 1.60-1.39 (m, 5H), 1.30-1.15 (m, 5H).

Example 216: cis-4-(((7-(Cyclopentylamino)-5-fluoro-4-oxo-3,4-dihydroquinazolin-2-yl)methyl)thio)cyclohexane-1-carboxylic acid and

Example 217: trans-4-(((7-(Cyclopentylamino)-5-fluoro-4-oxo-3,4-dihydroquinazolin-2-yl)methyl)thio)cyclohexane-1-carboxylic acid

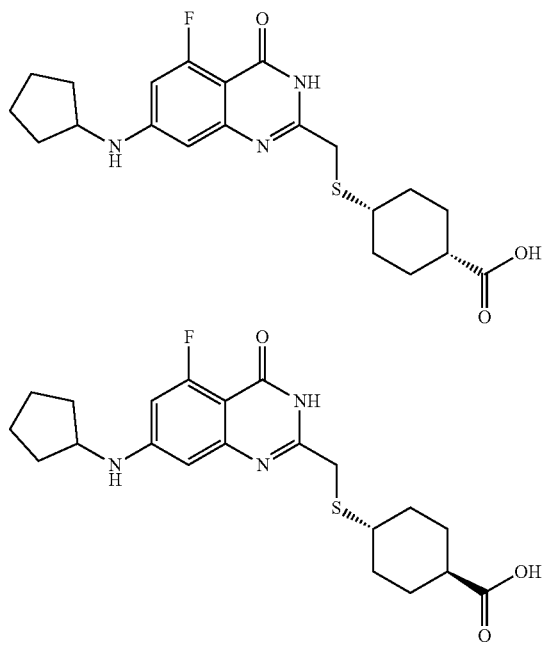

Step 1: 4-(((7-(Cyclopentylamino)-5-fluoro-4-oxo-3,4-dihydroquinazolin-2yl)methyl)thio)cyclohexane-1-carboxylic Acid Prepared from Int-A43 and Int-B14 according to the method described for Example 202. This coupling reaction proceeded with concomitant hydrolysis of the ester to give the title compound directly. LCMS: [M+H]+ 420.1.

Step 2: cis-4-(((7-(Cyclopentylamino)-5-fluoro-4-oxo-3,4-dihydroquinazolin-2-yl)methyl)thio)cyclohexane-1-carboxylic acid and trans-4-(((7-(Cyclopentylamino)-5-fluoro-4-oxo-3,4-dihydroquinazolin-2-yl)methyl)thio)cyclohexane-1-carboxylic Acid 4-(((7-(Cyclopentylamino)-5-fluoro-4-oxo-3,4-dihydroquinazolin-2yl)methyl)thio)cyclohexane-1-carboxylic acid was further purified by prep-HPLC (Agilent 10 prep-C18, 10 μm, 250×21.2 mm column, eluting with a gradient of MeOH in water with 0.1% TFA, at a flow rate of 20 mL/min) to afford the title compounds.

Example 216

LCMS: [M+H]+ 420.1;
$^1$H NMR (400 MHz, DMSO-d$_6$) δ 12.0 (br s, 1H), 6.90 (br s, 1H), 6.43 (d, J=13.6 Hz, 1H), 6.37 (s, 1H), 3.82-3.76 (m, 1H), 3.52 (s, 2H), 3.09 (m, 1H), 2.36-2.33 (m, 1H), 1.99-1.91 (m, 2H), 1.79-1.76 (m, 4H), 1.67-1.66 (m, 2H), 1.59-1.49 (m, 6H), 1.48-1.43 (m, 2H).

Example 217

LCMS: [M+H]+ 420.1;
$^1$H NMR (400 MHz, DMSO-d$_6$) δ 12.0 (br s, 1H), 7.07 (br s, 1H), 6.45 (dd, J=13.6, 2.0 Hz, 1H), 6.39 (d, J=1.6 Hz, 1H), 3.96 (s, 1H), 3.82-3.76 (m, 1H), 3.59 (s, 2H), 2.79-2.73 (m, 1H), 2.23-2.22 (m, 1H), 2.03-1.89 (m, 6H), 1.70-1.66 (m, 2H), 1.59-1.50 (m, 2H), 1.48-1.42 (m, 2H), 1.38-1.20 (m, 4H).

Example 218: trans-4-(((7-(Cyclopentylamino)-5-fluoro-4-oxo-3,4-dihydroquinazolin-2-yl)methyl)thio)cyclohexane-1-carboxamide

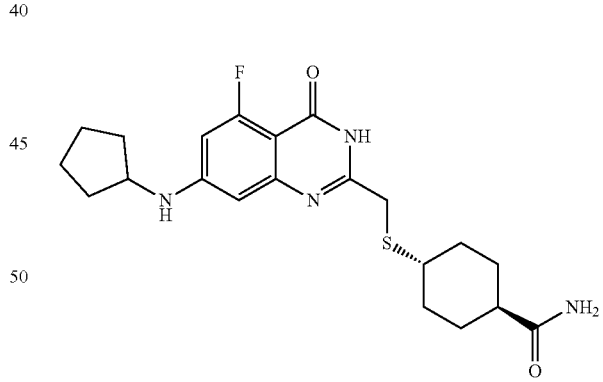

Prepared from trans-4-(((7-(Cyclopentylamino)-5-fluoro-4-oxo-3,4-dihydroquinazolin-2-yl)methyl)thio)cyclohexane-1-carboxylic acid and NH$_4$Cl according to the method described for Example 77, step 2. LCMS: [M+H]+ 419.1;
$^1$H NMR (400 MHz, DMSO-d$_6$) δ 11.6 (br s, 1H), 7.17 (s, 1H), 6.83 (d, J=6.4 Hz, 1H), 6.66 (s, 1H), 6.41 (d, J=14.0 Hz, 1H), 6.36 (s, 1H), 3.81-3.76 (m, 1H), 3.53 (s, 2H), 3.17 (d, J=5.2 Hz, 1H), 2.75-2.68 (m, 1H), 2.08-2.02 (m, 2H), 1.97-1.91 (m, 2H), 1.78-1.75 (m, 2H), 1.70-1.63 (m, 2H), 1.61-1.64 (m, 2H), 1.49-1.43 (m, 2H), 1.39-1.29 (m, 2H), 1.23-1.14 (m, 2H).

Example 219: 7-(Cyclopropylmethoxy)-2-(((tetrahydro-2H-pyran-4-yl)thio)methyl)quinazolin-4(3H)-one

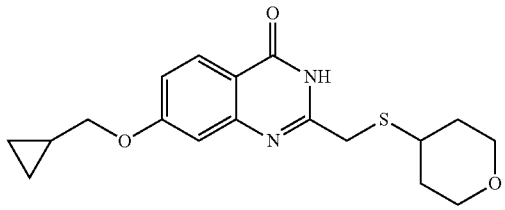 [SMILES: O=c1[nH]c(CSC2CCOCC2)nc2cc(OCC3CC3)ccc12]

To a solution of 7-bromo-2-((((tetrahydro-2H-pyran-4-yl)thio)methyl)-3-((2-(trimethylsilyl)ethoxy)methyl)quinazolin-4(3H)-one (200 mg, 0.41 mmol, 1.0 eq) in 1,4-dioxane (2 mL) and water (2 mL) under a $N_2$ atmosphere was added t-BuXPhos (70 mg, 0.16 mmol, 0.4 eq), $Pd_2(dba)_3$ (38 mg, 0.04 mmol, 0.1 eq) and sodium hydroxide (49 mg, 1.24 mmol, 3.0 eq) and the mixture was heated at 90° C. overnight. After cooling to RT, t-$Bu_4$NBr (322 mg, 1 mmol, 2.5 eq) and bromomethylcyclopropane (696 mg, 5.16 mmol, 12.0 eq) were added and the mixture was heated at 40° C. overnight. Loss of the SEM protecting group had also occurred in this reaction to give the title compound directly. After cooling to RT, the mixture was diluted with water (30 mL) and extracted with EtOAc (50 mL×3). The combined organic layers were dried over $Na_2SO_4$ and concentrated under reduced pressure. The residue was purified by prep-TLC (petroleum ether:EtOAc, 1:1, v/v) to afford the title compound (10 mg, 10%) as a white solid. LCMS: $[M+H]^+$ 347.1;

$^1$H NMR (400 MHz, DMSO-$d_6$) δ 12.1 (br s, 1H), 7.97 (d, J=8.8 Hz, 1H), 7.06 (dd, J=8.8, 2.4 Hz, 1H), 7.00 (d, J=2.4 Hz, 1H), 3.95 (d, J=7.2 Hz, 2H), 3.85-3.78 (m, 2H), 3.64 (s, 2H), 3.31-3.27 (m, 2H), 3.10-3.02 (m, 1H), 1.92-1.85 (m, 2H), 1.50-1.40 (m, 2H), 1.33-1.21 (m, 1H), 0.65-0.55 (m, 2H), 0.40-0.31 (m, 2H).

Example 220: 4-(((7-(Cyclopentylamino)-5-fluoro-4-oxo-3,4-dihydroquinazolin-2-yl)methyl)thio)-N,N-dimethylpiperidine-1-carboxamide

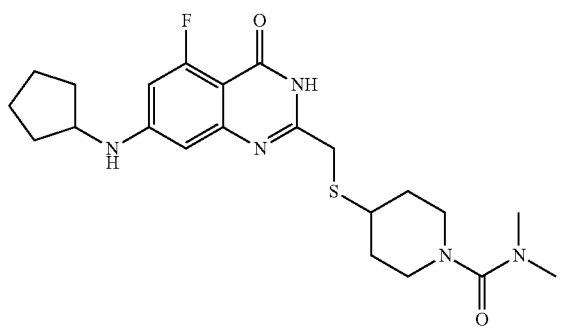 [SMILES: CN(C)C(=O)N1CCC(SCc2nc3cc(NC4CCCC4)cc(F)c3c(=O)[nH]2)CC1]

To a solution of 7-(cyclopentylamino)-5-fluoro-2-((piperidin-4-ylthio)methyl)quinazolin-4(3H)-one hydrochloride (100 mg, 0.24 mmol, 1.0 eq) and $Et_3N$ (74 mg, 0.72 mmol, 3.0 eq) in DCM (4.0 mL) under a $N_2$ atmosphere was added N,N-dimethylcarbamoyl chloride (31 mg, 0.29 mmol, 1.2 eq) and the mixture was stirred at 25° C. for 2 h. The mixture was diluted with water (30 mL) and extracted with EtOAc (40 mL×2). The combined organic layers were dried over $Na_2SO_4$ and concentrated under reduced pressure. The residue was purified by prep-TLC (DCM:MeOH, 15:1, v/v) to afford the title compound (50 mg, 46%) as a white solid. LCMS: $[M+H]^+$ 448.2;

$^1$H NMR (400 MHz, DMSO-$d_6$) δ 11.7 (s, 1H), 6.82 (d, J=6.4 Hz, 1H), 6.41 (d, J=14.0 Hz, 1H), 6.36 (s, 1H), 3.82-3.75 (m, 1H), 3.55 (s, 2H), 3.46-3.42 (m, 2H), 3.01-2.94 (m, 1H), 2.78-2.75 (m, 2H), 2.70 (s, 6H), 1.98-1.90 (m, 4H), 1.72-1.63 (m, 2H), 1.61-1.52 (m, 2H), 1.50-1.35 (m, 4H).

Example 221: 2-(((Cis-6-(Hydroxymethyl)tetrahydro-2H-pyran-3-yl)thio)methyl)-8-methylquinazolin-4(3H)-one

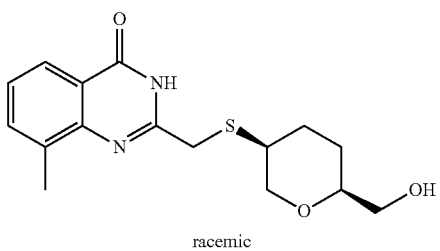 [SMILES: Cc1cccc2c(=O)[nH]c(CS[C@H]3CC[C@@H](CO)OC3)nc12]

racemic

Step 1: 6-(((tert-Butyldiphenylsilyl)oxy)methyl)tetrahydro-2H-pyran-3-ol

Prepared from 3,4-dihydro-2H-pyran-2-carbaldehyde according to literature Bioorg. Med. Chem. 2006, 14, 3953. The product was obtained as a 7:3 mixture of trans/cis isomers.

Step 2: trans-6-(((tert-butyldiphenylsilyl)oxy)methyl)tetrahydro-2H-pyran-3-yl methanesulfonate and cis-6-(((tert-butyldiphenylsilyl)oxy)methyl)tetrahydro-2H-pyran-3-yl Methanesulfonate To a solution of 6-(((tert-butyldiphenylsilyl)oxy)methyl)tetrahydro-2H-pyran-3-ol (1.1 g, 2.97 mmol, 1.0 eq) and $Et_3N$ (450 mg, 4.45 mmol, 1.5 eq) in DCM (25 mL) under a $N_2$ atmosphere was added methanesulfonyl chloride (408 mg, 3.56 mmol, 1.2 eq) and the mixture was stirred at RT for 2 h. The mixture was diluted with water (50 mL), extracted with DCM (20 mL×3) and the combined organic layers were dried over $Na_2SO_4$ and concentrated under reduced pressure. The residue was purified by column chromatography (petroleum ether:EtOAc, 1:0 to 10:1, v/v) to afford the trans isomer (730 mg, 55%) and cis isomer (330 mg, 25%) as white solids.

Trans isomer: $^1$H NMR (400 MHz, CDCl$_3$) δ 7.66-7.36 (m, 10H), 4.64-4.58 (m, 1H), 4.14-4.11 (m, 1H), 3.72-3.71 (m, 1H), 3.69-3.31 (m, 3H), 3.05 (s, 3H), 2.33-2.30 (m, 1H), 1.90-1.87 (m, 1H), 1.73-1.70 (m, 1H), 1.48-1.45 (m, 1H), 1.09 (s, 9H).

Cis isomer: $^1$H NMR (400 MHz, CDCl$_3$) δ 7.61-7.31 (m, 10H), 4.10-4.07 (m, 1H), 3.70-3.67 (m, 1H), 3.66-3.40 (m, 4H), 3.02 (s, 3H), 2.18-2.14 (m, 1H), 1.80-1.56 (m, 3H), 0.99 (s, 9H).

Step 3: 2-(((cis-6-(((tert-Butyldiphenylsilyl)oxy) methyl) tetrahydro-2H-pyran-3-yl)thio)methyl)-8-methylquinazolin-4(3H)-one Prepared from Int-C1 and trans-6-(((tert-butyldiphenylsilyl)oxy)methyl)tetrahydro-2H-pyran-3-yl methanesulfonate according to the method described for Example 210, step 3. LCMS: [M+H]+ 559.2.

Step 4: 2-(((cis-6-(Hydroxymethyl)tetrahydro-2H-pyran-3-yl)thio)methyl)-8-methylquinazolin-4(3H)-one To a solution of 2-(((cis 6-(((tert-butyldiphenylsilyl)oxy) methyl)tetrahydro-2H-pyran-3-yl)thio)methyl)-8-methylquinazolin-4(3H)-one (120 mg, 0.21 mmol, 1.0 eq) in DCM (2 mL) was added TBAF (0.64 mL, 0.64 mmol, 3.0 eq) and the mixture was stirred at RT for 16 h. The mixture was diluted with DCM (10 mL) and washed with water (5 mL) and brine (5 mL), dried over $Na_2SO_4$ and concentrated under reduced pressure. The residue was purified by prep-TLC (DCM:MeOH, 20:1, v/v) followed by C18 reverse phase column (Biotage, 0% to 40% MeCN in water) to afford the title compound (12 mg, 17%) as a white solid. LCMS: [M+H]+ 321.1;

$^1$H NMR (400 MHz, DMSO-$d_6$) δ 12.2 (s, 1H), 7.93 (d, J=8.0 Hz, 1H), 7.65 (d, J=7.2 Hz, 1H), 7.36 (t, J=7.6 Hz, 1H), 4.60 (t, J=5.6 Hz, 1H), 3.83 (d, J=12.0 Hz, 1H), 3.68 (dd, J=12.0, 2.4 Hz, 1H), 3.63 (d, J=2.0 Hz, 2H), 3.29-3.22 (m, 3H), 3.19 (m, 1H), 2.49 (3H, obscured by solvent peak), 1.93-1.85 (m, 2H), 1.52-1.38 (m, 2H).

Example 222: 7-(Cyclopentylamino)-5-fluoro-2-(((trans-3-(trifluoromethyl)piperidin-4-yl)thio) methyl)quinazolin-4(3H)-one Hydrochloride

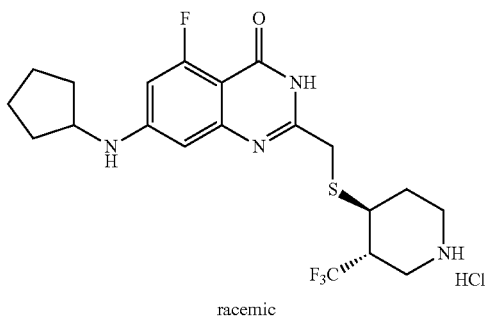 [SMILES: O=c1[nH]c(CS[C@H]2CCNC[C@@H]2C(F)(F)F)nc2cc(NC3CCCC3)cc(F)c12 ; Cl]

racemic

Step 1: tert-Butyl trans-4-(acetylthio)-3-(trifluoromethyl)piperidine-1-carboxylate Prepared from tert-butyl cis-4-hydroxy-3-(trifluoromethyl)piperidine-1-carboxylate according to the method described for Int-B3.

$^1$HNMR (400 MHz, CDCl$_3$) δ 5.23 (br s, 1H), 4.41 (br s, 1H), 3.94-3.89 (m, 2H), 2.34 (s, 3H), 1.62-1.58 (m, 2H), 1.42 (s, 9H).

Step 2: tert-Butyl trans-4-(((7-(cyclopentylamino)-5-fluoro-4-oxo-3,4-dihydroquinazolin-2-yl)methyl) thio)-3-(trifluoromethyl)piperidine-1-carboxylate Prepared from tert-butyl trans-4-(acetylthio)-3-(trifluoromethyl)piperidine-1-carboxylate and Int-A43 according to the method described for Example 202. LCMS: [M+H]+ 545.2.

Step 3: 7-(Cyclopentylamino)-5-fluoro-2-(((trans-3-(trifluoromethyl)piperidin-4-yl)thio)methyl)quinazolin-4(3H)-one Hydrochloride Prepared from tert-butyl trans-4-(((7-(cyclopentylamino)-5-fluoro-4-oxo-3,4-dihydroquinazolin-2-yl)methyl)thio)-3-(trifluoromethyl)piperidine-1-carboxylate according to the method described for Example 48, step 2. LCMS: [M+H]+ 445.1;

$^1$H NMR (400 MHz, DMSO-$d_6$) δ 9.52-9.18 (m, 2H), 7.08 (br s, 1H), 6.49-6.48 (m, 2H), 3.79-3.76 (m, 1H), 3.75-3.69 (m, 2H), 3.51-3.42 (m, 1H), 3.39-3.23 (m, 2H), 3.14-2.91 (m, 3H), 2.37-2.28 (m, 1H), 2.02-1.92 (m, 3H), 1.74-1.43 (m, 6H).

Example 223: 7-(Cyclopentylamino)-5-fluoro-2-(((cis-4-fluoropyrrolidin-3-yl)thio)methyl)quinazolin-4(3H)-one Trifluoroacetate

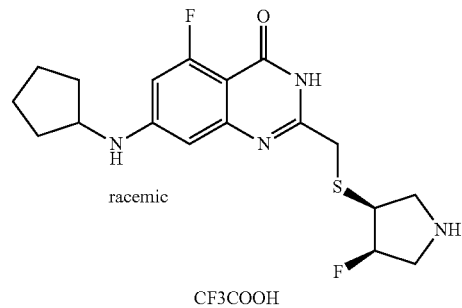 [SMILES: O=c1[nH]c(CS[C@H]2CNC[C@H]2F)nc2cc(NC3CCCC3)cc(F)c12 ; "CF3COOH"]

racemic

CF3COOH

Step 1: tert-Butyl cis-3-(benzoylthio)-4-fluoropyrrolidine-1-carboxylate

To a solution of tert-butyl trans-3-fluoro-4-hydroxy-pyrrolidine-1-carboxylate (500 mg, 2.44 mmol, 1.0 eq), benzenecarbothioic S-acid (673 mg, 4.87 mmol, 2.0 eq) and PPh$_3$ (1.28 g, 4.87 mmol, 2.0 eq) in THF (15 mL) was added DEAD (849 mg, 4.87 mmol, 2.0 eq) and the mixture was stirred at RT overnight under a N$_2$ atmosphere. The mixture was diluted with water (80 mL) and extracted with DCM (80 mL×3). The combined organic layers were dried over Na$_2$SO$_4$ and concentrated under reduced pressure. The residue was purified by column chromatography (petroleum ether:EtOAc, 8:1, v/v) to afford the title compound (550 mg, 24%) as a yellow solid.

$^1$H NMR (400 MHz, DMSO-$d_6$) δ 8.16-7.91 (m, 5H), 5.33 (d, J=52.8 Hz, 1H), 4.40-4.23 (m, 1H), 3.92-3.54 (m, 3H), 3.26-3.18 (m, 1H), 1.42 (s, 9H).

Step 2: tert-Butyl cis-3-(((7-(cyclopentylamino)-5-fluoro-4-oxo-3,4-dihydroquinazolin-2-yl)methyl)thio)-4-fluoropyrrolidine-1-carboxylate Prepared from Int-A43 and tert-butyl cis-3-(benzoylthio)-4-fluoropyrrolidine-1-carboxylate according to the method described for Example 202. LCMS: [M+H]$^+$ 481.2.

Step 3: 7-(Cyclopentylamino)-5-fluoro-2-(((cis-4-fluoropyrrolidin-3-yl)thio)methyl)quinazolin-4(3H)-one Trifluoroacetate Prepared from tert-butyl cis-3-(((7-(cyclopentylamino)-5-fluoro-4-oxo-3,4-dihydroquinazolin-2-yl)methyl)thio)-4-fluoropyrrolidine-1-carboxylate according to the method described for Example 48, step 2. Purification by prep-HPLC (Agilent 10 prep-C18, 10 μm, 250×21.2 mm column, eluting with a gradient of MeOH in water with 0.1% TFA, at a flow rate of 20 mL/min) afforded the title compound. LCMS: [M+H]$^+$ 381.1;
$^1$H NMR (400 MHz, DMSO-d$_6$) δ 11.8 (br s, 1H), 9.47 (br s, 1H), 9.27 (br s, 1H), 6.97 (br s, 1H), 6.43 (dd, J=14.0, 1.6 Hz, 1H), 6.38 (d, J=1.2 Hz, 1H), 5.34 (d, J=54.8 Hz, 1H), 3.79-3.67 (m, 5H), 3.64-3.36 (m, 2H), 3.09-2.96 (m, 1H), 2.00-1.88 (m, 2H), 1.74-1.63 (m, 2H), 1.63-1.51 (m, 2H), 1.51-1.40 (m, 2H).

Example 224: 7-(Cyclopentylamino)-5-(hydroxymethyl)-2-(((tetrahydro-2H-pyran-4-yl)thio)methyl)quinazolin-4(3H)-one

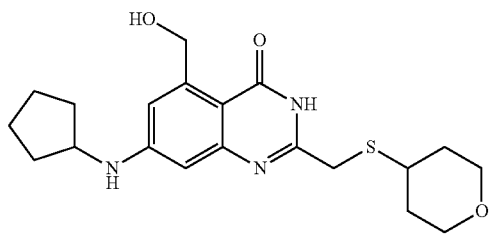

Step 1: Methyl 7-fluoro-4-oxo-2-(((tetrahydro-2H-pyran-4-yl)thio)methyl)-3,4-dihydroquinazoline-5-carboxylate To a suspension of 5-bromo-7-fluoro-2-(((tetrahydro-2H-pyran-4-yl)thio)methyl)quinazolin-4(3H)-one (300 mg, 0.80 mmol, 1.0 eq) in methanol (5 mL) was added Et$_3$N (163 mg, 1.61 mmol, 2.0 eq) and PdCl$_2$(dppf) (59 mg, 0.08 mmol, 0.1 eq) and the mixture was heated at 100° C. under a carbon monoxide atmosphere (50 psi) for 15 h. After cooling to RT, the mixture was filtered and the filtrate was dried over Na$_2$SO$_4$ and concentrated under reduced pressure to afford the title compound (230 mg, 81%) as a brown solid. LCMS: [M+H]$^+$ 353.1.

Step 2: 7-Fluoro-5-(hydroxymethyl)-2-(((tetrahydro-2H-pyran-4-yl)thio)methyl)quinazolin-4(3H)-one To a solution of methyl 7-fluoro-4-oxo-2-(((tetrahydro-2H-pyran-4-yl)thio)methyl)-3,4-dihydroquinazoline-5-carboxylate (30 mg, 0.09 mmol, 1.0 eq) in THF (3 mL) was added sodium borohydride (10 mg, 0.26 mmol, 3.0 eq) and the mixture was stirred at RT for 2 h. The mixture was diluted with water (5 mL) and extracted with EtOAc (20 mL×3). The combined organic layers were dried over Na$_2$SO$_4$ and concentrated under reduced pressure. The residue was purified by prep-TLC (petroleum ether:EtOAc, 1:1, v/v) to afford the title compound (10 mg, 36%) as a white solid. LCMS: [M+H]$^+$ 325.1.

Step 3: 7-(Cyclopentylamino)-5-(hydroxymethyl)-2-(((tetrahydro-2H-pyran-4-yl)thio)methyl)quinazolin-4(3H)-one Prepared from 7-fluoro-5-(hydroxymethyl)-2-(((tetrahydro-2H-pyran-4-yl)thio)methyl)quinazolin-4(3H)-one and cyclopentanamine according to the method described for Example 126. LCMS: [M+H]$^+$ 390.2;
$^1$HNMR (400 MHz, CD$_3$OD) δ 6.78 (d, J=2.4 Hz, 1H), 6.45 (s, 1H), 4.81 (s, 2H), 3.82-3.76 (m, 3H), 3.56-3.54 (m, 2H), 3.36-3.29 (m, 2H), 2.95-2.87 (m, 1H), 1.98-1.91 (m, 2H), 1.86-1.80 (m, 2H), 1.70-1.65 (m, 2H), 1.61-1.55 (m, 2H), 1.52-1.45 (m, 4H).

Example 225: 7-(cyclopentylamino)-5-(fluoromethyl)-2-(((tetrahydro-2H-pyran-4-yl)thio)methyl)quinazolin-4(3H)-one

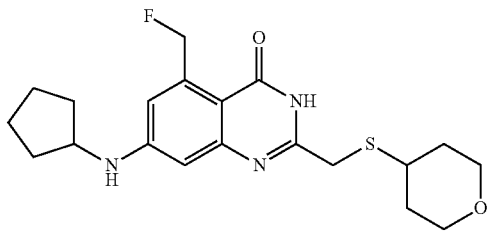 [SMILES: O=c1[nH]c(CSC2CCOCC2)nc2cc(NC3CCCC3)cc(CF)c12]

To a solution of 7-(cyclopentylamino)-5-(hydroxymethyl)-2-(((tetrahydro-2H-pyran-4-yl)thio)methyl)quinazolin-4(3H)-one (100 mg, 0.26 mmol, 1.0 eq) in DCM (5 mL) at −78° C. under a N$_2$ atmosphere was added Et$_3$N (52 mg, 0.51 mmol, 2.0 eq) and DAST (207 mg, 1.28 mmol, 5.0 eq) and the mixture was stirred at −78° C. for 2 h. After warming to RT, the reaction was quenched with water (5 mL) and the mixture was extracted with DCM (20 mL×3). The combined organic layers were dried over Na$_2$SO$_4$ and concentrated under reduced pressure. The residue was purified by prep-HPLC (Agilent 10 prep-C18, 10 μm, 250×21.2 mm column, eluting with a gradient of ACN in water with 0.1% TFA, at a flow rate of 20 mL/min) to afford the title compound (3.5 mg, 3%) as a white solid. LCMS: [M+H]$^+$ 392.1; $^1$HNMR (400 MHz, CD$_3$OD) δ 7.03 (s, 1H), 6.58 (d, J=2.0 Hz, 1H), 5.92 (d, J=48.4 Hz, 2H), 3.96-3.90 (m, 3H), 3.49-3.43 (m, 2H), 3.33 (2H, obscured by solvent peak), 3.12-3.06 (m, 1H), 2.10-2.04 (m, 2H), 1.98-1.95 (m, 2H), 1.80-1.58 (m, 8H).

Example 226: 7-(Cyclopentylamino)-6-fluoro-2-((piperidin-4-ylthio)methyl)quinazolin-4(3H)-one hydrochloride

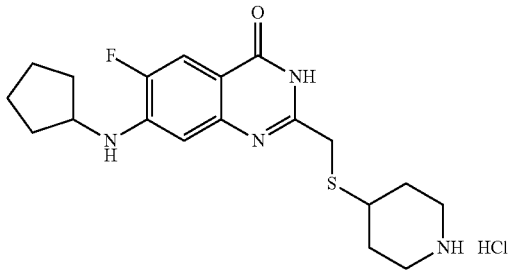 [SMILES: O=c1[nH]c(CSC2CCNCC2)nc2cc(NC3CCCC3)c(F)cc12 ; Cl]

Step 1: tert-Butyl 4-(((7-bromo-6-fluoro-4-oxo-3,4-dihydroquinazolin-2-yl)methyl)thio)piperidine-1-carboxylate Prepared from Int-A48 and Int-B2 according to the method described for Example 202. LCMS: [M+H]$^+$ 472.1.

Step 2: tert-Butyl 4-(((7-bromo-3-(2-(tert-butoxy)-2-oxoethyl)-6-fluoro-4-oxo-3,4-dihydroquinazolin-2-yl)methyl)thio)piperidine-1-carboxylate To a solution of tert-butyl 4-(((7-bromo-6-fluoro-4-oxo-3,4-dihydroquinazolin-2-yl)methyl)thio)piperidine-1-carboxylate (790 mg, 1.67 mmol, 1.0 eq) in DMF (12 mL) was added chloromethyl 2,2-dimethylpropanoate (302 mg, 2.01 mmol, 1.2 eq) and K$_2$CO$_3$ (347 mg, 2.51 mmol, 1.5 eq) and the mixture was heated at 80° C. under a N$_2$ atmosphere for 2 h. The mixture was diluted with water (60 mL) and extracted with EtOAc (50 mL×3). The combined organic layers were washed with water (20 mL×3), dried over Na$_2$SO$_4$ and concentrated under reduced pressure. The residue was purified by column chromatography (petroleum ether:EtOAc, 15:1, v/v) to afford the title compound (550 mg, 56%) as a brown oil. LCMS: [M+H]$^+$ 586.1.

Step 3: tert-Butyl 4-(((3-(2-(tert-butoxy)-2-oxoethyl)-7-(cyclopentylamino)-6-fluoro-4-oxo-3,4-dihydroquinazolin-2-yl)methyl)thio)piperidine-1-carboxylate To a solution of tert-butyl 4-(((7-bromo-3-(2-(tert-butoxy)-2-oxoethyl)-6-fluoro-4-oxo-3,4-dihydroquinazolin-2-yl)methyl)thio)piperidine-1-carboxylate (200 mg, 0.34 mmol, 1.0 eq) and cyclopentanamine (35 mg, 0.41 mmol, 1.2 eq) in toluene (5 mL) under a N$_2$ atmosphere was added Cs$_2$CO$_3$ (167 mg, 0.51 mmol, 1.5 eq), BINAP (42 mg, 0.07 mmol, 0.2 eq) and Pd$_2$(dba)$_3$ (31 mg, 0.03 mmol, 0.1 eq) and the mixture was heated at 100° C. for 2 h. After cooling to RT, the mixture was diluted with water (30 mL) and extracted with EtOAc (20 mL×3). The combined organic layers were dried over Na$_2$SO$_4$ and concentrated under reduced pressure. The residue was purified by prep-TLC (petroleum ether:EtOAc, 3:1, v/v) to afford the title compound (90 mg, 45%) as a yellow solid. LCMS: [M+H]$^+$ 591.3.

Step 4: tert-Butyl 4-(((7-(cyclopentylamino)-6-fluoro-4-oxo-3,4-dihydroquinazolin-2-yl)methyl)thio)piperidine-1-carboxylate To a solution of tert-butyl 4-(((3-(2-(tert-butoxy)-2-oxoethyl)-7-(cyclopentylamino)-6-fluoro-4-oxo-3,4-dihydroquinazolin-2-yl)methyl)thio)piperidine-1-carboxylate (90 mg, 0.15 mmol, 1.0 eq) in methanol (2 mL) was added 1 M NaOH (0.5 mL) and the mixture was stirred at RT for 0.5 h. The mixture was diluted with water (30 mL), extracted with EtOAc (20 mL×2) and the combined organic layers were dried over Na$_2$SO$_4$ and concentrated under reduced pressure. The residue was purified by prep-TLC (DCM:MeOH, 20:1, v/v) to afford the title compound (66 mg, 91%) as a white solid. LCMS: [M+H]$^+$ 477.2.

Step 5: 7-(Cyclopentylamino)-6-fluoro-2-((piperidin-4-ylthio)methyl)quinazolin-4(3H)-one hydrochloride Prepared from tert-butyl 4-(((7-(cyclopentylamino)-6-fluoro-4-oxo-3,4-dihydroquinazolin-2-yl)methyl)thio)piperidine-1-carboxylate according to the method described for Example 48, step 2. LCMS: [M+H]$^+$ 377.1;

$^1$H NMR (400 MHz, DMSO-d$_6$) δ 9.04-8.90 (m, 2H), 7.58 (d, J=11.6 Hz, 1H), 6.92 (d, J=7.2 Hz, 1H), 6.68 (br s, 1H), 3.85-3.78 (m, 3H), 3.24-3.14 (m, 3H), 2.94-2.86 (m, 2H), 2.17-2.13 (m, 2H), 2.03-1.95 (m, 2H), 1.71-1.53 (m, 8H).

Example 227: 7-(Cyclopentylamino)-5-fluoro-2-(((trans-2-(trifluoromethyl)piperidin-4-yl)thio)methyl)quinazolin-4(3H)-one bis Trifluoroacetate

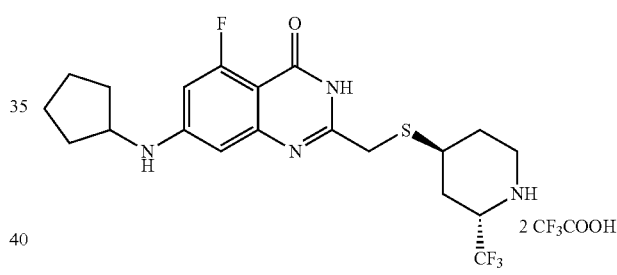

racemic

Step 1: tert-Butyl cis-4-hydroxy-2-(trifluoromethyl)piperidine-1-carboxylate

Prepared from tert-butyl 4-oxo-2-(trifluoromethyl)piperidine-1-carboxylate according to the procedure described in WO201391773.

Step 2: tert-Butyl cis-4-((methylsulfonyl)oxy)-2-(trifluoromethyl)piperidine-1-carboxylate Prepared from tert-butyl cis-4-hydroxy-2-(trifluoromethyl)piperidine-1-carboxylate according to the procedure described for Int-B3 step 1. LCMS: [M+H]$^+$ 348.1.

Step 3: tert-Butyl trans-4-(((7-(cyclopentylamino)-5-fluoro-4-oxo-3,4-dihydroquinazolin-2-yl)methyl)thio)-2-(trifluoromethyl)piperidine-1-carboxylate Prepared from Int-C12 and tert-butyl cis-4-((methylsulfonyl)oxy)-2-(trifluoromethyl)piperidine-1-carboxylate according to the method described for Example 210, step 3. LCMS: [M+H]$^+$ 545.2.

Step 4: 7-(Cyclopentylamino)-5-fluoro-2-(((trans-2-(trifluoromethyl)piperidin-4-yl)thio)methyl)quinazolin-4(3H)-one bis Trifluoroacetate Prepared from tert-butyl trans-4-(((7-(cyclopentylamino)-5-fluoro-4-oxo-3,4-dihydroquinazolin-2-yl)methyl)thio)-2-(trifluoromethyl)piperidine-1-carboxylate according to the method described for Example 48, step 2. Purification by prep-HPLC (Agilent 10 prep-C18, 10 μm, 250×21.2 mm column, eluting with a gradient of MeOH in water with 0.1% TFA, at a flow rate of 20 mL/min) afforded the title compound. LCMS: [M+H]$^+$ 445.1;
$^1$H NMR (400 MHz, CD$_3$OD) δ 6.49-6.43 (m, 2H), 4.52-4.43 (m, 1H), 3.87-3.81 (m, 1H), 3.69-3.65 (m, 1H), 3.49-3.40 (m, 2H), 2.71 (s, 2H), 2.41-2.33 (m, 1H), 2.27-2.16 (m, 2H), 2.15-2.00 (m, 3H), 1.82-1.53 (m, 6H). $^{19}$F NMR (400 MHz, CD$_3$OD) δ −75.9, −76.3, −77.3, −113.1.

Example 228: 7-(Cyclopentylamino)-5-fluoro-2-(((cis-2-(trifluoromethyl)piperidin-4-yl)thio)methyl)quinazolin-4(3H)-one hydrochloride

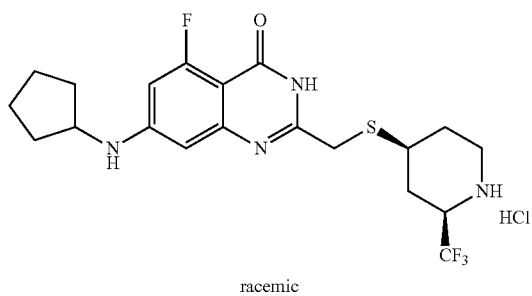 [SMILES: O=c1[nH]c(CS[C@H]2CCN[C@@H](C(F)(F)F)C2)nc2cc(NC3CCCC3)cc(F)c12 ; Cl]

racemic

Step 1: tert-Butyl trans-4-((4-nitrobenzoyl)oxy)-2-(trifluoromethyl)piperidine-1-carboxylate To a solution of tert-butyl cis-4-hydroxy-2-(trifluoromethyl)piperidine-1-carboxylate (500 mg, 1.86 mmol, 1.0 eq), 4-nitrobenzoic acid (621 mg, 3.71 mmol, 2.0 eq) and triphenylphosphine (974 mg, 3.71 mmol, 2.0 eq) in THF (15 mL) at 0° C. under a N$_2$ atmosphere was added DEAD (647 mg, 3.71 mmol, 2.0 eq) and the mixture was allowed to warm to RT and stirred overnight. The mixture was diluted with water (20 mL), extracted with EtOAc (15 mL×3) and the combined organic layers were washed with water (20 mL), brine (20 mL), dried over Na$_2$SO$_4$ and concentrated under reduced pressure. The residue was purified by column chromatography (petroleum ether:EtOAc, 20:1, v/v) to afford the title compound (430 mg, 55%) as a white solid. LCMS: [M+H]$^+$ 419.1.

Step 2: tert-Butyl trans-4-hydroxy-2-(trifluoromethyl)piperidine-1-carboxylate A mixture of tert-butyl trans-4-(4-nitrobenzoyl)oxy)-2-(trifluoromethyl)piperidine-1-carboxylate (400 mg, 0.96 mmol, 1.0 eq) and 2 M NaOH (8.0 mL) in methanol (16 mL) was stirred at 20° C. for 2 h. The mixture was diluted with water (30 mL) and extracted with EtOAc (25 mL×3). The combined organic layers were washed with brine (20 mL), dried over Na$_2$SO$_4$ and concentrated under reduced pressure to afford the title compound (200 mg, 78%) as an off white solid.

$^1$HNMR (400 MHz, DMSO-d$_6$) δ 4.96 (br s, 1H), 4.93-4.73 (m, 1H), 4.10-3.96 (m, 1H), 3.77-3.65 (m, 1H), 2.94-2.69 (m, 1H), 2.06-1.98 (m, 1H), 1.88-1.78 (m, 1H), 1.58-1.44 (m, 1H), 1.40 (s, 9H), 1.24-1.65 (m, 1H).

Step 3. tert-Butyl trans-4-((methylsulfonyl)oxy)-2-(trifluoromethyl)piperidine-1-carboxylate Prepared from tert-butyl trans-4-hydroxy-2-(trifluoromethyl)piperidine-1-carboxylate according to the procedure described for Int-B3 step 1. LCMS: [M+H]$^+$ 348.1.

Step 4: tert-Butyl cis-4-(((7-(cyclopentylamino)-5-fluoro-4-oxo-3,4-dihydroquinazolin-2-yl)methyl)thio)-2-(trifluoromethyl)piperidine-1-carboxylate Prepared from Int-C12 and tert-butyl trans-4-((methylsulfonyl)oxy)-2-(trifluoromethyl)piperidine-1-carboxylate according to the method described for Example 210, step 3. LCMS: [M+H]$^+$ 545.2.

Step 5: 7-(Cyclopentylamino)-5-fluoro-2-(((cis-2-(((cis-2-(trifluoromethyl)piperidin-4-yl)thio)methyl)quinazolin-4(3H)-one Hydrochloride Prepared from tert-butyl cis-4-(((7-(cyclopentylamino)-5-fluoro-4-oxo-3,4-dihydroquinazolin-2-yl)methyl)thio)-2-(trifluoromethyl)piperidine-1-carboxylate according to the method described for Example 48, step 2. LCMS: [M+H]$^+$ 445.1;
$^1$H NMR (400 MHz, DMSO-d$_6$) δ 12.1 (br s, 1H), 10.0 (br s, 2H), 7.07 (br s, 1H), 6.53-6.40 (m, 2H), 4.40-4.31 (m, 1H), 3.78-3.69 (m, 3H), 3.43-3.36 (m, 1H), 3.18-3.04 (m, 2H), 2.54-2.52 (m, 1H), 2.21-2.13 (m, 1H), 1.99-1.91 (m, 2H), 1.72-1.54 (m, 6H), 1.51-1.42 (m, 2H).

Example 229: 7-(Cyclopropylmethoxy)-2-((piperidin-4-ylthio)methyl)pyrido[2,3-d]pyrimidin-4(3H)-one Hydrochloride

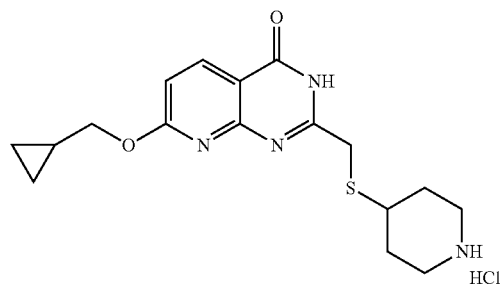 [SMILES: O=c1[nH]c(CSC2CCNCC2)nc2nc(OCC3CC3)ccc12 ; Cl]

Step 1: tert-Butyl 4-(((7-chloro-4-oxo-3,4-dihydropyrido[2,3-d]pyrimidin-2-yl)methyl)thio)piperidine-1-carboxylate Prepared from Int-A44 and Int-B2 according to the method described for Example 202. LCMS: [M+H]$^+$ 411.1.

Step 2: tert-Butyl 4-(((7-(cyclopropylmethoxy)-4-oxo-3,4-dihydropyrido[2,3-d]pyrimidin-2-yl)methyl)thio)piperidine-1-carboxylate To a solution of cyclopropylmethanol (53 mg, 0.73 mmol, 5.5 eq) in THF (3 mL) at 0° C. was added NaH (60% w/w dispersion in oil, 58 mg, 1.46 mmol, 10 eq) portion-wise and the mixture was stirred for 30 min. A solution of tert-butyl 4-(((7-chloro-4-oxo-3,4-dihydropyrido[2,3-d]pyrimidin-2-yl)methyl)thio)piperidine-1-carboxylate (60 mg, 0.15 mmol, 1.0 eq) in THF (0.5 mL) was then added and the mixture was allowed to warm to RT and stirred for 1 h. The mixture was cooled to 0° C., diluted with water (10 mL) and extracted with EtOAc (15 mL×3). The combined organic layers were washed with brine (20 mL), dried over $Na_2SO_4$ and concentrated under reduced pressure. The residue was purified by prep-TLC (DCM:MeOH, 60:1, v/v) to afford the title compound (30 mg, 46%) as a light-yellow solid. LCMS: [M+H]$^+$ 447.1.

Step 3: 7-(Cyclopropylmethoxy)-2-((piperidin-4-ylthio)methyl)pyrido[2,3-d]pyrimidin-4(3H)-one hydrochloride Prepared from tert-butyl 4-(((7-(cyclopropylmethoxy)-4-oxo-3,4-dihydropyrido[2,3-d]pyrimidin-2-yl)methyl)thio)piperidine-1-carboxylate according to the method described for Example 48, step 2. LCMS: [M+H]$^+$ 347.1;

$^1$H NMR (400 MHz, DMSO-d$_6$) δ 12.5 (br s, 1H), 8.60 (br s, 2H), 8.29 (d, J=8.8 Hz, 1H), 6.93 (d, J=8.4 Hz, 1H), 4.21 (d, J=7.2 Hz, 2H), 3.72 (s, 2H), 3.27-3.20 (m, 2H), 3.13-3.05 (m, 1H), 2.96-2.87 (m, 2H), 2.17-2.07 (m, 2H), 1.69-1.59 (m, 2H), 1.32-1.23 (m, 1H), 0.60-0.55 (m, 2H), 0.40-0.32 (m, 2H).

Example 230: 7-((Cyclobutylmethyl)amino)-6-methoxy-2-((piperidin-4-ylthio)methyl)quinazolin-4(3H)-one Hydrochloride

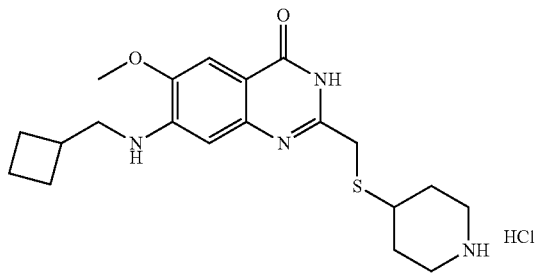 [SMILES: COc1cc2c(=O)[nH]c(CSC3CCNCC3)nc2cc1NCC1CCC1 ; Cl]

Step 1: tert-Butyl 4-(((7-bromo-6-methoxy-4-oxo-3,4-dihydroquinazolin-2-yl)methyl)thio)piperidine-1-carboxylate Prepared from Int-A45 and Int-B2 according to the method described for Example 202. LCMS: [M+H]$^+$ 484.1.

Step 2: tert-Butyl 4-(((7-((cyclobutylmethyl)amino)-6-methoxy-4-oxo-3,4-dihydroquinazolin-2-yl)methyl)thio)piperidine-1-carboxylate Prepared from tert-butyl 4-(((7-bromo-6-methoxy-4-oxo-3,4-dihydroquinazolin-2-yl)methyl)thio)piperidine-1-carboxylate and cyclobutylmethanamine according to the method described for Example 226, step 2, 3 and 4. LCMS: [M+H]$^+$ 489.2.

Step 3: 7-((Cyclobutylmethyl)amino)-6-methoxy-2-((piperidin-4-ylthio)methyl)quinazolin-4(3H)-one Hydrochloride Prepared from tert-butyl 4-(((7-((cyclobutylmethyl)amino)-6-methoxy-4-oxo-3,4-dihydroquinazolin-2-yl)methyl)thio)piperidine-1-carboxylate according to the method described for Example 48, step 2. LCMS: [M+H]$^+$ 389.1;

$^1$H NMR (400 MHz, DMSO-d$_6$) δ 13.5 (br s, 1H), 9.11-8.88 (m, 2H), 7.25 (s, 1H), 6.88 (s, 1H), 6.64 (br s, 1H), 3.96 (s, 2H), 3.93 (s, 3H), 3.28-3.18 (m, 5H), 2.94-2.85 (m, 2H), 2.69-2.60 (m, 1H), 2.22-2.12 (m, 2H), 2.07-1.95 (m, 2H), 1.90-1.80 (m, 2H), 1.77-1.60 (m, 4H).

Example 231: 7-((2,2-Difluorocyclopentyl)amino)-5-fluoro-2-(((tetrahydro-2H-pyran-4-yl)thio)methyl)quinazolin-4(3H)-one

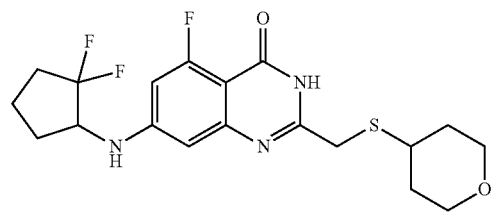 [SMILES: O=c1[nH]c(CSC2CCOCC2)nc2cc(NC3CCCC3(F)F)cc(F)c12]

Step 1: 7-Bromo-5-fluoro-2-(((tetrahydro-2H-pyran-4-yl)thio)methyl)quinazolin-4(3H)-one Prepared from Int-A46 and Int B1 according to the method described for Example 202. LCMS: [M+H]$^+$ 373.0.

Step 2: 7-((2, 2-Difluorocyclopentyl)amino)-5-fluoro-2-(((tetrahydro-2H-pyran-4-yl)thio)methyl)quinazolin-4(3H)-one Prepared from 7-bromo-5-fluoro-2-(((tetrahydro-2H-pyran-4-yl)thio)methyl)quinazolin-4(3H)-one and 2,2-difluorocyclopentan-1-amine according to the method described for Example 226, step 2, 3 and 4. LCMS: [M+H]$^+$ 414.1;

$^1$H NMR (400 MHz, DMSO-d$_6$) δ 11.7 (s, 1H), 6.93 (d, J=8.0 Hz, 1H), 6.57-6.54 (m, 2H), 4.22-4.15 (m, 1H), 3.82-3.79 (m, 2H), 3.55 (s, 2H), 3.36-3.27 (m, 2H), 3.06-3.00 (m, 1H), 2.25-2.03 (m, 3H), 1.89-1.86 (m, 2H), 1.78-1.72 (m, 2H), 1.65-1.60 (m, 1H), 1.48-1.38 (m, 2H).

Example 232: 7-(Cyclopentylamino)-5,6-difluoro-2-((piperidin-4-ylthio)methyl)quinazolin-4(3H)-one Hydrochloride

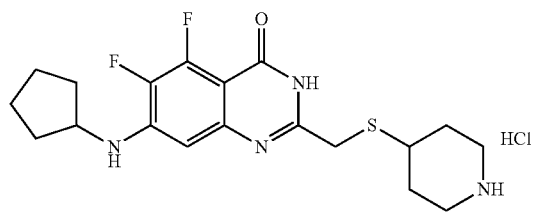 [SMILES: O=c1[nH]c(CSC2CCNCC2)nc2cc(NC3CCCC3)c(F)c(F)c12 ; Cl]

Step 1: tert-Butyl 4-(((7-(cyclopentylamino)-5,6-difluoro-4-oxo-3,4-dihydroquinazolin-2-yl)methyl)thio)piperidine-1-carboxylate Prepared from Int-A47 and Int-B2 according to the method described for Example 202. LCMS: [M+H]$^+$ 495.2.

Step 2: 7-(Cyclopentylamino)-5,6-difluoro-2-((piperidin-4-ylthio)methyl)quinazolin-4(3H)-one hydrochloride Prepared from tert-butyl 4-(((7-(cyclopentylamino)-5,6-difluoro-4-oxo-3,4-dihydroquinazolin-2-yl)methyl)thio)piperidine-1-carboxylate according to the method described for Example 48, step 2. LCMS: [M+H]$^+$ 395.1;

$^1$H NMR (400 MHz, DMSO-d$_6$) δ 12.2 (br s, 1H), 8.95 (br s, 1H), 8.83 (br s, 1H), 6.81 (br s, 1H), 6.63 (d, J=7.2 Hz, 1H), 3.91-3.82 (m, 1H), 3.67 (s, 2H), 3.21-3.17 (m, 2H), 3.16-3.04 (m, 1H), 2.95-2.85 (m, 2H), 2.19-2.06 (m, 2H), 2.04-1.91 (m, 2H), 1.78-1.53 (m, 8H).

Example 233: 5-Fluoro-7-((trans-4-morpholinocyclohexyl)amino)-2-(((tetrahydro-2H-pyran-4-yl)thio)methyl)quinazolin-4(3H)-one Trifluoroacetate and

Example 234: 5-Fluoro-7-((cis-4-morpholinocyclohexyl)amino)-2-(((tetrahydro-2H-pyran-4-yl)thio)methyl)quinazolin-4(3H)-one Trifluoroacetate

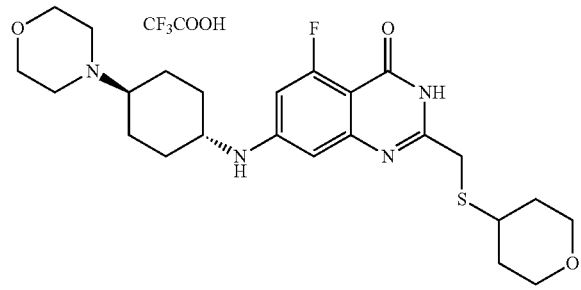

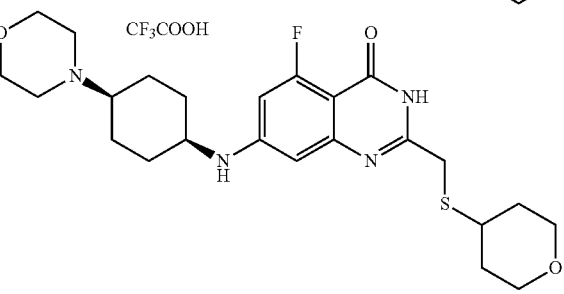

Step 1: 7-((1,4-Dioxaspiro[4.5]decan-8-yl)amino)-5-fluoro-2-(((tetrahydro-2H-pyran-4-yl)thio)methyl)quinazolin-4(3H)-one Prepared from 7-bromo-5-fluoro-2-(((tetrahydro-2H-pyran-4-yl)thio)methyl)quinazolin-4(3H)-one and 1,4-dioxaspiro[4.5]decan-8-amine according to the method described for Example 226, step 2, 3, 4. LCMS: [M+H]$^+$ 450.2.

Step 2: 5-Fluoro-7-((4-oxocyclohexyl)amino)-2-(((tetrahydro-2H-pyran-4-yl)thio)methyl)quinazolin-4(3H)-one Prepared from 7-((1,4-dioxaspiro[4.5]decan-8-yl)amino)-5-fluoro-2-(((tetrahydro-2H-pyran-4-yl)thio)methyl)quinazolin-4(3H)-one according to the method described for Example 21, step 3.
LCMS: [M+H]$^+$ 406.1.

Step 3: 5-Fluoro-7-((4-morpholinocyclohexyl)amino)-2-(((tetrahydro-2H-pyran-4-yl)thio)methyl)quinazolin-4(3H)-one To a solution of 5-fluoro-7-((4-oxocyclohexyl)amino)-2-(((tetrahydro-2H-pyran-4-yl)thio)methyl)quinazolin-4(3H)-one (30 mg, 0.07 mmol, 1.0 eq) in methanol (2 mL) was added morpholine (32 mg, 0.37 mmol, 5.0 eq) and the mixture was stirred at RT for 30 min. NaCNBH$_3$ (24 mg, 0.38 mmol, 5.0 eq) was then added and the mixture was stirred at RT overnight. The reaction was quenched with a saturated aqueous NaHCO$_3$ solution (20 mL) and the mixture was extracted with EtOAc (30 mL×2). The combined organic layers were washed with brine (40 mL), dried over Na$_2$SO$_4$ and concentrated under reduced pressure to afford the title compound (10 mg, 28%) as a white solid. LCMS: [M+H]$^+$ 477.2.

Step 4: 5-Fluoro-7-((trans-4-morpholinocyclohexyl)amino)-2-(((tetrahydro-2H-pyran-4-yl)thio)methyl)quinazolin-4(3H)-one trifluoroacetate and 5-Fluoro-7-((cis-4-morpholinocyclohexyl)amino)-2-(((tetrahydro-2H-pyran-4-yl)thio)methyl)quinazolin-4(3H)-one Trifluoroacetate 5-Fluoro-7-((4-morpholinocyclohexyl)amino)-2-(((tetrahydro-2H-pyran-4-yl)thio)methyl)quinazolin-4(3H)-one further purified by prep-HPLC (Agilent 10 prep-C18, 10 μm, 250×21.2 mm column, eluting with a gradient of ACN in water with 0.1% TFA, at a flow rate of 20 mL/min) to afford the title compounds.

Example 233

LCMS: [M+H]$^+$ 477.2;
$^1$H NMR (400 MHz, CD$_3$OD) δ 6.63-6.58 (m, 2H), 4.10 (d, J=12.0 Hz, 2H), 3.93-3.89 (m, 2H), 3.82-3.73 (m, 2H), 3.51-3.41 (m, 5H), 3.35-3.31 (m, 2H), 3.26-3.20 (m, 3H), 3.09-3.04 (m, 1H), 2.28-2.25 (m, 4H), 1.98-1.93 (m, 2H), 1.78-1.69 (m, 2H), 1.63-1.54 (m, 2H), 1.49-1.37 (m, 2H).

Example 234

LCMS: [M+H]$^+$ 477.2;
$^1$H NMR (400 MHz, CD$_3$OD) δ 6.63-6.58 (m, 2H), 4.10 (d, J=13.2 Hz, 2H), 3.93-3.90 (m, 2H), 3.83-3.77 (m, 3H), 3.51-3.41 (m, 4H), 3.35-3.31 (m, 2H), 3.27-3.22 (m, 3H), 3.10-3.03 (m, 1H), 2.15-2.12 (m, 2H), 2.05-2.02 (m, 2H), 1.97-1.94 (m, 2H), 1.88-1.77 (m, 4H), 1.63-1.53 (m, 2H).

Example 235: 7-(Cyclopropylmethoxy)-5-fluoro-2-(((trans-4-hydroxycyclohexyl)thio)methyl)quinazolin-4(3H)-one

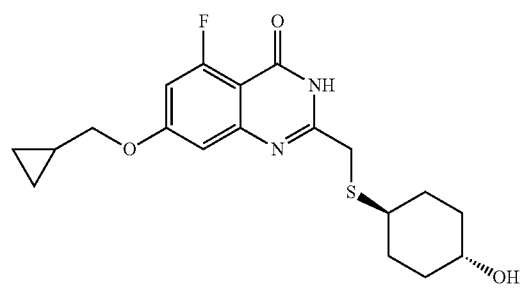 [SMILES: O=c1[nH]c(CS[C@H]2CC[C@H](O)CC2)nc2cc(OCC3CC3)cc(F)c12]

To a solution of Int-A49 (300 mg, 1.06 mmol, 1.0 eq) in THF (5 mL) under a N₂ atmosphere was added Int-B11 (168 mg, 1.27 mmol, 1.2 eq) and 2 M NaOH (2 mL) and the mixture was stirred at RT overnight. The mixture was poured into water (30 mL) and extracted with EtOAc (20 mL×3). The combined organic layers were washed with brine (30 mL), dried over Na₂SO₄ and concentrated under reduced pressure. The residue was purified by C18 reverse phase column (Biotage, 40% ACN in water) to afford the title compound (130 mg, 32%) as a white solid. LCMS: [M+H]⁺ 379.1;

¹H NMR (400 MHz, DMSO-d₆) δ 12.1 (s, 1H), 6.89-6.86 (m, 2H), 4.52 (d, J=4.4 Hz, 1H), 3.96 (d, J=7.2 Hz, 2H), 3.57 (s, 2H), 3.40-3.38 (m, 1H), 2.74-2.67 (m, 1H), 1.97-1.94 (m, 2H), 1.82-1.80 (m, 2H), 1.28-1.11 (m, 5H), 0.60-0.58 (m, 2H), 0.37-0.33 (m, 2H).

Example 236: 5-Fluoro-7-(((tetrahydro-2H-pyran-4-yl)methoxy)-2-(((tetrahydro-2H-pyran-4-yl)thio)methyl)quinazolin-4(3H)-one

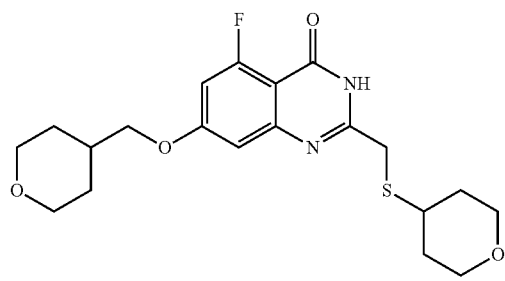 [SMILES: O=c1[nH]c(CSC2CCOCC2)nc2cc(OCC3CCOCC3)cc(F)c12]

Prepared from Int-A50 and Int-B1 according to the method described for Example 202. LCMS: [M+H]⁺ 409.1;

¹H NMR (400 MHz, DMSO-d₆) δ 12.2 (s, 1H), 6.95-6.84 (m, 2H), 3.99 (d, J=6.4 Hz, 2H), 3.92-3.77 (m, 4H), 3.61 (s, 2H), 3.38-3.32 (m, 2H), 3.31-3.27 (m, 2H), 3.10-3.00 (m, 1H), 2.08-1.97 (m, 1H), 1.93-1.84 (m, 2H), 1.72-1.63 (m, 2H), 1.51-1.27 (m, 4H).

Example 237: 7-(Cyclobutylmethoxy)-5-methyl-2-(((tetrahydro-2H-pyran-4-yl)thio)methyl)quinazolin-4(3H)-one

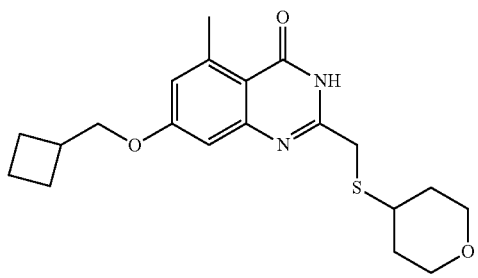 [SMILES: Cc1cc(OCC2CCC2)cc2nc(CSC3CCOCC3)[nH]c(=O)c12]

Prepared from Int-A51 and Int-B1 according to the method described for Example 202. LCMS: [M+H]⁺ 375.1;

¹H NMR (400 MHz, DMSO-d₆) δ 11.9 (s, 1H), 6.85 (s, 1H), 6.82 (s, 1H), 4.05 (d, J=6.4 Hz, 2H), 3.83-3.80 (m, 2H), 3.60 (s, 2H), 3.35-3.32 (m, 2H), 3.08-3.01 (m, 1H), 2.77-2.70 (m, 1H), 2.70 (s, 3H), 2.11-2.04 (m, 2H), 1.95-1.79 (m, 6H), 1.49-1.40 (m, 2H).

Example 238: 5-Fluoro-2-(((tetrahydro-2H-pyran-4-yl)thio)methyl)-7-((tetrahydrofuran-3-yl)methoxy)quinazolin-4(3H)-one

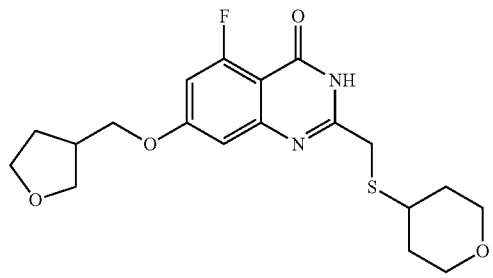

racemic

Prepared from Int-A52 and Int-B1 according to the method described for Example 202. LCMS: [M+H]⁺ 395.0;

¹H NMR (400 MHz, DMSO-d₆) δ 12.2 (s, 1H), 6.94-6.84 (m, 2H), 4.10-4.00 (m, 2H), 3.84-3.72 (m, 4H), 3.69-3.62 (m, 1H), 3.60 (s, 2H), 3.55-3.48 (m, 1H), 3.37-3.34 (m, 1H), 3.30-3.27 (m, 1H), 3.08-2.99 (m, 1H), 2.70-2.63 (m, 1H), 2.07-1.96 (m, 1H), 1.92-1.83 (m, 2H), 1.70-1.62 (m, 1H), 1.48-1.37 (m, 2H).

Example 239: (R)-5-fluoro-2-(((tetrahydro-2H-pyran-4-yl)thio)methyl)-7-((tetrahydrofuran-3-yl)methoxy)quinazolin-4(3H)-one and (S)-5-fluoro-2-(((tetrahydro-2H-pyran-4-yl)thio)methyl)-7-((tetrahydrofuran-3-yl)methoxy)quinazolin-4(3H)-one

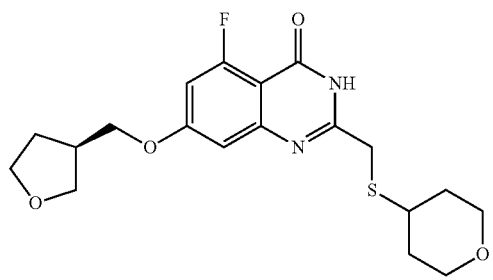

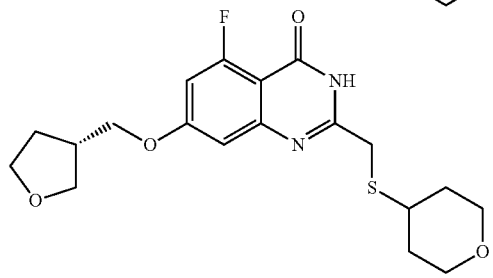

Example 238 was further purified by chiral prep-HPLC (Chiralpak IE-3, 3 μm, 0.46×5 cm column, eluting with a gradient of hexane:DCM (0.1% DEA):MeOH 50:50 at a flow rate of 1.0 mL/min) to afford the title compounds with retention times of 2.09 minutes (239a) and 3.35 minutes (239b).

Example 239a

LCMS: [M+H]$^+$ 395.2;
$^1$HNMR (400 MHz, DMSO-d$_6$) δ 12.2 (s, 1H), 6.91-6.87 (m, 2H), 4.11-4.01 (m, 2H), 3.84-3.75 (m, 4H), 3.69-3.63 (m, 1H), 3.62 (s, 2H), 3.56-3.52 (m, 1H), 3.34-3.33 (m, 1H), 3.30-3.27 (m, 1H), 3.06-2.99 (m, 1H), 2.68-2.63 (m, 1H), 2.04-1.96 (m, 1H), 1.91-1.88 (m, 2H), 1.70-1.65 (m, 1H), 1.49-1.40 (m, 2H).

Example 239b

LCMS: [M+H]$^+$ 395.2;
$^1$H NMR (400 MHz, DMSO-d$_6$) δ 12.2 (s, 1H), 6.88-6.82 (m, 2H), 4.10-4.02 (m, 2H), 3.84-3.75 (m, 4H), 3.69-3.63 (m, 1H), 3.62 (s, 2H), 3.56-3.52 (m, 1H), 3.34-3.33 (m, 1H), 3.30-3.27 (m, 1H), 3.09-3.03 (m, 1H), 2.68-2.63 (m, 1H), 2.04-1.96 (m, 1H), 1.91-1.88 (m, 2H), 1.70-1.65 (m, 1H), 1.49-1.42 (m, 2H).

Example 240: 7-(Cyclopentylamino)-5-fluoro-2-(((trans-6-fluoroazepan-4-yl)thio)methyl)quinazolin-4(3H)-one

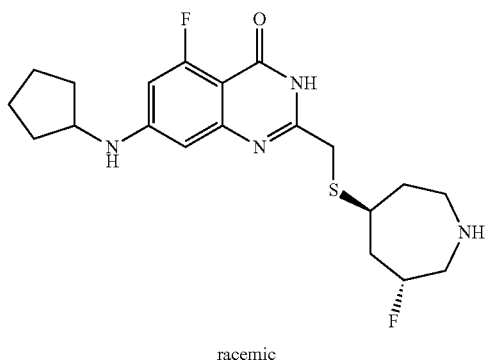 [SMILES: O=c1[nH]c(CS[C@H]2CCNC[C@H](F)C2)nc2cc(NC3CCCC3)cc(F)c12]

racemic

Step 1: tert-Butyl 3-fluoro-5-hydroxyazepane-1-carboxylate

Prepared from 1,3-dichloropropan-2-one according to procedure described in US2015197493.

Step 2: tert-Butyl 3-fluoro-5-((methylsulfonyl)oxy)azepane-1-carboxylate

Prepared from tert-butyl 3-fluoro-5-hydroxyazepane-1-carboxylate according to the method described for Int-B3, step 1. LCMS: [M+H]$^+$ 312.1.

Step 3: tert-Butyl 5-(((7-(cyclopentylamino)-5-fluoro-4-oxo-3,4-dihydroquinazolin-2-yl)methyl)thio)-3-fluoroazepane-1-carboxylate Prepared from Int-C12 and tert-butyl 3-fluoro-5-((methylsulfonyl)oxy)azepane-1-carboxylate according to the method described for Example 210, step 3. LCMS: [M+H]$^+$ 509.2.

Step 4: tert-Butyl trans-5-(((7-(cyclopentylamino)-5-fluoro-4-oxo-3,4-dihydroquinazolin-2-yl)methyl)thio)-3-fluoroazepane-1-carboxylate and tert-Butyl cis-5-(((7-(cyclopentylamino)-5-fluoro-4-oxo-3,4-dihydroquinazolin-2-yl)methyl)thio)-3-fluoroazepane-1-carboxylate tert-Butyl 5-(((7-(cyclopentylamino)-5-fluoro-4-oxo-3,4-dihydroquinazolin-2-yl)methyl)thio)-3-fluoroazepane-1-carboxylate was further purified by prep-HPLC (Agilent 10 prep-C18, 10 m, 250×21.2 mm column, eluting with a gradient of MeOH in water with 0.1% TFA, at a flow rate of 20 mL/min) to afford the titled trans isomer, LCMS: [M+H]$^+$ 509.2 and cis isomer, LCMS: [M+H]$^+$ 509.2. (Cis and trans assignments were made arbitrarily).

Step 5: 7-(Cyclopentylamino)-5-fluoro-2-(((trans-6-fluoroazepan-4-yl)thio)methyl)quinazolin-4(3H)-one Prepared from tert-butyl trans-5-(((7-(cyclopentylamino)-5-fluoro-4-oxo-3,4-dihydroquinazolin-2-yl)methyl)thio)-3-fluoroazepane-1-carboxylate according to the method described for Example 48, step 2. The crude product was partitioned between a saturated aqueous Na$_2$CO$_3$ solution (10 mL) and EtOAc (30 mL). The layers were separated and the organic layer was dried over Na$_2$SO$_4$ and concentrated under reduced pressure. The residue was purified by prep-TLC (DCM/MeOH, 10:1, v/v) to afford the title compound. LCMS: [M+H]$^+$ 409.1;
$^1$H NMR (400 MHz, DMSO-d$_6$) δ 11.7 (s, 1H), 6.85 (d, J=6.0 Hz, 1H), 6.42 (d, J=13.6 Hz, 1H), 6.36 (s, 1H), 4.96 (d, J=43.6 Hz, 1H), 3.78-3.75 (m, 1H), 3.57 (s, 2H), 3.17-2.85 (m, 4H), 2.40-2.30 (m, 1H), 2.17-2.08 (m, 2H), 2.00-1.87 (m, 3H), 1.76-1.68 (m, 3H), 1.58-1.54 (m, 2H), 1.47-1.42 (m, 2H).

Example 241: 7-(Cyclopentylamino)-5-fluoro-2-(((cis-6-fluoroazepan-4-yl)thio)methyl)quinazolin-4(3H)-one

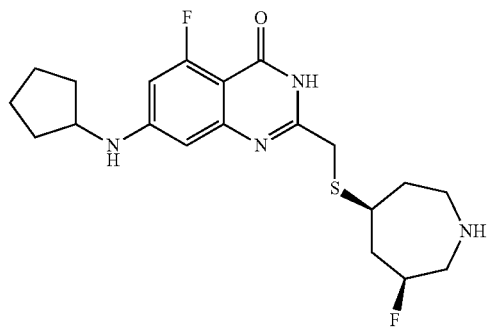

racemic

Prepared from tert-butyl cis-5-(((7-(cyclopentylamino)-5-fluoro-4-oxo-3,4-dihydroquinazolin-2-yl)methyl)thio)-3-fluoroazepane-1-carboxylate according to the method described for Example 48, step 2. The crude product was partitioned between a saturated aqueous Na$_2$CO$_3$ solution (10 mL) and EtOAc (30 mL). The layers were separated and the organic layer was dried over Na$_2$SO$_4$ and concentrated under reduced pressure. The residue was purified by prep-TLC (DCM/MeOH, 10:1, v/v) to afford the title compound. LCMS: [M+H]$^+$ 409.1;

¹H NMR (400 MHz, DMSO-d₆) δ 11.7 (s, 1H), 6.86 (d, J=6.0 Hz, 1H), 6.42 (d, J=14.0 Hz, 1H), 6.36 (s, 1H), 4.96 (d, J=48.0 Hz, 1H), 3.78-3.75 (m, 1H), 3.56 (s, 2H), 3.11-3.01 (m, 4H), 2.76-2.70 (m, 1H), 2.43-2.34 (m, 1H), 2.05-1.93 (m, 4H), 1.73-1.62 (m, 3H), 1.58-1.54 (m, 2H), 1.47-1.42 (m, 2H).

Example 242: 2-((((cis)-6-(Aminomethyl)tetrahydro-2H-pyran-3-yl)thio)methyl)-7-(cyclopentylamino)-5-fluoroquinazolin-4(3H)-one bis Hydrochloride

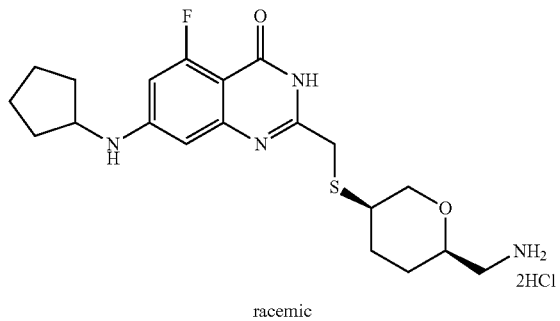 [SMILES: NC[C@H]1CC[C@@H](SCc2nc3cc(NC4CCCC4)cc(F)c3c(=O)[nH]2)CO1]

racemic

Step 1: (3,4-Dihydro-2H-pyran-2-yl)methanol

Prepared from 3,4-dihydro-2H-pyran-2-carbaldehyde according to literature Bioorg. Med. Chem. 2006, 14, 3953.

Step 2: (3,4-Dihydro-2H-pyran-2-yl)methyl Methanesulfonate

Prepared from (3,4-dihydro-2H-pyran-2-yl)methanol according to the method described for Int B3, step 1.
¹H NMR (400 MHz, CDCl₃) δ 6.36 (d, J=6.0 Hz, 1H), 4.80-4.72 (m, 1H), 4.32-4.29 (m, 2H), 4.14-4.06 (m, 1H), 3.07 (s, 3H), 2.18-2.08 (m, 1H), 2.08-2.03 (m, 1H), 1.91-1.84 (m, 1H), 1.78-1.67 (m, 1H).

Step 3: 2-((3,4-Dihydro-2H-pyran-2-yl)methyl)isoindoline-1,3-dione

To a mixture of 3,4-dihydro-2H-pyran-2-ylmethyl methanesulfonate (500 mg, 2.6 mmol, 1.0 eq) in DMSO (3 mL) was added potassium phthalimide (578 mg, 3.12 mmol, 1.2 eq) and the mixture was heated at 90° C. for 16 h. After cooling to RT, the mixture was poured into water (20 mL) and extracted with EtOAc (10 mL×3). The combined organic layers were washed with brine (10 mL), dried over Na₂SO₄ and concentrated under reduced pressure. The residue was purified by column chromatography (petroleum ether/EtOAc, 1:0 to 10:1, v/v) to afford the title compound (350 mg, 55%) as a white solid. LCMS: [M+H]⁺ 244.0.

Step 4: (3,4-Dihydro-2H-pyran-2-yl)methanamine

To a mixture of 2-(3,4-dihydro-2H-pyran-2-ylmethyl)isoindoline-1,3-dione (500 mg, 2.06 mmol) in methanol (5 mL) at 0° C. was added hydrazine hydrate (0.25 mL, 4.11 mmol, 2.0 eq) and the mixture was heated at 50° C. for 16 h. The mixture was concentrated under reduced pressure and the residue was triturated with DCM (20 mL) and filtered. The filtrate was concentrated under reduced pressure to afford the title compound (230 mg, 99%) as a light yellow solid, which was used in next step directly.

Step 5: tert-Butyl ((3,4-dihydro-2H-pyran-2-yl)methyl)carbamate

To a solution of (3,4-dihydro-2H-pyran-2-yl)methanamine (230 mg, 2.03 mmol, 1.0 eq) in DCM (4 mL) at RT was added Et₃N (0.34 mL, 2.44 mmol, 2.2 eq) followed by di-tert-butyl dicarbonate (532 mg, 2.44 mmol, 2.2 eq) and the mixture was stirred at RT for 5 h. The mixture was diluted with DCM (10 mL) and washed with water (5 mL). The organic layer was dried over Na₂SO₄ and concentrated under reduced pressure. The residue was purified by column chromatography (petroleum ether:EtOAc, 1:0 to 10:1, v/v) to afford the title compound (200 mg, 46%) as a colorless oil.
¹H NMR (400 MHz, CDCl₃) δ 6.34 (d, J=6.0 Hz, 1H), 4.89 (br s, 1H), 4.73-4.65 (m, 1H), 3.91-3.81 (m, 1H), 3.47-3.38 (m, 1H), 3.25-3.11 (m, 1H), 2.16-2.03 (m, 1H), 2.01-1.92 (m, 1H), 1.87-1.77 (m, 1H), 1.68-1.59 (m, 1H), 1.45 (s, 9H).

Step 6: tert-Butyl ((5-hydroxytetrahydro-2H-pyran-2-yl)methyl)carbamate

To a solution of tert-butyl ((3,4-dihydro-2H-pyran-2-yl)methyl)carbamate (800 mg, 3.75 mmol, 1.0 eq) in THF (3 mL) at 0° C. was added a 1 M BH₃/THF solution (18.8 mL, 18.8 mmol, 5.0 eq) dropwise and the mixture was allowed to warm to RT and stirred for 16 h. 3 M NaOH (6 mL) and H₂O₂ (30% aqueous solution, 8 mL) were then added dropwise and the mixture was heated at 55° C. for 1 h. After cooling to 0° C., the reaction was quenched with water (15 mL) and the mixture was extracted with EtOAc (30 mL×3). The combined organic layers were dried over Na₂SO₄ and concentrated under reduced pressure to afford the title compound (700 mg, 80%) as colorless oil, which was used in next step directly without further purification.

Step 7: trans-6-(((tert-Butoxycarbonyl)amino)methyl)tetrahydro-2H-pyran-3-yl methanesulfonate and cis-6-(((tert-Butoxycarbonyl)amino)methyl)tetrahydro-2H-pyran-3-yl methanesulfonate To a solution of tert-butyl ((5-hydroxytetrahydro-2H-pyran-2-yl)methyl)carbamate (700 mg, 3.03 mmol, 1.0 eq) in DCM (10 mL) was added Et₃N (0.63 mL, 4.54 mmol, 1.5 eq) followed by methanesulfonyl chloride (0.28 mL, 3.63 mmol, 1.2 eq) and the mixture was stirred at RT for 2 h. The mixture was diluted with water (30 mL) and extracted with EtOAc (50 mL×3). The combined organic extracts were dried over Na₂SO₄ and concentrated under reduced pressure. The residue was purified by column chromatography (petroleum ether:EtOAc, 5:1 to 1:1, v/v) to afford the titled trans isomer (150 mg, 16%) and cis isomer (200 mg, 21%) as white solids. Trans isomer: ¹H NMR (400 MHz, CDCl₃) δ 4.86 (br s, 1H), 4.66-4.59 (m, 1H), 4.18-4.05 (m, 1H), 3.40-3.30 (m, 2H), 3.02 (s, 3H), 3.02-2.93 (m, 1H), 2.32-2.08 (m, 1H), 1.84-1.66 (m, 2H), 1.48-1.38 (m, 10H), 1.31-1.15 (m, 1H).
Cis isomer: ¹H NMR (400 MHz, CDCl₃) δ 4.77 (br s, 1H), 4.20-4.07 (m, 1H), 3.65-3.60 (m, 1H), 3.48-3.32 (m, 2H), 3.07 (s, 3H), 3.06-2.98 (m, 1H), 2.25-2.18 (m, 1H), 1.89-1.63 (m, 4H), 1.44 (s, 9H).

Step 8: tert-Butyl ((cis-5-(((7-(cyclopentylamino)-5-fluoro-4-oxo-3,4-dihydroquinazolin-2-yl)methyl)thio) tetrahydro-2H-pyran-2-yl)methyl)carbamate Prepared from Int-C12 and trans-6-(((tert-butoxycarbonyl)amino)methyl)tetrahydro-2H-pyran-3-yl methanesulfonate according to the method described for Example 210, step 3. LCMS: [M+H]+ 507.1.

Step 9: 2-((((cis)-6-(Aminomethyl)tetrahydro-2H-pyran-3-yl)thio)methyl)-7-(cyclopentylamino)-5-fluoroquinazolin-4(3H)-one Bis Hydrochloride Prepared from tert-butyl ((cis-5-(((7-(cyclopentylamino)-5-fluoro-4-oxo-3,4-dihydroquinazolin-2-yl)methyl)thio)tetrahydro-2H-pyran-2-yl)methyl)carbamate according to the method described for Example 48, step 2. LCMS: [M+H]+ 407.1;
$^1$H NMR (400 MHz, DMSO-d$_6$) δ 12.0 (br s, 1H), 7.89 (br s, 4H), 7.09 (br s, 1H), 6.54-6.38 (m, 2H), 3.87-3.84 (m, 1H), 3.80-3.71 (m, 3H), 3.22 (s, 1H), 2.91 (m, 2H), 2.76 (m, 2H), 1.97-1.85 (m, 3H), 1.73-1.35 (m, 9H).

Example 243: 2-(((trans-4-(Aminomethyl)-4-fluorocyclohexyl)thio)methyl)-7-(cyclopentylamino)-5-fluoroquinazolin-4(3H)-one Trifluoroacetate

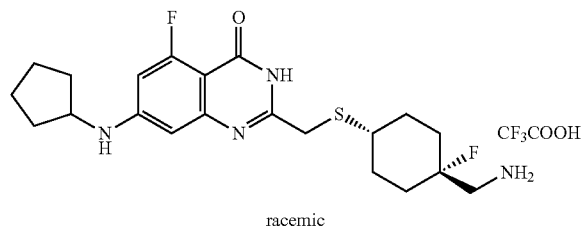 [SMILES: NC[C@]1(F)CC[C@@H](SCc2nc3cc(NC4CCCC4)cc(F)c3c(=O)[nH]2)CC1 ; "CF3COOH"]

racemic

Step 1:
(((4-Methylenecyclohexyl)oxy)methyl)benzene

To a mixture of methyl (triphenyl)phosphonium bromide (10.5 g, 29.4 mmol, 1.5 eq) in anhydrous THF (70 mL) at −10° C. under N$_2$ was added n-BuLi (2.5 M solution in hexanes, 11.0 mL, 27.4 mmol, 1.4 eq) and the mixture was stirred at −10° C. for 1 h. A solution of 4-benzyloxycyclohexanone (4.0 g, 19.6 mmol, 1.0 eq) in THF (10 mL) was then added dropwise and the mixture was allowed to warm to RT and stirred for 3 h. The reaction was quenched with water (100 mL) and the mixture was extracted with EtOAc (80 mL×3). The combined organic extracts were washed with brine (50 mL), dried over Na$_2$SO$_4$ and concentrated under reduced pressure. The residue was purified by column chromatography (petroleum ether/EtOAc, 1:0 to 20:1, v/v) to afford the title compound (3.4 g, 86%) as a colorless oil.
$^1$HNMR (400 MHz, CDCl$_3$) δ 7.29-7.17 (m, 5H), 4.56 (s, 2H), 4.49 (s, 2H), 3.49-3.45 (m, 1H), 2.33-2.27 (m, 2H), 2.00-1.94 (m, 2H), 1.85-1.82 (m, 2H), 1.58-1.49 (m, 2H).

Step 2: (((4-(Bromomethyl)-4-fluorocyclohexyl)oxy)methyl)benzene

To a solution of (((4-methylenecyclohexyl)oxy)methyl)benzene (2.4 g, 11.9 mmol, 1.0 eq) in DCM (24 mL) at 0° C. was added triethylamine trihydrofluoride (2.9 mL, 17.8 mmol, 1.5 eq) and NBS (2.32 g, 13.1 mmol, 1.1 eq) and the mixture was allowed to warm to RT and stirred for 5 h. The mixture was diluted with DCM (80 mL) and washed with 0.5 M HCl (20 mL) and brine (20 mL). The organic layer was dried over Na$_2$SO$_4$ and concentrated under reduced pressure to afford the title compound (3.55 g, 99%) as light yellow oil, which was used directly in the next step without further purification.

Step 3: (((cis-4-(Azidomethyl)-4-fluorocyclohexyl)oxy)methyl)benzene and (((trans-4-(Azidomethyl)-4-fluorocyclohexyl)oxy)methyl)benzene To the solution of (((4-(bromomethyl)-4-fluorocyclohexyl)oxy)methyl)benzene (3.55 g, 11.8 mmol, 1.0 eq) in DMSO (20 mL) was added KI (2.94 g, 17.7 mmol, 1.5 eq) and NaN$_3$ (1.15 g, 17.7 mmol, 1.5 eq) and the mixture was heated at 120° C. for 16 h. The mixture was poured into ice-water (20 mL) and extracted with DCM (100 mL×3). The combined organic layers were washed with brine (50 mL), dried over dried over Na$_2$SO$_4$ and concentrated under reduced pressure. The residue was purified by column chromatography (petroleum:EtOAc, 1:0 to 10:1, v/v) to afford the titled trans isomer (1.5 g, 48%) and the cis isomer (700 mg, 23%) as light yellow solids. (Cis and trans assignments were made arbitrarily).
Cis isomer $^1$HNMR (400 MHz, CDCl$_3$) δ 7.35-7.33 (m, 5H), 4.62-4.54 (m, 1H), 4.51 (s, 2H), 3.33-3.28 (m, 2H), 2.20-1.76 (m, 8H).
Trans isomer $^1$H NMR (400 MHz, CDCl$_3$) δ 7.35-7.34 (m, 5H), 4.58 (s, 2H), 3.41-3.27 (m, 3H), 2.10-2.07 (m, 2H), 2.06-2.05 (m, 2H), 2.04-2.02 (m, 2H), 1.78-1.48 (m, 2H).

Step 4:
cis-4-(Aminomethyl)-4-fluorocyclohexan-1-ol

The mixture of (((cis-4-(azidomethyl)-4-fluorocyclohexyl)oxy)methyl)benzene (1 g, 3.8 mmol, 1.0 eq) and 10% Pd(OH)$_2$/C (200 mg) in methanol (10 mL) was heated at 50° C. under a H$_2$ atmosphere (100 atm) for 24 h. After cooling to RT, the mixture was filtered through Celite and the filtrate was concentrated under reduced pressure to afford the title compound (500 g, 90%) as light yellow oil, which was used for the next step directly without further purification.

Step 5: tert-Butyl (((trans)-1-fluoro-4-hydroxycyclohexyl)methyl)carbamate

Prepared from cis-4-(aminomethyl)-4-fluorocyclohexan-1-ol according to the method described for Example 242, step 5 and used directly in the next step.

Step 6: cis-4-(((tert-Butoxycarbonyl)amino)methyl)-4-fluorocyclohexyl Methanesulfonate Prepared from tert-butyl (((trans)-1-fluoro-4-hydroxycyclohexyl)methyl)carbamate according to the method described for Int-B3, step 1. LCMS: [M+H]+ 326.1.

Step 7: tert-Butyl (((cis)-4-(((7-(cyclopentylamino)-5-fluoro-4-oxo-3,4-dihydroquinazolin-2-yl)methyl)thio)-1-fluorocyclohexyl)methyl)carbamate Prepared from Int-C12 and cis-4-(((tert-butoxycarbonyl)amino)methyl)-4-fluorocyclohexyl methanesulfonate according to the method described for Example 210, step 3. LCMS: [M+H]+ 523.1.

Step 8: 2-(((trans-4-(Aminomethyl)-4-fluorocyclohexyl)thio)methyl)-7-(cyclopentylamino)-5-fluoroquinazolin-4(3H)-one Trifluoroacetate Prepared from tert-butyl (((cis)-4-(((7-(cyclopentylamino)-5-fluoro-4-oxo-3,4-dihydroquinazolin-2-yl)methyl)thio)-1-fluorocyclohexyl)methyl)carbamate according to the method described for Example 48, step 2. Purification by prep-HPLC (Agilent 10 prep-C18, 10 µm, 250×21.2 mm column, eluting with a gradient of MeOH in water with 0.1% TFA, at a flow rate of 20 mL/min) afforded the title compound. LCMS: [M+H]$^+$ 423.1;
$^1$H NMR (400 MHz, DMSO-d$_6$) δ 11.7 (br s, 1H), 7.96 (br s, 3H), 6.86 (br s, 1H), 6.42 (dd, J=13.8, 2.2 Hz, 1H), 6.35 (d, J=2.1 Hz, 1H), 3.79 (m, 1H), 3.53 (s, 2H), 3.24-3.05 (m, 3H), 2.01-1.87 (m, 4H), 1.86-1.54 (m, 9H), 1.49-1.43 (m, 3H).

Example 244: 2-(((cis-4-(Aminomethyl)-4-fluorocyclohexyl)thio)methyl)-7-(cyclopentylamino)-5-fluoroquinazolin-4(3H)-one Trifluoroacetate

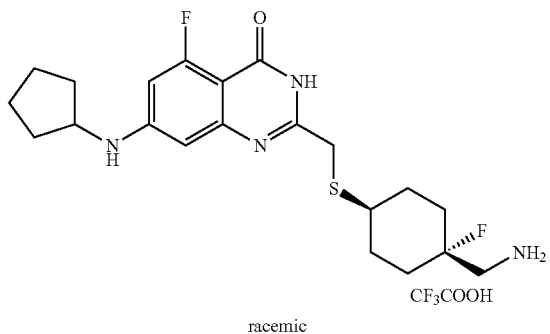 [SMILES: NC[C@]1(F)CC[C@H](SCc2nc3cc(NC4CCCC4)cc(F)c3c(=O)[nH]2)CC1 ; "CF3COOH"]

racemic

Step 1: trans-4-(Aminomethyl)-4-fluorocyclohexan-1-ol

Prepared from (((trans-4-(azidomethyl)-4-fluorocyclohexyl)oxy)methyl)benzene according to the method described for Example 243, step 4 and used directly in the next step.

Step 2: tert-Butyl ((cis-1-fluoro-4-hydroxycyclohexyl)methyl)carbamate

Prepared from trans-4-(aminomethyl)-4-fluorocyclohexan-1-ol according to the method described for Example 242, step 5.
$^1$HNMR (400 MHz, CDCl$_3$) δ 4.81 (br s, 1H), 4.05-3.98 (m, 1H), 3.36-3.29 (m, 2H), 1.87-1.78 (m, 2H), 1.78-1.58 (m, 2H), 1.55-1.49 (m, 2H), 1.47 (s, 9H).

Step 3: trans-4-(((tert-Butoxycarbonyl)amino)methyl)-4-fluorocyclohexyl Methanesulfonate Prepared from tert-butyl ((cis-1-fluoro-4-hydroxycyclohexyl)methyl)carbamate according to the method described for Int-B3, step 1. LCMS: [M+H]$^+$ 326.1.

Step 4: tert-Butyl (((trans)-4-(((7-(cyclopentylamino)-5-fluoro-4-oxo-3,4-dihydroquinazolin-2-yl)methyl)thio)-1-fluorocyclohexyl)methyl)carbamate Prepared from Int-C12 and trans-4-(((tert-butoxycarbonyl)amino)methyl)-4-fluorocyclohexyl methanesulfonate according to the method described for Example 210, step 3. LCMS: [M+H]$^+$ 523.1.

Step 5: 2-(((cis-4-(Aminomethyl)-4-fluorocyclohexyl)thio)methyl)-7-(cyclopentylamino)-5-fluoroquinazolin-4(3H)-one Trifluoroacetate Prepared from tert-butyl (((trans)-4-(((7-(cyclopentylamino)-5-fluoro-4-oxo-3,4-dihydroquinazolin-2-yl)methyl)thio)-1-fluorocyclohexyl)methyl)carbamate according to the method described for Example 48, step 2. Purification by prep-HPLC (Agilent 10 prep-C18, 10 m, 250×21.2 mm column, eluting with a gradient of MeOH in water with 0.1% TFA, at a flow rate of 20 mL/min) afforded the title compound. LCMS: [M+H]$^+$ 423.1;
$^1$H NMR (400 MHz, DMSO-d$_6$) δ 11.6 (br s, 1H), 7.99 (br s, 3H), 6.86 (br s, 1H), 6.42 (dd, J=13.8, 2.1 Hz, 1H), 6.35 (d, J=2.1 Hz, 1H), 3.82-3.74 (m, 1H), 3.58 (s, 2H), 3.10-3.00 (m, 2H), 2.77 (m, 1H), 2.05-1.82 (m, 6H), 1.75-1.36 (m, 10H).

Further example compounds of the invention prepared by the methods described herein are provided in Table 10.

TABLE 10

| Example | Structure/name | MS [M + H]$^+$ |
|---|---|---|
| Example 245 | 6-Fluoro-7-((tetrahydro-2H-pyran-4-yl)amino)-2-(((tetrahydro-2H-pyran-4-yl)thio)methyl)quinazolin-4(3H)-one | 394.2 |

TABLE 10-continued

| Example | Structure/name | MS [M + H]+ |
|---|---|---|
| Example 246 | 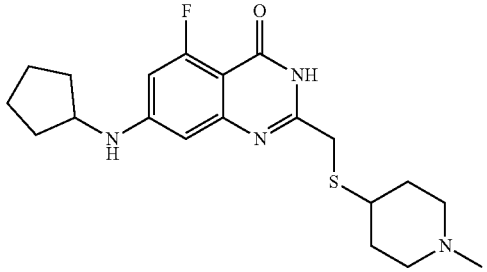 [SMILES: CN1CCC(SCc2nc3cc(NC4CCCC4)cc(F)c3c(=O)[nH]2)CC1]<br>7-(Cyclopentylamino)-5-fluoro-2-(((1-methylpiperidin-4-yl)thio)methyl)quinazolin-4(3H)-one | 391.2 |
| Example 247 | 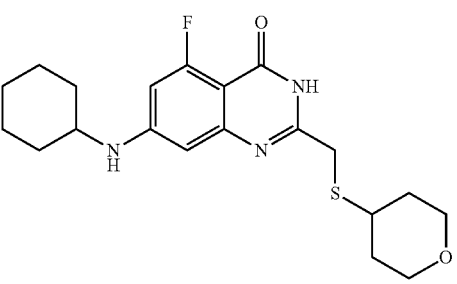 [SMILES: O=c1[nH]c(CSC2CCOCC2)nc2cc(NC3CCCCC3)cc(F)c12]<br>7-(Cyclohexylamino)-5-fluoro-2-(((tetrahydro-2H-pyran-4-yl)thio)methyl)quinazolin-4(3H)-one | 392.2 |
| Example 248 | 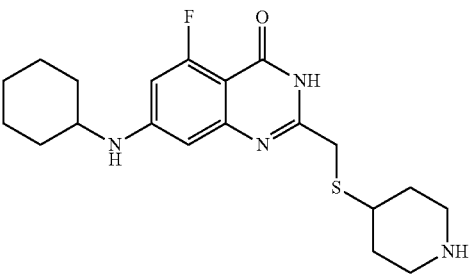 [SMILES: O=c1[nH]c(CSC2CCNCC2)nc2cc(NC3CCCCC3)cc(F)c12]<br>7-(Cyclohexylamino)-5-fluoro-2-((piperidin-4-ylthio)methyl)quinazolin-4(3H)-one | 391.1 |
| Example 249 | 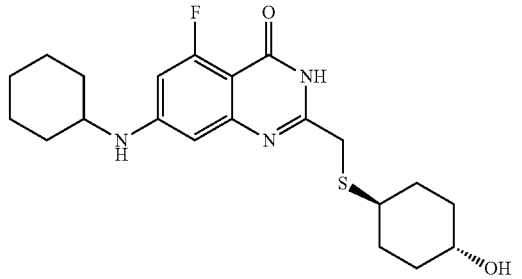 [SMILES: O=c1[nH]c(CS[C@H]2CC[C@H](O)CC2)nc2cc(NC3CCCCC3)cc(F)c12]<br>7-(Cyclohexylamino)-5-fluoro-2-((((1r,4r)-4-hydroxycyclohexyl)thio)methyl)quinazolin-4(3H)-one | 406.1 |

TABLE 10-continued

| Example | Structure/name | MS [M + H]+ |
|---|---|---|
| Example 250 | (R)-5-fluoro-7-((1-(methylsulfonyl)piperidin-3-yl)amino)-2-(((tetrahydro-2H-pyran-4-yl)thio)methyl)quinazolin-4(3H)-one | 471.2 |
| Example 251 | 7-(Cyclobutylamino)-5-fluoro-2-(((tetrahydro-2H-pyran-4-yl)thio)methyl)quinazolin-4(3H)-one | 364.1 |
| Example 252 | 7-((2-Cyclopentylethyl)amino)-2-(((tetrahydro-2H-pyran-4-yl)thio)methyl)quinazolin-4(3H)-one | 388.2 |
| Example 253 | 5-Chloro-7-(cyclopentylamino)-2-(((tetrahydro-2H-pyran-4-yl)thio)methyl)quinazolin-4(3H)-one | 394.1 |
| Example 254 | 7-(Cyclopentylamino)-2-(((1-(2,2,2-trifluoroethyl)piperidin-4-yl)thio)methyl)quinazolin-4(3H)-one | 441.2 |

TABLE 10-continued

| Example | Structure/name | MS [M + H]+ |
|---|---|---|
| Example 255 | 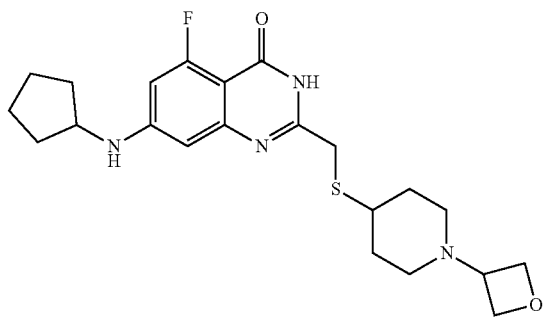 [SMILES: O=c1[nH]c(CSC2CCN(C3COC3)CC2)nc2cc(NC3CCCC3)cc(F)c12]
7-(Cyclopentylamino)-5-fluoro-2-(((1-(oxetan-3-yl)piperidin-4-yl)thio)methyl)quinazolin-4(3H)-one | 433.2 |
| Example 256 | 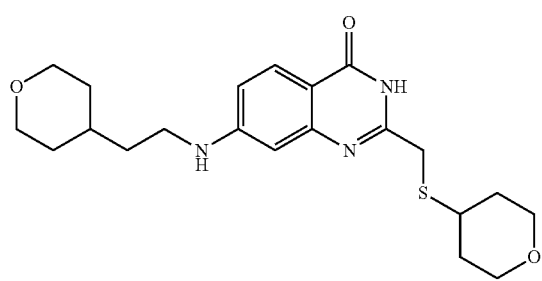 [SMILES: O=c1[nH]c(CSC2CCOCC2)nc2cc(NCCC3CCOCC3)ccc12]
7-((2-(Tetrahydro-2H-pyran-4-yl)ethyl)amino)-2-(((tetrahydro-2H-pyran-4-yl)thio)methyl)quinazolin-4(3H)-one | 404.1 |
| Example 257 | 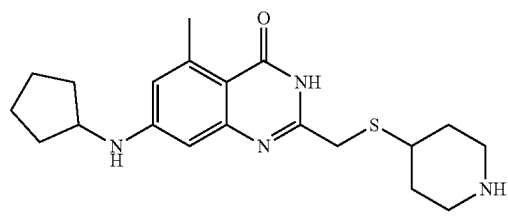
7-(Cyclopentylamino)-5-methyl-2-((piperidin-4-ylthio)methyl)quinazolin-4(3H)-one hydrochloride | 373.2 |
| Example 258 | 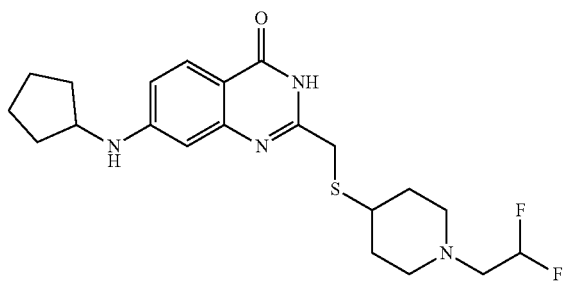 [SMILES: O=c1[nH]c(CSC2CCN(CC(F)F)CC2)nc2cc(NC3CCCC3)ccc12]
7-(Cyclopentylamino)-2-(((1-(2,2-difluoroethyl)piperidin-4-yl)thio)methyl)quinazolin-4(3H)-one | 423.1 |

TABLE 10-continued

| Example | Structure/name | MS [M + H]+ |
| --- | --- | --- |
| Example 259 | 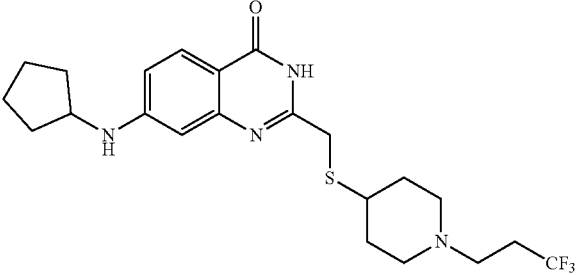 [SMILES: O=c1[nH]c(CSC2CCN(CCC(F)(F)F)CC2)nc2cc(NC3CCCC3)ccc12]<br>7-(Cyclopentylamino)-2-(((1-(3,3,3-trifluoropropyl)piperidin-4-yl)thio)methyl)quinazolin-4(3H)-one | 455.2 |
| Example 260 | 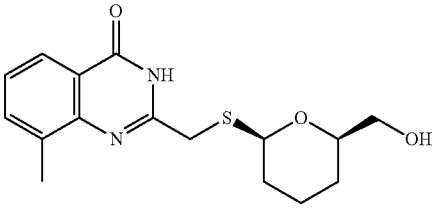 [SMILES: Cc1cccc2c(=O)[nH]c(CS[C@@H]3CCC[C@H](CO)O3)nc12]<br>2-(((Cis-6-(hydroxymethyl)tetrahydro-2H-pyran-2-yl)thio)methyl)-8-methylquinazolin-4(3H)-one | 321.1 |
| Example 261 | 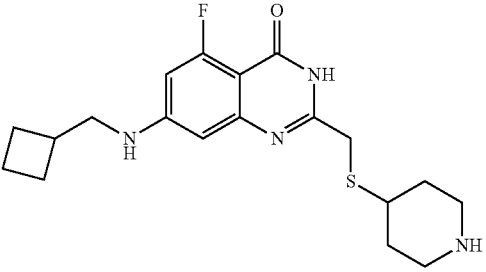 [SMILES: O=c1[nH]c(CSC2CCNCC2)nc2cc(NCC3CCC3)cc(F)c12]<br>7-((Cyclobutylmethyl)amino)-5-fluoro-2-((piperidin-4-ylthio)methyl)quinazolin-4(3H)-one | 377.2 |
| Example 262 | 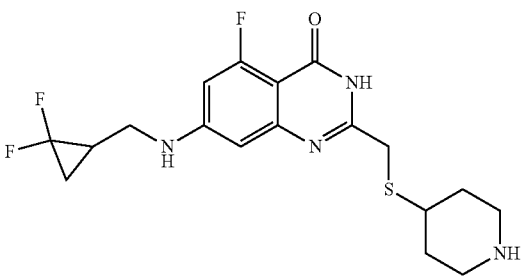 [SMILES: O=c1[nH]c(CSC2CCNCC2)nc2cc(NCC3CC3(F)F)cc(F)c12]<br>7-(((2,2-Difluorocyclopropyl)methyl)amino)-5-fluoro-2-((piperidin-4-ylthio)methyl)quinazolin-4(3H)-one | 399.1 |

TABLE 10-continued

| Example | Structure/name | MS [M + H]+ |
|---|---|---|
| Example 263 | 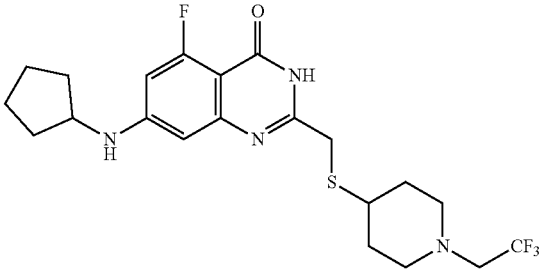 [SMILES: O=c1[nH]c(CSC2CCN(CC(F)(F)F)CC2)nc2cc(NC3CCCC3)cc(F)c12]<br>7-(Cyclopentylamino)-5-fluoro-2-(((1-(2,2,2-trifluoroethyl)piperidin-4-yl)thio)methyl)quinazolin-4(3H)-one | 459.2 |
| Example 264 | 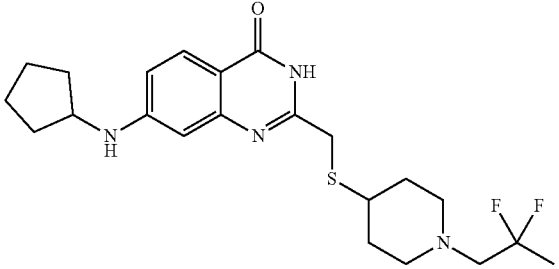 [SMILES: CC(F)(F)CN1CCC(SCc2nc3cc(NC4CCCC4)ccc3c(=O)[nH]2)CC1]<br>7-(Cyclopentylamino)-2-(((1-(2,2-difluoropropyl)piperidin-4-yl)thio)methyl)quinazolin-4(3H)-one | 437.2 |
| Example 265 | 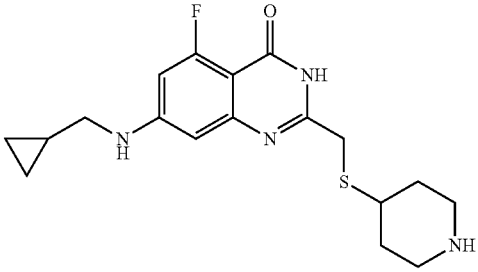 [SMILES: O=c1[nH]c(CSC2CCNCC2)nc2cc(NCC3CC3)cc(F)c12]<br>7-((Cyclopropylmethyl)amino)-5-fluoro-2-((piperidin-4-ylthio)methyl)quinazolin-4(3H)-one | 363.1 |
| Example 266 | 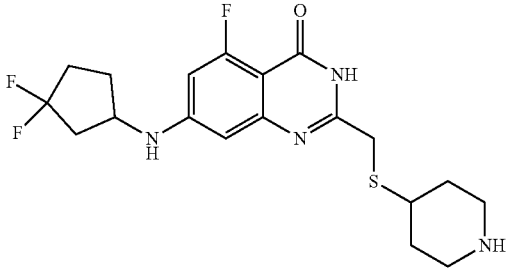 [SMILES: O=c1[nH]c(CSC2CCNCC2)nc2cc(NC3CCC(F)(F)C3)cc(F)c12]<br>7-((3,3-Difluorocyclopentyl)amino)-5-fluoro-2-((piperidin-4-ylthio)methyl)quinazolin-4(3H)-one | 413.1 |

TABLE 10-continued

| Example | Structure/name | MS [M + H]+ |
|---|---|---|
| Example 267 | 2-(((Trans-4-hydroxycyclohexyl)thio)methyl)-7-(((R)-1-(methylsulfonyl)piperidin-3-yl)amino)quinazolin-4(3H)-one | 467.1 |
| Example 268 | (R)-2-(((1-acetylpiperidin-4-yl)thio)methyl)-7-((1-(methylsulfonyl)piperidin-3-yl)amino)quinazolin-4(3H)-one | 494.1 |
| Example 269 | 5-Fluoro-2-(((trans-4-hydroxycyclohexyl)thio)methyl)-7-(((R)-1-(methylsulfonyl)piperidin-3-yl)amino)quinazolin-4(3H)-one | 485.1 |
| Example 270 | 7-(Cyclopentylamino)-2-(((1,1-dioxidotetrahydro-2H-thiopyran-4-yl)thio)methyl)-5-fluoroquinazolin-4(3H)-one | 426.0 |

TABLE 10-continued

| Example | Structure/name | MS [M + H]+ |
|---|---|---|
| Example 271 | 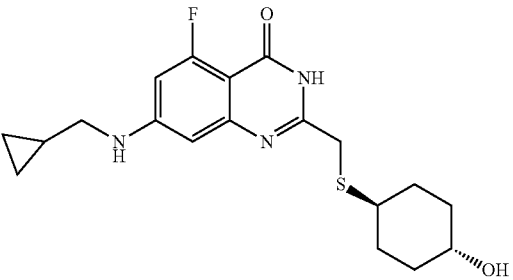 [SMILES: O=c1[nH]c(CS[C@H]2CC[C@H](O)CC2)nc2cc(NCC3CC3)cc(F)c12]<br>7-((Cyclopropylmethyl)amino)-5-fluoro-2-(((trans-4-hydroxycyclohexyl)thio)methyl)quinazolin-4(3H)-one | 378.1 |
| Example 272 | 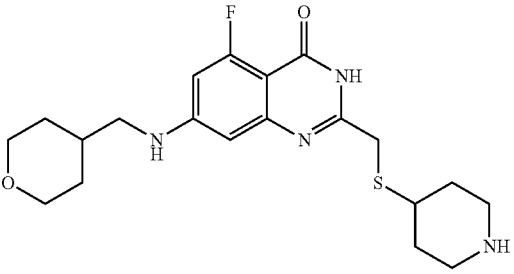 [SMILES: O=c1[nH]c(CSC2CCNCC2)nc2cc(NCC3CCOCC3)cc(F)c12]<br>5-Fluoro-2-((piperidin-4-ylthio)methyl)-7-(((tetrahydro-2H-pyran-4-yl)methyl)amino)quinazolin-4(3H)-one | 407.1 |
| Example 273 | 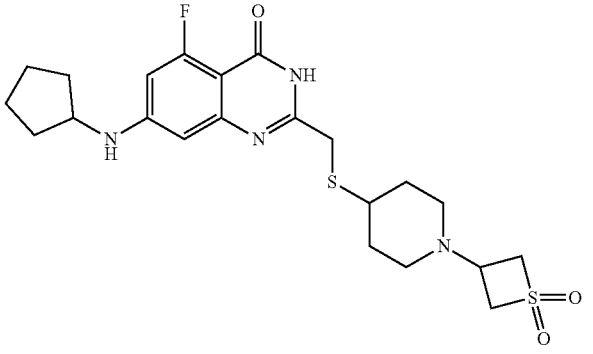 [SMILES: O=c1[nH]c(CSC2CCN(C3CS(=O)(=O)C3)CC2)nc2cc(NC3CCCC3)cc(F)c12]<br>7-(Cyclopentylamino)-2-(((1-(1,1-dioxidothietan-3-yl)piperidin-4-yl)thio)methyl)-5-fluoroquinazolin-4(3H)-one | 481.1 |
| Example 274 | 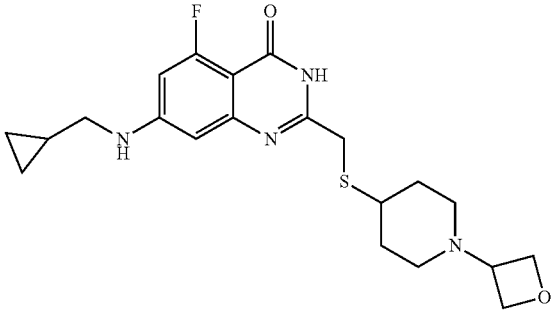 [SMILES: O=c1[nH]c(CSC2CCN(C3COC3)CC2)nc2cc(NCC3CC3)cc(F)c12]<br>7-((Cyclopropylmethyl)amino)-5-fluoro-2-(((1-(oxetan-3-yl)piperidin-4-yl)thio)methyl)quinazolin-4(3H)-one | 419.1 |

TABLE 10-continued

| Example | Structure/name | MS [M + H]⁺ |
|---|---|---|
| Example 275 | 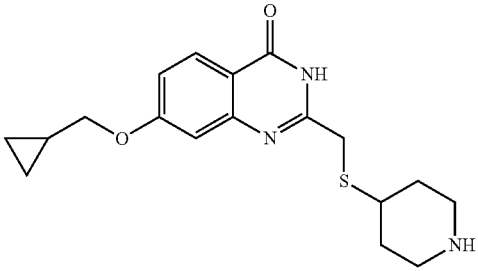 [SMILES: O=c1[nH]c(CSC2CCNCC2)nc2cc(OCC3CC3)ccc12]<br>7-(Cyclopropylmethoxy)-2-((piperidin-4-ylthio)methyl)quinazolin-4(3H)-one | 346.1 |
| Example 276 | 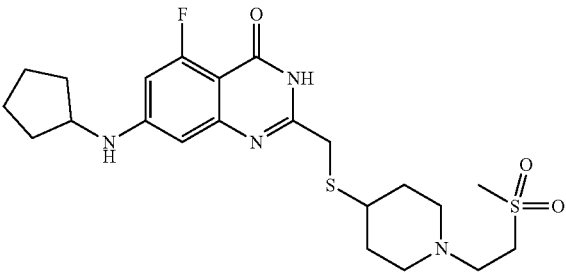 [SMILES: CS(=O)(=O)CCN1CCC(SCc2nc3cc(NC4CCCC4)cc(F)c3c(=O)[nH]2)CC1]<br>7-(Cyclopentylamino)-5-fluoro-2-(((1-(2-(methylsulfonyl)ethyl)piperidin-4-yl)thio)methyl)quinazolin-4(3H)-one | 483.1 |
| Example 277 | 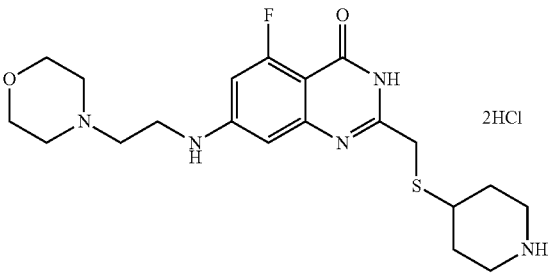 [SMILES: O=c1[nH]c(CSC2CCNCC2)nc2cc(NCCN3CCOCC3)cc(F)c12]<br>5-Fluoro-7-((2-morpholinoethyl)amino)-2-((piperidin-4-ylthio)methyl)quinazolin-4(3H)-one dihydrochloride | 422.1 |
| Example 278 | 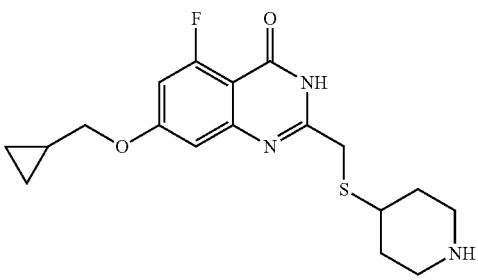 [SMILES: O=c1[nH]c(CSC2CCNCC2)nc2cc(OCC3CC3)cc(F)c12]<br>7-(Cyclopropylmethoxy)-5-fluoro-2-((piperidin-4-ylthio)methyl)quinazolin-4(3H)-one | 364.0 |

TABLE 10-continued

| Example | Structure/name | MS [M + H]+ |
|---|---|---|
| Example 279 | 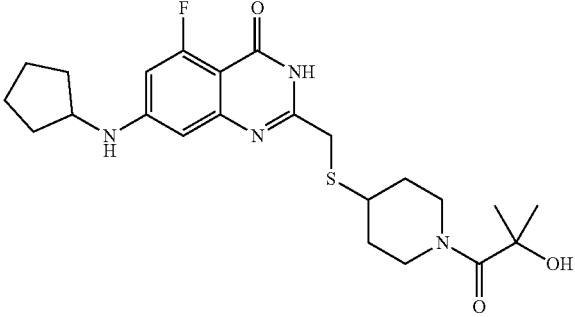 [SMILES: CC(C)(O)C(=O)N1CCC(SCc2nc3cc(NC4CCCC4)cc(F)c3c(=O)[nH]2)CC1]<br>7-(Cyclopentylamino)-5-fluoro-2-(((1-(2-hydroxy-2-methylpropanoyl)piperidin-4-yl)thio)methyl)quinazolin-4(3H)-one | 463.1 |
| Example 280 | 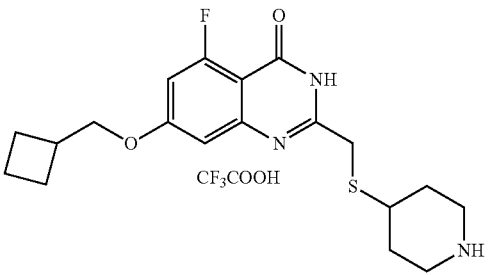 [SMILES: O=c1[nH]c(CSC2CCNCC2)nc2cc(OCC3CCC3)cc(F)c12 ; "CF3COOH"]<br>7-(Cyclobutylmethoxy)-5-fluoro-2-((piperidin-4-ylthio)methyl)quinazolin-4(3H)-one 2,2,2-trifluoroacetate | 378.1 |
| Example 281 | 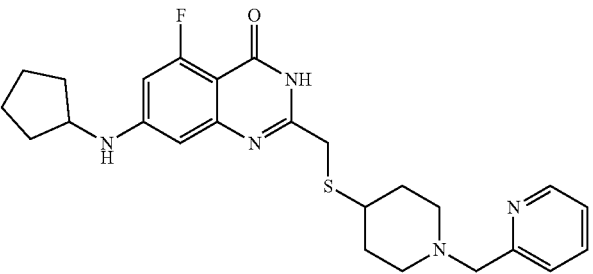 [SMILES: O=c1[nH]c(CSC2CCN(Cc3ccccn3)CC2)nc2cc(NC3CCCC3)cc(F)c12]<br>7-(Cyclopentylamino)-5-fluoro-2-(((1-(pyridin-2-ylmethyl)piperidin-4-yl)thio)methyl)quinazolin-4(3H)-one | 468.1 |
| Example 282 | 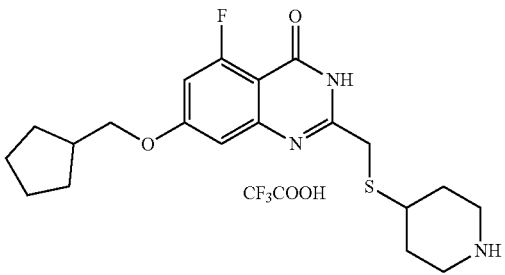 [SMILES: O=c1[nH]c(CSC2CCNCC2)nc2cc(OCC3CCCC3)cc(F)c12 ; "CF3COOH"]<br>7-(Cyclopentylmethoxy)-5-fluoro-2-((piperidin-4-ylthio)methyl)quinazolin-4(3H)-one 2,2,2-trifluoroacetate | 392.1 |

TABLE 10-continued

| Example | Structure/name | MS [M + H]+ |
|---|---|---|
| Example 283 | 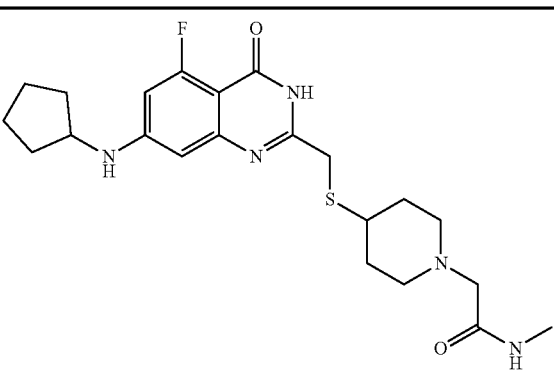<br>2-(4-(((7-(Cyclopentylamino)-5-fluoro-4-oxo-3,4-dihydroquinazolin-2-yl)methyl)thio)piperidin-1-yl)-N-methylacetamide hydrochloride | 448.1 |
| Example 284 | 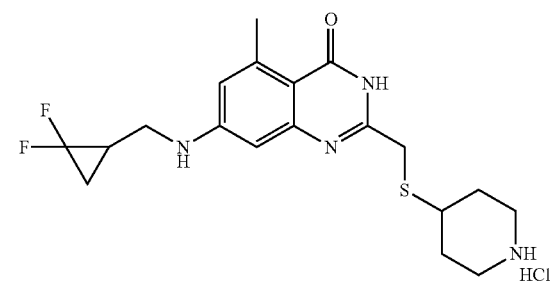 [SMILES: Cc1cc(NCC2CC2(F)F)cc2nc(CSC3CCNCC3)[nH]c(=O)c12 ; Cl]<br>7-(((2,2-Difluorocyclopropyl)methyl)amino)-5-methyl-2-((piperidin-4-ylthio)methyl)quinazolin-4(3H)-one hydrochloride | 395.1 |
| Example 285 | 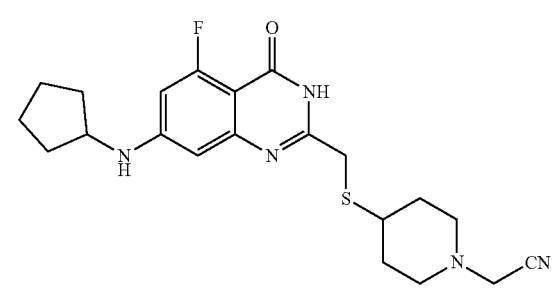 [SMILES: N#CCN1CCC(SCc2nc3cc(NC4CCCC4)cc(F)c3c(=O)[nH]2)CC1]<br>2-(4-(((7-(Cyclopentylamino)-5-fluoro-4-oxo-3,4-dihydroquinazolin-2-yl)methyl)thio)piperidin-1-yl)acetonitrile | 416.1 |
| Example 286 | 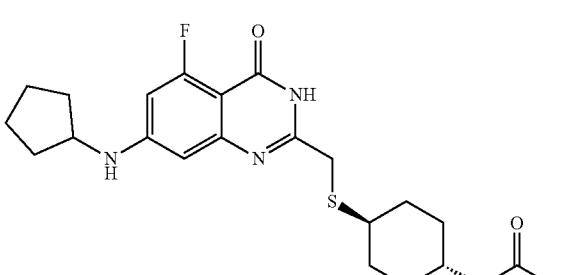<br>2-(Trans-4-(((7-(cyclopentylamino)-5-fluoro-4-oxo-3,4-dihydroquinazolin-2-yl)methyl)thio)cyclohexyl)acetamide | 433.1 |

TABLE 10-continued

| Example | Structure/name | MS [M + H]⁺ |
|---|---|---|
| Example 287 | 5-Fluoro-7-((2-morpholinoethyl)amino)-2-(((tetrahydro-2H-pyran-4-yl)thio)methyl)quinazolin-4(3H)-one | 423.1 |
| Example 288 | 5-Fluoro-2-(((tetrahydro-2H-pyran-4-yl)thio)methyl)-7-((1-(2,2,2-trifluoroethyl)piperidin-4-yl)amino)quinazolin-4(3H)-one | 475.1 |
| Example 289 | 7-((Cyclobutylmethyl)amino)-6-fluoro-2-((piperidin-4-ylthio)methyl)quinazolin-4(3H)-one hydrochloride | 377.1 |
| Example 290 | 7-(Cyclohexylamino)-6-fluoro-2-(((tetrahydro-2H-pyran-4-yl)thio)methyl)quinazolin-4(3H)-one | 392.1 |

TABLE 10-continued

| Example | Structure/name | MS [M + H]+ |
|---|---|---|
| Example 291 | 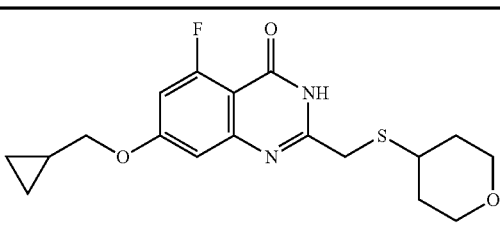<br>7-(Cyclopropylmethoxy)-5-fluoro-2-(((tetrahydro-2H-pyran-4-yl)thio)methyl)quinazolin-4(3H)-one | 365.0 |
| Example 292 | 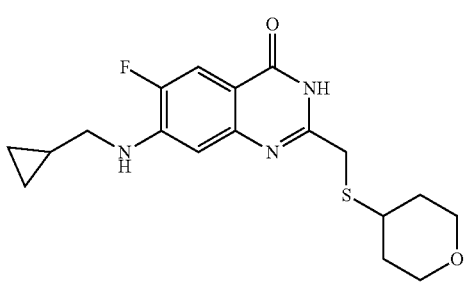 [SMILES: O=c1[nH]c(CSC2CCOCC2)nc2cc(NCC3CC3)c(F)cc12]<br>7-(((Cyclopropylmethyl)amino)-6-fluoro-2-((((tetrahydro-2H-pyran-4-yl)thio)methyl)quinazolin-4(3H)-one | 364.0 |
| Example 293 | 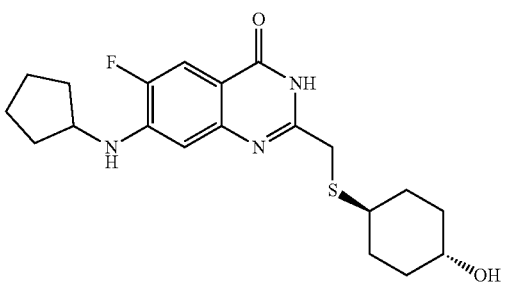 [SMILES: O=c1[nH]c(CS[C@H]2CC[C@H](O)CC2)nc2cc(NC3CCCC3)c(F)cc12]<br>7-(Cyclopentylamino)-6-fluoro-2-(((trans-4-hydroxycyclohexyl)thio)methyl)quinazolin-4(3H)-one | 392.1 |
| Example 294 | 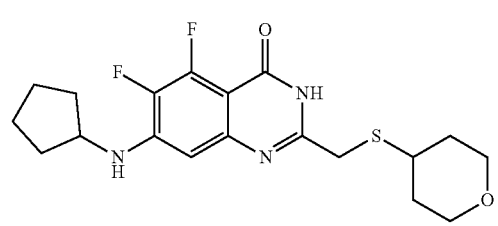 [SMILES: O=c1[nH]c(CSC2CCOCC2)nc2cc(NC3CCCC3)c(F)c(F)c12]<br>7-(Cyclopentylamino)-5,6-difluoro-2-(((tetrahydro-2H-pyran-4-yl)thio)methyl)quinazolin-4(3H)-one | 396.1 |
| Example 295 | 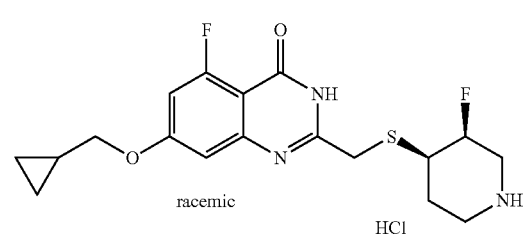 [SMILES: O=c1[nH]c(CS[C@@H]2CCNC[C@@H]2F)nc2cc(OCC3CC3)cc(F)c12 ; Cl]<br>7-(Cyclopropylmethoxy)-5-fluoro-2-(((cis-3-fluoropiperidin-4-yl)thio)methyl)quinazolin-4(3H)-one hydrochloride | 382.0 |

TABLE 10-continued

| Example | Structure/name | MS [M + H]+ |
|---|---|---|
| Example 296 | 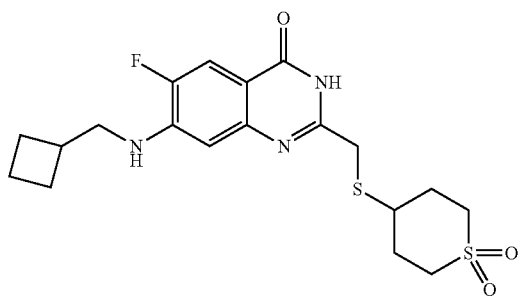 [SMILES: O=c1[nH]c(CSC2CCS(=O)(=O)CC2)nc2cc(NCC3CCC3)c(F)cc12]<br>7-((Cyclobutylmethyl)amino)-2-(((1,1-dioxidotetrahydro-2H-thiopyran-4-yl)thio)methyl)-6-fluoroquinazolin-4(3H)-one | 426.0 |
| Example 297 | 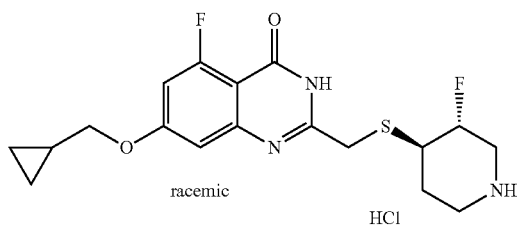 [SMILES: O=c1[nH]c(CS[C@@H]2CCNC[C@H]2F)nc2cc(OCC3CC3)cc(F)c12 ; Cl]<br>racemic HCl<br>7-(Cyclopropylmethoxy)-5-fluoro-2-(((trans-3-fluoropiperidin-4-yl)thio)methyl)quinazolin-4(3H)-one hydrochloride | 382.0 |
| Example 298 | 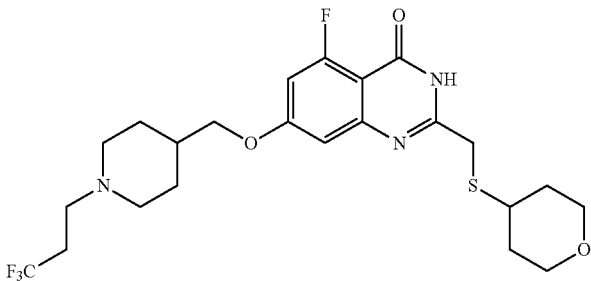 [SMILES: O=c1[nH]c(CSC2CCOCC2)nc2cc(OCC3CCN(CCC(F)(F)F)CC3)cc(F)c12]<br>5-Fluoro-2-(((tetrahydro-2H-pyran-4-yl)thio)methyl)-7-((1-(3,3,3-trifluoropropyl)piperidin-4-yl)methoxy)quinazolin-4(3H)-one | 504.1 |
| Example 299 | 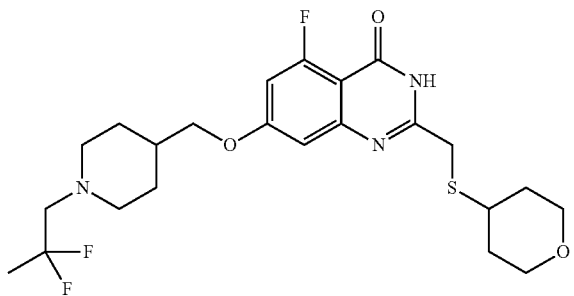 [SMILES: CC(F)(F)CN1CCC(COc2cc(F)c3c(=O)[nH]c(CSC4CCOCC4)nc3c2)CC1]<br>7-((1-(2,2-Difluoropropyl)piperidin-4-yl)methoxy)-5-fluoro-2-(((tetrahydro-2H-pyran-4-yl)thio)methyl)quinazolin-4(3H)-one | 486.1 |

TABLE 10-continued

| Example | Structure/name | MS [M + H]+ |
|---|---|---|
| Example 300 | 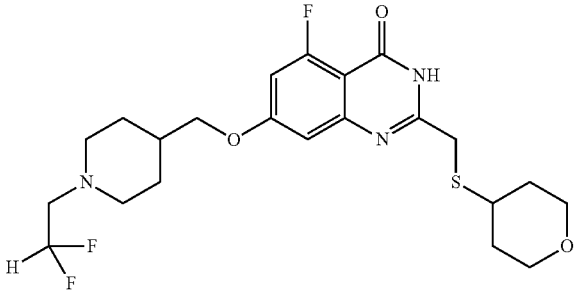 [SMILES: O=c1[nH]c(CSC2CCOCC2)nc2cc(OCC3CCN(CC(F)F)CC3)cc(F)c12]<br>7-((1-(2,2-Difluoroethyl)piperidin-4-yl)methoxy)-5-fluoro-2-(((tetrahydro-2H-pyran-4-yl)thio)methyl)quinazolin-4(3H)-one | 472.1 |
| Example 301 | 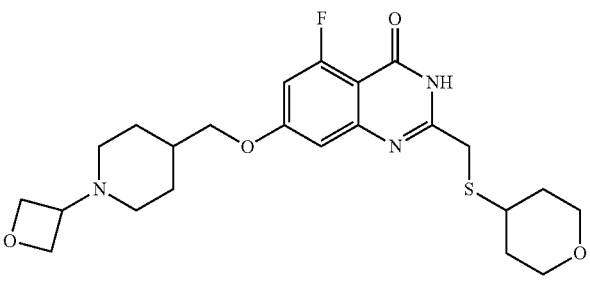 [SMILES: O=c1[nH]c(CSC2CCOCC2)nc2cc(OCC3CCN(C4COC4)CC3)cc(F)c12]<br>5-Fluoro-7-((1-(oxetan-3-yl)piperidin-4-yl)methoxy)-2-(((tetrahydro-2H-pyran-4-yl)thio)methyl)quinazolin-4(3H)-one | 464.1 |
| Example 302 | 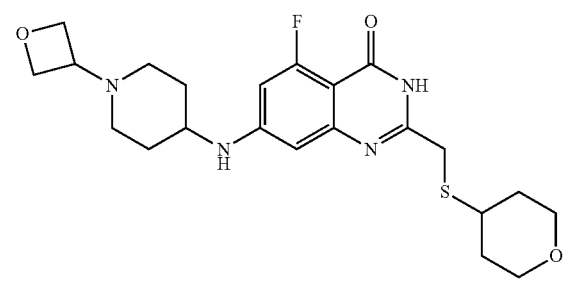 [SMILES: O=c1[nH]c(CSC2CCOCC2)nc2cc(NC3CCN(C4COC4)CC3)cc(F)c12]<br>5-Fluoro-7-((1-(oxetan-3-yl)piperidin-4-yl)amino)-2-(((tetrahydro-2H-pyran-4-yl)thio)methyl)quinazolin-4(3H)-one | 449.1 |
| Example 303 | 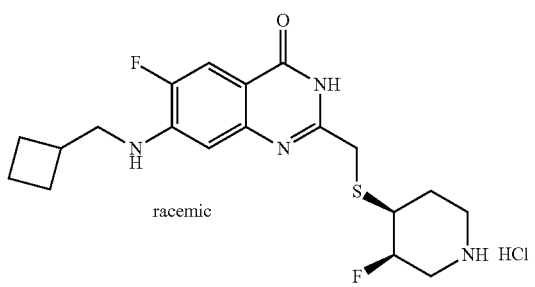 [SMILES: O=c1[nH]c(CS[C@H]2CCNC[C@H]2F)nc2cc(NCC3CCC3)c(F)cc12 ; Cl]<br>7-((Cyclobutylmethyl)amino)-6-fluoro-2-(((cis-3-fluoropiperidin-4-yl)thio)methyl)quinazolin-4(3H)-one hydrochloride | 395.1 |

TABLE 10-continued

| Example | Structure/name | MS [M + H]+ |
|---|---|---|
| Example 304 | 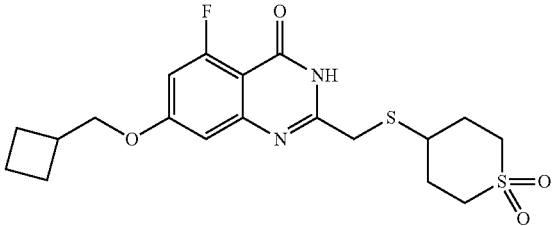 [SMILES: O=c1[nH]c(CSC2CCS(=O)(=O)CC2)nc2cc(OCC3CCC3)cc(F)c12]<br>7-(cyclobutylmethoxy)-2-(((1,1-dioxidotetrahydro-2H-thiopyran-4-yl)thio)methyl)-5-fluoroquinazolin-4(3H)-one | 427.0 |
| Example 305 | 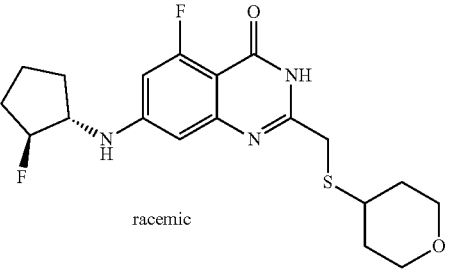 [SMILES: O=c1[nH]c(CSC2CCOCC2)nc2cc(N[C@H]3CCC[C@@H]3F)cc(F)c12]<br>racemic<br>5-Fluoro-7-((trans-2-fluorocyclopentyl)amino)-2-(((tetrahydro-2H-pyran-4-yl)thio)methyl)quinazolin-4(3H)-one | 396.1 |
| Example 306 | 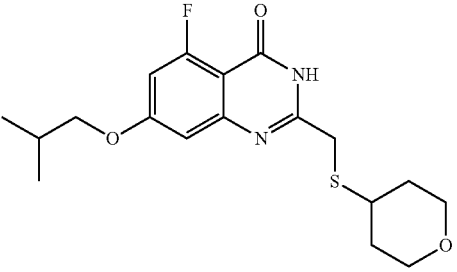 [SMILES: CC(C)COc1cc(F)c2c(=O)[nH]c(CSC3CCOCC3)nc2c1]<br>5-Fluoro-7-isobutoxy-2-(((tetrahydro-2H-pyran-4-yl)thio)methyl)quinazolin-4(3H)-one | 367.1 |
| Example 307 | 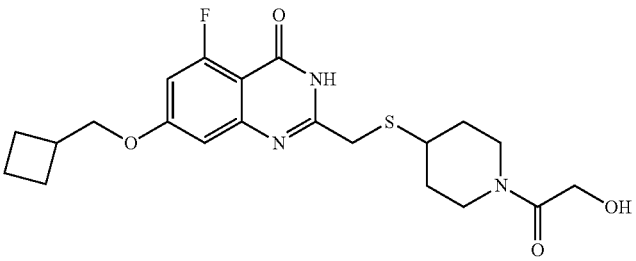 [SMILES: O=C(CO)N1CCC(SCc2nc3cc(OCC4CCC4)cc(F)c3c(=O)[nH]2)CC1]<br>7-(Cyclobutylmethoxy)-5-fluoro-2-(((1-(2-hydroxyacetyl)piperidin-4-yl)thio)methyl)quinazolin-4(3H)-one | 436.1 |

TABLE 10-continued

| Example | Structure/name | MS [M + H]+ |
|---|---|---|
| Example 308 | 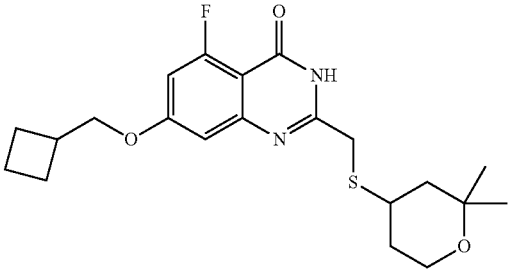 [SMILES: CC1(C)CC(SCc2nc3cc(OCC4CCC4)cc(F)c3c(=O)[nH]2)CCO1]<br>7-(Cyclobutylmethoxy)-2-(((2,2-dimethyltetrahydro-2H-pyran-4-yl)thio)methyl)-5-fluoroquinazolin-4(3H)-one | 407.1 |
| Example 309 | 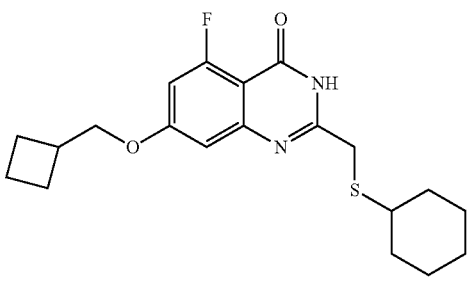 [SMILES: O=c1[nH]c(CSC2CCCCC2)nc2cc(OCC3CCC3)cc(F)c12]<br>7-(Cyclobutylmethoxy)-2-((cyclohexylthio)methyl)-5-fluoroquinazolin-4(3H)-one | 377.1 |
| Example 310 | 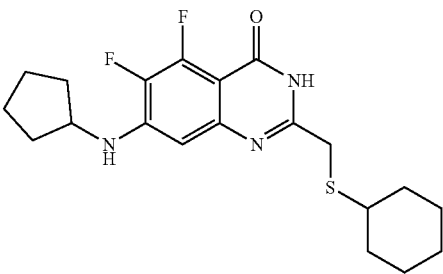 [SMILES: O=c1[nH]c(CSC2CCCCC2)nc2cc(NC3CCCC3)c(F)c(F)c12]<br>2-((Cyclohexylthio)methyl)-7-(cyclopentylamino)-5,6-difluoroquinazolin-4(3H)-one | 394.1 |
| Example 311 | 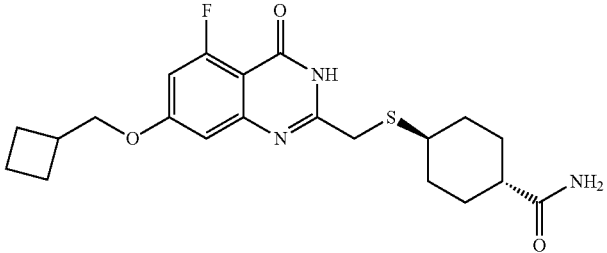 [SMILES: NC(=O)[C@H]1CC[C@H](SCc2nc3cc(OCC4CCC4)cc(F)c3c(=O)[nH]2)CC1]<br>Trans-4-(((7-(cyclobutylmethoxy)-5-fluoro-4-oxo-3,4-dihydroquinazolin-2-yl)methyl)thio)cyclohexane-1-carboxamide | 420.0 |

TABLE 10-continued

| Example | Structure/name | MS [M + H]+ |
|---|---|---|
| Example 312 | 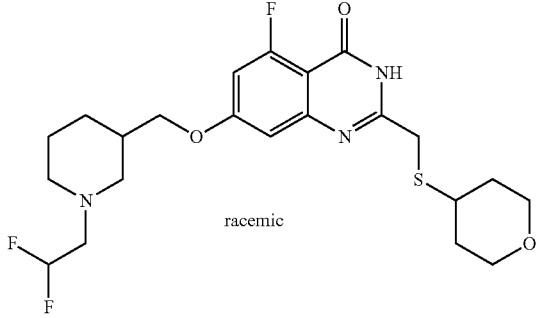 [SMILES: O=c1[nH]c(CSC2CCOCC2)nc2cc(OCC3CCCN(CC(F)F)C3)cc(F)c12]<br>racemic<br>7-((1-(2,2-Difluoroethyl)piperidin-3-yl)methoxy)-5-fluoro-2-(((tetrahydro-2H-pyran-4-yl)thio)methyl)quinazolin-4(3H)-one | 472.1 |
| Example 313 | 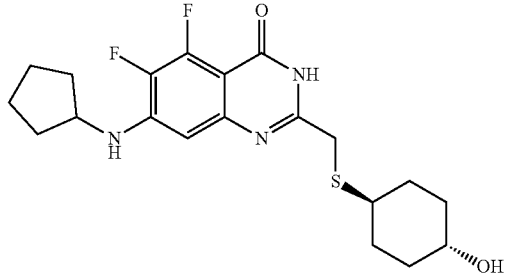 [SMILES: O=c1[nH]c(CS[C@H]2CC[C@H](O)CC2)nc2cc(NC3CCCC3)c(F)c(F)c12]<br>7-(Cyclopentylamino)-5,6-difluoro-2-(((trans-4-hydroxycyclohexyl)thio)methyl)quinazolin-4(3H)-one | 410.1 |
| Example 314 | 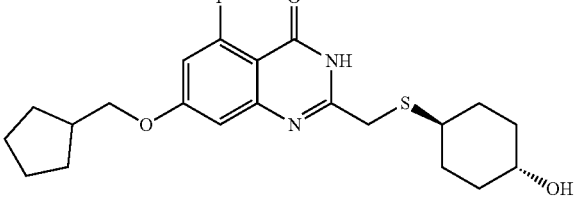<br>7-(Cyclopentylmethoxy)-5-fluoro-2-(((trans-4-hydroxycyclohexyl)thio)methyl)quinazolin-4(3H)-one | 407.1 |
| Example 315 | 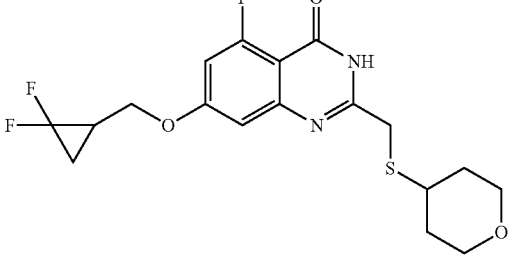<br>7-((2,2-Difluorocyclopropyl)methoxy)-5-fluoro-2-(((tetrahydro-2H-pyran-4-yl)thio)methyl)quinazolin-4(3H)-one | 401.0 |

TABLE 10-continued

| Example | Structure/name | MS [M + H]+ |
|---|---|---|
| Example 316 | 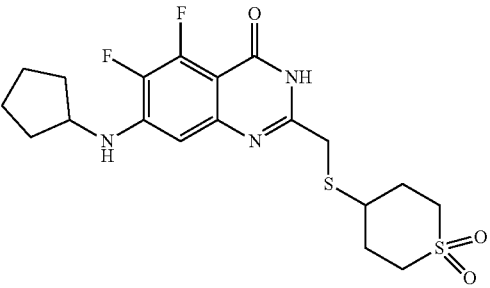 [SMILES: O=c1[nH]c(CSC2CCS(=O)(=O)CC2)nc2cc(NC3CCCC3)c(F)c(F)c12]<br>7-(Cyclopentylamino)-2-(((1,1-dioxidotetrahydro-2H-thiopyran-4-yl)thio)methyl)-5,6-difluoroquinazolin-4(3H)-one | 444.0 |
| Example 317 | 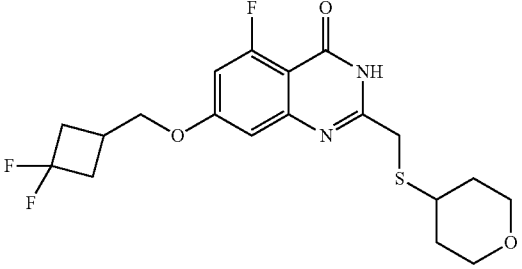 [SMILES: O=c1[nH]c(CSC2CCOCC2)nc2cc(OCC3CC(F)(F)C3)cc(F)c12]<br>7-((3,3-Difluorocyclobutyl)methoxy)-5-fluoro-2-(((tetrahydro-2H-pyran-4-yl)thio)methyl)quinazolin-4(3H)-one | 415.0 |
| Example 318 | 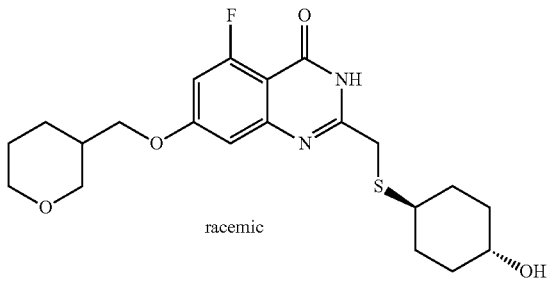 [SMILES: O=c1[nH]c(CS[C@H]2CC[C@H](O)CC2)nc2cc(OCC3CCCOC3)cc(F)c12]<br>5-Fluoro-2-(((trans-4-hydroxycyclohexyl)thio)methyl)-7-((tetrahydro-2H-pyran-3-yl)methoxy)quinazolin-4(3H)-one | 423.1 |
| Example 319 | 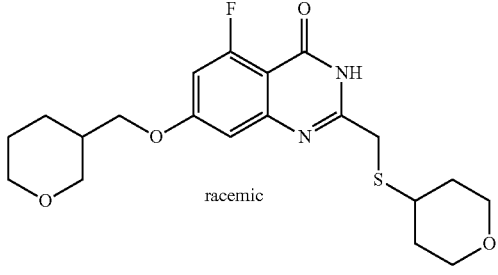 [SMILES: O=c1[nH]c(CSC2CCOCC2)nc2cc(OCC3CCCOC3)cc(F)c12]<br>5-Fluoro-7-((tetrahydro-2H-pyran-3-yl)methoxy)-2-(((tetrahydro-2H-pyran-4-yl)thio)methyl)quinazolin-4(3H)-one | 409.1 |

TABLE 10-continued

| Example | Structure/name | MS [M + H]⁺ |
|---|---|---|
| Example 320 | 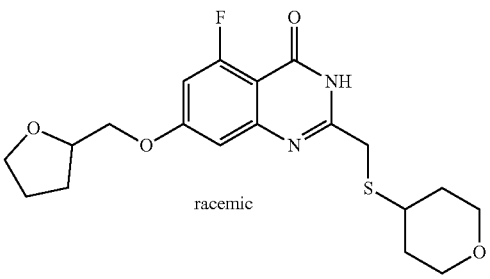 [SMILES: O=c1[nH]c(CSC2CCOCC2)nc2cc(OCC3CCCO3)cc(F)c12]<br>racemic<br>5-Fluoro-2-(((tetrahydro-2H-pyran-4-yl)thio)methyl)-7-((tetrahydrofuran-2-yl)methoxy)quinazolin-4(3H)-one | 395.1 |

Example 321: (R)-5-Fluoro-2-(((tetrahydro-2H-pyran-4-yl)thio)methyl)-7-((tetrahydrofuran-2-yl)methoxy)quinazolin-4(3H)-one and (S)-5-Fluoro-2-(((tetrahydro-2H-pyran-4-yl)thio)methyl)-7-((tetrahydrofuran-2-yl)methoxy)quinazolin-4(3H)-one

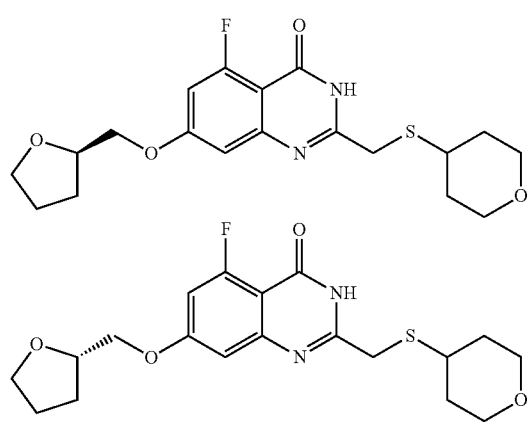

Example 320 was further purified by chiral prep-HPLC (Chiralpak IG-3, 3 μm, 0.46×5 cm column, eluting with a gradient of (hexane:DCM 1:1)(0.1% diethylamine): EtOH 50:50 at a flow rate of 1.0 mL/min) to afford the title compounds with retention times of 2.50 minutes and 3.70 minutes.

Example 321a

LCMS: [M+H]⁺ 395.2; ¹H NMR (400 MHz, DMSO) δ 12.18 (br s, 1H), 6.90-6.87 (m, 2H), 4.19-4.16 (m, 2H), 4.15-4.06 (m, 1H), 3.83-3.76 (m, 3H), 3.71-3.65 (m, 1H), 3.61 (s, 2H), 3.32-3.29 (m, 2H), 3.08-3.03 (m, 1H), 2.01-1.99 (m, 1H), 1.90-1.82 (m, 4H), 1.71-1.67 (m, 1H), 1.49-1.39 (m, 2H).

Example 321b

LCMS: [M+H]⁺ 395.2; ¹H NMR (400 MHz, DMSO) δ 12.18 (br s, 1H), 6.91-6.88 (m, 2H), 4.17-4.15 (m, 2H), 4.15-4.05 (m, 1H), 3.83-3.78 (m, 3H), 3.70-3.65 (m, 1H), 3.62 (s, 2H), 3.33-3.30 (m, 2H), 3.08-3.03 (m, 1H), 2.01-1.99 (m, 1H), 1.90-1.82 (m, 4H), 1.72-1.67 (m, 1H), 1.49-1.39 (m, 2H).

Example 322: 5,6-Difluoro-2-(((tetrahydro-2H-pyran-4-yl)thio)methyl)-7-(((tetrahydrofuran-3-yl)methyl)amino)quinazolin-4(3H)-one

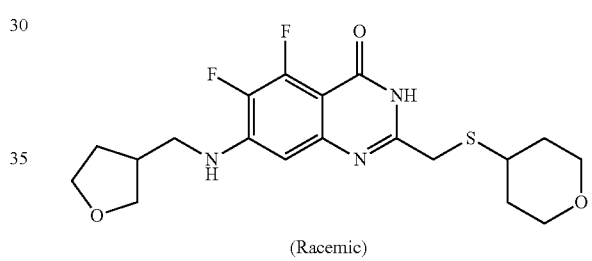

(Racemic)

Step 1: 2-(Chloromethyl)-5, 6, 7-trifluoroquinazolin-4(3H)-one

Prepared from methyl 6-amino-2,3,4-trifluorobenzoate and chloroacetonitrile according to the method described for Int-A16. LCMS: [M+H]⁺ 249.0.

Step 2: 5, 6, 7-Trifluoro-2-(((tetrahydro-2H-pyran-4-yl)thio)methyl)quinazolin-4(3H)-one Prepared from 2-(chloromethyl)-5,6,7-trifluoroquinazolin-4(3H)-one and Int-B1 according to the method described for Example 28. LCMS: [M+H]⁺ 331.0.

Step 3: 5, 6, 7-Trifluoro-2-(((tetrahydro-2H-pyran-4-yl)thio)methyl)-3-((2-(trimethylsilyl)ethoxy)methyl)quinazolin-4(3H)-one To a solution of 5,6,7-trifluoro-2-(tetrahydropyran-4-yl-sulfanylmethyl)-3H-quinazolin-4-one (52.0 g, 157 mmol) in anhydrous THF (650 mL) at 0° C. under a N₂ atmosphere was added KHMDS (1 M solution in THF, 236 mL, 236 mmol) and the mixture was stirred at 0° C. for 1 h. 2-(Chloromethoxy)ethyl-trimethylsilane (41.8 mL, 236 mmol) was then added and the mixture was stirred for a further 1.5 h. The reaction was quenched with water (100 mL) and the mixture was extracted with EtOAc (500 mL×3). The combined organic layers were dried over Na₂SO₄ and concentrated under reduced pressure. The residue was purified by column chromatography (Petroleum ether:EtOAc, 10:1, v/v) to afford the title compound (58.0 g, 80%) as a brown oil. ¹H NMR (400 MHz, DMSO-$d_6$) δ 7.59-7.55 (m, 1H), 5.57 (s, 2H), 3.99 (s, 2H), 3.87-3.77 (m, 2H), 3.63 (t, J=8.0 Hz, 2H), 3.32-3.29 (m, 2H), 3.15-3.04 (m, 1H), 1.91-1.88 (m, 2H), 1.54-1.40 (m, 2H), 0.90 (t, J=8.0 Hz, 2H), 0.04 (s, 9H).

Step 4: 5,6-Difluoro-2-(((tetrahydro-2H-pyran-4-yl)thio)methyl)-7-(((tetrahydrofuran-3-yl)methyl)amino)-3-((2-(trimethylsilyl)ethoxy)methyl)quinazolin-4(3H)-one To a solution of 5,6,7-trifluoro-2-(tetrahydropyran-4-yl-sulfanylmethyl)-3-(2-trimethylsilylethoxy-methyl)quinazolin-4-one (1.5 g, 3.3 mmol) in DMSO (15 mL) was added K₂CO₃ (0.99 g, 7.2 mmol) and tetrahydrofuran-3-ylmethanamine (0.40 g, 3.9 mmol) and the mixture was heated at 50° C. overnight. The mixture was diluted with water (20 mL), extracted with EtOAc (30 mL×3) and the combined organic layers were washed with water (40 mL), dried over Na₂SO₄ and concentrated under reduced pressure. The residue was purified by preparative TLC (Petroleum ether:EtOAc, 3/1, v/v) to afford title compound (560 mg, 32%) as a yellow oil. LCMS: [M+H]⁺ 542.1.

Step 5: 5,6-Difluoro-2-(((tetrahydro-2H-pyran-4-yl)thio)methyl)-7-(((tetrahydrofuran-3-yl)methyl)amino)quinazolin-4(3H)-one To a solution of 5,6-difluoro-7-(tetrahydrofuran-3-ylmethylamino)-2-(tetrahydropyran-4-ylsulfanylmethyl)-3-(2-trimethylsilylethoxymethyl)quinazolin-4-one (560 mg, 1.03 mmol) in DCM (10 mL) was added TFA (5 mL) and the mixture was stirred at RT for 2 h. The mixture was then concentrated under reduced pressure and the residue was purified by column chromatography (DCM:MeOH, 20/1, v/v) to afford the title compound (220 mg, 50%) as a yellow solid. LCMS: [M+H]⁺ 412.1. ¹H NMR (400 MHz, DMSO-$d_6$) δ 11.9 (s, 1H), 7.00-6.98 (m, 1H), 6.58 (d, J=7.2 Hz, 1H), 3.83-3.68 (m, 4H), 3.64-3.61 (m, 1H), 3.59 (s, 2H), 3.50-3.47 (m, 1H), 3.31-3.28 (m, 2H), 3.19-3.16 (m, 2H), 3.06-2.99 (m, 1H), 2.59-2.50 (m, 1H), 2.02-1.94 (m, 1H), 1.88-1.86 (m, 2H), 1.65-1.57 (m, 1H), 1.48-1.39 (m, 2H).

Example 323: (S)-5,6-Difluoro-2-(((tetrahydro-2H-pyran-4-yl)thio)methyl)-7-(((tetrahydrofuran-3-yl)methyl)amino)quinazolin-4(3H)-one and (R)-5,6-Difluoro-2-(((tetrahydro-2H-pyran-4-yl)thio)methyl)-7-(((tetrahydrofuran-3-yl)methyl)amino)quinazolin-4(3H)-one

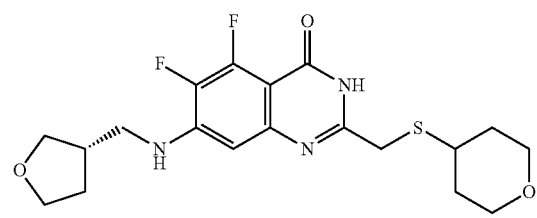

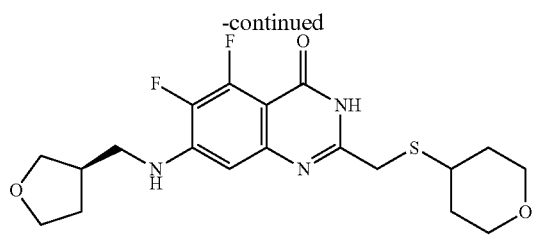

Example 322 was further purified by chiral prep-HPLC (Chiralpak IA-3, 3 μm, 0.46×5 cm column, eluting with a gradient of (hexane:DCM 3:1)(0.1% diethylamine): EtOH 50:50 at a flow rate of 1.0 mL/min) to afford the title compounds with retention times of 2.79 minutes and 4.83 minutes.

Example 323a

LCMS: [M+H]⁺ 412.2; ¹H NMR (400 MHz, DMSO) δ 11.9 (s, 1H), 7.01-7.00 (m, 1H), 6.60-6.58 (m, 1H), 3.83-3.69 (m, 4H), 3.65-3.60 (m, 1H), 3.58 (s, 2H), 3.51-3.46 (m, 1H), 3.30-3.29 (m, 2H), 3.20-3.17 (m, 2H), 3.07-3.00 (m, 1H), 2.59-2.51 (m, 1H), 2.00-1.96 (m, 1H), 1.90-1.86 (m, 2H), 1.64-1.63 (m, 1H), 1.49-1.43 (m, 2H).

Example 323b

LCMS: [M+H]⁺ 412.2; ¹H NMR (400 MHz, DMSO) δ 11.9 (s, 1H), 7.01-7.00 (m, 1H), 6.60-6.58 (m, 1H), 3.84-3.69 (m, 4H), 3.65-3.59 (m, 1H), 3.58 (s, 2H), 3.51-3.47 (m, 1H), 3.32-3.29 (m, 2H), 3.20-3.17 (m, 2H), 3.07-2.99 (m, 1H), 2.60-2.51 (m, 1H), 2.00-1.96 (m, 1H), 1.90-1.86 (m, 2H), 1.64-1.63 (m, 1H), 1.47-1.42 (m, 2H).

Example 324: 5-Fluoro-2-((((trans)-4-hydroxycyclohexyl)thio)methyl)-7-((tetrahydrofuran-3-yl)methoxy)quinazolin-4(3H)-one

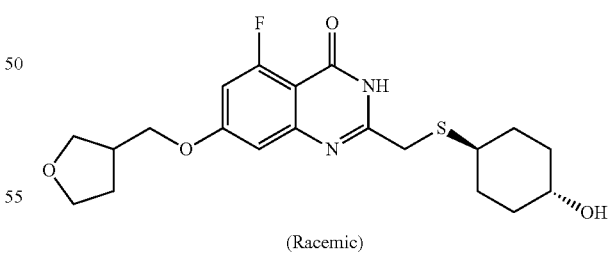

(Racemic)

Prepared from Int-A52 and Int-B11 according to the method described for Example 235. LCMS: [M+H]⁺ 409.1; ¹H NMR (400 MHz, CD₃OD) δ 6.94 (s, 1H), 6.83 (dd, J=12.6, 2.0 Hz, 1H), 4.13-4.02 (m, 2H), 3.93-3.88 (m, 2H), 3.81-3.77 (m, 1H), 3.72-3.66 (m, 1H), 3.65 (s, 2H), 3.55-3.49 (m, 1H), 2.80-2.67 (m, 2H), 2.20-2.18 (m, 1H), 2.08-2.04 (m, 2H), 1.96-1.93 (m, 2H), 1.78-1.75 (m, 1H), 1.42-1.23 (m, 4H).

Example 325: 5-Fluoro-2-((((trans)-4-hydroxycyclo-
hexyl)thio)methyl)-7-(((R)-tetrahydrofuran-3-yl)
methoxy)quinazolin-4(3H)-one and 5-Fluoro-2-
((((trans)-4-hydroxycyclohexyl)thio)methyl)-7-(((S)-
tetrahydrofuran-3-yl)methoxy)quinazolin-4(3H)-one

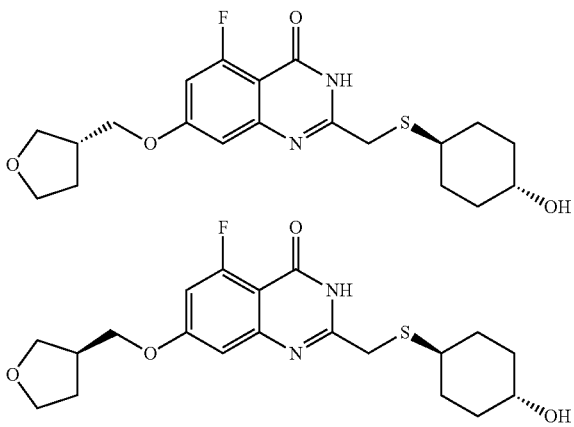

Example 324 was further purified by chiral prep-HPLC (Chiralpak IE-3, 3 μm, 0.46×5 cm column, eluting with a gradient of MTBE (0.1% diethylamine): MeOH 50:50 at a flow rate of 1.0 mL/min) to afford the title compounds with retention times of 2.22 minutes and 3.1 minutes.

Example 325a

LCMS: [M+H]$^+$ 409.2; $^1$H NMR (400 MHz, CD$_3$OD) δ 6.93 (s, 1H), 6.82 (dd, J=12.6, 2.0 Hz, 1H), 4.12-4.02 (m, 2H), 3.93-3.88 (m, 2H), 3.81-3.77 (m, 1H), 3.72-3.66 (m, 1H), 3.63 (s, 2H), 3.53-3.50 (m, 1H), 2.80-2.71 (m, 2H), 2.18-2.09 (m, 1H), 2.08-2.04 (m, 2H), 1.96-1.93 (m, 2H), 1.78-1.77 (m, 1H), 1.37-1.26 (m, 4H).

Example 325b

LCMS: [M+H]$^+$ 409.2; $^1$H NMR (400 MHz, CD$_3$OD) δ 6 6.93 (s, 1H), 6.82 (dd, J=12.6, 2.0 Hz, 1H), 4.13-4.02 (m, 2H), 3.93-3.88 (m, 2H), 3.81-3.76 (m, 1H), 3.72-3.65 (m, 1H), 3.64 (s, 2H), 3.53-3.50 (m, 1H), 2.80-2.70 (m, 2H), 2.18-2.08 (m, 1H), 2.07-2.04 (m, 2H), 1.96-1.93 (m, 2H), 1.81-1.77 (m, 1H), 1.37-1.26 (m, 4H).

Example 326: 5-Fluoro-7-(((trans)-3-fluoro-1-meth-
ylpiperidin-4-yl)methoxy)-2-(((tetrahydro-2H-pyran-
4-yl)thio)methyl)quinazolin-4(3H)-one

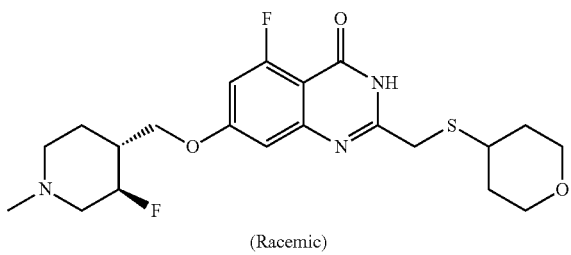 [SMILES: CN1CC[C@H](COc2cc(F)c3c(=O)[nH]c(CSC4CCOCC4)nc3c2)[C@@H](F)C1]

(Racemic)

Step 1: trans-tert-Butyl
3-fluoro-4-(hydroxymethyl)piperidine-1-carboxylate

The title compound was prepared in two steps from tert-butyl 3-fluoro-4-oxo-piperidine-1-carboxylate in 8% overall yield according to the procedure described in *Eur. J. Med. Chem.* 2012, 53, 408. $^1$H NMR (400 MHz, CDCl$_3$) δ 4.46-4.27 (m, 2H), 4.08-4.02 (m, 1H), 3.80 (dd, J=10.8, 4.0 Hz, 1H), 3.70 (dd, J=10.8, 5.2 Hz, 1H), 2.78-2.68 (m, 2H), 1.82-1.78 (m, 2H), 1.45 (s, 9H), 1.38-1.32 (m, 1H).

Step 2: tert-Butyl (trans)-3-fluoro-4-(methylsulfony-
loxymethyl)piperidine-1-carboxylate To a solution of trans-tert-butyl 3-fluoro-4-(hydroxymethyl)piperidine-1-carboxylate (800 mg, 3.43 mmol) and Et$_3$N (520 mg, 5.14 mmol) in DCM (5 mL) at 0° C. was added MsCl (471 mg, 4.12 mmol) and the mixture was stirred at RT for 2 h. Water (20 mL) was added and the mixture was extracted with EtOAc (30 mL×3). The combined organic layers were dried over Na$_2$SO$_4$ and concentrated under reduced pressure to afford the title compound (1.0 g, 94%) as a white solid. $^1$H NMR (400 MHz, CDCl$_3$) δ 4.44-4.25 (m, 4H), 4.10-4.07 (m, 1H), 3.03 (s, 3H), 2.82-2.66 (m, 2H), 2.02-1.95 (m, 1H), 1.88-1.84 (m, 1H), 1.52-1.45 (m, 10H).

Step 3: 5-Fluoro-7-hydroxy-2-(((tetrahydro-2H-
pyran-4-yl)thio)methyl)quinazolin-4(3H)-one Prepared from Int-A53 and Int-B1 according to the method described for Example 202. $^1$HNMR (400 MHz, DMSO-d$_6$) δ 12.0 (s, 1H), 10.9 (s, 1H), 6.70 (d, J=2.0 Hz, 1H), 6.66-6.62 (m, 1H), 3.83-3.80 (m, 2H), 3.59 (s, 2H), 3.31-3.28 (m, 2H), 3.07-3.00 (m, 1H), 1.90-1.86 (m, 2H), 1.49-1.39 (m, 2H).

Step 4: trans-tert-Butyl 3-fluoro-4-(((5-fluoro-4-
oxo-2-(((tetrahydro-2H-pyran-4-yl)thio)methyl)-3,4-
dihydroquinazolin-7-yl) oxy)methyl)piperidine-1-
carboxylate A mixture of tert-butyl (trans)-3-fluoro-4-(methylsulfonyloxymethyl)piperidine-1-carboxylate (800 mg, 2.57 mmol), K$_2$CO$_3$ (540 mg, 3.87 mmol) and 5-fluoro-7-hydroxy-2-(((tetrahydro-2H-pyran-4-yl)thio)methyl)quinazolin-4(3H)-one (957 mg, 3.08 mmol) in DMSO (30 mL) was heated at 60° C. overnight. The mixture was allowed to cool to RT, diluted with water (20 mL) and extracted with EtOAc (30 mL×3). The combined organic layers were washed with brine (10 mL×3), dried over Na$_2$SO$_4$ and concentrated under reduced pressure. The residue was purified by reverse phase column (Biotage, C18 column, 0%-60% ACN in water, 0.1% TFA) to afford the title compound (380 mg, 28%) as a brown solid. LCMS: [M+H]$^+$ 526.2.

Step 5: 5-Fluoro-7-(((trans)-3-fluoropiperidin-4-yl)
methoxy)-2-(((tetrahydro-2H-pyran-4-yl)thio)
methyl)quinazolin-4(3H)-one hydrochloride To a mixture of trans-tert-butyl 3-fluoro-4-(((5-fluoro-4-oxo-2-(((tetrahydro-2H-pyran-4-yl)thio)methyl)-3,4-dihydroquinazolin-7-yl)oxy)methyl)piperidine-1-carboxylate (380 mg, 0.720 mmol) in EtOAc (5 mL) was added a 2 M solution of HCl in EtOAc (5 mL) and the mixture was stirred at RT for 2 h. The mixture was concentrated under reduced pressure to afford the title compound (320 mg, 95%) as a brown solid. 1H NMR (400 MHz, DMSO-d$_6$) δ 9.39 (s, 1H), 6.98 (s, 1H), 6.94-6.91 (m, 1H), 4.96-4.84 (m, 1H), 4.28-4.21 (m, 2H), 3.84-3.80 (m, 2H), 3.65 (s, 2H), 3.49-3.47 (m, 1H), 3.35-3.30 (m, 2H), 3.26-3.18 (m, 1H), 3.17-3.03 (m, 2H), 3.03-2.92 (m, 1H), 2.47-2.35 (m, 1H), 2.12-2.02 (m, 1H), 1.91-1.88 (m, 2H), 1.80-1.69 (m, 1H). 1.49-1.39 (m, 2H). Two protons not observed (C—NH$_2^+$—C).

Step 6: 5-Fluoro-7-(((trans)-3-fluoro-1-methylpiperidin-4-yl)methoxy)-2-(((tetrahydro-2H-pyran-4-yl)thio)methyl)quinazolin-4(3H)-one To a solution of 5-fluoro-7-(((trans)-3-fluoropiperidin-4-yl)methoxy)-2-(((tetrahydro-2H-pyran-4-yl)thio)methyl)quinazolin-4(3H)-one hydrochloride (320 mg, 0.690 mmol) in methanol (20 mL) was added a 30% aqueous formaldehyde solution (0.2 mL) and NaCNBH$_3$ (435 mg, 6.93 mmol) and the mixture was stirred at RT for 1 h. Water (5 mL) was then added and the mixture was extracted with EtOAc (20 mL×3). The combined organic layers were dried over Na$_2$SO$_4$ and concentrated under reduced pressure. The residue was purified by column chromatography (DCM:MeOH, 35/1, v/v) to afford the title compound (80 mg, 25%) as a yellow solid. LCMS: [M+H]$^+$ 440.1; $^1$HNMR (400 MHz, DMSO-d$_6$) δ 12.2 (s, 1H), 6.91-6.88 (m, 2H), 4.64-4.46 (m, 1H), 4.25-4.11 (m, 2H), 3.83-3.80 (m, 2H), 3.62 (s, 2H), 3.35-3.34 (m, 1H), 3.29-3.28 (m, 1H), 3.12-3.03 (m, 2H), 2.75-2.67 (m, 1H), 2.23 (s, 3H), 2.02-1.87 (m, 6H), 1.55-1.38 (m, 3H).

Example 327: 5-Fluoro-7-(((3S,4S)-3-fluoro-1-methylpiperidin-4-yl)methoxy)-2-(((tetrahydro-2H-pyran-4-yl)thio)methyl)quinazolin-4(3H)-one and 5-Fluoro-7-(((3R,4R)-3-fluoro-1-methylpiperidin-4-yl)methoxy)-2-(((tetrahydro-2H-pyran-4-yl)thio)methyl)quinazolin-4(3H)-one

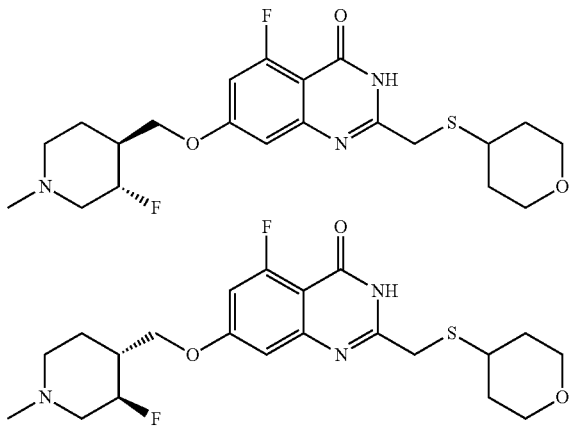

Example 326 was further purified by chiral prep-HPLC (Chiralpak IE-3, 3 μm, 0.46×5 cm column, eluting with a gradient of (hexane:DCM 1:1): MeOH 50:50 at a flow rate of 1.0 mL/min) to afford the title compounds with retention times of 2.05 minutes and 3.48 minutes.

Example 327a

Chiral prep-HPLC (Chiralpak IE-3, 3 μm, 0.46×5 cm column, eluting with a gradient of [hexane:DCM 1:1]: MeOH 50:50 at a flow rate of 1.0 mL/min) retention time: 2.05 minutes; LCMS: [M+H]$^+$ 440.2; $^1$H NMR (400 MHz, DMSO) δ 12.18 (s, 1H), 6.91-6.88 (m, 2H), 4.68-4.54 (m, 1H), 4.24-4.15 (m, 2H), 3.84-3.80 (m, 2H), 3.62 (s, 2H) 3.35-3.34 (m, 1H), 3.29-3.28, (m, 1H), 3.11-3.04 (m, 2H), 2.72-2.68 (m, 1H), 2.23 (s, 3H), 2.08-1.83 (m, 6H), 1.52-1.41 (m, 3H); [α]$_D$=25.6° (c 0.082 g/100 mL, MeOH).

Example 327b

Chiral prep-HPLC (Chiralpak IE-3, 3 μm, 0.46×5 cm column, eluting with a gradient of [hexane:DCM 1:1]: MeOH 50:50 at a flow rate of 1.0 mL/min) retention time: 3.48 minutes; LCMS: [M+H]$^+$ 440.2; $^1$H NMR (400 MHz, DMSO) δ 12.18 (s, 1H), 6.91-6.88 (m, 2H), 4.62-4.54 (m, 1H), 4.24-4.15 (m, 2H), 3.84-3.80 (m, 2H), 3.62 (s, 2H) 3.36-3.35 (m, 1H), 3.32-3.29, (m, 1H), 3.11-3.04 (m, 2H), 2.72-2.70 (m, 1H), 2.23 (s, 3H), 2.08-1.83 (m, 6H), 1.52-1.41 (m, 3H); [α]$_D$=−27.4° (c 0.084 g/100 mL, MeOH).

Example 328: 5,6-Difluoro-7-(((cis)-3-methoxycyclobutyl)amino)-2-(((tetrahydro-2H-pyran-4-yl)thio)methyl)quinazolin-4(3H)-one

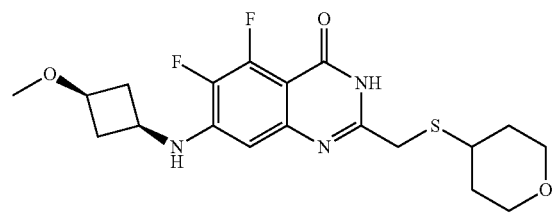 [SMILES: CO[C@H]1C[C@@H](Nc2cc3nc(CSC4CCOCC4)[nH]c(=O)c3c(F)c2F)C1]

Step 1: 5, 6-Difluoro-7-(((cis)-3-methoxycyclobutyl)amino)-2-(((tetrahydro-2H-pyran-4-yl)thio)methyl)-3-((2-(trimethylsilyl)ethoxy)methyl)quinazolin-4(3H)-one Prepared from 5,6,7-trifluoro-2-(((tetrahydro-2H-pyran-4-yl)thio)methyl)-3-((2-(trimethylsilyl)ethoxy)-methyl)quinazolin-4(3H)-one and cis-3-methoxycyclobutanamine hydrochloride according to the method described for Example 322, step 4. $^1$H NMR (400 MHz, DMSO-d$_6$) δ 7.22 (d, J=6.0 Hz, 1H), 6.49 (d, J=7.2 Hz, 1H), 5.56 (s, 2H), 3.96 (s, 2H), 3.90-3.85 (m, 2H), 3.75-3.59 (m, 4H), 3.34-3.20 (m, 2H), 3.19 (s, 3H), 3.12-3.08 (m, 1H), 2.78-2.66 (m, 2H), 2.00-1.98 (m, 4H), 1.57-1.45 (m, 2H), 0.98-0.84 (m, 2H), 0.00 (s, 9H).

Step 2: 5, 6-Difluoro-7-(((cis)-3-methoxycyclobutyl)amino)-2-(((tetrahydro-2H-pyran-4-yl)thio)methyl)quinazolin-4(3H)-one Prepared from 5,6-difluoro-7-(((cis)-3-methoxycyclobutyl)amino)-2-(((tetrahydro-2H-pyran-4-yl)thio)methyl)-3-((2-(trimethylsilyl)ethoxy)methyl)quinazolin-4(3H)-one according to the method described for Example 322, step 5. LCMS: [M+H]$^+$ 412.1;
$^1$H NMR (400 MHz, DMSO-d$_6$) δ 11.9 (s, 1H), 7.03 (d, J=6.0 Hz, 1H), 6.44 (d, J=6.8 Hz, 1H), 3.81-3.79 (m, 2H), 3.68-3.57 (m, 4H), 3.37-3.34 (m, 1H), 3.28-3.27 (m, 1H), 3.14 (s, 3H), 3.07-3.00 (m, 1H), 2.77-2.65 (m, 2H), 1.95-1.85 (m, 4H), 1.47-1.37 (m, 2H).

Example 329: N-((cis)-4-(((7-(Cyclopropyl-methoxy)-5-fluoro-4-oxo-3,4-dihydroquinazolin-2-yl)methyl)thio)cyclohexyl)acetamide

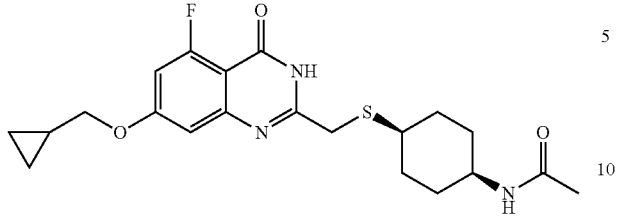

Step 1: tert-Butyl ((cis)-4-(((7-(cyclopropyl-methoxy)-5-fluoro-4-oxo-3,4-dihydroquinazolin-2-yl)methyl)thio)cyclohexyl)carbamate Prepared from Int-A49 and Int-B5-cis according to the method described for Example 202. LCMS: [M+H]+ 478.1.

Step 2: 2-((((cis)-4-Aminocyclohexyl)thio)methyl)-7-(cyclopropylmethoxy)-5-fluoroquinazolin-4(3H)-one Hydrochloride A mixture of tert-butyl ((cis)-4-(((7-(cyclopropyl-methoxy)-5-fluoro-4-oxo-3,4-dihydroquinazolin-2-yl)methyl)thio)cyclohexyl)carbamate (150 mg, 0.31 mmol) and a 2 M solution of HCl in EtOAc (10 mL, 20 mmol) was stirred at RT overnight. The solvent was removed under reduced pressure to afford the title compound (80 mg, 67%) as a yellow solid. LCMS: [M+H]+ 378.1.

Step 3: N-((cis)-4-(((7-(Cyclopropylmethoxy)-5-fluoro-4-oxo-3,4-dihydroquinazolin-2-yl)methyl)thio)cyclohexyl)acetamide To a solution of 2-((((cis)-4-aminocyclohexyl)thio)methyl)-7-(cyclopropylmethoxy)-5-fluoroquinazolin-4(3H)-one hydrochloride (80 mg, 0.21 mmol) and Et$_3$N (96 mg, 0.95 mmol) in DCM (2 mL) was added acetic anhydride (48 mg, 0.48 mmol) and the mixture was stirred at RT for 1 h. Water (5 mL) was added and the mixture was extracted with EtOAc (20 mL×3). The combined organic layers were dried over Na$_2$SO$_4$ and concentrated under reduced pressure to afford the title compound (50 mg, 57%) as a white solid. LCMS: [M+H]+ 420.1;
$^1$H NMR (400 MHz, DMSO-d$_6$) δ 12.1 (br s, 1H), 7.75 (d, J=7.6 Hz, 1H), 6.90-6.85 (m, 2H), 3.96 (d, J=7.6 Hz, 2H), 3.63-3.57 (m, 1H), 3.56 (s, 2H), 3.12-3.05 (m, 1H), 1.77 (s, 3H), 1.71-1.69 (m, 4H), 1.51-1.50 (m, 4H), 1.25-1.20 (m, 1H), 0.59-0.56 (m, 2H), 0.35-0.34 (m, 2H).

Example 330: N-((trans)-4-(((7-(Cyclopropyl-methoxy)-5-fluoro-4-oxo-3,4-dihydroquinazolin-2-yl)methyl)thio)cyclohexyl)acetamide

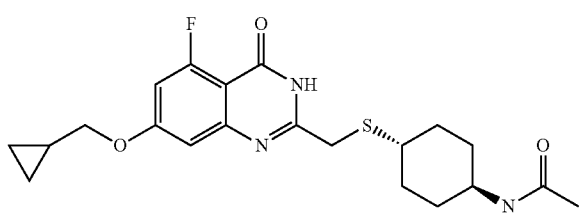

Step 1: tert-Butyl ((trans)-4-(((7-(cyclopropyl-methoxy)-5-fluoro-4-oxo-3,4-dihydroquinazolin-2-yl)methyl)thio)cyclohexyl)carbamate Prepared from Int-A49 and Int-B5-trans according to the method described for Example 202. LCMS: [M+H]+ 478.1

Step 2: 2-((((trans)-4-Aminocyclohexyl)thio)methyl)-7-(cyclopropylmethoxy)-5-fluoroquinazolin-4(3H)-one Hydrochloride Prepared from tert-butyl ((trans)-4-(((7-(cyclopropyl-methoxy)-5-fluoro-4-oxo-3,4-dihydroquinazolin-2-yl)methyl)thio)cyclohexyl)carbamate according to the method described for Example 329, step 2. LCMS: [M+H]+ 378.1.

Step 3: N-((trans)-4-(((7-(Cyclopropylmethoxy)-5-fluoro-4-oxo-3,4-dihydroquinazolin-2-yl)methyl)thio)cyclohexyl)acetamide Prepared from 2-((((trans)-4-aminocyclohexyl)thio)methyl)-7-(cyclopropylmethoxy)-5-fluoroquinazolin-4(3H)-one hydrochloride according to the method described for Example 329, step 3. LCMS: [M+H]+ 420.1; $^1$H NMR (400 MHz, DMSO-d$_6$) δ 12.1 (br s, 1H), 7.69 (d, J=7.6 Hz, 1H), 6.97-6.73 (m, 2H), 3.95 (d, J=7.2 Hz, 2H), 3.58 (s, 2H), 3.53-3.41 (m, 1H), 2.73-2.67 (m, 1H), 2.03-1.93 (m, 2H), 1.79-1.75 (m, 2H), 1.75 (s, 3H), 1.34-1.10 (m, 5H), 0.63-0.55 (m, 2H), 0.37-0.32 (m, 2H).

Example 331: 7-(((cis)-3-Ethoxycyclobutyl)amino)-5,6-difluoro-2-(((tetrahydro-2H-pyran-4-yl)thio)methyl)quinazolin-4(3H)-one

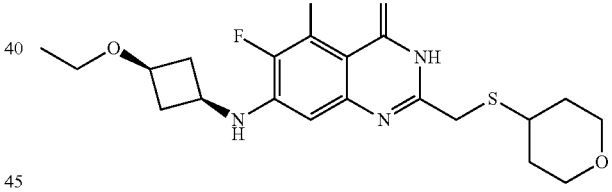

Step 1: 7-(((cis)-3-Ethoxycyclobutyl)amino)-5,6-difluoro-2-(((tetrahydro-2H-pyran-4-yl)thio)methyl)-3-((2-(trimethylsilyl)ethoxy)methyl)quinazolin-4(3H)-one Prepared from 5,6,7-trifluoro-2-(((tetrahydro-2H-pyran-4-yl)thio)methyl)-3-((2-(trimethylsilyl)ethoxy)-methyl)quinazolin-4(3H)-one and cis-3-ethoxycyclobutanamine hydrochloride according to the method described for Example 322 step 4. LCMS: [M+H]+ 556.3.

Step 2: 7-(((cis)-3-Ethoxycyclobutyl)amino)-5,6-difluoro-2-(((tetrahydro-2H-pyran-4-yl)thio)methyl)quinazolin-4(3H)-one Prepared from 7-(((cis)-3-ethoxycyclobutyl)amino)-5,6-difluoro-2-(((tetrahydro-2H-pyran-4-yl)thio)methyl)-3-((2-(trimethylsilyl)ethoxy)methyl)quinazolin-4(3H)-one according to the method described for Example 322 step 5. LCMS: [M+H]+ 426.1.

$^1$H NMR (400 MHz, DMSO-d$_6$) δ 11.9 (s, 1H), 7.03 (d, J=6.4 Hz, 1H), 6.44 (d, J=6.4 Hz, 1H), 3.84-3.77 (m, 2H), 3.76-3.67 (m, 1H), 3.65-3.55 (m, 1H), 3.55 (s, 2H), 3.38-3.29 (m, 4H), 3.05-3.01 (m, 1H), 2.77-2.66 (m, 2H), 1.96-1.82 (m, 4H), 1.50-1.38 (m, 2H), 1.10 (t, J=6.8 Hz, 3H).

Example 332: 5-Fluoro-2-(((((cis)-4-hydroxy-4-methylcyclohexyl)thio)methyl)-7-((tetrahydro-2H-pyran-4-yl)methoxy)quinazolin-4(3H)-one

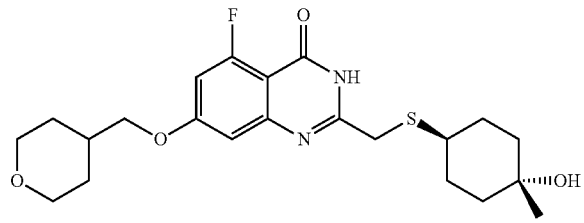 [SMILES: C[C@]1(O)CC[C@H](SCc2nc3cc(OCC4CCOCC4)cc(F)c3c(=O)[nH]2)CC1]

Prepared from Int-A50 and Int-B16 according to the method described for Example 202. LCMS: [M+H]$^+$ 437.1; $^1$H NMR (400 MHz, DMSO-d$_6$) δ 12.2 (br s, 1H), 6.89-6.86 (m, 2H), 3.98 (d, J=6.0 Hz, 2H), 3.88-3.85 (m, 2H), 3.55 (s, 2H), 3.33-3.30 (m, 2H), 2.98-2.90 (m, 1H), 2.04-1.89 (m, 3H), 1.68-1.65 (m, 2H), 1.56-1.48 (m, 2H), 1.42-1.28 (m, 6H), 1.07 (s, 3H). One signal (OH) not observed.

Example 333: 7-((1-Acetylpiperidin-4-yl)methoxy)-5-fluoro-2-(((tetrahydro-2H-pyran-4-yl)thio)methyl) quinazolin-4(3H)-one

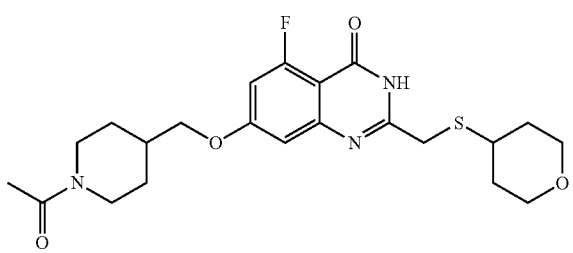 [SMILES: CC(=O)N1CCC(COc2cc(F)c3c(=O)[nH]c(CSC4CCOCC4)nc3c2)CC1]

Step 1: 1-[4-(Hydroxymethyl)-1-piperidyl]ethanone

The title compound was synthesized from piperidin-4-ylmethanol according to the procedure described in U.S. Pat. No. 4,898,871.

Step 2: (1-Acetylpiperidin-4-yl)methyl Methanesulfonate

To a solution of 1-[4-(hydroxymethyl)-1-piperidyl]ethanone (3.0 g, 19.1 mmol) and Et$_3$N (3.86 g, 38.2 mmol) in DCM (15 mL) at 0° C. under a N$_2$ atmosphere was added a solution of MsCl (2.22 mL, 28.6 mmol) in DCM (5 mL) and the mixture was allowed to warm to RT and stirred for 1 h. The mixture was diluted with DCM (20 mL) and washed with water (10 mL) and brine (10 mL). The organic layer was dried over Na$_2$SO$_4$ and concentrated under reduced pressure to afford the title compound (4.5 g, 100%) as a brown oil. $^1$H NMR (400 MHz, DMSO-d$_6$) δ 4.43-4.35 (m, 1H), 4.06 (d, J=6.4 Hz, 2H), 3.84-3.78 (m, 1H), 3.16 (s, 3H), 3.03-2.96 (m, 1H), 2.53-2.46 (m, 1H), 1.98 (s, 3H), 1.95-1.83 (m, 1H), 1.72-1.63 (m, 2H), 1.20-0.99 (m, 2H).

Step 3: 2,6-Difluoro-4-hydroxybenzoic Acid

The title compound was synthesized from 2,6-difluoro-4-hydroxybenzonitrile according to the procedure described in WO201742380.

Step 4: Methyl 2,6-difluoro-4-hydroxybenzoate

The title compound was synthesized from 2,6-difluoro-4-hydroxybenzoic acid according to the procedure described in WO201123989.

Step 5: Methyl 4-((1-acetylpiperidin-4-yl)methoxy)-2,6-difluorobenzoate

A mixture of (1-acetylpiperidin-4-yl)methyl methanesulfonate (4.55 g, 19.4 mmol), methyl 2,6-difluoro-4-hydroxybenzoate (2.6 g, 13.8 mmol) and K$_2$CO$_3$ (4.77 g, 34.6 mmol) in DMSO (26 mL) was heated at 80° C. under a N$_2$ atmosphere overnight. The mixture was diluted with water (100 mL) and extracted with EtOAc (35 mL×3). The combined organic extracts were washed with water (25 mL), brine (25 mL), dried over Na$_2$SO$_4$ and concentrated under reduced pressure to afford the title compound (4.52 g, 100%) as a pale yellow oil. LCMS: [M+H]$^+$ 328.1.

Step 6: Methyl 4-((1-acetylpiperidin-4-yl)methoxy)-2-((2,4-dimethoxybenzyl)amino)-6-fluorobenzoate A mixture of methyl 4-((1-acetylpiperidin-4-yl)methoxy)-2,6-difluorobenzoate (13.0 g, 39.7 mmol), (2,4-dimethoxyphenyl)methanamine (8.95 mL, 59.6 mmol) and K$_2$CO$_3$ (13.7 g, 99.3 mmol) in NMP (80 mL) was heated at 80° C. for 16 h. After cooling to RT, the mixture was diluted with water (200 mL) and extracted with EtOAc (100 mL×3). The combined organic extracts were dried over Na$_2$SO$_4$ and concentrated under reduced pressure. The residue was purified by column chromatography (Petroleum ether:EtOAc, 3/1, v/v) to afford the title compound (15.0 g, 80%) as a yellow solid. LCMS: [M+H]$^+$ 475.3.

Step 7: Methyl 4-((1-acetylpiperidin-4-yl)methoxy)-2-amino-6-fluorobenzoate

A solution of methyl 4-((1-acetylpiperidin-4-yl)methoxy)-2-((2,4-dimethoxybenzyl)amino)-6-fluorobenzoate (12.0 g, 25.3 mmol), triethylsilane (2.94 g, 25.3 mmol) and TFA (50.0 mL, 25.3 mmol) in DCM (100 mL) was stirred at 25° C. for 1 h. The mixture was concentrated under reduced pressure and the residue was diluted with DCM (50 mL), adjusted to pH 8 with a saturated aqueous Na$_2$CO$_3$ solution and extracted with DCM (50 mL×3). The combined organic extracts were dried over Na$_2$SO$_4$ and concentrated under reduced pressure. The residue was purified by column chromatography (DCM:MeOH, 100/1 to 50/1, v/v) to afford the title compound (6.2 g, 76%) as a yellow solid. LCMS: [M+H]$^+$ 325.2.

Step 8: 7-((1-Acetylpiperidin-4-yl)methoxy)-2-(chloromethyl)-5-fluoroquinazolin-4(3H)-one A mixture of methyl 4-((1-acetylpiperidin-4-yl)methoxy)-2-amino-6-fluorobenzoate (20.0 g, 55.5 mmol), 2-chloroacetonitrile (10.5 mL, 166 mmol) and a 2 M HCl in dioxane solution (90.0 mL, 180 mmol) was heated at 80° C. for 2 h. The mixture was filtered and the collected solid was slurried with water (80 mL) for 1 h then filtered. The solid was then slurried with a 60/1 DCM/MeOH solution (40 mL) followed by a 100/1 DCM/EtOH solution (60 mL) to afford the title compound (12.0 g, 55%) as a pale yellow solid. LCMS: [M+H]+ 368.1.

Step 9: 7-((1-Acetylpiperidin-4-yl)methoxy)-5-fluoro-2-(((tetrahydro-2H-pyran-4-yl)thio)methyl) quinazolin-4(3H)-one A mixture of 7-((1-acetylpiperidin-4-yl)methoxy)-2-(chloromethyl)-5-fluoroquinazolin-4(3H)-one (10.0 g, 27.2 mmol), 2 M aqueous NaOH (54.4 mL, 109 mmol) and Int-B1 (5.23 g, 32.6 mmol) in THF (100 mL) was stirred at RT under a $N_2$ atmosphere for 3 h. The mixture was diluted with water (1 L) and adjusted to pH 1 with a 2 M aqueous HCl solution. The mixture was stirred for 15 min and then allowed to stand undisturbed for 1 day. The resulting suspension was filtered and the filter cake was washed with EtOAc (50 mL) and dried to afford the title compound (10.0 g, 82%) as a pale yellow solid. LCMS: [M+H]+ 450.1;
$^1$H NMR (400 MHz, DMSO-$d_6$) δ 12.2 (s, 1H), 6.92-6.96 (m, 2H), 4.40-4.35 (m, 1H), 4.00 (d, J=6.4 Hz, 2H), 3.85-3.79 (m, 3H), 3.61 (s, 2H), 3.35-3.29 (m, 2H), 3.10-2.97 (m, 2H), 2.57-2.50 (m, 1H), 2.05-1.96 (m, 1H), 1.99 (s, 3H), 1.92-1.86 (m, 2H), 1.81-1.73 (m, 2H), 1.49-1.39 (m, 2H), 1.30-1.05 (m, 2H).

Example 334: 5-Fluoro-7-(((trans)-3-fluoro-1-methylpiperidin-4-yl)methoxy)-2-((((trans)-4-hydroxycyclohexyl)thio)methyl)quinazolin-4(3H)-one trifluoroacetic acid

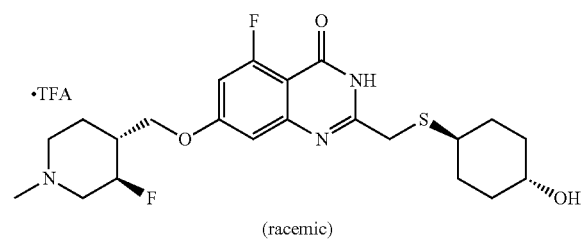 [SMILES: CN1CC[C@H](COc2cc(F)c3c(=O)[nH]c(CS[C@H]4CC[C@H](O)CC4)nc3c2)[C@@H](F)C1]

(racemic)

Step 1: 5-Fluoro-7-hydroxy-2-((((trans)-4-hydroxycyclohexyl)thio)methyl)quinazolin-4(3H)-one To a solution of Int-A53 (500 mg, 2.19 mmol) and Int-B11 (434 mg, 3.28 mmol) in DMSO (6 mL) under a nitrogen atmosphere was added $K_2CO_3$ (604 mg, 4.37 mmol) and the mixture was stirred at RT overnight. The mixture was diluted with water (20 mL) and extracted with EtOAc (20 mL×3). The combined organic extracts were dried over $Na_2SO_4$ and concentrated under reduced pressure. The residue was purified by column chromatography (DCM:MeOH, 30/1 to 10/1, v/v) to afford the title compound (480 mg, 68%) as a brown solid. LCMS: [M+H]+ 325.1.

Step 2: tert-Butyl (trans)-3-fluoro-4-(((5-fluoro-2-((((trans)-4-hydroxycyclohexyl)thio)methyl)-4-oxo-3,4-dihydroquinazolin-7-yl) oxy)methyl)piperidine-1-carboxylate Prepared from 5-fluoro-7-hydroxy-2-((((trans)-4-hydroxycyclohexyl)thio)methyl)quinazolin-4(3H)-one and tert-butyl (trans)-3-fluoro-4-(methylsulfonyloxymethyl)piperidine-1-carboxylate according to the method described for Example 326, step 4. LCMS: [M+H]+ 540.3.

Step 3: 5-Fluoro-7-(((trans)-3-fluoropiperidin-4-yl)methoxy)-2-((((trans)-4-hydroxycyclohexyl)thio)methyl)quinazolin-4(3H)-one Hydrochloride Prepared from tert-butyl (trans)-3-fluoro-4-(((5-fluoro-2-((((trans)-4-hydroxycyclohexyl)thio)methyl)-4-oxo-3,4-dihydroquinazolin-7-yl)oxy)methyl)piperidine-1-carboxylate according to the procedure described for Example 326, step 5. LCMS: [M+H]+ 440.2.

Step 4: 5-Fluoro-7-(((trans)-3-fluoro-1-methylpiperidin-4-yl)methoxy)-2-((((trans)-4-hydroxycyclohexyl)thio)methyl)quinazolin-4(3H)-one Trifluoroacetic Acid Prepared from 5-fluoro-7-(((trans)-3-fluoropiperidin-4-yl)methoxy)-2-((((trans)-4-hydroxycyclohexyl)thio)methyl) quinazolin-4(3H)-one hydrochloride according to the procedure described for Example 326, step 6. Purification by prep-HPLC (Agilent 10 prep-C18, 10 μm, 250×21.2 mm column, eluting with a gradient of MeOH in water with 0.1% TFA, at a flow rate of 20 mL/min) gave the title compound in 48% yield. LCMS: [M+H]+ 454.1;
$^1$HNMR (400 MHz, DMSO-$d_6$) δ 12.2 (br s, 1H), 10.2-9.67 (m, 1H), 7.01-6.84 (m, 2H), 5.21-4.68 (m, 1H), 4.34-4.21 (m, 2H), 3.83-3.64 (m, 1H), 3.58 (s, 2H), 3.50-3.27 (m, 2H), 3.24-2.97 (m, 2H), 2.85-2.81 (m, 3H), 2.76-2.67 (m, 1H), 2.59-2.47 (m, 1H), 2.33-2.07 (m, 2H), 2.03-1.63 (m, 5H), 1.30-1.10 (m, 4H).

Example 335: 5-fluoro-7-(((3S,4S)-3-fluoro-1-methylpiperidin-4-yl)methoxy)-2-((((trans)-4-hydroxycyclohexyl)thio)methyl)quinazolin-4(3H)-one and 5-fluoro-7-(((3R,4R)-3-fluoro-1-methylpiperidin-4-yl)methoxy)-2-((((trans)-4-hydroxycyclohexyl)thio) methyl)quinazolin-4(3H)-one

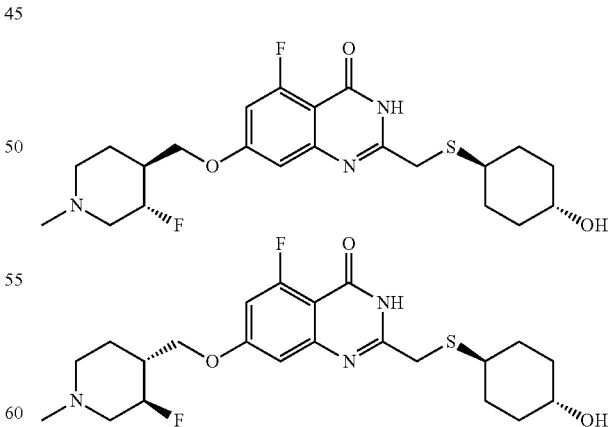

Example 334 was further purified by chiral prep-HPLC (Chiralpak IE-3, 3 μm, 0.46×10 cm column, eluting with a gradient of MeOH:DCM 50:50 at a flow rate of 1.0 mL/min) to afford the title compounds with retention times of 1.85 minutes and 4.13 minutes.

Example 335a

LCMS: [M+H]⁺ 454.2;
¹HNMR (400 MHz, DMSO-d₆) δ 12.15 (s, 1H), 6.91-6.88 (m, 2H), 4.62-4.48 (m, 2H), 4.24-4.14 (m, 2H), 3.58 (s, 1H), 3.40-3.33 (m, 1H), 3.11-3.07 (m, 1H), 2.75-2.67 (m, 2H), 2.22 (s, 3H), 1.97-1.79 (m, 8H), 1.54-1.45 (m, 1H), 1.26-1.11 (m, 5H).

Example 335b

LCMS: [M+H]⁺ 454.2;
¹H NMR (400 MHz, DMSO-d₆) δ 12.16 (s, 1H), 6.91-6.88 (m, 2H), 4.62-4.52 (m, 2H), 4.24-4.15 (m, 2H), 3.58 (s, 1H), 3.39-3.35 (m, 1H), 3.11-3.07 (m, 1H), 2.75-2.67 (m, 2H), 2.23 (s, 3H), 1.98-1.79 (m, 8H), 1.54-1.45 (m, 1H), 1.28-1.11 (m, 5H).

Further example compounds of the invention prepared by the methods described herein are provided in Table 11.

TABLE 11

| Example | Structure/Name | MS [M + H]⁺ |
|---|---|---|
| Example 336 | 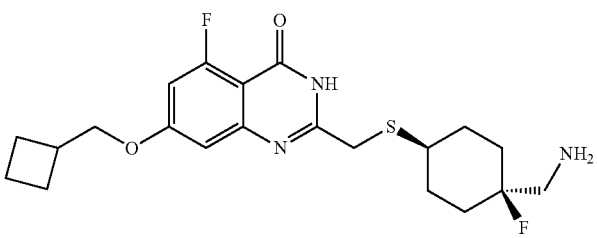<br>2-((((trans)-4-(Aminomethyl)-4-fluorocyclohexyl)thio)methyl)-7-(cyclobutylmethoxy)-5-fluoroquinazolin-4(3H)-one | 424.1 |
| Example 337 | 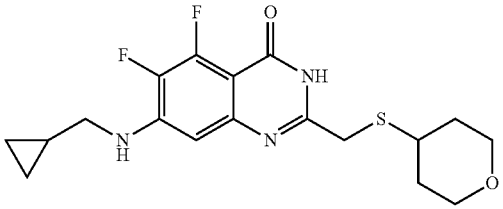<br>7-((Cyclopropylmethyl)amino)-5,6-difluoro-2-(((tetrahydro-2H-pyran-4-yl)thio)methyl)quinazolin-4(3H)-one | 382.0 |
| Example 338 | 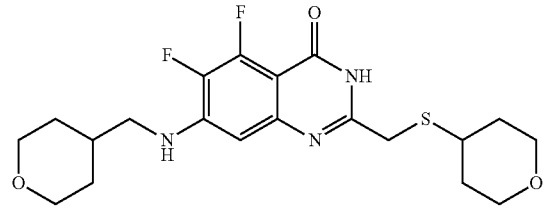<br>5,6-Difluoro-7-((((tetrahydro-2H-pyran-4-yl)methyl)amino)-2-(((tetrahydro-2H-pyran-4-yl)thio)methyl)quinazolin-4(3H)-one | 426.1 |
| Example 339 | 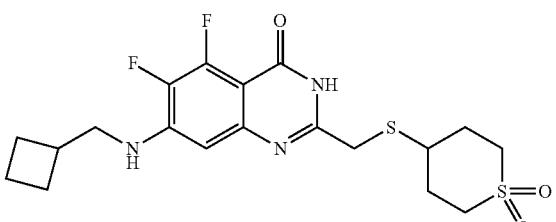<br>7-((Cyclobutylmethyl)amino)-2-(((1,1-dioxidotetrahydro-2H-thiopyran-4-yl)thio)methyl)-5,6-difluoroquinazolin-4(3H)-one | 444.0 |

TABLE 11-continued

| Example | Structure/Name | MS [M + H]+ |
|---|---|---|
| Example 340 | 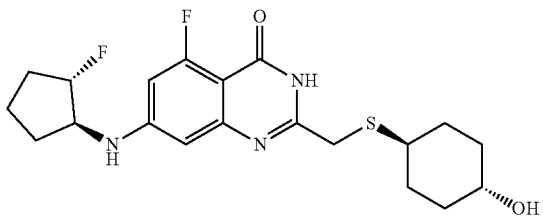<br>(racemic)<br>5-Fluoro-7-(((trans)-2-fluorocyclopentyl)amino)-2-((((trans)-4-hydroxycyclohexyl)thio)methyl)quinazolin-4(3H)-one | 410.1 |
| Example 341 | 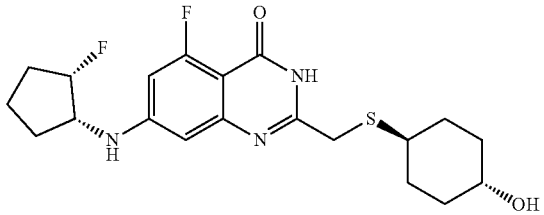<br>(racemic)<br>5-Fluoro-7-(((cis)-2-fluorocyclopentyl)amino)-2-((((trans)-4-hydroxycyclohexyl)thio)methyl)quinazolin-4(3H)-one | 410.1 |
| Example 342 | 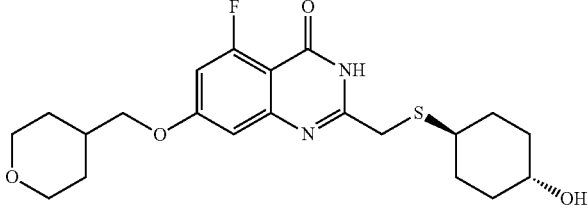<br>5-Fluoro-2-((((trans)-4-hydroxycyclohexyl)thio)methyl)-7-((tetrahydro-2H-pyran-4-yl)methoxy)quinazolin-4(3H)-one | 423.0 |
| Example 343 | 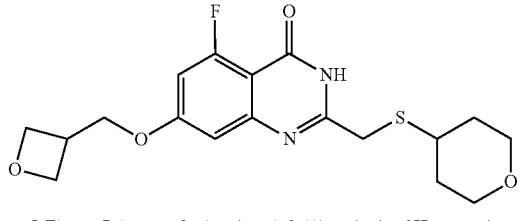<br>5-Fluoro-7-(oxetan-3-ylmethoxy)-2-(((tetrahydro-2H-pyran-4-yl)thio)methyl)quinazolin-4(3H)-one | 381.1 |
| Example 344 | 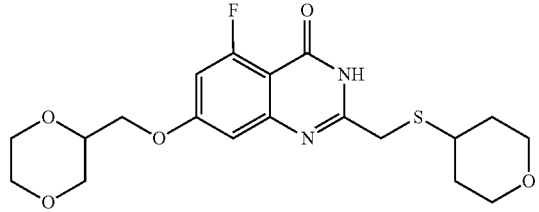<br>(racemic)<br>7-((1,4-Dioxan-2-yl)methoxy)-5-fluoro-2-(((tetrahydro-2H-pyran-4-yl)thio)methyl)quinazolin-4(3H)-one | 411.0 |

TABLE 11-continued

| Example | Structure/Name | MS [M + H]+ |
|---|---|---|
| Example 345 | 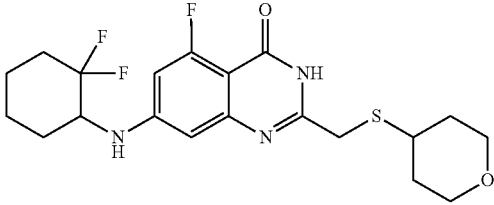<br>(racemic)<br>7-((2,2-Difluorocyclohexyl)amino)-5-fluoro-2-(((tetrahydro-2H-pyran-4-yl)thio)methyl)quinazolin-4(3H)-one | 428.1 |
| Example 346 | 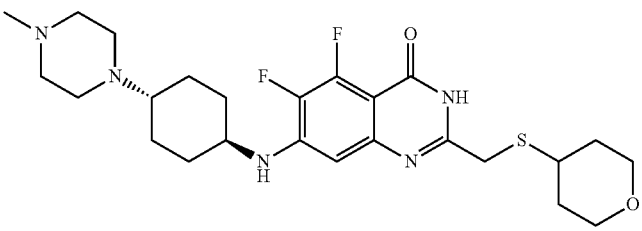<br>5,6-Difluoro-7-(((trans)-4-(4-methylpiperazin-1-yl)cyclohexyl)amino)-2-(((tetrahydro-2H-pyran-4-yl)thio)methyl)quinazolin-4(3H)-one | 508.1 |
| Example 347 | 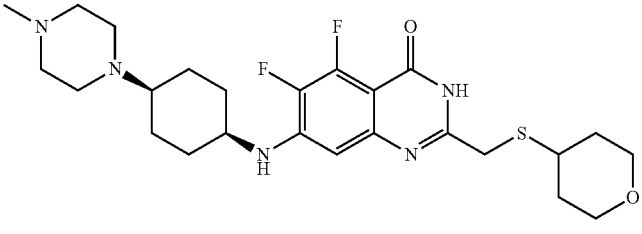<br>5,6-Difluoro-7-(((cis)-4-(4-methylpiperazin-1-yl)cyclohexyl)amino)-2-(((tetrahydro-2H-pyran-4-yl)thio)methyl)quinazolin-4(3H)-one | 508.1 |
| Example 348 | 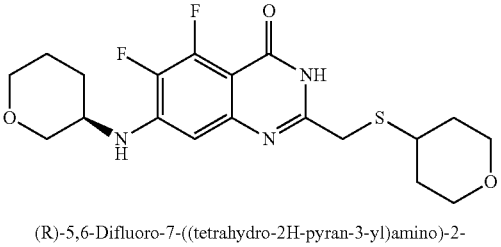<br>(R)-5,6-Difluoro-7-((tetrahydro-2H-pyran-3-yl)amino)-2-(((tetrahydro-2H-pyran-4-yl)thio)methyl)quinazolin-4(3H)-one | 412.0 |
| Example 349 | 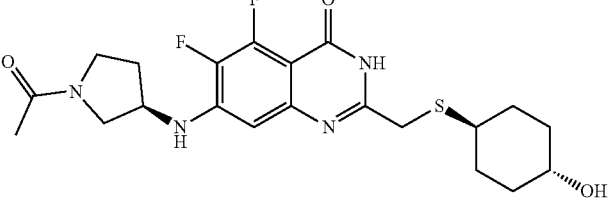<br>7-(((R)-1-Acetylpyrrolidin-3-yl)amino)-5,6-difluoro-2-((((trans)-4-hydroxycyclohexyl)thio)methyl)quinazolin-4(3H)-one | 453.0 |

TABLE 11-continued

| Example | Structure/Name | MS [M + H]+ |
|---|---|---|
| Example 350 | 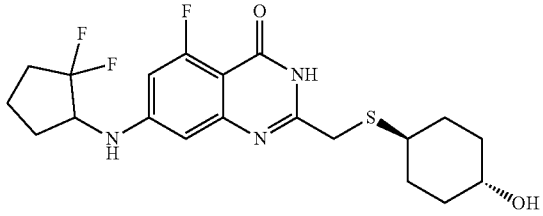<br>(racemic)<br>7-((2,2-Difluorocyclopentyl)amino)-5-fluoro-2-((((trans)-4-hydroxycyclohexyl)thio)methyl)quinazolin-4(3H)-one | 428.0 |
| Example 351 | 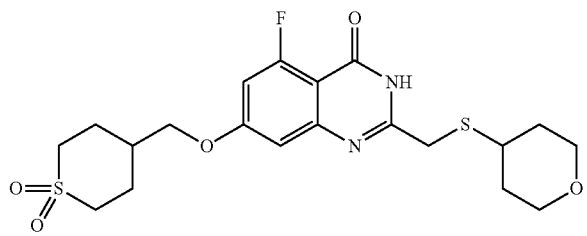<br>7-((1,1-Dioxidotetrahydro-2H-thiopyran-4-yl)methoxy)-5-fluoro-2-(((tetrahydro-2H-pyran-4-yl)thio)methyl)quinazolin-4(3H)-one | 457.0 |
| Example 352 | 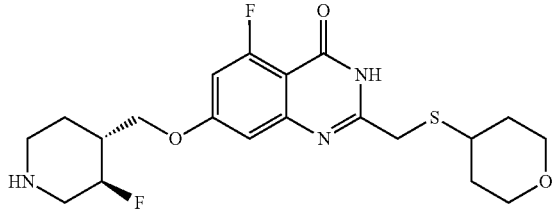<br>(racemic)<br>5-Fluoro-7-(((trans)-3-fluoropiperidin-4-yl)methoxy)-2-(((tetrahydro-2H-pyran-4-yl)thio)methyl)quinazolin-4(3H)-one | 426.0 |
| Example 353 | 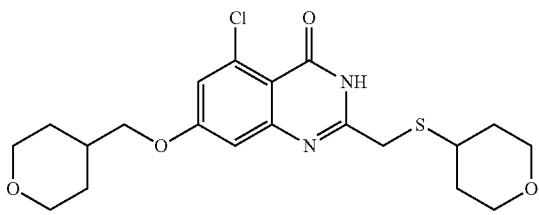<br>5-Chloro-7-((tetrahydro-2H-pyran-4-yl)methoxy)-2-(((tetrahydro-2H-pyran-4-yl)thio)methyl)quinazolin-4(3H)-one | 425.0 |
| Example 354 | 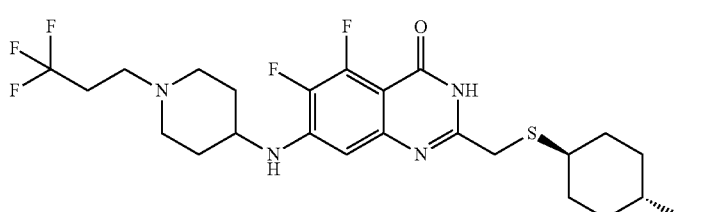<br>5,6-Difluoro-2-((((trans)-4-hydroxycyclohexyl)thio)methyl)-7-((1-(3,3,3-trifluoropropyl)piperidin-4-yl)amino)quinazolin-4(3H)-one | 521.0 |

TABLE 11-continued

| Example | Structure/Name | MS [M + H]+ |
|---|---|---|
| Example 355 | 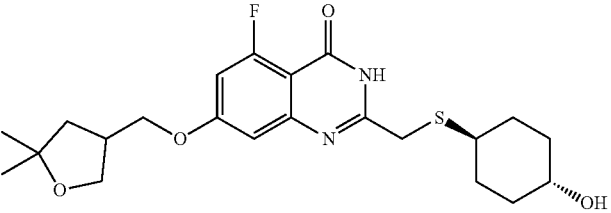<br>(racemic)<br>7-((5,5-Dimethyltetrahydrofuran-3-yl)methoxy)-5-fluoro-2-(((((trans)-4-hydroxycyclohexyl)thio)methyl)quinazolin-4(3H)-one | 437.1 |
| Example 356 | 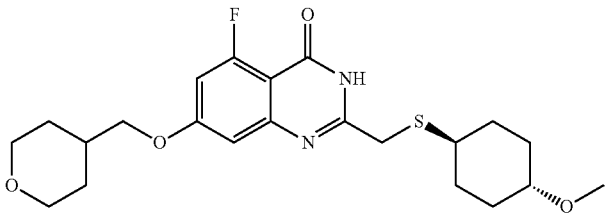<br>5-Fluoro-2-((((trans)-4-methoxycyclohexyl)thio)methyl)-7-((tetrahydro-2H-pyran-4-yl)methoxy)quinazolin-4(3H)-one | 437.1 |
| Example 357 | 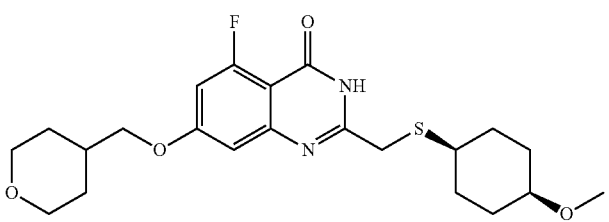<br>5-Fluoro-2-(((((cis)-4-methoxycyclohexyl)thio)methyl)-7-((tetrahydro-2H-pyran-4-yl)methoxy)quinazolin-4(3H)-one | 437.1 |
| Example 358 | 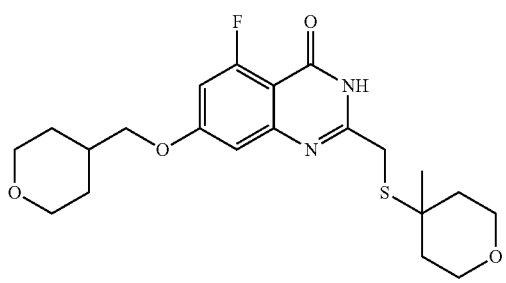<br>5-Fluoro-2-(((4-methyltetrahydro-2H-pyran-4-yl)thio)methyl)-7-((tetrahydro-2H-pyran-4-yl)methoxy)quinazolin-4(3H)-one | 423.1 |
| Example 359 | 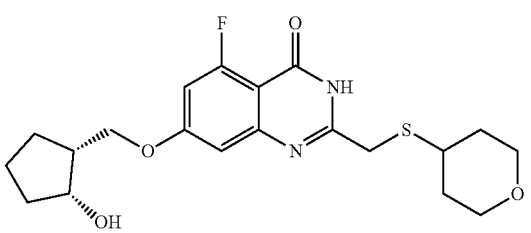<br>(racemic)<br>5-Fluoro-7-(((cis)-2-hydroxycyclopentyl)methoxy)-2-(((tetrahydro-2H-pyran-4-yl)thio)methyl)quinazolin-4(3H)-one | 409.1 |

TABLE 11-continued

| Example | Structure/Name | MS [M + H]+ |
|---|---|---|
| Example 360 | (trans)-4-((5,6-Difluoro-4-oxo-2-(((tetrahydro-2H-pyran-4-yl)thio)methyl)-3,4-dihydroquinazolin-7-yl)amino)cyclohexane-1-carbonitrile | 435.1 |
| Example 361 | (cis)-4-((5,6-Difluoro-4-oxo-2-(((tetrahydro-2H-pyran-4-yl)thio)methyl)-3,4-dihydroquinazolin-7-yl)amino)cyclohexane-1-carbonitrile | 435.1 |
| Example 362 | 5,6-Difluoro-7-(((trans)-3-methoxycyclobutyl)amino)-2-(((tetrahydro-2H-pyran-4-yl)thio)methyl)quinazolin-4(3H)-one | 412.0 |
| Example 363 | 5,6-Difluoro-2-((((trans)-4-hydroxycyclohexyl)thio)methyl)-7-(((cis)-3-methoxycyclobutyl)amino)quinazolin-4(3H)-one | 426.0 |
| Example 364 | 5-Methyl-7-((tetrahydro-2H-pyran-4-yl)methoxy)-2-(((tetrahydro-2H-pyran-4-yl)thio)methyl)quinazolin-4(3H)-one | 405.0 |

TABLE 11-continued

| Example | Structure/Name | MS [M + H]+ |
| --- | --- | --- |
| Example 365 | 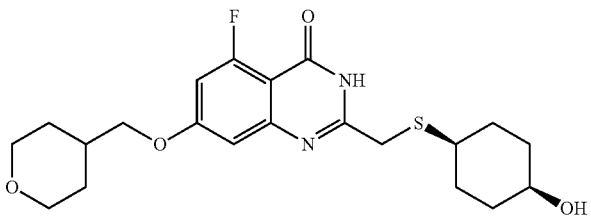<br>5-Fluoro-2-((((cis)-4-hydroxycyclohexyl)thio)methyl)-7-((tetrahydro-2H-pyran-4-yl)methoxy)quinazolin-4(3H)-one | 423.1 |
| Example 366 | 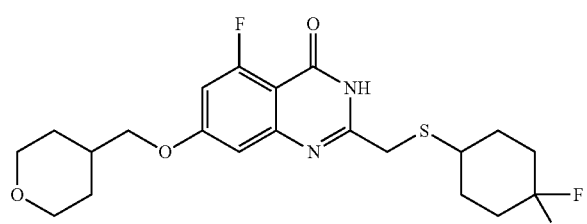<br>2-(((4,4-Difluorocyclohexyl)thio)methyl)-5-fluoro-7-((tetrahydro-2H-pyran-4-yl)methoxy)quinazolin-4(3H)-one | 443.0 |
| Example 367 | 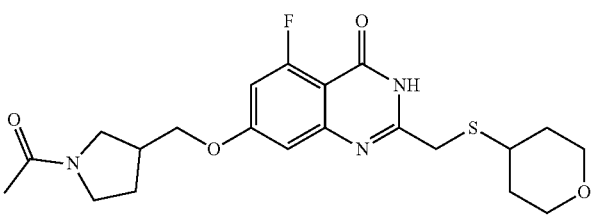<br>(racemic)<br>7-((1-Acetylpyrrolidin-3-yl)methoxy)-5-fluoro-2-(((tetrahydro-2H-pyran-4-yl)thio)methyl)quinazolin-4(3H)-one | 436.1 |
| Example 368 | 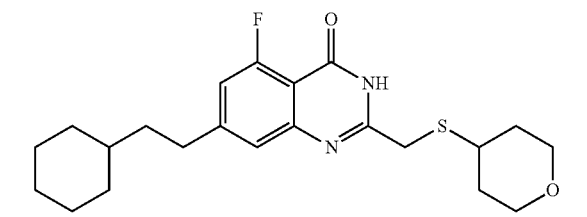<br>7-(2-Cyclohexylethyl)-5-fluoro-2-(((tetrahydro-2H-pyran-4-yl)thio)methyl)quinazolin-4(3H)-one | 405.1 |
| Example 369 | 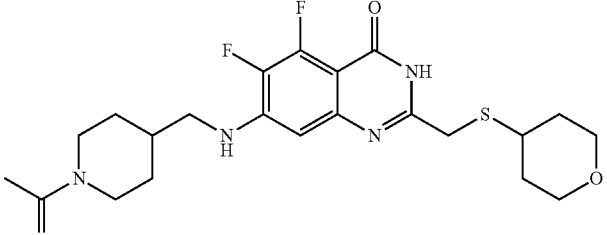<br>7-(((1-Acetylpiperidin-4-yl)methyl)amino)-5,6-difluoro-2-(((tetrahydro-2H-pyran-4-yl)thio)methyl)quinazolin-4(3H)-one | 467.1 |

TABLE 11-continued

| Example | Structure/Name | MS [M + H]+ |
|---|---|---|
| Example 370 | 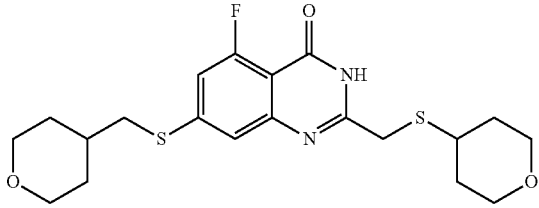<br>5-Fluoro-7-((((tetrahydro-2H-pyran-4-yl)methyl)thio)-2-(((tetrahydro-2H-pyran-4-yl)thio)methyl)quinazolin-4(3H)-one | 425.0 |
| Example 371 | 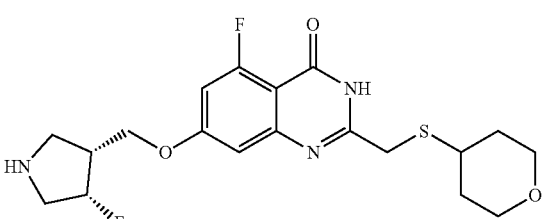<br>(racemic)<br>5-Fluoro-7-(((cis)-4-fluoropyrrolidin-3-yl)methoxy)-2-(((tetrahydro-2H-pyran-4-yl)thio)methyl)quinazolin-4(3H)-one | 412.1 |
| Example 372 | 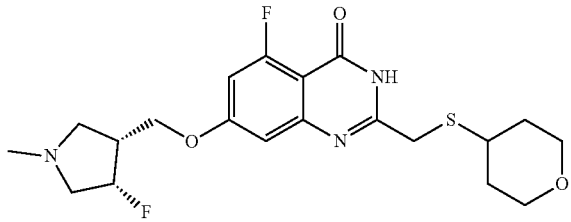<br>(racemic)<br>5-Fluoro-7-(((cis)-4-fluoro-1-methylpyrrolidin-3-yl)methoxy)-2-(((tetrahydro-2H-pyran-4-yl)thio)methyl)quinazolin-4(3H)-one | 426.1 |
| Example 373 | 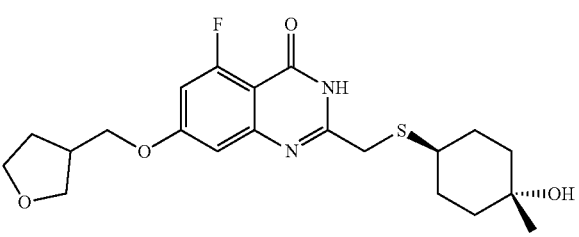<br>(racemic)<br>5-Fluoro-2-((((cis)-4-hydroxy-4-methylcyclohexyl)thio)methyl)-7-((tetrahydrofuran-3-yl)methoxy)quinazolin-4(3H)-one | 423.1 |
| Example 374 | 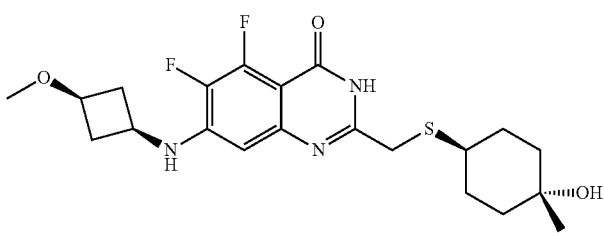<br>5,6-Difluoro-2-((((cis)-4-hydroxy-4-methylcyclohexyl)thio)methyl)-7-(((cis)-3-methoxycyclobutyl)amino)quinazolin-4(3H)-one | 440.1 |

TABLE 11-continued

| Example | Structure/Name | MS [M + H]+ |
|---|---|---|
| Example 375 | 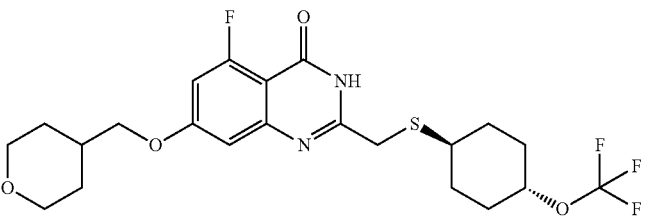<br>5-Fluoro-7-((tetrahydro-2H-pyran-4-yl)methoxy)-2-((((trans)-4-(trifluoromethoxy)cyclohexyl)thio)methyl)quinazolin-4(3H)-one | 491.0 |
| Example 376 | 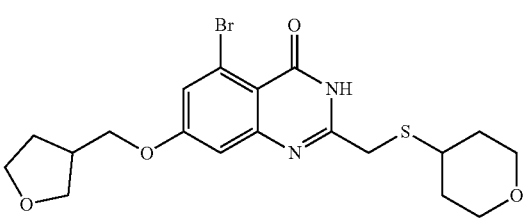<br>(racemic)<br>5-Bromo-2-((((tetrahydro-2H-pyran-4-yl)thio)methyl)-7-((tetrahydrofuran-3-yl)methoxy)quinazolin-4(3H)-one | 455.0 |
| Example 377 | 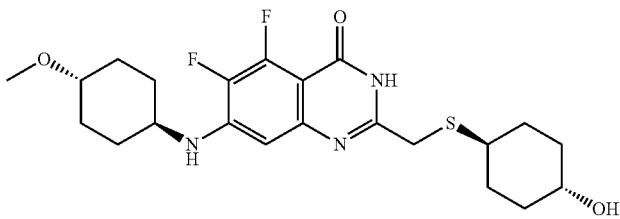<br>5,6-Difluoro-2-((((trans)-4-hydroxycyclohexyl)thio)methyl)-7-(((trans)-4-methoxycyclohexyl)amino)quinazolin-4(3H)-one | 454.1 |
| Example 378 | 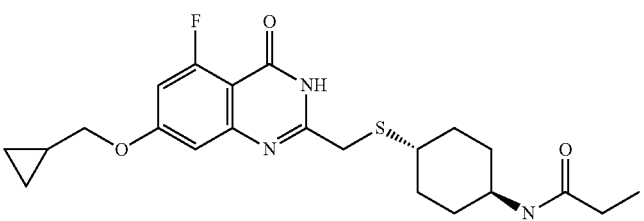<br>N-((trans)-4-(((7-(Cyclopropylmethoxy)-5-fluoro-4-oxo-3,4-dihydroquinazolin-2-yl)methyl)thio)cyclohexyl)propionamide | 434.1 |
| Example 379 | 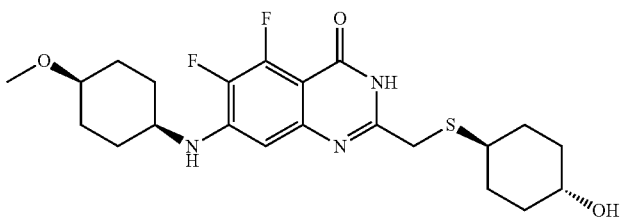<br>5,6-Difluoro-2-((((trans)-4-hydroxycyclohexyl)thio)methyl)-7-(((cis)-4-methoxycyclohexyl)amino)quinazolin-4(3H)-one | 454.1 |

TABLE 11-continued

| Example | Structure/Name | MS [M + H]+ |
|---|---|---|
| Example 380 | N-(4-(((7-(Cyclopropylmethoxy)-5-fluoro-4-oxo-3,4-dihydroquinazolin-2-yl)methyl)thio)-1-methylcyclohexyl)acetamide | 434.1 |
| Example 381 | 5,6-Difluoro-2-((((trans)-4-hydroxycyclohexyl)thio)methyl)-7-(((R)-tetrahydro-2H-pyran-3-yl)amino)quinazolin-4(3H)-one | 426.1 |
| Example 382 | 5-Fluoro-2-((((trans)-3-hydroxycyclobutyl)thio)methyl)-7-((tetrahydro-2H-pyran-4-yl)methoxy)quinazolin-4(3H)-one | 395.1 |
| Example 383 | (racemic) 4-Oxo-2-(((tetrahydro-2H-pyran-4-yl)thio)methyl)-7-((tetrahydrofuran-3-yl)methoxy)-3,4-dihydroquinazoline-5-carbonitrile | 402.1 |
| Example 384 | 5,6-Difluoro-7-(neopentylamino)-2-(((tetrahydro-2H-pyran-4-yl)thio)methyl)quinazolin-4(3H)-one | 398.1 |

TABLE 11-continued

| Example | Structure/Name | MS [M + H]+ |
| --- | --- | --- |
| Example 385 | 5-Fluoro-7-(((cis)-3-hydroxy-3-methylcyclobutyl)methoxy)-2-(((tetrahydro-2H-pyran-4-yl)thio)methyl)quinazolin-4(3H)-one | 409.1 |
| Example 386 | 5-Fluoro-7-(((trans)-3-hydroxy-3-methylcyclobutyl)methoxy)-2-(((tetrahydro-2H-pyran-4-yl)thio)methyl)quinazolin-4(3H)-one | 409.1 |
| Example 387 | N-((cis)-3-(((5-Fluoro-4-oxo-7-((tetrahydro-2H-pyran-4-yl)methoxy)-3,4-dihydroquinazolin-2-yl)methyl)thio)cyclobutyl)acetamide | 436.1 |
| Example 388 | (racemic) 5-Fluoro-7-(((cis)-3-fluoro-1-methylpiperidin-4-yl)methoxy)-2-(((tetrahydro-2H-pyran-4-yl)thio)methyl)quinazolin-4(3H)-one | 440.1 |
| Example 389 | N-((trans)-4-(((5,6-Difluoro-7-(((cis)-3-methoxycyclobutyl)amino)-4-oxo-3,4-dihydroquinazolin-2-yl)methyl)thio)cyclohexyl)acetamide | 467.1 |

TABLE 11-continued

| Example | Structure/Name | MS [M + H]+ |
|---|---|---|
| Example 390 | 7-((1-(Cyclopropanecarbonyl)piperidin-4-yl)methoxy)-5-fluoro-2-(((tetrahydro-2H-pyran-4-yl)thio)methyl)quinazolin-4(3H)-one | 476.1 |
| Example 391 | (racemic)<br>N-((trans-4-(((5-Fluoro-4-oxo-7-((tetrahydrofuran-3-yl)methoxy)-3,4-dihydroquinazolin-2-yl)methyl)thio)cyclohexyl)acetamide | 450.1 |
| Example 392 | N-((trans)-4-(((7-(Cyclobutylamino)-5,6-difluoro-4-oxo-3,4-dihydroquinazolin-2-yl)methyl)thio)cyclohexyl)acetamide | 437.1 |
| Example 393 | N-((trans)-3-(((5-Fluoro-4-oxo-7-((tetrahydro-2H-pyran-4-yl)methoxy)-3,4-dihydroquinazolin-2-yl)methyl)thio)cyclobutyl)acetamide | 436.1 |
| Example 394 | (racemic)<br>7-(1-Cyclopentylethoxy)-5-fluoro-2-(((tetrahydro-2H-pyran-4-yl)thio)methyl)-5,6,7,8-tetrahydroquinazolin-4(3H)-one | 407.1 |

TABLE 11-continued

| Example | Structure/Name | MS [M + H]+ |
|---|---|---|
| Example 395 | 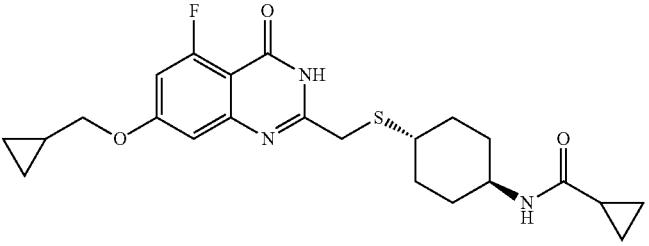<br>N-((trans)-4-(((7-(Cyclopropylmethoxy)-5-fluoro-4-oxo-3,4-dihydroquinazolin-2-yl)methyl)thio)cyclohexyl)cyclopropanecarboxamide | 446.1 |
| Example 396 | 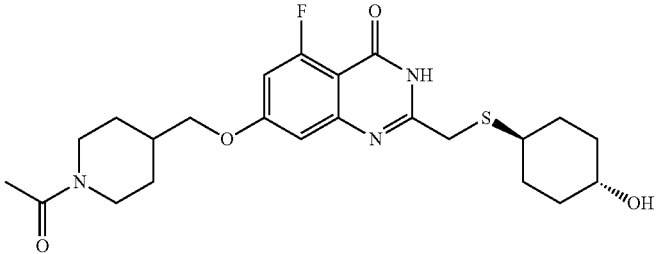<br>7-((1-Acetylpiperidin-4-yl)methoxy)-5-fluoro-2-((((trans)-4-hydroxycyclohexyl)thio)methyl)quinazolin-4(3H)-one | 464.1 |
| Example 397 | 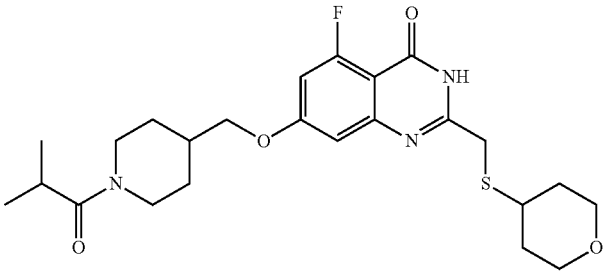<br>5-Fluoro-7-((1-isobutyrylpiperidin-4-yl)methoxy)-2-(((tetrahydro-2H-pyran-4-yl)thio)methyl)quinazolin-4(3H)-one | 478.1 |
| Example 398 | 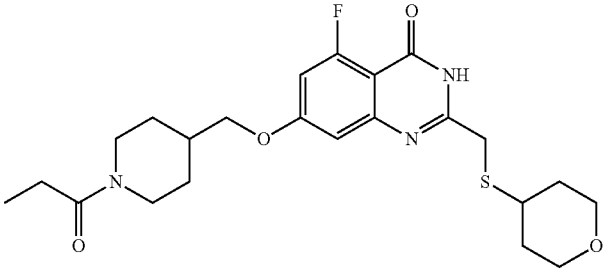<br>5-Fluoro-7-((1-propionylpiperidin-4-yl)methoxy)-2-(((tetrahydro-2H-pyran-4-yl)thio)methyl)quinazolin-4(3H)-one | 464.1 |
| Example 399 | 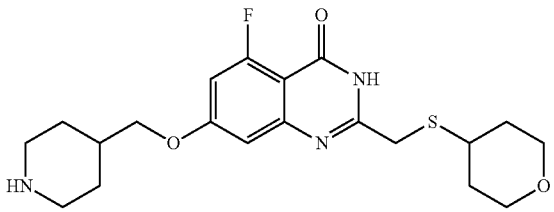<br>5-Fluoro-7-(piperidin-4-ylmethoxy)-2-(((tetrahydro-2H-pyran-4-yl)thio)methyl)quinazolin-4(3H)-one | 408.1 |

TABLE 11-continued

| Example | Structure/Name | MS [M + H]+ |
|---|---|---|
| Example 400 | (racemic)<br>5,6-Difluoro-7-((1-(tetrahydro-2H-pyran-4-yl)ethyl)amino)-2-(((tetrahydro-2H-pyran-4-yl)thio)methyl)quinazolin-4(3H)-one | 440.1 |
| Example 401 | (racemic)<br>7-((1-Acetylpiperidin-3-yl)methoxy)-5-fluoro-2-(((tetrahydro-2H-pyran-4-yl)thio)methyl)quinazolin-4(3H)-one | 450.1 |
| Example 402 | 5,6-Difluoro-2-(((tetrahydro-2H-pyran-4-yl)thio)methyl)-7-(((cis)-3-(trifluoromethoxy)cyclobutyl)amino)quinazolin-4(3H)-one | 466.0 |
| Example 403 | 7-Amino-5,6-difluoro-2-(((tetrahydro-2H-pyran-4-yl)thio)methyl)quinazolin-4(3H)-one | 328.0 |
| Example 404 | 7-(Cyclopropylmethoxy)-2-(((((trans)-4-(dimethylamino)cyclohexyl)thio)methyl)-5-fluoro-7,8-dihydroquinazolin-4(3H)-one | 406.1 |

TABLE 11-continued

| Example | Structure/Name | MS [M + H]+ |
|---|---|---|
| Example 405 | 5-Fluoro-2-((((cis)-3-hydroxycyclobutyl)thio)methyl)-7-((tetrahydro-2H-pyran-4-yl)methoxy)quinazolin-4(3H)-one | 395.1 |
| Example 406 | 5,6-Difluoro-7-((tetrahydro-2H-pyran-4-yl)methoxy)-2-(((tetrahydro-2H-pyran-4-yl)thio)methyl)quinazolin-4(3H)-one | 427.0 |
| Example 407 | 5,6-Difluoro-7-((2-methoxy-2-methylpropyl)amino)-2-(((tetrahydro-2H-pyran-4-yl)thio)methyl)quinazolin-4(3H)-one | 414.1 |
| Example 408 | (racemic) 5,6-Difluoro-7-(((((cis)-3-fluoro-1-methylpiperidin-4-yl)methyl)amino)-2-(((tetrahydro-2H-pyran-4-yl)thio)methyl)quinazolin-4(3H)-one | 457.1 |
| Example 409 | 7-((1-Acetylpiperidin-4-yl)methoxy)-5-fluoro-2-((((cis)-4-hydroxy-4-methylcyclohexyl)thio)methyl)quinazolin-4(3H)-one | 478.1 |

TABLE 11-continued

| Example | Structure/Name | MS [M + H]+ |
|---|---|---|
| Example 410 | 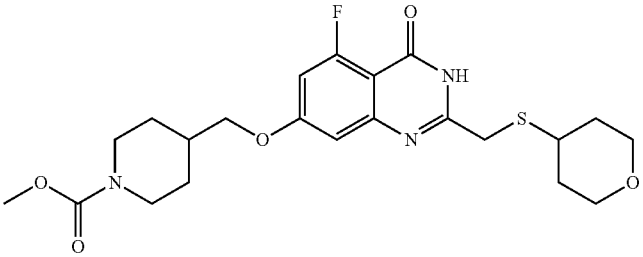<br>Methyl 4-(((5-fluoro-4-oxo-2-((((tetrahydro-2H-pyran-4-yl)thio)methyl)-3,4-dihydroquinazolin-7-yl)oxy)methyl)piperidine-1-carboxylate | 466.0 |
| Example 411 | 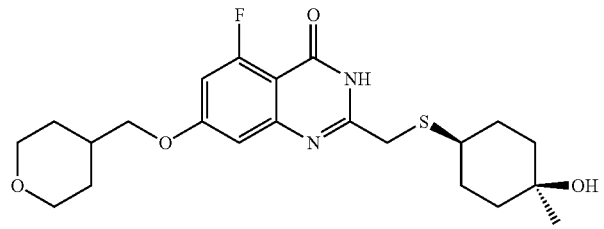<br>5-Fluoro-2-(((((trans)-4-hydroxy-4-methylcyclohexyl)thio)methyl)-7-((tetrahydro-2H-pyran-4-yl)methoxy)quinazolin-4(3H)-one | 437.1 |
| Example 412 | 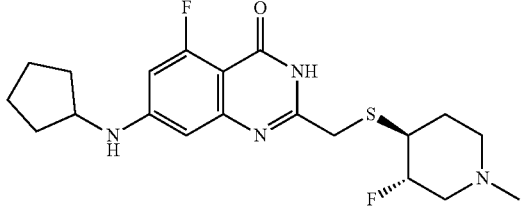<br>(racemic)<br>7-(Cyclopentylamino)-5-fluoro-2-(((((trans)-3-fluoro-1-methylpiperidin-4-yl)thio)methyl)quinazolin-4(3H)-one | 409.2 |
| Example 413 | 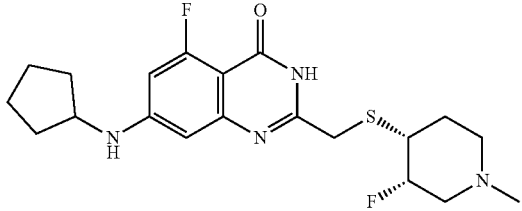<br>(racemic)<br>7-(Cyclopentylamino)-5-fluoro-2-(((((cis)-3-fluoro-1-methylpiperidin-4-yl)thio)methyl)quinazolin-4(3H)-one | 409.0 |
| Example 414 | 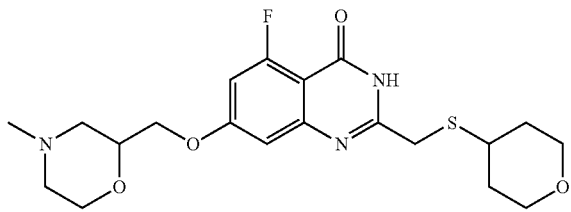<br>(racemic)<br>5-Fluoro-7-((4-methylmorpholin-2-yl)methoxy)-2-((((tetrahydro-2H-pyran-4-yl)thio)methyl)quinazolin-4(3H)-one | 424.0 |

TABLE 11-continued

| Example | Structure/Name | MS [M + H]+ |
| --- | --- | --- |
| Example 415 | 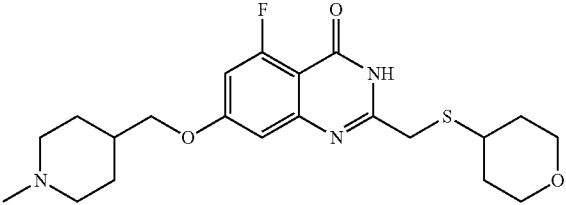<br>5-Fluoro-7-((1-methylpiperidin-4-yl)methoxy)-2-(((tetrahydro-2H-pyran-4-yl)thio)methyl)quinazolin-4(3H)-one | 422.1 |
| Example 416 | 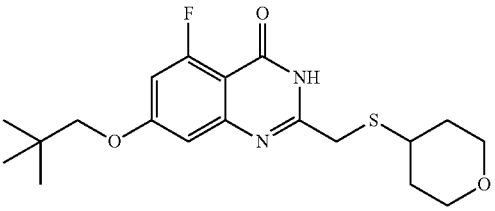<br>5-Fluoro-7-(neopentyloxy)-2-(((tetrahydro-2H-pyran-4-yl)thio)methyl)quinazolin-4(3H)-one | 381.1 |
| Example 417 | 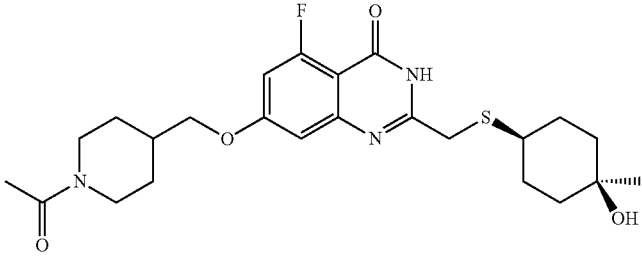<br>7-((1-Acetylpiperidin-4-yl)methoxy)-5-fluoro-2-((((trans)-4-hydroxy-4-methylcyclohexyl)thio)methyl)quinazolin-4(3H)-one | 478.1 |
| Example 418 | 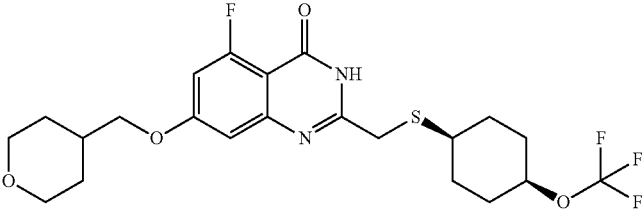<br>5-Fluoro-7-((tetrahydro-2H-pyran-4-yl)methoxy)-2-((((cis)-4-(trifluoromethoxy)cyclohexyl)thio)methyl)quinazolin-4(3H)-one | 491.1 |
| Example 419 | 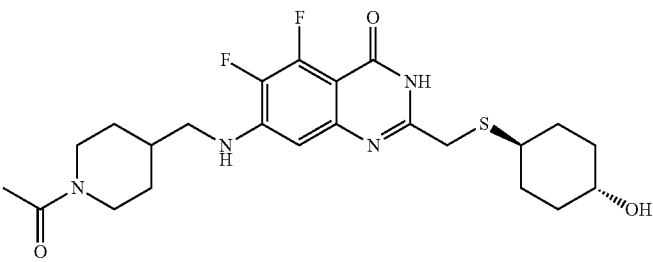<br>7-(((1-Acetylpiperidin-4-yl)methyl)amino)-5,6-difluoro-2-((((trans)-4-hydroxycyclohexyl)thio)methyl)quinazolin-4(3H)-one | 481.0 |

TABLE 11-continued

| Example | Structure/Name | MS [M + H]+ |
|---|---|---|
| Example 420 | 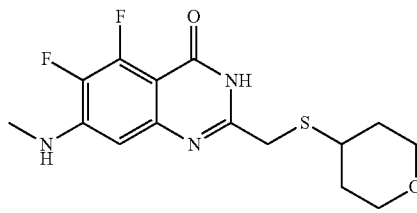<br>5,6-Difluoro-7-(methylamino)-2-(((tetrahydro-2H-pyran-4-yl)thio)methyl)quinazolin-4(3H)-one | 341.9 |
| Example 421 | 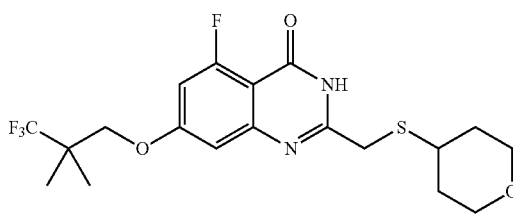<br>5-Fluoro-2-(((tetrahydro-2H-pyran-4-yl)thio)methyl)-7-(3,3,3-trifluoro-2,2-dimethylpropoxy)quinazolin-4(3H)-one | 435.0 |
| Example 422 | 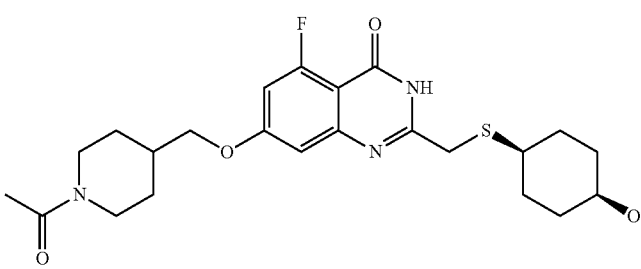<br>7-((1-Acetylpiperidin-4-yl)methoxy)-5-fluoro-2-(((((cis)-4-hydroxycyclohexyl)thio)methyl)quinazolin-4(3H)-one | 464.1 |
| Example 423 | 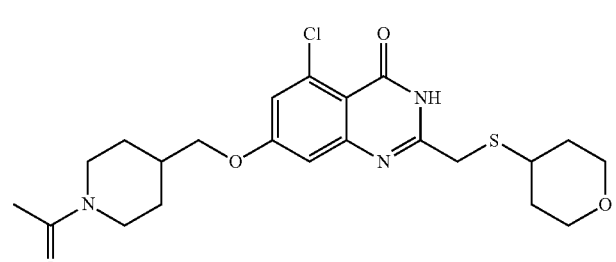<br>7-((1-Acetylpiperidin-4-yl)methoxy)-5-chloro-2-(((tetrahydro-2H-pyran-4-yl)thio)methyl)quinazolin-4(3H)-one | 466.0 |
| Example 424 | 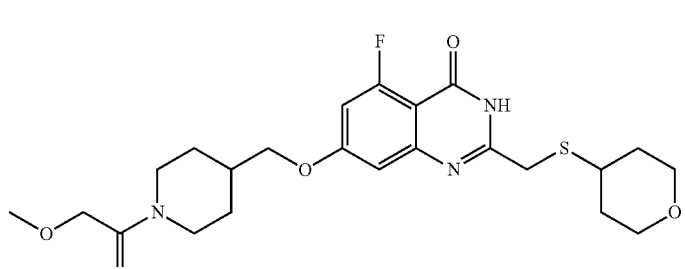<br>5-Fluoro-7-((1-(2-methoxyacetyl)piperidin-4-yl)methoxy)-2-(((tetrahydro-2H-pyran-4-yl)thio)methyl)quinazolin-4(3H)-one | 480.0 |

TABLE 11-continued

| Example | Structure/Name | MS [M + H]+ |
|---|---|---|
| Example 425 | 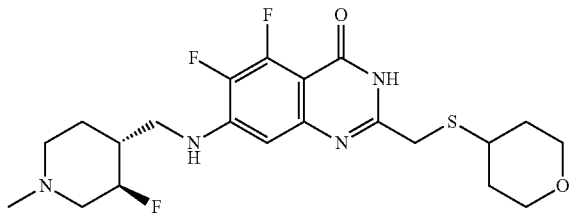<br>(racemic)<br>5,6-Difluoro-7-((((trans)-3-fluoro-1-methylpiperidin-4-yl)methyl)amino)-2-(((tetrahydro-2H-pyran-4-yl)thio)methyl)quinazolin-4(3H)-one | 457.0 |
| Example 426 | 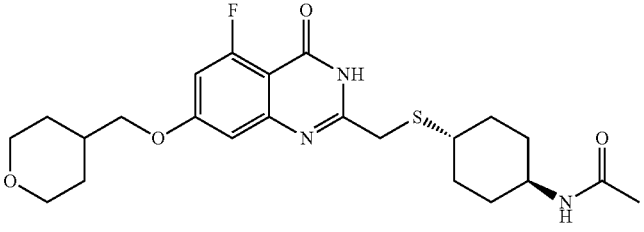<br>N-((trans)-4-(((5-Fluoro-4-oxo-7-((tetrahydro-2H-pyran-4-yl)methoxy)-3A-dihydroquinazolin-2-yl)methyl)thio)cyclohexyl)acetamide | 464.1 |
| Example 427 | 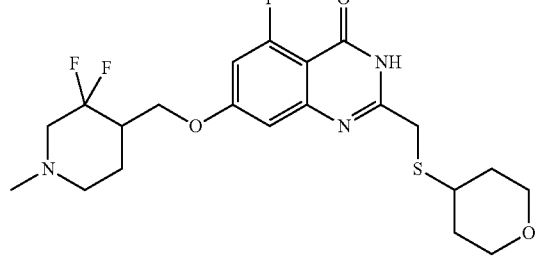<br>(Racemic)<br>7-((3,3-Difluoro-1-methylpiperidin-4-yl)methoxy)-5-fluoro-2-(((tetrahydro-2H-pyran-4-yl)thio)methyl)quinazolin-4(3H)-one | 458.0 |

Example A. Enzymatic Assay for Inhibition of PARP14

The catalytic domain of human PARP14 (residues 1611 to 1801, GenBank Accession No. NM_017554) was overexpressed in *Escherichia coli* cells. An N-terminal His-TEV fusion tag was used to purify the protein from cell lysates. The His-TEV tag was left on the protein for use in the enzymatic assay.

Enzymatic inhibition of PARP14 was measured using a dissociation-enhanced lanthanide fluorescence immunoassay (DELFIA) monitoring the auto-modification of PARP14 by biotinylated nicotinamide adenine dinucleotide (biotin-NAD). 1 µL of a dose response curve of each test compound was spotted in 384-well nickel-coated white microplates (Thermo) using a Mosquito (TTP Labtech). Reactions were performed in a 50 µL volume by adding 40 µL of PARP14 in assay buffer (20 mM HEPES pH=8, 100 mM NaCl, 0.1% bovine serum albumin, 2 mM DTT and 0.002%0 Tween20), incubating with test compound at 25° C. for 30 min, then adding 10 µL of biotin-NAD (Biolog). The final concentrations of PARP14 and biotin-NAD are 50 nM and 3 µM, respectively. Reactions proceeded at 25° C. for 3 h, then were quenched with 5 µL of 10 mM unmodified nicotinamide adenine dinucleotide (Sigma-Aldrich). The quenched reactions were washed 3 times with 100 µL of TBST wash buffer (50 mM Tris-HCl, 150 mM NaCl and 0.1% Tween20). Next, to the washed and dried plate was added 25 µL of DELFIA Europium-N1 streptavidin (Perkin Elmer) diluted in DELFIA assay buffer (Perkin Elmer). After a 30 min incubation at 25° C., the plate was washed 5 times with TBST wash buffer. Finally, 25 µL of DELFIA enhancement solution was added. After a 5 min incubation the plate was read on an Envision platereader equipped with a LANCE/DELFIA top mirror (Perkin Elmer) using excitation of 340 nm and emission of 615 nm to measure the amount of Europium present in each well, informing on the amount of biotin-NAD that was transferred in the automodification reaction. Control wells containing a negative control of 2% DMSO vehicle or a positive control of 100 µM rucaparib were used to calculate the 0% inhibition as described below:

$$\% \text{ inhibition} = 100 \times \frac{ex615_{cmpd} - ex615_{min}}{ex615_{max} - ex615_{min}}$$

where ex615$_{cmpd}$ is the emission from the compound treated well, ex615$_{min}$ is the emission from the rucaparib treated positive control well and ex615$_{max}$ is the emission from the DMSO treated negative control well.

The % inhibition values were plotted as a function of compound concentration and the following 4-parameter fit was applied to derive the IC$_{50}$ values:

$$Y = \text{Bottom} + \frac{(\text{Top} - \text{Bottom})}{\left(1 + \left(\frac{X}{IC_{50}}\right)^{\text{Hill Coefficient}}\right)}$$

where top and bottom are normally allowed to float, but may be fixed at 100 or 0 respectively in a 3-parameter fit. The Hill Coefficient is normally allowed to float but may also be fixed at 1 in a 3-parameter fit. Y is the % inhibition and X is the compound concentration.

IC$_{50}$ data for the Example compounds is provided below in Table A-1 ("+" is <1 µM; "++" is ≥1 µM<10 µM; and "+++" is ≥10 µM).

TABLE A-1

| Example No. | IC$_{50}$ PARP14 (µM) |
| --- | --- |
| 1 | +++ |
| 2 | + |
| 3 | ++ |
| 4 | +++ |
| 5 | ++ |
| 6 | ++ |
| 7 | +++ |
| 8 | + |
| 9 | ++ |
| 10 | +++ |
| 11 | +++ |
| 12 | ++ |
| 13 | + |
| 14 | ++ |
| 15 | ++ |
| 16 | ++ |
| 17 | ++ |
| 18 | + |
| 19 | +++ |
| 20 | + |
| 21 | + |
| 22 | + |
| 23 | + |
| 24 | ++ |
| 25 | +++ |
| 26 | ++ |
| 27 | ++ |
| 28 | +++ |
| 29 | ++ |
| 30 | ++ |
| 31 | ++ |
| 32 | ++ |
| 33 | + |
| 34 | + |
| 35 | + |
| 36 | +++ |
| 37 | +++ |
| 38 | +++ |
| 39 | +++ |
| 40 | +++ |
| 41 | +++ |
| 42 | +++ |
| 43 | +++ |
| 44 | + |
| 45 | ++ |
| 46 | ++ |
| 47 | ++ |
| 48 | ++ |
| 49 | ++ |
| 50 | ++ |
| 51 | + |
| 52 | ++ |
| 53 | + |
| 54 | ++ |
| 55 | ++ |
| 56 | + |
| 57 | + |
| 58 | + |
| 59 | + |
| 60 | + |
| 61 | + |
| 62 | + |
| 63 | ++ |
| 64 | + |
| 65 | ++ |
| 66 | + |
| 67 | + |
| 68 | ++ |
| 69 | + |
| 70 | ++ |
| 71 | ++ |
| 72 | +++ |
| 73 | + |
| 74 | +++ |
| 75 | +++ |
| 76 | ++ |
| 77 | +++ |
| 78 | +++ |
| 79 | + |
| 80 | + |
| 81 | ++ |
| 82 | ++ |
| 83 | ++ |
| 84 | ++ |
| 85 | ++ |
| 86 | ++ |
| 87 | ++ |
| 88 | +++ |
| 89 | ++ |
| 90 | ++ |
| 91 | ++ |
| 92 | ++ |
| 93 | +++ |
| 94 | + |
| 95 | ++ |
| 96 | ++ |
| 97 | ++ |
| 98 | + |
| 99 | ++ |
| 100 | + |
| 101 | + |
| 102 | + |
| 103 | + |
| 104 | ++ |
| 105 | + |
| 106 | ++ |
| 107 | + |
| 108 | + |
| 109 | ++ |
| 110 | ++ |
| 111 | ++ |
| 112 | ++ |
| 113 | +++ |
| 114 | ++ |
| 115 | + |
| 116 | + |
| 117 | ++ |
| 118 | ++ |
| 119 | + |
| 120 | +++ |
| 121 | + |
| 122 | + |
| 123 | + |
| 124 | + |
| 125 | ++ |
| 126 | ++ |

TABLE A-1-continued

| Example No. | IC$_{50}$ PARP14 (µM) |
|---|---|
| 127 | +++ |
| 128 | ++ |
| 129 | ++ |
| 130 | ++ |
| 131 | ++ |
| 132 | +++ |
| 133 | +++ |
| 134 | ++ |
| 135 | +++ |
| 136 | + |
| 137 | + |
| 138 | + |
| 139 | + |
| 140 | + |
| 141 | ++ |
| 142 | + |
| 143 | ++ |
| 144 | ++ |
| 145 | + |
| 146 | + |
| 147 | + |
| 148 | + |
| 149 | ++ |
| 150 | ++ |
| 151 | + |
| 152 | + |
| 153 | + |
| 154 | + |
| 155 | + |
| 156 | ++ |
| 157 | + |
| 158 | ++ |
| 159 | ++ |
| 160 | ++ |
| 161 | ++ |
| 162 | + |
| 163 | ++ |
| 164 | ++ |
| 165 | + |
| 166 | + |
| 167 | ++ |
| 168 | ++ |
| 169 | + |
| 170 | + |
| 171 | + |
| 172 | + |
| 173 | ++ |
| 174 | + |
| 175 | ++ |
| 176 | + |
| 177 | + |
| 178 | ++ |
| 179 | + |
| 180 | + |
| 181 | + |
| 182 | ++ |
| 183 | ++ |
| 184 | + |
| 185 | + |
| 186 | + |
| 187 | + |
| 188 | +++ |
| 189 | ++ |
| 190 | + |
| 191 | ++ |
| 192 | + |
| 193 | + |
| 194 | + |
| 195 | + |
| 196 | + |
| 197 | + |
| 198 | ++ |
| 199 | + |
| 200 | + |
| 201 | + |
| 202 | ++ |
| 203 | + |

TABLE A-1-continued

| Example No. | IC$_{50}$ PARP14 (µM) |
|---|---|
| 204 | ++ |
| 205 | + |
| 206 | + |
| 207 | +++ |
| 208 | + |
| 209 | + |
| 210 | + |
| 211a | + |
| 211b | + |
| 212 | + |
| 213a | + |
| 213b | + |
| 214 | + |
| 215 | + |
| 216 | ++ |
| 217 | + |
| 218 | + |
| 219 | + |
| 220 | + |
| 221 | ++ |
| 222 | + |
| 223 | + |
| 224 | ++ |
| 225 | +++ |
| 226 | + |
| 227 | ++ |
| 228 | ++ |
| 229 | + |
| 230 | ++ |
| 231 | + |
| 232 | + |
| 233 | + |
| 234 | ++ |
| 235 | + |
| 236 | + |
| 237 | + |
| 238 | + |
| 239a | + |
| 239b | + |
| 240 | + |
| 241 | + |
| 242 | ++ |
| 243 | + |
| 244 | + |
| 245 | ++ |
| 246 | + |
| 247 | + |
| 248 | + |
| 249 | + |
| 250 | + |
| 251 | + |
| 252 | + |
| 253 | + |
| 254 | + |
| 255 | + |
| 256 | + |
| 257 | + |
| 258 | + |
| 259 | + |
| 260 | +++ |
| 261 | + |
| 262 | + |
| 263 | + |
| 264 | + |
| 265 | + |
| 266 | + |
| 267 | + |
| 268 | + |
| 269 | + |
| 270 | + |
| 271 | + |
| 272 | ++ |
| 273 | + |
| 274 | + |
| 275 | + |
| 276 | + |
| 277 | + |

TABLE A-1-continued

| Example No. | IC$_{50}$ PARP14 (μM) |
|---|---|
| 278 | + |
| 279 | + |
| 280 | + |
| 281 | + |
| 282 | + |
| 283 | + |
| 284 | + |
| 285 | + |
| 286 | + |
| 287 | + |
| 288 | + |
| 289 | ++ |
| 290 | + |
| 291 | + |
| 292 | + |
| 293 | + |
| 294 | + |
| 295 | + |
| 296 | + |
| 297 | ++ |
| 298 | + |
| 299 | + |
| 300 | + |
| 301 | + |
| 302 | + |
| 303 | + |
| 304 | + |
| 305 | + |
| 306 | ++ |
| 307 | + |
| 308 | + |
| 309 | + |
| 310 | + |
| 311 | ++ |
| 312 | + |
| 313 | + |
| 314 | + |
| 315 | + |
| 316 | + |
| 317 | + |
| 318 | + |
| 319 | + |
| 320 | + |
| 321a | + |
| 321b | + |
| 322 | + |
| 323a | + |
| 323b | + |
| 324 | + |
| 325a | + |
| 325b | + |
| 326 | + |
| 327a | + |
| 327b | + |
| 328 | + |
| 329 | + |
| 330 | + |
| 331 | + |
| 332 | + |
| 333 | + |
| 334 | + |
| 335a | + |
| 335b | + |
| 336 | ++ |
| 337 | + |
| 338 | + |
| 339 | + |
| 340 | + |
| 341 | + |
| 342 | + |
| 343 | + |
| 344 | + |
| 345 | + |
| 346 | + |
| 347 | + |
| 348 | + |
| 349 | + |
| 350 | + |
| 351 | + |
| 352 | ++ |
| 353 | + |
| 354 | + |
| 355 | + |
| 356 | + |
| 357 | + |
| 358 | + |
| 359 | + |
| 360 | + |
| 361 | + |
| 362 | + |
| 363 | + |
| 364 | + |
| 365 | + |
| 366 | + |
| 367 | + |
| 368 | ++ |
| 369 | + |
| 370 | + |
| 371 | + |
| 372 | + |
| 373 | + |
| 374 | + |
| 375 | + |
| 376 | + |
| 377 | + |
| 378 | + |
| 379 | + |
| 380 | + |
| 381 | + |
| 382 | + |
| 383 | + |
| 384 | + |
| 385 | + |
| 386 | + |
| 387 | + |
| 388 | + |
| 389 | + |
| 390 | + |
| 391 | + |
| 392 | + |
| 393 | + |
| 394 | + |
| 395 | + |
| 396 | + |
| 397 | + |
| 398 | + |
| 399 | + |
| 400 | +++ |
| 401 | + |
| 402 | + |
| 403 | +++ |
| 404 | + |
| 405 | + |
| 406 | + |
| 407 | ++ |
| 408 | ++ |
| 409 | + |
| 410 | + |
| 411 | + |
| 412 | + |
| 413 | + |
| 414 | + |
| 415 | + |
| 416 | + |
| 417 | + |
| 418 | + |
| 419 | + |
| 420 | + |
| 421 | + |
| 422 | + |

TABLE A-1-continued

| Example No. | IC$_{50}$ PARP14 (µM) |
|---|---|
| 423 | + |
| 424 | + |
| 425 | + |
| 426 | + |
| 427 | + |

Example B: mRNA Expression Levels of PARP14 in Various Cancer Types

FIG. 1 illustrates the mRNA expression levels of PARP14 in various cancer types, compared to their matched normal tissue. RNA sequencing data were downloaded from The Cancer Genome Consortium (TCGA) and analyzed. Individual dots represent values from individual samples, boxes represent the interquartile or middle 50% of the data with horizontal lines being the group median, vertical lines representing the upper and lower quartiles of the data. It is apparent that PARP14 mRNA is higher, compared to normal tissue, in several cancer types. BLCA=bladder cancer, BRCA=breast cancer, ESCA=esophageal cancer, HNSC=head and neck cancer, KIRP=papillary kidney cancer, KIRC=clear cell kidney cancer, READ=rectal cancer, STAD=stomach cancer, THCA=thyroid cancer, UCEC—uterine cancer. *p<0.05, p<0.01, *p<0.001, Wilcoxon test.

Figure 2A:
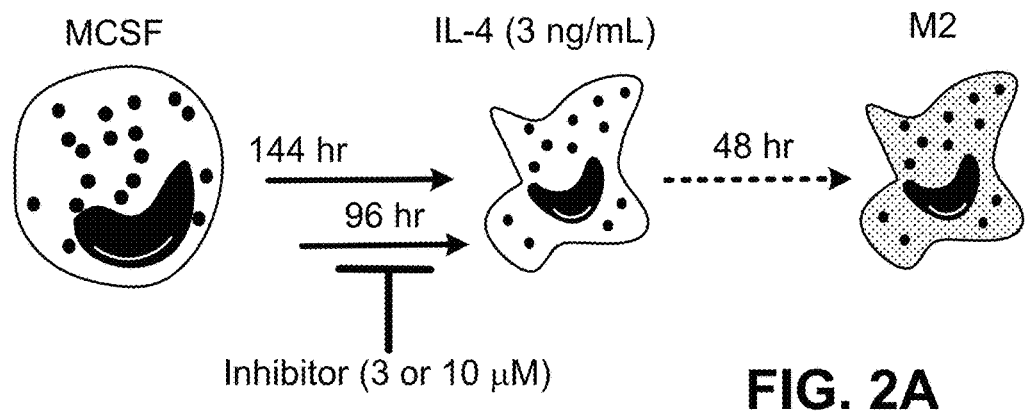
FIGS. 2A and 2B illustrate that in vitro treatment with various PARP14 inhibitors decreases IL-10 production in IL-4 stimulated M2-like macrophages.
Figure 2B:
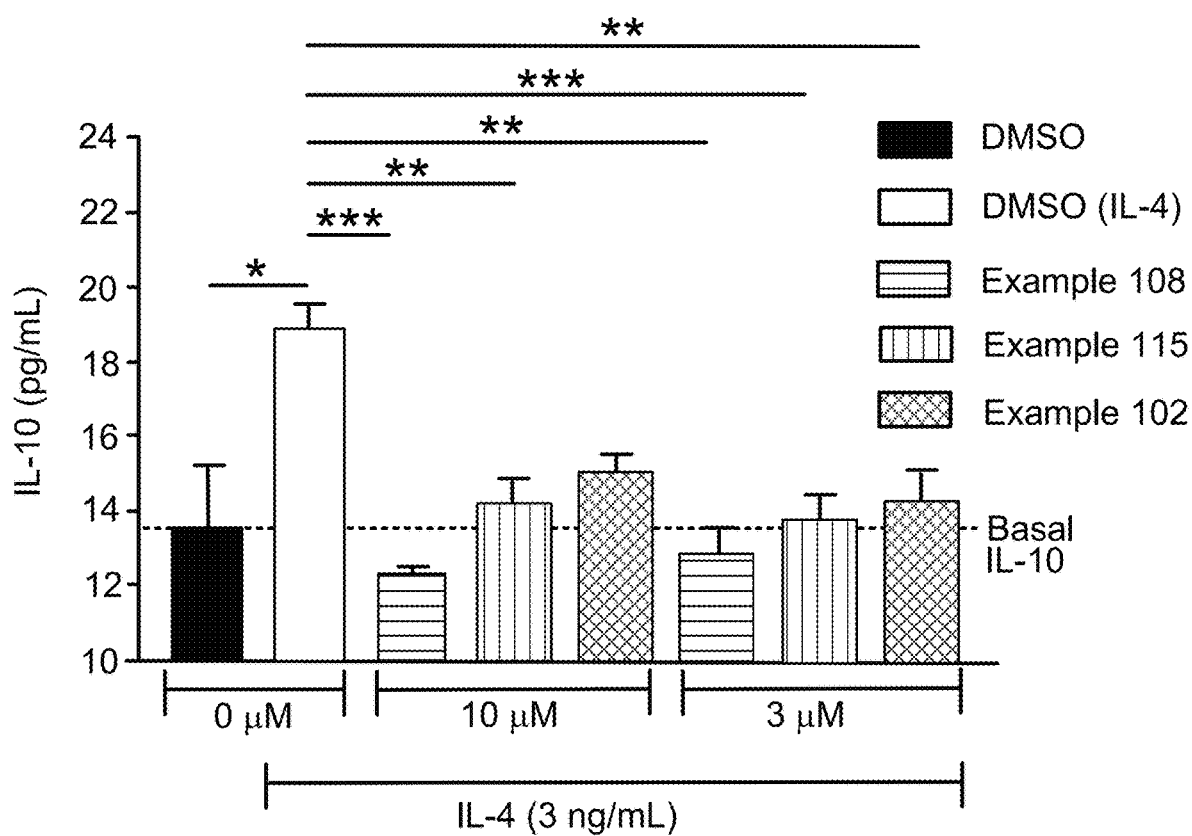

Example C: Reduction of IL-10 Production in Cells by Treatment with PARP14 Inhibitors FIGS. 2A and 2B illustrate that in vitro treatment with various PARP14 inhibitors decreases IL-10 production in IL-4 stimulated M2-like macrophages. Figure A) Experimental layout. Monocytes were isolated from peripheral human blood and cultured in the presence of M-CSF and PARP14 inhibitors (at 10 or 3 µM) for 96 h. M-CSF differentiates monocytes into M-0 macrophages. Subsequently medium was replaced with fresh medium containing IL-4 and PARP14 inhibitors (at 10 or 3 µM), and cells were incubated for another 48 h. Figure B) IL-10 levels in tissue culture supernatant, measured by ELISA, of cells treated as described under A. *p<0.5, p<0.01, *p<0.001; statistical significance was determined by the Holm-Sidak method.

Isolation of primary human monocytes from whole blood: Primary monocytes were isolated from whole blood (iSPECIMEN; 500 mL) collected from healthy donors. Blood was diluted at a 1:1 ratio with EasySep buffer (STEMCELL Technologies 20144) and layered onto lymphoprep (STEMCELL Technologies 07811) in SepMate tubes (STEMCELL Technologies 85450) for PBMC isolation according to the manufacturer's instructions. The isolated PBMCs were pooled, washed with EasySep buffer, resuspended in the appropriate volume of ammonium chloride solution (STEMCELL Technologies 07850; 10-15 mL) for RBC lysis, and gently shaken for 10 minutes. The total volume was increased to 40 mL with EasySep buffer to dilute the RBC lysis, then cells were centrifuged at 1500 rpm for 5 minutes. Fresh EasySep buffer was used to resuspend PBMCs for counting. The EasySep human monocyte isolation kit (STEMCELL Technologies 19359) was used to isolate monocytes from the PBMC cell population according to the manufacturer's instructions. The enriched monocyte cell population was resuspended in fresh EasySep buffer for counting and seeding for subsequent assays.

Monocyte to macrophage differentiation, M2 polarization, and PARP14 inhibition: Monocytes were seeded on day 0 in ImmunoCult SF macrophage medium (STEMCELL Technologies 10961) containing 50 ng/mL M-CSF (STEMCELL Technologies 78057) at a density of 1 million cells per 1 mL of media in 12-well plates and allowed to grow and differentiate into macrophages for 6 days. On day 4, one half of the initial volume of media was added to each well. Six days after monocyte seeding, cells were treated with 3 ng/mL human recombinant IL-4 (STEMCELL Technologies 78045) and samples were collected (media and cells) at 24, 48, and 72 hours. Cells were treated with PARP14 inhibitors (Examples 102, 108, and 115) or DMSO on day 2 or day 4 after seeding at 10 µmol/L and 3 µmol/L.

IL-10 determination: Levels of IL-10 in the supernatants of human primary M2 macrophages were determined with the IL-10 ELISA kit (STEMCELL Technologies 02013) according to the manufacturer's instructions. Briefly, supernatants were collected at the indicated time points and depleted of any floating cells before being stored at −80° C. until ready to use. Supernatants were diluted at a ratio of 1:3 for the assay and concentrations were determined from the kit's IL-10 standard curve and normalized to total cell protein.

Example D: Inhibition of Tumor Growth by Treatment with a PARP14 Inhibitor

Figure 3A:
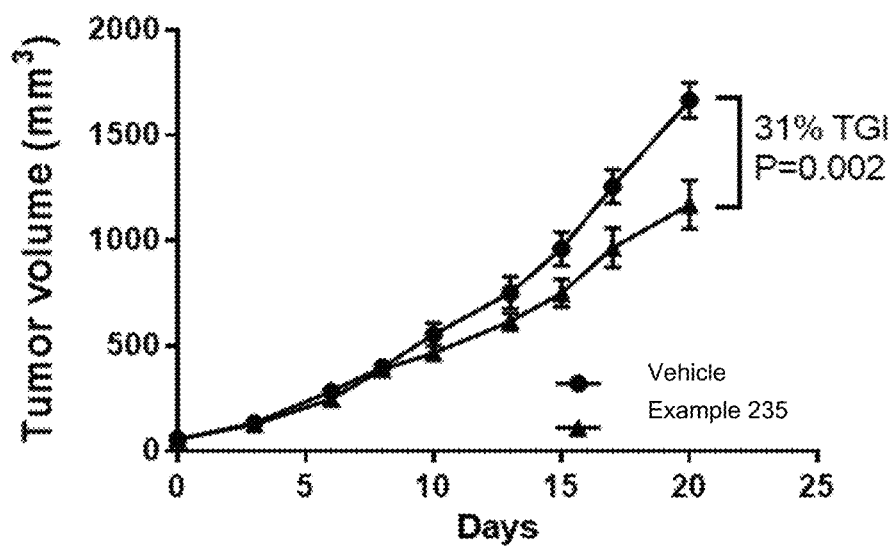
FIG. 3A illustrates that a PARP14 inhibitor reduces tumor growth in a 4T1 murine syngeneic model.
Figure 3B:
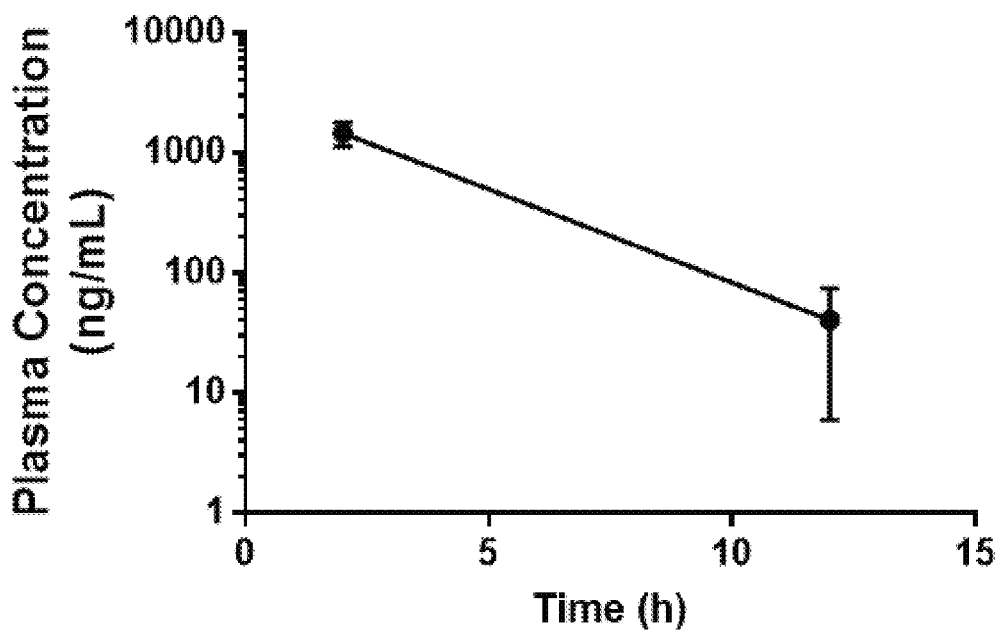
FIG. 3B shows the plasma concentration of the PARP14 inhibitor following the last dose at the study endpoint.
Figure 4A:
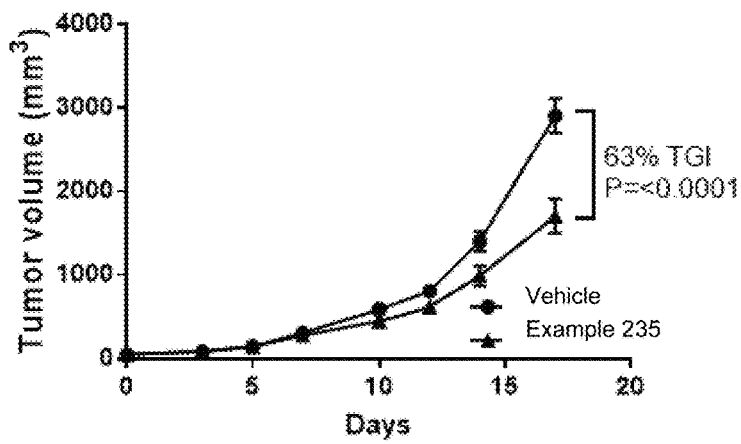
FIG. 4A illustrates that a PARP14 inhibitor reduces tumor growth in a LL/2 murine syngeneic model.

FIGS. 3A and 4A illustrate that a PARP14 inhibitor (Example 235) reduces tumor growth in the murine syngeneic models (A) 4T1 and (B) LL/2. For the 4T1 study (FIGS. 3A and 3B), female BALB/c mice were inoculated orthotopically in the mammary fat pad with 1×10$^5$ 4T1 cells (ATCC, CRL-2539™) for tumor development. Seven days after tumor inoculation, 16 mice with tumor size ranging from 41-78 mm$^3$ (average tumor size 56 mm$^3$) were selected and assigned into 2 groups using stratified randomization with 8 mice in each group based upon their tumor volumes. The treatments were started from the next day post randomization (defined as randomization day DO) and were treated with vehicle (0.5% methylcellulose +0.2% Tween 80), or the compound of Example 235 (500 mg/kg PO BID*21 days). The tumor sizes were measured three times per week during the treatment. The entire study was terminated on D20. Tumor growth inhibition of 31% was observed for the treatment group versus the vehicle group.

For the LL/2 study (FIGS. 4A-4C), female C57BL/6 mice were inoculated subcutaneously in the right flank with 5×10$^5$ LL/2 cells (ATCC, CRL-1642™) for tumor development. Five days after tumor inoculation, 16 mice with tumor size ranging from 37-72 mm$^3$ (average tumor size 51 mm$^3$) were selected and assigned into 2 groups using stratified randomization with 8 mice in each group based upon their tumor volumes. The treatments were started from the next day post randomization (defined as randomization day DO) and were treated with vehicle (0.5% methylcellulose +0.2% Tween 80), or the compound of Example 235 (500 mg/kg PO BID*21 days). The tumor sizes were measured three times per week during the treatment. The entire study was terminated on D21. Tumor growth inhibition of 63% was observed for the treatment group versus the vehicle group.

Figure 4B:
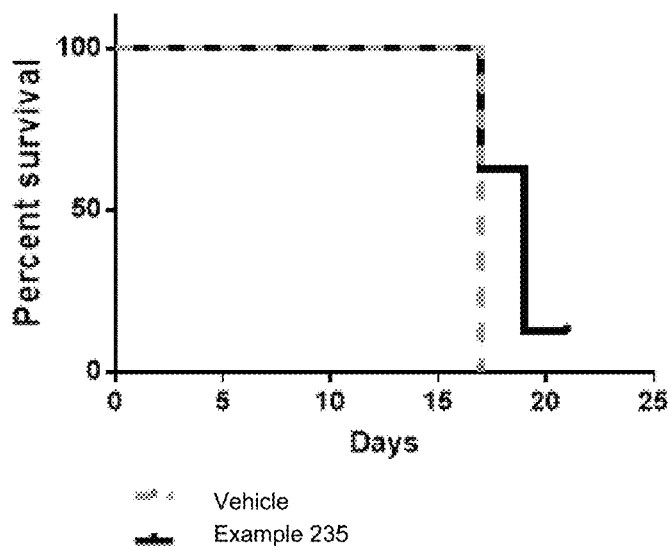
FIG. 4B shows the survival benefit of administration of the PARP14 inhibitor in the LL/2 syngeneic model.
Figure 4C:
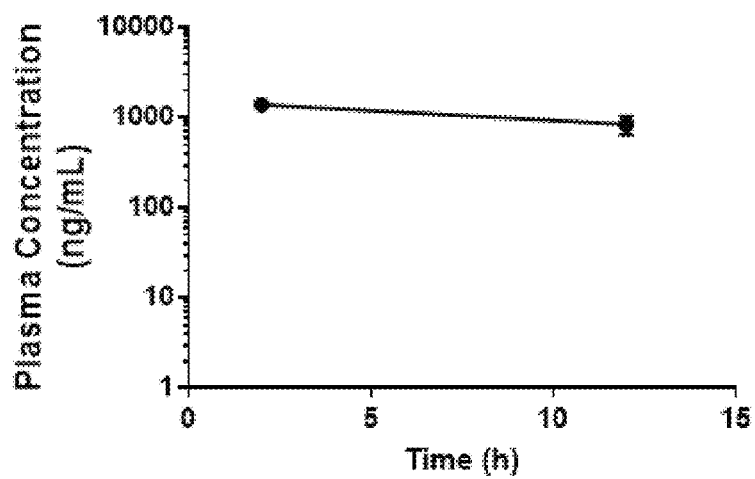
FIG. 4C shows the plasma concentration of the PARP14 inhibitor following the last dose at the study endpoint.

Mean tumor volume and SEM for both studies were plotted and are shown in FIGS. 3A and 4A. Statistical significance, calculated using 2way ANOVA multiple comparisons in which each treatment group was compared to vehicle control, is indicated by an asterisk. Statistics were performed on groups with less than 20% animal loss (D20 for 4T1, D17 for LL/2). Survival benefit was determined for the LL/2 study (FIG. 4B). Individual mice were euthanized once they reached the termination endpoint (TV>2000 mm3). The time from treatment initiation to termination was deemed as its survival time and plotted in a Kaplan-Meier survival curve format. Mice remaining at study end date of 21 days were euthanized at day 21 after treatment initiation. The plasma concentration of the compound of Example 235 at 2 and 12 hours following the last dose at study endpoint is plotted (FIGS. 3B and 4C).

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound which is 7-((1-acetylpiperidin-4-yl)methoxy)-5-fluoro-2-(((tetrahydro-2H-pyran-4-yl)thio)methyl)quinazolin-4(3H)-one, or a pharmaceutically acceptable salt thereof.

2. A compound which is 7-((1-acetylpiperidin-4-yl)methoxy)-5-fluoro-2-(((tetrahydro-2H-pyran-4-yl)thio)methyl)quinazolin-4(3H)-one.

3. A pharmaceutical composition comprising a compound of claim 1, or a pharmaceutically acceptable salt thereof, and at least one pharmaceutically acceptable carrier.

4. A pharmaceutical composition comprising a compound of claim 2 and at least one pharmaceutically acceptable carrier.

* * * * *